United States Patent [19]
Breitman et al.

[11] Patent Number: 5,998,187
[45] Date of Patent: Dec. 7, 1999

[54] RECEPTOR TYROSINE KINASE

[75] Inventors: Martin L. Breitman, Willowdale; Janet Rossant, Toronto; Daniel J. Dumont, Oakville; Terry P. Yamaguchi, Toronto, all of Canada; Jo-Ann Breitman, Toronto, Canada, executor of said Martin L. Breitman, deceased

[73] Assignee: Mount Sinai Hospital Corporation, Toronto, Canada

[21] Appl. No.: 08/838,957

[22] Filed: Apr. 23, 1997

Related U.S. Application Data

[60] Division of application No. 08/278,089, Jul. 20, 1994, Pat. No. 5,687,714, which is a continuation-in-part of application No. 08/235,408, Apr. 29, 1994, abandoned, which is a continuation-in-part of application No. 07/921,795, Jul. 30, 1992, abandoned.

[51] Int. Cl.⁶ .................................................. C07K 14/705
[52] U.S. Cl. ........................ 435/194; 435/69.1; 435/69.7; 530/350; 530/402
[58] Field of Search .................................. 530/350, 300, 530/326, 402; 435/194, 69.1, 69.7

[56] References Cited

FOREIGN PATENT DOCUMENTS

| | | |
|---|---|---|
| WO94/00469 | 1/1994 | WIPO . |
| WO96/11269 | 4/1996 | WIPO . |
| WO96/11664 | 4/1996 | WIPO . |

OTHER PUBLICATIONS

Kramer, H., Cagan, R.L. & Zipursky, S.L. (1991), Nature, 352, 207–212.
Schejter, E.D. & Shilo, B.Z. (1989), Cell, 56, 1093–1104.
Geissler, E.N., Rayn, M.A. & Housman, D.E. (1988), Cell, 185–192.
Chabot, B., Stephenson, D.A., Chapman, V.M., Besmer, P. & Bernstein, A. (1988), Nature, 335, 88–89.
Russell, E.S. (1979), Adv. Genet., 20, 357–459.
Dubreuil et al., (1990), Ann. N.Y. Acad. Sci., 599, 58–65.
Williams et al., (1990), Cell, 63, 167–174.
Copeland et a., (1990), Cell, 63, 175–183.
Flanagan, J.G., & Leder, P. (1990), Cell, 63, 185–194.
Stephenson et al., (1991), Proc. Natl. Acad. Sci. 88, 6–10.
Pawson, T. & Bernstein, A. (1991), Trends Gen., 6, 350–356.
Noden, D.M. (1988) Development,103, 121–140.
Tomasi, V., Manica, F. & Spisni, E. (1990), BioFactors, 2, 213–217.
Maher, P.A. (1991), J. Cell Biol., 112, 955–963.
Runyan et al., (1990), Cell Reg. 1, 301–313.
Rodrigues, G.A., Naujokas, M.A. & Park, M. (1991), Mol. Cell. Biol., 11, 2962–2970.
Tahira, T., Ishizaka, Y., Itoh, F., Sugimura, T. & Nagano, M. (1990), Oncogene, 5, 97–102.
Reid et al, (1990), Proc. Natl. Acad. Sci., 87, 1596–1600.
Bernard, O., Li, M. & Reid, H.H. (1991), Proc. Natl. Acad. Sci. USA, 88, 7625–7629.

Eisemann, A., Ahn, J.A., Graziani, G., Tronick, S.R. & Ron, D. (1991), Oncogene, 6, 1195–1202.
Fujita, H., Ohta, M., Kawaski, T. & Itoh, N. (1991), Biochem. Biophis. Res. Comm., 174, 946–951.
Vu et al., (1989), Mol. Cell Biol., 9, 4563–4567.
Pardanaud et al., (1987), Development, 100, 339–349.
Coffin, J.D. & Poole, T.J. (1988). Development, 102, 735–748.
Noden, D.M. (1989), Am. Rev. Respir. Dis., 140, 1097–1103.
Noden, D.M. (1990), Ann. N.Y. Acad. Sci., 236–249.
Wagner, R.C. (1980), Adv. Microcirc., 9, 45–75.
Beddington, R.S.P. & Martin, P. (1989), Mol. Cell. Med., 6, 263–274.
Sadowski, I. et al., Mol. Cell, Biol. 6, 4396 (1986).
Koch et al., Science 252:668–674, (1991).
Moran et al., PNAS USA 87:8622, (1990).
Anderson et al., Science 250:979, (1990).
Muslin, A.J. & Williams, L.T. (1991). Development, 112, 1095–1101.
Hanks, S.K., Quinn, A.M. & Hunter, T. (1988), Science, 241, 42–52.
Takahashi, M. & Cooper, G.M. (1987). Mol. Cell. Biol., 7, 1378–1385.
Partanen et al., (1990), Proc. Natl. Acad. Sci., 87, 8913–8917.
Safran et al., (1990), Oncogene, 5, 635–643.
Dumont et al. Abstracts, 20th Annual Meeting J. of Cell Biochem. 15C, Jan. 24–Feb. 3, (1991).
Dumont et al., J. of Cell Biochem. Supplement 16F, Apr. 3–16, (1992).
Dumont, D.J. et al. (1993), Oncogene, 7:1471–1480.
Dumont, D.J. et al. (1992), Oncogene, 8:1293–1301.
Dumont, D.J. et al., The Eastern Canadian Conference on Development and Cancer, Sep. 23–25, (1991).
Iwana, A. et al., Biochem. Biophys. Res. Com. 195:301, (1993).
Horita, et al., Biochem. Biophys. Res. Co. 189: 1747–1753, (1992).
Lyon & Searle, Genetic Variants and Strains of the Laboratory Mouse, New York: Oxford University Press, (1989), pp. 47, 87, 151, 179, 210, 270, 294 and 419.
S.J. O'Brien, Genetic Maps, Locus Maps of Complex Genomics, (Aug. 1991).
Sambrook et al., Molecular Cloning, A Lab Manual, Sec. Edition. vol. 3, pp. 1610–1630 and 17.2–17.28, Cold Spring Harbor Lab. Press, 1989.

(List continued on next page.)

Primary Examiner—Sally Teng
Attorney, Agent, or Firm—Merchant & Gould P.C.

[57] ABSTRACT

Novel receptor tyrosine kinase protein and isoforms thereof which are expressed in cells of the endothelial lineage, and DNA segments encoding the novel protein and isoforms thereof are disclosed. Methods for identifying ligands which are capable of binding to the receptor protein and methods for screening for agonist or antagonist substances of the interaction of the protein and a ligand are also disclosed.

5 Claims, 70 Drawing Sheets

OTHER PUBLICATIONS

Klagsbrun, M. and P.A. D'Amore, Annu. Rev. Physiol. 53:217–39, 1991.

Lewin, Science, 237, 1570, Sep. 25, 1987.

Reeck et al., Cell, 50, 667, Aug. 28, 1987.

George et al., Macromolecular Sequencing and Synthesis, Selected Methods and Applications, pp. 127–149, 1988, Alan R. Liss, Inc.

```
   1 ATCAAGTTTCAAGACGTGATCGGAGAGGGCAACTTTGGCCAGGTTCTGAAGGCACGCATCAAGAAGGATG    70
     I  K  F  Q  D  V  I  G  E  G  N  F  G  Q  V  L  K  A  R  I  K  K  D  G
  71 GGTTACGGATGGATGCCGCCATCAAGAGGATGAAAGAGTATGCCTCCAAAGATGATCACAGGGACTTCGC   140
     L  R  M  D  A  A  I  K  R  M  K  E  Y  A  S  K  D  D  H  R  D  F  A
 141 AGGAGAACTGGAGGTTCTTTGTAAACTTGGACACCATCCAAACATCATTAATCTCTTGGGAGCATGTGAA   210
     G  E  L  E  V  L  C  K  L  G  H  H  P  N  I  I  N  L  L  G  A  C  E
 211 CACCGAGGCTATTTGTACCTAGCTATTGAGTATGCCCCGCATGGAAACCTCCTGGACTTCCTGCGTAAGA   280
     H  R  G  Y  L  Y  L  A  I  E  Y  A  P  H  G  N  L  L  D  F  L  R  K  S
 281 GCAGAGTGCTAGAGACAGACCCTGCTTTTGCCATCGCCAACAGTACAGCTTCCACACTGTCCTCCCAACA   350
     R  V  L  E  T  D  P  A  F  A  I  A  N  S  T  A  S  T  L  S  S  Q  Q
 351 GCTTCTTCATTTTGCTGCAGATGTGGCCCGGGGGATGGACTACTTGAGCCAGAAACAGTTTATCCACAGG   420
     L  L  H  F  A  A  D  V  A  R  G  M  D  Y  L  S  Q  K  Q  F  I  H  R
 421 GACCTGGCTGCCAGAAACATTTTAGTTGGTGAAAACTACATAGCCAAAATAGCAGATTTTGGATTGTCAC   490
     D  L  A  A  R  N  I  L  V  G  E  N  Y  I  A  K  I  A  D  F  G  L  S  R
 491 GAGGTCAAGAAGTGTATGTGAAAAAGACAATGGGAAGGCTCCCAGTGCGTTGGATGGCAATCGAATCACT   560
     G  Q  E  V  Y  V  K  K  T  M  G  R  L  P  V  R  W  M  A  I  E  S  L
 561 GAACTATAGTGTCTATACAACCAACAGTGATGTCTGGTCCTATGGTGTATTGCTCTGGGAGATTGTTAGC   630
     N  Y  S  V  Y  T  T  N  S  D  V  W  S  Y  G  V  L  L  W  E  I  V  S
 631 TTAGGAGGCACCCCCTACTGCGGCATGACGTGCGCGGAGCTCTATGAGAAGCTACCCCAGGGCTACAGGC   700
     L  G  G  T  P  Y  C  G  M  T  C  A  E  L  Y  E  K  L  P  Q  G  Y  R  L
 701 TGGAGAAGCCCCTGAACTGTGATGATGAGGTGTATGATCTAATGAGACAGTGCTGGAGGGAGAAGCCTTA   770
     E  K  P  L  N  C  D  D  E  V  Y  D  L  M  R  Q  C  W  R  E  K  P  Y
 771 TGAGAGACCATCATTTGCCCAGATATTGGTGTCCTTAAACAGGATGCTGGAAGAACGGAAGACATACGTG   840
     E  R  P  S  F  A  Q  I  L  V  S  L  N  R  M  L  E  E  R  K  T  Y  V
 841 AACACCACACTGTATGAGAAGTTTACCTATGCAGGAATTGACTGCTCTGCGGAAGAAGCAGCCTAGAGCA   910
     N  T  T  L  Y  E  K  F  T  Y  A  G  I  D  C  S  A  E  E  A  A  *
 911 GAACTCTTCATGTACAACGGCCATTTCTCCTCACTGGCGCGAGAGCCTTGACACCTGTACCAAGCAAGCC   980
 981 ACCCACTGCCAAGAGATGTGATATATAAGTGTATATATTGTGCTGTGTTTGGGACCCTCCTCATACAGCT  1050
1051 CGTGCGGATCTGCAGTGTGTTCTGACTCTAATGTGACTGTATATACTGCTCGGAGTAAGAATGTGCTAAG  1120
1121 ATCAGAATGCCTGTTCGTGGTTTCATATAATATATTTTTCTAAAAGCATAGATTGCACAGGAAGGTATGA  1190
1191 GTACAAATACTGTAATGCATAACTTGTTATTGTCCTAGATGTGTTTGACATTTTTCCTTTACAACTGAAT  1260
1261 GCTATAAAAGTGTTTTGCTGTGTGCGCGTAAGATACTGTTCGTTAAAATAAGCATTCCCTTGACAGCACA  1330
1331 GGAAGAAAAGCGAGGGAAATGTATGGATTATATTAAATGTGGGTTACTACACAAGAGGCCGAACATTCCA  1400
1401 AGTAGCAGAAGAGAGGGTCTCTCAACTCTGCTCCTCACCTGCAGAAGCCAGTTTGTTTGGCCATGTGACA  1470
1471 ATTGTCCTGTGTTTTTATAGCACCCAAATCATTCTAAAATATGAACATCTAAAAACTTTGCTAGGAGACT  1540
1541 AAGAACCTTTGGAGAGATAGATATAAGTACGGTCAAAAAACAAAACTGCGCCATGGTACCC  1601
```

FIG. 3

```
                                                                                                                            85
     IKFQDVIGEGNFGQVLKAR---IKKD  GLR--MDAAIKRMKEYASKD  DHRDFAGELEVLCKLG  HHPNIINLLGACEHR  GYLYLAIEYAPHG
Tek
Jtk14
Ret   LVLGKTL...E..K.V..TAFHL.GR  AGY--TTV.V.ML..N..PS  EL..LLS.FN...QV   N..HV.K.Y...SQD  .P.L.IK...KY.           543
FlgM  LVLGKPL....C....VL.EAIGLD..  KPMRVTKV.V.ML.SD.TEK  .LS.LIS.M.MMKMI.  K.K........TQQ   .P.VIV..SK.            567
             I                            II                   III                 IV                V

MLLDFL  RKSRVLETDPAFAIAMSTAST-------  LSSQQLLHFAADVARGMDYLSQKQFIHRDLAARNILVGENY   IAKIADFGLSR---GQEV         169
Tek                                                           .V....L                  AS............            32
Jtk14
Ret   S.RG..  .E..KVGPGYLGSGGSRNS.SLOHPDERA  .TMGD.IS..MQISQ..Q..AEMKLV............A.GR  KM.S.......DVYEEDP        638
FlgM  ..REY.  QAR.PPGLFYCYNPSHMPEEQ-------  ...KD.VSC.YQ.....E..AS.KC.....V.T.DM        VM.......A.DIMMIDY        654
                   Insert                                           VI                       VII YVKK  TMGRLPVRMAIESL  MYSVYTT-MSDVMSYGVLLMEIVSLGGIPYCG  MTCADVYEKLPQGYRLEKPLN   CDDEVYHVMRQCWREKPYER          260
Tek
Jtk14  ...R  SQ..I..K.....  FDMI....Q.....F.......T..N..P.   IPPERLFML.KT.H.M.R.D.   SE.M.R..L...KQE.DK.           65
Ret    .K.T  .M.....K...P.A.  FDRI...HQ.....F.......FT..S..P.  VPVEELFKL.KE.H.MQ..S.   .TM.L.MM.D..HAV.SQ.          729
FlgM                                                                                                              745
                  VIII                                                     X                  XI PSFAQILYSL  -NRML-EERKTYWNTLYEKFIVAGI-DC-SAEEAA  301
Tek
Jtk14
Ret   .V..D.SKD.  E.M.VK--.RD.LDLAASTPSDSLIYD.GL.E..TP  772
FlgM  .T.K.LVED.  DHIV..TSMQE.LQLSIPLDQYSPSFP.TR.SICSS  790
                          IX
```

```
RCEAQKWGPDGSRPCTT---CKNNGVCHEDT-----GECICPPGFMGRTCEK  tek 1
ACEPHTFCRTCKERCSGPEGCKSYVFQLPDP-----YGCSCATGWRGLQCNE  tek 2
ACPSCYYCPDCKLRCH----CTNEEIQDRFQ-----CLCSQGWQGLQCEK   tek 3
GCGAGRWGPGCQTKECPG--CLHGGVCHDHD-----GECVCPPGFTGTRCEQ tie 1
ACREGRFCQSCQEQCPGISQRGLTFCLPDP-----YGCSCGSWRCSQCQE   tie 2
ACAPCHFCADCRLQCQ----CQNGGTCDRF-----SGCVCPSGWHGVHCEK  tie 3
NSDSECPLSHDGYCLHDGVCMYIEALDK-YACNCVVGYIGERCQY        EGF
GRYCDEDIDECSLSSPCRNGASCLNVPGS---YRCLCTNYEGRDCAI      Notch
c---g----c----C-------C-----------C--C---G--C---    Consensus
```

FIG. 12 B

```
TekFn1    468 EPYPGDG-PIKSKKLFYKPVNQA------WKYIEVTN-EIFTLNYLEPRTDYELCVQLARPGEGGEGH--------PGPVRR              533
T1eFn1    471 PSGDG-PISTVRLHYRPQDSTMD----WSTIVDPSENVTLMNLRPKTGYSVRVQLSRPGEGGEGA--------WGPPTL              537
TekFn2    534 FTTACIGLPPP--RGLSLLPKSQTALNLTWQPIFTNS---EDEPYVEVERRSLQTTSDQQNIKVPGNLTSVLLSNLV-------PREQYTVRARV-NTK  619
T1eFn2    539 TTDC-PEPLLQPWLEGWHVEGTDRLRVSWSLPLVPGPLVGDGFLLRL-WDGTRGQERRENVSSPQARTA-LLTGLT-------PGTHYQLDVQLYHCT  626
TekFn3    633 LSDILPPQPENIKISNITDST-AMVS---WTIVDGY--SISSIIRYKVQGKNE--D-QHIDVKIKNATVTQYQLKGLE------PETTYHVDIFAENNI  717
T1eFn3    639 LPPSGPPAPRHLHAQALSDSEIQLT----WKHPEALPGPISKYVV--EVQVAGAGDPLMIDVDRPEETST--IIRGLN------ASTRYLPRMRA--S  721
Pinc-rat 1537 VSDV----PRDLEVIASTPTSLLIS---WEPPAVSVRYYRITYGETGGNSP---VQEFT-VPGSKSTATINNIK-------PGADYTITLYAVT--   1612
DLar      610 PGA-P--PRNITAIATSSTTISLS---WLPPPVERSNGRIIYY--KVFPVE--VGREDDEATTMTLNMTSIVLDELKRWTEYKIWVLAGTSV-----   691
Consensus     PGA-P                       W           V                                          P TekFn1        AQGEWSEELRAWT                           632
T1eFn1        LLGPASPPAHVL                            638
TekFn2        --GSSNPAFSHELRTL                        731
T1eFn2        IQGLGDWSNTV                             732
TekFn3        --GRGDSPASSKPVSINYQTEIDKPSQMQV         1640
T1eFn3        --GDGPRSHPIILRTQ                        705
                G
```

RECEPTOR TYROSINE KINASE

This application is a division of application Ser. No. 08/278,089, filed Jul. 20, 1994, now U.S. Pat. No. 5,681, 714, which is a continuation-in-part of U.S. Ser. No. 08/235, 408, filed Apr. 29, 1994, now abandoned, which is a continuation-in-part of U.S. Ser. No. 07/921,795, filed Jul. 30, 1992, now abandoned.

FIELD OF THE INVENTION

The invention relates to a novel receptor tyrosine kinase protein, isoforms and parts thereof, nucleic acid molecules encoding the novel protein and fragments thereof, and uses of the protein and nucleic acid molecules.

BACKGROUND OF THE INVENTION

Transmembrane receptor tyrosine kinases (RTKs) comprise a large and evolutionarily conserved family of structurally related proteins capable of transducing extracellular signals to the cytoplasm. The latent oncogenic potential of these molecules and the molecular mechanisms by which they function in signalling pathways have been the subject of extensive study.

In addition, genetic and biochemical analyses of a variety of developmental mutants have led to recognition of the pivotal roles played by RTK-mediated signalling pathways in the regulation of cell determination, migration, and proliferation. Notable examples in Drosophila include the role of sevenless and its ligand, bride of sevenless, in R7 photoreceptor determination (Krämer, H., Cagan, R. L. & Zipursky, S. L. (1991), *Nature*, 352, 207–212), and of DE R/flb in early morphogenetic events during gastrulation (Schejter, E. D. & Shilo, B.-Z. (1989), *Cell*, 56, 1093–1104). Similarly, in the mouse, loss of function mutations at the W/c-kit (Geissler, E. N., Rayn, M. A. & Housman, D. E. (1988), *Cell*, 55, 185–192; Chabot, B., Stephenson, D. A., Chapman, V. M., Besmer, P. & Bernstein, A. (1988), *Nature*, 335, 88–89) and Sl (Russell, E. S. (1979), *Adv.Genet.*, 20, 357–459) loci have revealed the importance of the Kit receptor and its ligand in melanogenesis, hematopoiesis, and gametogenesis (Dubreuil, P., Rottapel, R., Reith, A. D., Forrester, L. & Bernstein, A. (1990), *Ann. N.Y. Acad. Sci.*, 599, 58–65; Williams, D. E., Eisenman, J., Baird, A., Rauch, C., Ness, K. V., March, C. J., Park, L. S., Martin, U., Mochizuki, D. Y., Boswell, H. S., Burgess, G. S., Cosman, D. & Lyman, S. D. (1990), *Cell*, 63, 167–174; Copeland, N. G., Gilbert, D. J., Cho, B. C., Donovan, P. J., Jenkins, N. A., Cosman, D. Anderson, D., Lyman, S. D. & Williams, D. E. (1990), *Cell*, 63, 175–183 and Flanagan, J. G. & Leder, P. (1990), *Cell*, 63, 185–194) while a deletion in the gene encoding PDGFR-α has been correlated with the Patch mutation, which also causes a defect in melanogenesis (Stephenson, D. A., Mercola, M., Anderson, E., Wang, C., Stiles, C. D., Bowen-Pope, D. F. & Chapman, V. M. (1991), *Proc.Natl.Acad.Sci.*, 88, 6–10). These observations, together with others (reviewed in Pawson, T. & Bernstein, A. (1991), *Trends Gen.*, 6, 350–356), have established the importance of receptor-ligand interactions in the regulation of development.

Angiogenesis in both the embryo and adult requires the differentiation, proliferation, and migration of endothelial cells. Tissue transplantation studies with quail/chick chimeras have established that the developmental cues for both endothelial cell differentiation and proper patterning of vessels are extracellular and not pre-programmed within the cell (Noden, D. M. (1988) Development, 103, 121–140) Several peptide hormones, such as bFGF, VEGF and PD-EGF, have been shown to have both mitogenic and chemotactic effects on cultured endothelial cells (see Tomasi, V., Manica, F. & Spisni, E. (1990), *BioFactors*, 2, 213–217; Klagsbrun, M. & D'Amore, P. (1991), *Annu.Rev.Physiol.*, 53, 217–239, for reviews). However, many of these factors also show similar effects on other cell types, implying that receptors for these factors are also expressed by such cells.

Studies have demonstrated that both tyrosine kinase activity and phosphotyrosine-containing proteins are increased in embryonic chicken heart relative to the adult (Maher, P. A. (1991). *J.Cell Biol.*, 112, 955–963), and that inhibitors of kinase activity impede inductive processes during in vitro differentiation of cardiac explants derived from chicken embryos (Runyan, R. B., Potts, J. D., Sharma, R. V., Loeber, C. P., Chiang, J. J. & Bhalla, R. C. (1990), *Cell Reg.*, 1, 301–313).

SUMMARY OF THE INVENTION

The present inventors have identified and characterized a receptor tyrosine kinase protein that plays a critical role in murine cardiogenesis. The heart forms early in mouse embryogenesis and its development is known to be accompanied by the differentiation from mesoderm of myocytes and endothelial cells that subsequently form the myocardium and endocardium, respectively (Manasek, F. J. (1976), in The Cell Surface in Animal Embryogenesis and Development, p.545–598, Elsevier/North-Holland Biomedical Press; Kaufman, M. H. & Navaratnam, V. (1981), *J.Anat.*, 133, 235–246). There have not hitherto been any reports of directed screens for tyrosine kinases expressed during murine cardiogenesis.

In particular, the present inventors using reverse transcription coupled to the polymerase chain reaction (RT-PCR) isolated from murine embryonic heart a cDNA, designated tek, whose deduced amino acid sequence corresponds to a novel RTK. The tek locus of mouse was mapped to chromosome 4. The present inventors have also shown by in situ hybridization that tek is expressed in the endocardium as well as the endothelial lining of the vasculature. tek was also found to be expressed in both mature endothelial cells and their progenitors, suggesting that the signalling pathways regulated by tek may be important to both the determination and proliferation of cells of the endothelial lineage. The tek locus of humans was mapped to the human chromosome 9p21 region. This region is deleted or rearranged in many types of neoplasia, suggesting that the tek locus may play a role in oncogenesis.

The present inventors have cloned and sequenced a 4.2-kb murine cDNA encoding the novel receptor tyrosine kinase. Conceptual translation of the 4.2-kb cDNA revealed a single large open reading frame from a putative initiation codon at nucleotide 124 to an in-frame stop codon at nucleotide 3490. The inventors have determined the primary structure of the deduced receptor tyrosine kinase protein. The 1,122 residue polypeptide corresponds to a receptor tyrosine kinase protein containing a kinase region interrupted by a 21 amino acid insert linked via a transmembrane domain to a remarkably complex novel extracellular domain. The extracellular domain comprises three Fibronectin type III (FNIII) repeats, immediately following the transmembrane domain, fused to two immunoglobulin-like (Ig-like) loops that are themselves separated by three tandem epidermal growth factor-like (EGF-like) repeats.

The present inventors have also demonstrated that the 4.2-kb cDNA encodes a 140-kDa protein that co-migrates with a polypeptide specifically detected by antibody directed against the novel receptor tyrosine kinase protein in both cultured endothelial cells and highly vascularized embryonic tissues. A 140-kDa protein was also specifically precipitated from cells transfected with the cDNA.

The present inventors have further elucidated the role of the novel receptor tyrosine kinase within the endothelial cell lineage by disrupting its signalling pathway using two different genetic approaches. First, transgenic mice expressing a dominant-negative form of the novel receptor tyrosine kinase protein were constructed. Second, a null allele of the tek locus was created by homologous recombination in embryonic stem cells. Transgenic mice expressing dominant-negative alleles of tek or homozygous for the null allele of the tek locus both died in utero. Analysis of mice carrying either dominant-negative or null mutations of the tek gene confirmed that the tek signalling pathway plays a critical role in the differentiation, proliferation and survival of endothelial cells in the mouse embryo.

The present invention therefore provides a purified and isolated nucleic acid molecule, preferably a DNA molecule, having a sequence which codes for a receptor tyrosine kinase protein which is expressed in cells of endothelial lineage, or an oligonucleotide fragment of the nucleic acid molecules which is unique to the receptor tyrosine kinase protein of the invention. In a preferred embodiment of the invention, the purified and isolated nucleic acid molecule has the sequence as shown in SEQ ID NO:1 and in SEQ ID NO:5.

The invention also contemplates a double stranded nucleic acid molecule comprising a nucleic acid molecule of the invention or an oligonucleotide fragment thereof hydrogen bonded to a complementary nucleotide base sequence.

The present invention provides in one embodiment, an isolated and purified nucleic acid molecule comprising: (a) a sequence encoding a protein having the amino acid sequence as shown in SEQ ID NO:6 and FIG. 11B, wherein T can also be U; (b) nucleic acid sequences complementary to (a); (c) nucleic acid sequences which are at least 95% homologous to (a); or, (d) a fragment of (a) or (b) that is at least 18 bases and which will hybridize to (a) or (b) under stringent conditions. In a particular embodiment, the fragment is a sequence encoding a receptor tyrosine kinase extracellular domain having the amino acid sequence as shown in SEQ ID NO:6 from amino acid number 19 to 744 and sequences having at least 97% homology thereto.

The present invention also provides a purified and isolated nucleic acid molecule comprising: (a) a sequence as shown in SEQ ID NO: 5 and FIG. 11B; (b) nucleic acid sequences complementary to (a); (c) nucleic acid sequences which are at least 95% homologous to (a); or, (d) a fragment of (a) or (b) that is at least 18 bases and which will hybridize to (a) or (b) under stringent conditions.

It is contemplated that a nucleic acid molecule of the invention may be prepared having a structural mutation including, replacement, deletion or insertion mutations. For example, the signal peptide may be deleted, in particular, the first 17 amino acids of tek as shown in SEQ ID NO. 6 and FIG. 11B, may be deleted. As another example, lysine$^{853}$ to alanine$^{853}$ may be altered to generate a protein that is still competent to bind ligand, but which is catalytically inactive and thus unable to transduce a signal.

The invention further contemplates a recombinant molecule comprising a nucleic acid molecule of the invention or an oligonucleotide fragment thereof and an expression control sequence operatively linked to the nucleic acid molecule or oligonucleotide fragment. A transformant host cell including a recombinant molecule of the invention is also provided.

Still further, this invention provides plasmids which comprise the nucleic acid molecules of the invention.

The invention further provides a method of preparing a novel receptor tyrosine kinase protein or isoforms thereof utilizing the purified and isolated nucleic acid molecule of the invention. The method comprises culturing a transformant host cell including a recombinant molecule comprising a nucleic acid molecule of the invention and an expression control sequence operatively linked to the nucleic acid molecule, in a suitable medium until the protein is formed and thereafter isolating the protein.

The invention further broadly contemplates a substantially pure receptor tyrosine kinase protein or a part thereof, which is expressed in cells of endothelial lineage.

The receptor tyrosine kinase protein of the invention is further characterized as containing an extracellular domain comprising at least one fibronectin III repeat, at least one immunoglobulin-like loop and at least one epidermal growth factor-like repeat. The extracellular domain comprises three fibronectin III repeats, two immunoglobulin-like loops and three fibronectin III repeats. The three fibronectin III repeats are fused to the two immunoglobulin-like loops and the two immunoglobulin-like loops are separated by the three fibronectin III repeats.

In an embodiment, the invention provides a purified and isolated protein having an amino acid sequence as shown in SEQ ID NO: 6 or a sequence having at least 97% homology thereto, or a part of the protein having at least 20 amino acids. The part of the protein preferably comprises an extracellular domain of a receptor tyrosine kinase having the amino acid sequence as shown in SEQ ID NO: 6 from amino acid number 19 to 744 or a sequence having at least 97% homology thereto. Conjugates of the Tek protein of the invention, or parts thereof may be prepared. This may be accomplished, for example by the synthesis of N-terminal or C-terminal fusion proteins. The invention therefore also relates to fusion proteins comprising a part of the protein as described herein and, optionally a marker protein, such as the Fc portion of an immunoglobulin.

The present invention also includes a receptor tyrosine kinase protein of the invention or part thereof, preferably the catalytic domain, which is enzymatically active. The catalytically active form of the protein or part thereof is also referred to herein as an "activated receptor tyrosine kinase protein or part thereof".

The invention further contemplates antibodies having specificity against an epitope of the receptor tyrosine kinase protein of the invention or part of the protein. Antibodies may be labelled with a detectable substance and they may be used to detect the novel receptor tyrosine kinase of the invention in tissues and cells. The antibodies may therefore be used to monitor angiogenesis, cardiogenesis and tumorigenesis.

The invention also permits the construction of nucleotide probes which are unique to the novel receptor tyrosine kinase protein of the invention or a part of the protein. Thus, the invention also relates to a probe comprising a nucleotide sequence coding for a protein, which displays the properties of the novel receptor tyrosine kinase of the invention or a peptide unique to the protein. The probe may be labelled, for example, with a radioactive substance and it may be used to select from a mixture of nucleotide sequences a nucleotide sequence coding for a protein which displays the properties of the novel receptor tyrosine kinase protein of the invention.

The present invention also provides a transgenic non-human animal or embryo all of whose germ cells and somatic cells contain a recombinant molecule of the invention preferably a recombinant molecule comprising the nucleic acid molecules of the invention containing a sequence encoding the receptor tyrosine kinase protein of the invention or part thereof with a structural mutation or comprising the nucleic acid molecules of the invention containing a sequence encoding the receptor tyrosine kinase protein of the invention or part thereof and one or more regulatory elements which differ from the regulatory elements of the native protein.

The invention still further provides a method for identifying a substance, which is capable of binding to the novel receptor tyrosine kinase protein of the invention, comprising reacting the novel receptor tyrosine kinase protein of the invention or part of the protein under conditions which permit the formation of a complex between the substance and the novel receptor tyrosine kinase protein or part of the protein and assaying for substance-receptor complexes, for free substance, for non-complexed receptor tyrosine kinase protein, or for activation of the receptor tyrosine kinase protein.

An embodiment of the invention provides a method for identifying ligands which are capable of binding to the novel receptor tyrosine kinase protein of the invention, isoforms thereof, or part of the protein, comprising reacting the novel receptor kinase protein of the invention, isoforms thereof, or part of the protein, with at least one ligand which potentially is capable of binding to the protein, isoform or part of the protein, under conditions which permit the formation of ligand-receptor protein complexes, and assaying for ligand-receptor protein complexes, for free ligand, for non-complexed proteins or for activation of the receptor tyrosine kinase protein. In a preferred embodiment of the method, ligands are identified which are capable of binding to and activating the novel receptor tyrosine kinase protein of the invention, isoforms thereof, or part of the protein. The ligands which bind to and activate the novel receptor tyrosine kinase receptor of the invention are identified by assaying for protein tyrosine kinase activity i.e. by assaying for phosphotyrosine.

In addition, the invention provides a method of using the novel proteins of the invention for assaying a medium for the presence of a substance that affects a tek effector system. In accordance with one embodiment, a method is provided which comprises providing a known concentration of a receptor tyrosine kinase protein of the invention, or a part thereof, incubating the protein, or a part thereof, with a substance which is capable of binding to the protein or part thereof, and thereby activating the tek effector system, and a suspected agonist or antagonist substance under conditions which permit the formation of ligand-receptor protein complexes, and assaying for ligand-receptor protein complexes, for free ligand or for non-complexed protein or for activation of the receptor tyrosine kinase protein.

The invention also relates to a method for assaying a medium for the presence of an agonist or antagonist of the interaction of the novel receptor tyrosine kinase protein and a substance which is capable of binding to the receptor tyrosine kinase protein, which comprises providing a known concentration of the receptor tyrosine kinase protein, reacting the receptor tyrosine kinase protein with a substance which is capable of binding to the receptor tyrosine kinase protein and a suspected agonist or antagonist under conditions which permit the formation of substance-receptor tyrosine kinase complexes, and assaying for substance-receptor tyrosine kinase complexes, for free substance, for non-complexed proteins, or for activation of the receptor tyrosine kinase.

The methods of the invention make it possible to screen a large number of potential ligands for their ability to bind to the novel receptor tyrosine kinase protein of the present invention. The methods of the invention will also be useful for identifying substances which may affect cardiogenesis and angiogenesis and/or maintenance of cells of the endothelial lineage and which may play a role in tumorigenesis.

Substances which affect angiogenesis, cardiogenesis or tumorigenesis may be identified using the methods of the invention by comparing the pattern and level of expression of the novel receptor tyrosine kinase protein of the invention in tissues and cells in the presence and in the absence of the substance.

The invention further contemplates a method for identifying a substance which is capable of binding to an activated receptor tyrosine kinase protein of the invention or an isoform or part of the activated protein, comprising reacting an activated receptor tyrosine kinase protein of the invention, or an isoform, or part of the protein, with at least one substance which potentially can bind with the receptor tyrosine kinase protein, isoform or part of the protein, under conditions which permit the formation of substance-receptor kinase protein complexes, and assaying for substance-receptor kinase protein complexes, for free substance, for non-complexed receptor kinase proteins, or for phosphorylation of the substance. The method may be used to identify intracellular ligands such as Src homology region 2 (SH2) containing proteins which bind to an activated receptor tyrosine kinase of the invention or parts thereof or intracellular ligands which may be phosphorylated by the protein.

DESCRIPTION OF THE DRAWINGS

The invention will be better understood with reference to the drawings in which:

FIG. 1 shows a nucleotide and deduced amino acid sequence of a receptor tyrosine kinase protein of the invention as shown in SEQ ID NOS:1 and 2;

FIG. 2 shows a nucleotide and deduced amino sequence of a 1601 bp DNA molecule of the invention as shown in SEQ ID NOS:3 and 4;

FIG. 3 shows a comparison of a portion of the deduced amino acid sequence of the novel receptor tyrosine kinase protein of the invention (SEQ ID NO:4) with that of other tyrosine kinases (SEQ ID NO:1, 14 to 16);

FIG. 11B shows the nucleotide and deduced amino acid sequence of a 4177-nucleotide tek cDNA as shown in SEQ ID NO: 4 and 5;

FIG. 12A shows a sequence comparison of Tek receptor tyrosine kinase protein (SEQ ID NO:17 to 19) and Tie EGF-like repeats (SEQ ID NO:20–22);

FIG. 12B shows a sequence comparison of Tek receptor tyrosine kinase protein (SEQ ID NO:25, 27, 29) and Tie fibronectin type III repeats (SEQ ID NO:26, 28, and 30);

DETAILED DESCRIPTION OF THE INVENTION

Figure 4:
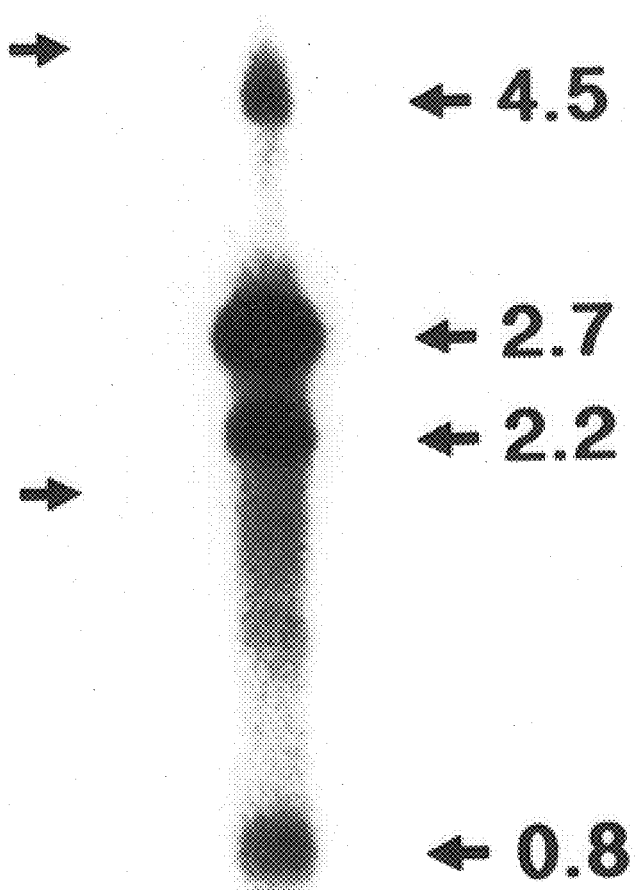
FIG. 4 shows a Northern blot hybridization analysis of expression of a DNA molecule of the invention in 12.5 day murine embryonic heart.

I. Characterization of Nucleic Acid Molecules and Proteins of the Invention

The present inventors have isolated a gene encoding a novel receptor tyrosine kinase protein, designated tek, expressed during murine cardiogenesis. By analysing the segregation of an AccI restriction site polymorphism in AKR/J:DBA recombinant inbred mice, the present inventors mapped the tek locus to chromosome 4, between the brown and pmv-23 loci. This region is syntenic with human chromosomal regions 1p22-23, 9q31-33, and 9p22-13. In mice and humans, these regions do not contain any previously described loci known to be involved with the biology of the endothelial cell lineage (Lyon, M. F. & Searle, A. G. *Genetic Variants and Strains of the Laboratory Mouse*, New York:Oxford University Press, 1989, 2nd, Ed.; O'Brien, 1990).

The human tek locus was mapped, by the present inventors, to human chromosome 9p21, a region which is deleted or rearranged in many types of neoplasia (Fountain et al., 1992; Taguchi et al., 1993; Olopade et al., 1992; Rowley and Diaz, 1992), suggesting a role for the tek locus in oncogenesis.

The novel gene products of the invention were identified as mouse receptor tyrosine kinase protein based on the structural homology of the protein to the known mouse and human receptor tyrosine kinases. The deduced amino acid sequence of Tek protein predicts that it encodes a putative receptor tyrosine kinase that contains a 21 amino acid kinase insert and which is most closely related in its catalytic domain to FGFR1 (mouse fibroblast growth factor) and the product of the ret proto-oncogene.

Northern blot hybridization analysis of RNA from 12.5 day embryonic heart using the 1.6 kb cDNA as probe suggested that the tek locus gives rise to at least 4 different transcripts of approximately 4.5, 2.7, 2.2, and 0.8 kb. Differential splicing of primary transcripts is known to occur for several genes encoding RTKs, including met (Rodrigues, G. A., Naujokas, M. A. & Park, M. (1991), Mol.Cell.Biol., 11, 2962–2970), trkB (Middlemas, D. S., Lindberg, R. A. & Hunter, T. (1991), Mol.Cell.Biol., 11, 143–153), ret (Tahira, T., Ishizaka, Y., Itoh, F., Sugimura, T. & Nagao, M. (1990), Oncogene, 5, 97–102), and flg (Reid et al., 1990, Proc.Natl.Acad.Sci., 87,1596–1600; Bernard, O., Li, M. & Reid, H. H. (1991), Proc.Natl.Acad Sci.USA, 88, 7625–7629; Eisemann, A., Ahn, J. A., Graziani, G., Tronick, S. R. & Ron, D. (1991), Oncogene, 6, 1195–1202; Fujita, H., Ohta, M., Kawasaki, T. & Itoh, N. (1991), Biochem. Biophis. Res. Comm., 174, 946–951; Meng, B. & Reid, H. H. (1991), Proc.Natl.Acad.Sci., 7625–7629), favoring the possibility that at least some of the smaller transcripts hybridizing with the tek cDNA are differentially spliced. The 4.5 kb tek transcript is of the appropriate size to encode a molecule with an extensive extracellular domain. In contrast, the smallest transcript, at 0.8 kb, is sufficient to encode only a significantly truncated version of the protein. Since this transcript was detected with a probe comprised entirely of sequences from the catalytic domain and 3' untranslated region, it is possible that the 0.8 kb message codes for an isoform completely lacking an extracellular domain. Truncated molecules of this type have recently been shown to be encoded by the trkB gene in rats (Middlemas et al., 1991, Mol.Cell.Biol., 11, 143–153) and by pdgfb in murine ES cells (Vu, T. H., Martin, G. R., Lee, P., Mark, D., Wang, A. & Williams, L. T. (1989), Mol.Cell.Biol., 9, 4563–4567). These small isoforms may act as catalytically deregulated molecules during periods of rapid growth (Middlemas et al., 1991). The detection of multiple tek transcripts may indicate potential differential expression of different tek isoforms during embryogenes is.

Overlapping cDNAs from tek hybridizing clones were used to assemble a 4177 nucleotide contiguous cDNA (FIG. 11B and SEQ ID NO: 5). The sequence of this cDNA predicts a 1122-residue protein having several structural motifs that distinguish it from other receptor tyrosine kinases. In particular the Tek tyrosine kinase protein has an extracellular domain within which three distinct types of structural motifs can be identified, including immunoglobulin-like loops between residues 19 and 209 and 344 and 467 (FIG. 11B and SEQ ID NO: 6). The two immunoglobulin-like loops are separated from one another by three tandem cysteine-rich epidermal growth factor (EGF)-like repeats (SEQ ID NO:17–19) that show homology to similar motifs found in other cell-surface proteins, such as Tie (SEQ ID NO:20–22) and Notch (SEQ ID NO:24) (FIG. 12A). Moreover, the second immunoglobulin-like loop is followed by three regions (SEQ ID NO:25, 27 and 29) showing homology to fibronectin type III (FNIII) repeats found in polypeptides such as Drosophila leukocyte common antigen-related molecule (DLAR) (SEQ ID NO:33) and fibronectin (FIG. 12B). The extracellular domain of Tek receptor tyrosine kinase protein represents a composite of three different structural motifs that are usually not found collectively within a single receptor tyrosine kinase.

It is likely that the unusual structure of the Tek receptor tyrosine kinase protein reflects some aspect of its role in endothelial cell biology. In addition to playing potential roles in regulating endothelial cell proliferation and differentiation, the complex structure of the Tek receptor tyrosine kinase protein extracellular domain likely also plays a role in guiding the proper patterning of endothelial cells during blood vessel formation, both in the embryo and in the adult.

Tie, a receptor tyrosine kinase protein expressed in cells of the endothelial lineage (Partenan et al, 1992, Mol. Cell Biol. 12:1698–1707) shows a similar juxtaposition of structural motifs within the extracellular domain as Tek receptor tyrosine kinase protein. Despite the structural homology between Tek and Tie proteins, these two molecules show only modest sequence similarity in their extracellular domains (FIGS. 12A and 12B), suggesting that they interact with distinct ligands. In addition, Tek and Tie proteins are more divergent within their carboxy terminal tails and kinase insert regions than in their ATP-binding and phosphotransferase domains, suggesting that these two receptors likely utilize non-identical signalling pathways.

Figure 15A:
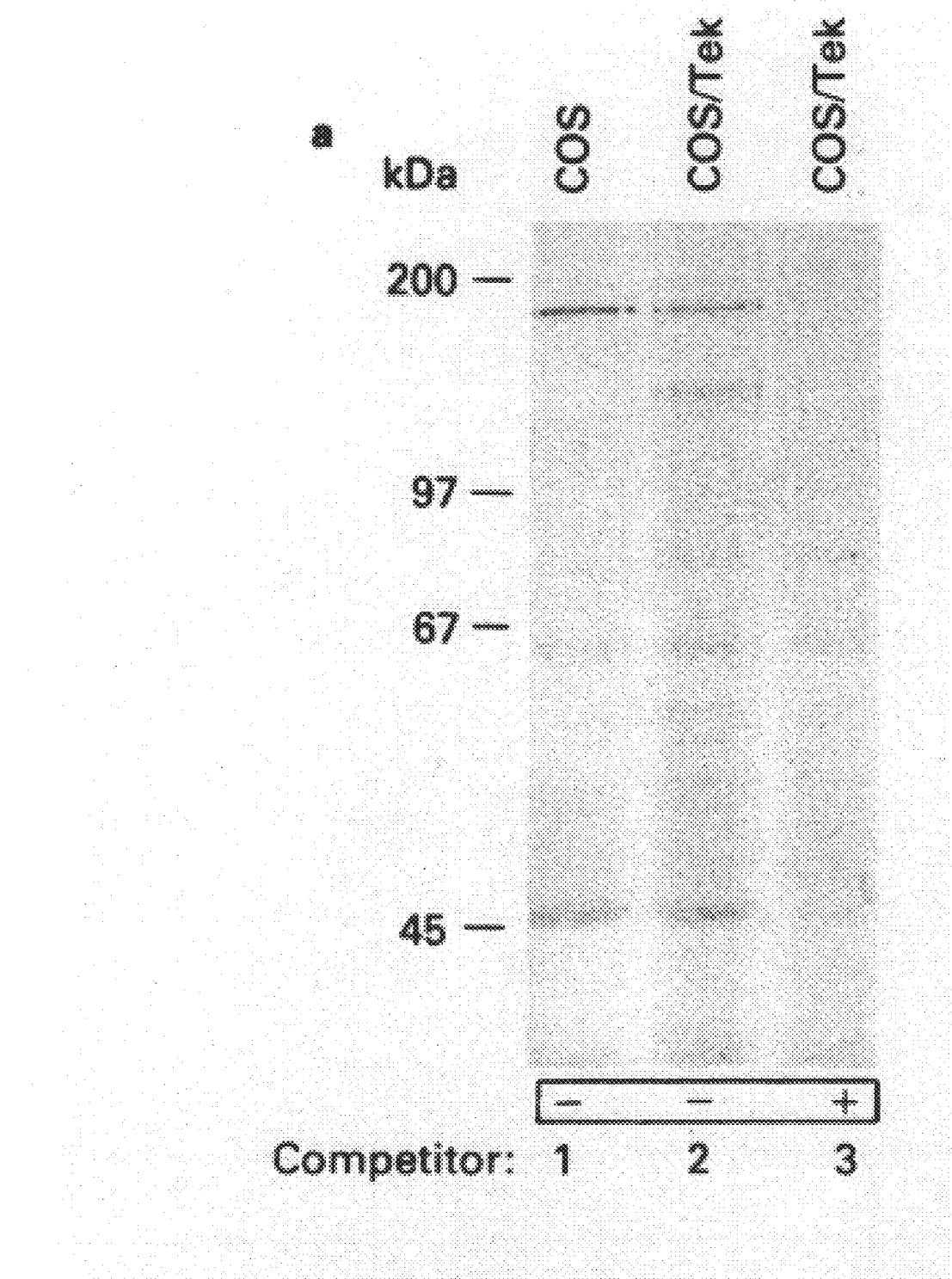
FIG. 15A shows that tek directs synthesis of a 140-kDa protein by immunoprecipitation with anti-tek serum.

A 140-kDa protein was specifically precipitated from a cell line transfected with tek cDNA (FIG. 15A). Moreover, this 140 kDa protein could be detected immunologically by Western analysis (FIG. 15B, lane 2) and its immunoprecipitation could be competed by a GST fusion protein containing the 43-residue carboxy terminal segment to which the antibody was raised (FIG. 15A, lane 3). The apparent size of the encoded Tek receptor tyrosine kinase protein, 140 kDa, is approximately 20 kDa greater than that predicted by the deduced amino acid sequence (126 kDa). The larger size of the detected protein indicates that Tek receptor tyrosine kinase protein may be a glycosylated cell surface protein.

Cell lysates prepared from umbilical vein, Py4-1 cells, and Day 13.5 embryonic heart all contained a 140 kDa protein that reacted specifically with Tek antibody and which comigrated with the species detected in transfected COS cells. Taken together, the results indicate that the 4.2 Kb tek cDNA contains the complete coding information for the native Tek receptor tyrosine kinase protein.

The tek cDNA encodes a 140 kDa protein which comigrates with the polypeptide specifically detected by Tek antibody in both cultured endothelial cells (Py4-1) and highly vascularized embryonic tissues (heart and umbilical vein). The Tek receptor tyrosine kinase protein cytoplasmic domain expressed in E. coli was shown to react with phosphotyrosine receptor tyrosine kinase protein antibodies.

Figure 1:
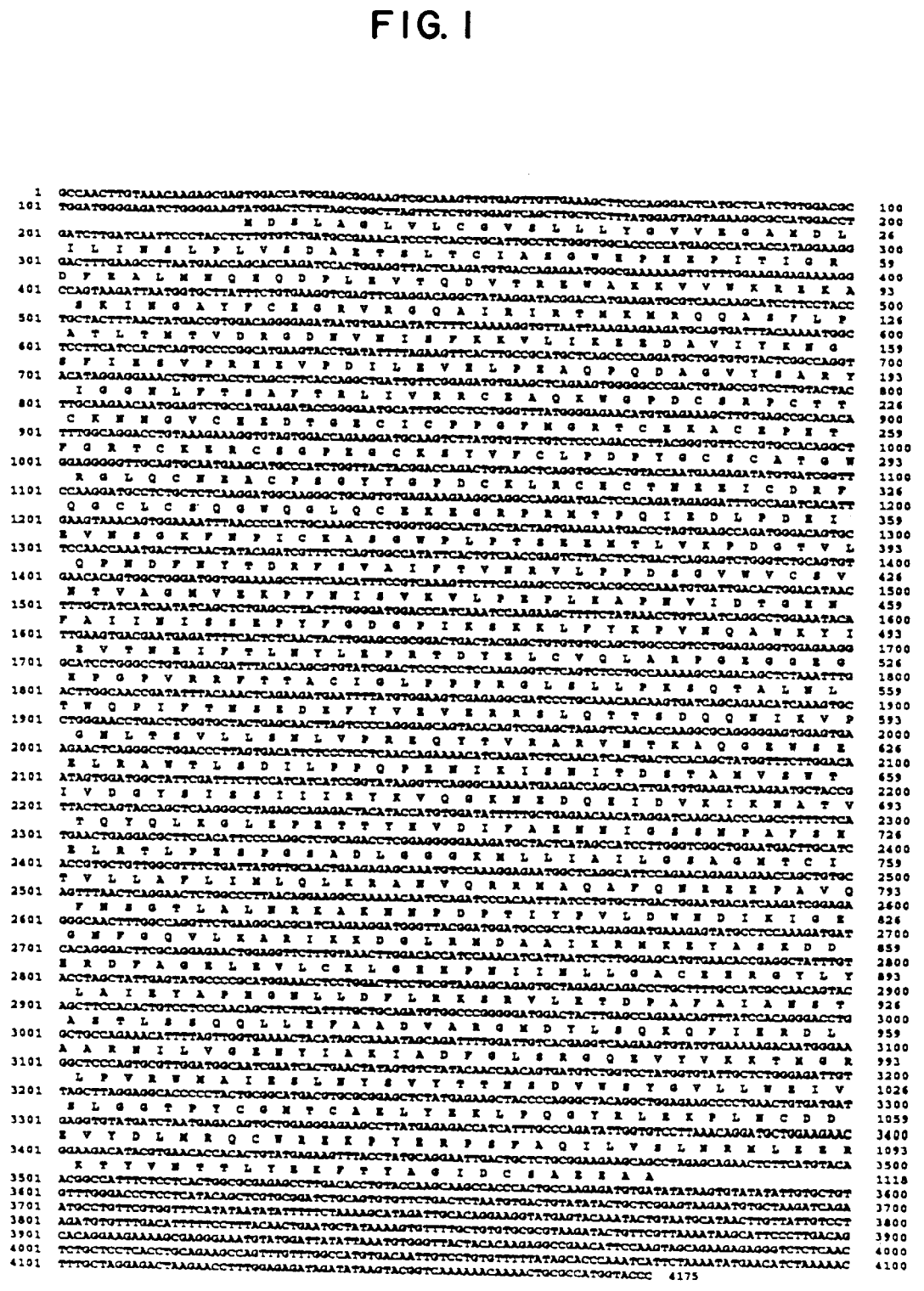

The DNA sequence and deduced amino acid sequence of tek are shown in SEQ ID NOS: 1 and 2 and FIG. 1, and in SEQ ID NOS: 5 and 6 and FIG. 11B. The DNA sequence and deduced amino acid sequence of a 1601 bp segment are shown in SEQ ID NOS: 3 and 4 and in FIG. 2. The DNA and deduced amino acid sequence of tek shown in FIG. 1 and SEQ ID NOS: 1 and 2 are the same as those shown in FIG. 11B and SEQ ID NOS: 5 and 6, with the exception that FIG. 11B and SEQ ID NOS: 5 and 6 have an additional short segment of 12 nucleotides, (coding for the amino acids Phe, Gln, Asp, Val) commencing at nucleotide number 2592. This short segment is also shown in FIG. 2 and SEQ ID NO: 3 commencing at nucleotide number 7.

It will be appreciated that the invention includes nucleotide or amino acid sequences which have substantial sequence homology with the nucleotide and amino acid sequences shown in SEQ ID NOS:1–6 and in FIGS. 1, 2 and 11B. The term "sequences having substantial sequence homology" means those nucleotide and amino acid sequences which have slight or inconsequential sequence variations from the sequences disclosed in FIGS. 1, 2 and 11B and SEQ ID NOS: 1–6, i.e. the homologous sequences function in substantially the same manner to produce substantially the same polypeptides as the actual sequences. The variations may be attributable to local mutations or structural modifications.

Sequences having substantial homology include nucleic acid sequences which encode proteins having at least 95% sequence homology with the amino acid sequences as shown in SEQ ID NOS: 2, 4 and 6 or portions thereof; and nucleic acid sequences having at least 85% homology, preferably at least 90% with the nucleic acid sequences as shown in SEQ ID NOS: 1 and 5 or fragments thereof. An example of such a sequence includes the sequence encoding Tek receptor tyrosine kinase protein in humans and in other mammals.

Sequences having substantial homology also include fragments of the nucleic acid sequences of the invention having at least 18 bases which will hybridize to the nucleic acid sequences under stringent conditions. Stringent hybridization conditions are those which are stringent enough to provide specificity, reduce the number of mismatches and yet are sufficiently flexible to allow formation of stable hybrids at an acceptable rate. Such conditions are known to those skilled in the art and are described, for example, in Sambrook, et al, (1989, Molecular Cloning, A Laboratory Manual, Cold Spring Harbor). By way of example only, stringent hybridization with short nucleotides may be carried out at 5–10° below the $T_m$ using high concentrations of probe such as 0.01–1.0 pmole/ml.

The invention also provides amino acid sequences having substantial sequence homology with the amino acid sequence shown in SEQ ID NO: 2, 4 or 6. Substantially homologous sequences include sequences having at least 95% sequence homology. Peptides which are unique to the receptor tyrosine kinase protein of the invention are also contemplated, preferably peptides having at least 10 amino acids.

It will also be appreciated that a double stranded nucleotide sequence comprising a nucleic acid molecule of the invention or an oligonucleotide fragment thereof, hydrogen bonded to a complementary nucleotide base sequence, an RNA made by transcription of this double stranded nucleotide sequence, and an antisense strand of the nucleic acid molecule of the invention or an oligonucleotide fragment of the nucleic acid molecule, are contemplated within the scope of the invention.

The sequence of the nucleic acid molecule of the invention or a fragment thereof, may be inverted relative to its normal presentation for transcription to produce antisense nucleic acid molecules. The antisense nucleic acid molecules may be constructed using chemical synthesis and enzymatic ligation reactions using procedures known in the art.

A number of unique restriction sequences for restriction enzymes are incorporated in the nucleic acid sequences identified in SEQ ID NOS: 1, 3 and 5 and in FIGS. 1, 2 and 11B and these provide access to nucleotide sequences which code for polypeptides unique to the receptor tyrosine kinase protein of the invention. DNA sequences unique to the receptor tyrosine kinase protein of the invention or isoforms thereof, can also be constructed by chemical synthesis and enzymatic ligation reactions carried out by procedures known in the art.

The present invention includes conjugates of the receptor tyrosine kinase protein of the invention. For example, the receptor tyrosine kinase protein or parts thereof may be conjugated with selected proteins to produce fusion proteins. Examples of proteins which may be selected include lymphokines such as gamma interferon, tumor necrosis factor, IL-1, IL-2, IL-3, Il-4, IL-5, IL-6, IL-7, IL-8, IL-9, IL-10, IL-11, GM-CSF, CSF-1 and G-CSF. Particularly preferred molecules include the Fc portion of immunoglobulin molecules.

II. Expression Pattern of the Receptor Tyrosine Kinase Protein of the Invention

In the adult and all stages of embryonic development examined, tek expression was primarily restricted to cells of the endothelial lineage. Tek transcripts have also been found by the present inventors in the mesoderm of the amnion of developing embryos. The amnion is comprised of two cell layers, one mesodermal and the other ectodermal in origin. This membrane shares several features with the endothelial lining of blood vessels, such as having an epithelial-like morphology and the requirement to contain fluid within an enclosed cavity. Thus, this tissue may utilize Tek receptor tyrosine kinase protein to accomplish this.

Specifically, in situ hybridization analysis of adult tissues, as well as sectioned and whole mount embryos, showed that tek is specifically expressed in the endocardium, the leptomeninges and the endothelial lining of the vasculature from the earliest stages of their development. Moreover, examination of the morphology of tek-expressing cells, and staging of tek expression relative to that of the endothelial cell marker von Willebrand factor, revealed that tek is expressed prior to von Willebrand factor and appears to mark the embryonic progenitors of mature endothelial cells. Thus, tek encodes a novel putative receptor tyrosine kinase that may be critically involved in the determination and/or maintenance of cells of the endothelial lineage.

Overall, the pattern of expression observed in sectioned and whole mount mouse embryos was similar to that described previously for quail embryos stained with a monoclonal antibody specific for cells of the endothelial lineage (Pardanaud, L., Altmann, C., Kitos, P., Dieterlen-Lievre, F. & Buck, C. A. (1987). *Development*, 100, 339–349; Coffin, J. D. & Poole, T. J. (1988). *Development*, 102, 735–748). Thus, it is likely that orchestration of vascularization in the two vertebrate species is very similar. Studies on cell lineage relations carried out primarily in the chick (Noden, D. M. (1989), *Am.Rev.Respir.Dis.*, 140, 1097–1103, and Noden, D. M. (1990), *Ann. N.Y. Acad. Sci.*, 1, 236–249; O'Brien, S. J. *Genetic Maps, Locus Maps of Complex Genomes*. Cold Spring Harbor Laboratory Press, 1990) have established that endothelial cells are derived from angioblasts, which migrate from mesoderm and populate the embryo with precursor cells that eventually contribute to the formation of the intraembryonic blood vessels.

Figure 10:
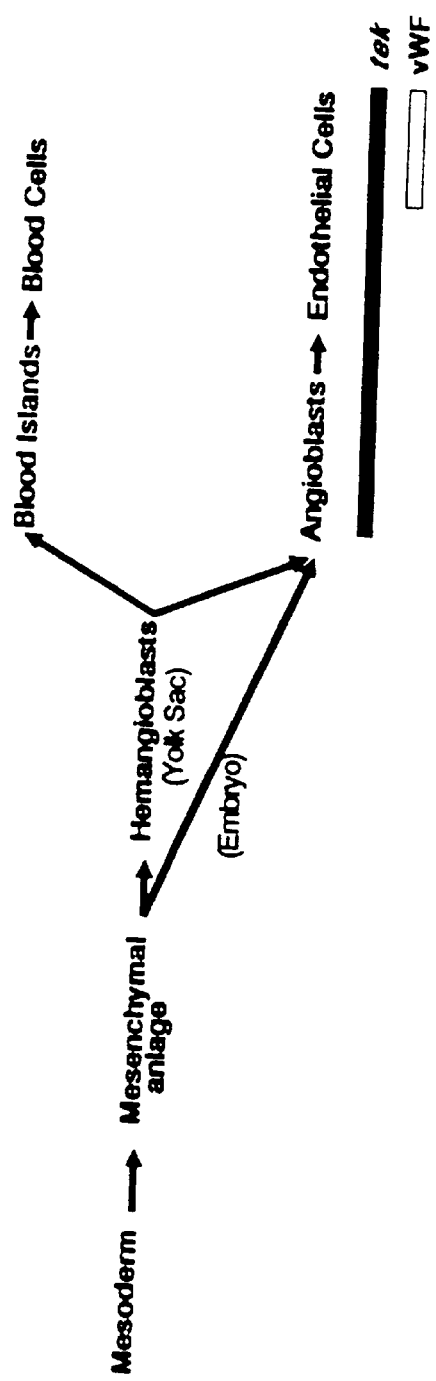
FIG. 10 shows the hierarchy of the endothelial cell lineage.

FIG. 10 shows the hierarchy of the endothelial cell lineage. Horizontal bars denote the relationship between cellular determination and onset of expression of tek and von Willebrand factor within the lineage (adapted from (Wagner, R. C. (1980). *Adv.Microcirc.*, 9, 45–75). In the yolk sac, angioblasts are thought to originate from hemangioblasts, ill-defined cells of mesenchymal origin that are also believed to give rise to primitive blood cells in the developing blood islets. In the embryo, on the other hand, angioblasts are thought to arise directly from cells of the mesenchymal anlage (Wagner, 1980).

Several cell lines of endothelial origin were also examined for expression of tek and of Flk-1. Flk-1 encodes a receptor tyrosine kinase protein which is expressed in cells of the endothelial lineage. Tek and Flk-1 were differentially expressed in endothelial cell lines (FIG. 14), suggesting that tek and Flk-1 are differentially regulated.

Figure 6A:
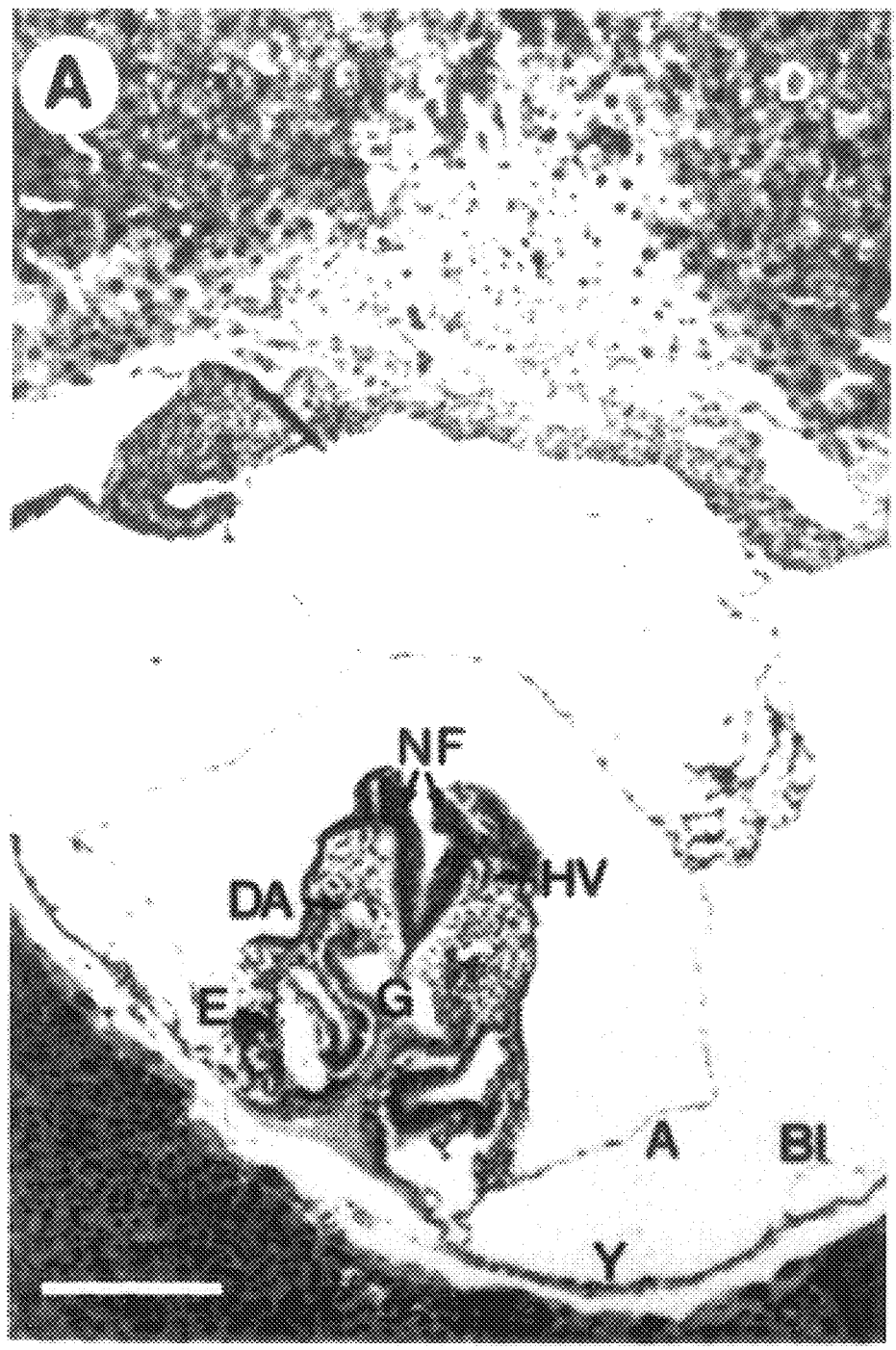
FIG. 6 shows the expression of a DNA molecule of the invention precedes that of von Willebrand factor in 8.5 day embryos, (A) bright field illumination, (B) dark field illumination, (C) blood island, (D) showing absence of expression of von Willebrand factor in the embryo, (E) showing expression of von Willebrand factor in the endothelial lining of the blood vessels of the maternal decidua, (F) cephalic region, (G) saggital section (H) dark field illumination of (G), (I) heart region, (J) tek-expressing cells beneath the ventral surface of the somites.
Figure 6B:
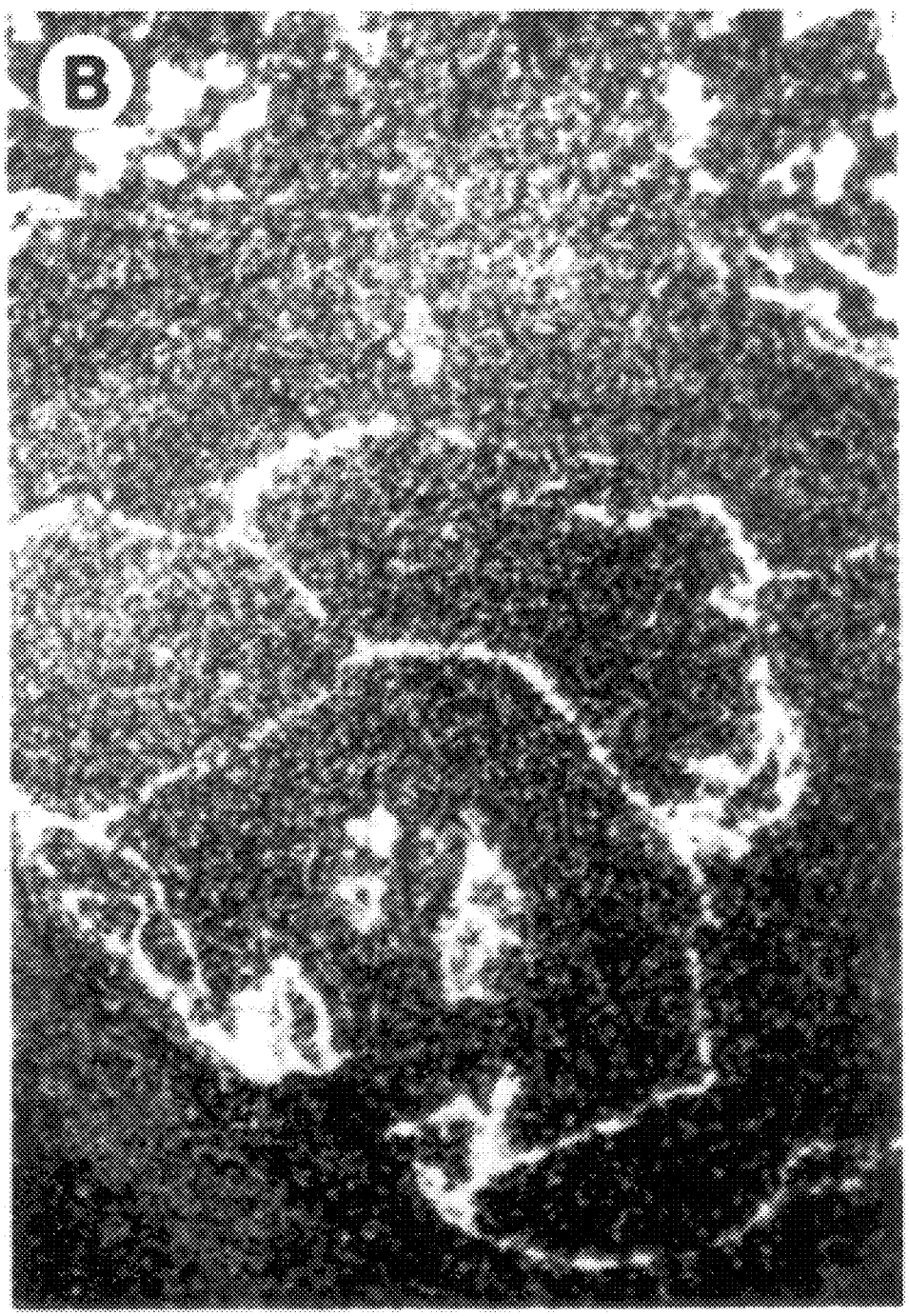
Figure 6C:
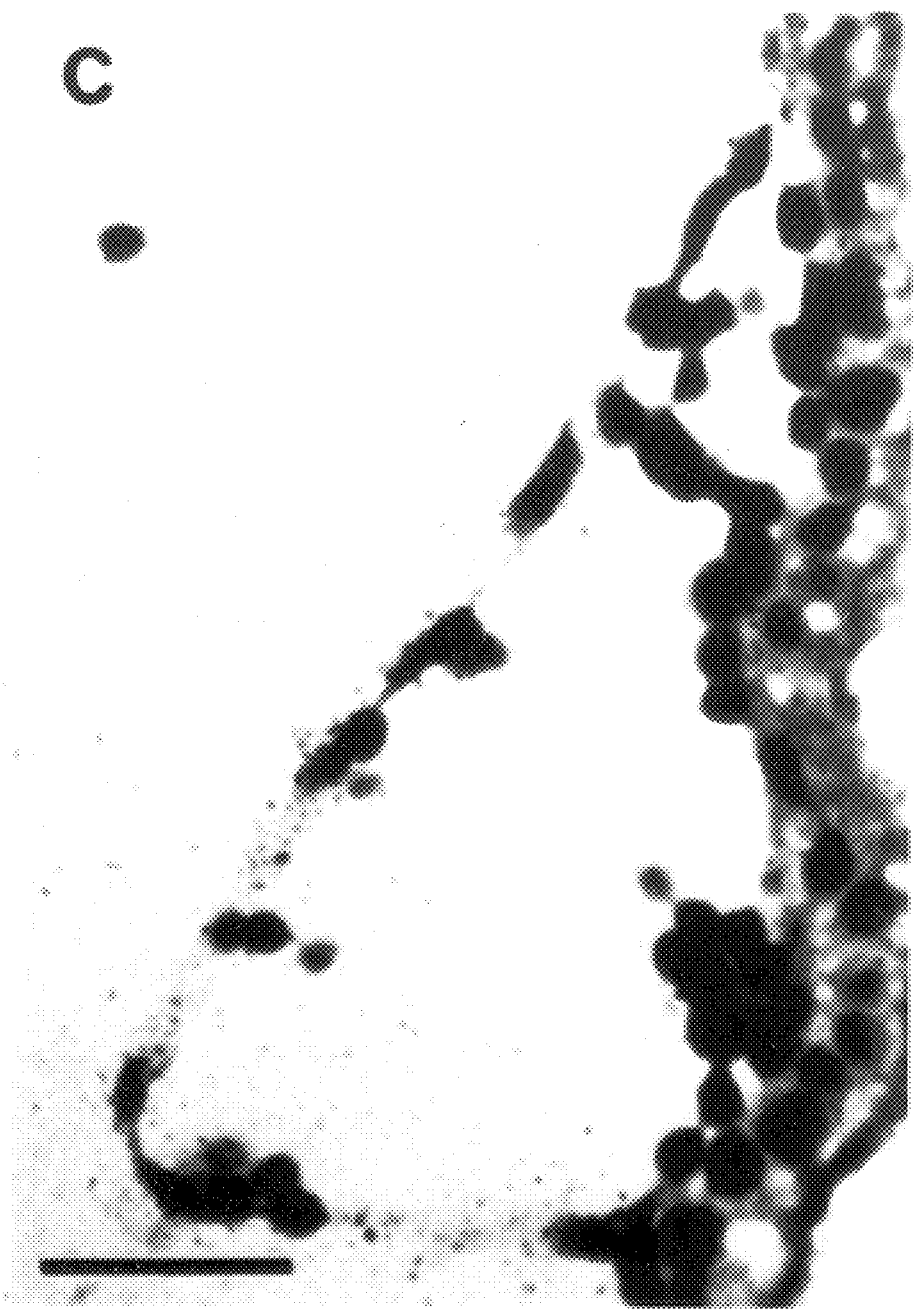
Figure 6D:
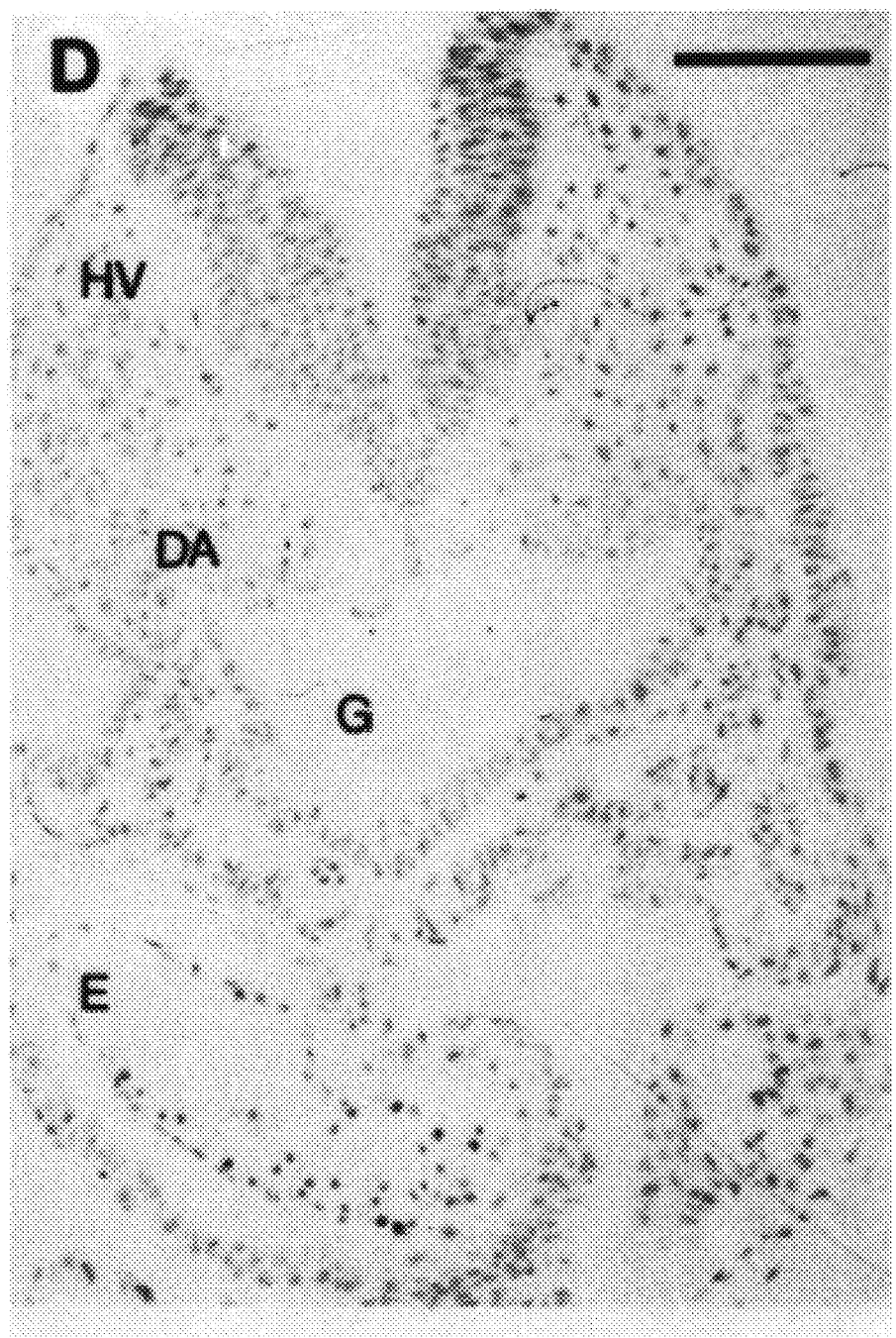
Figure 6E:
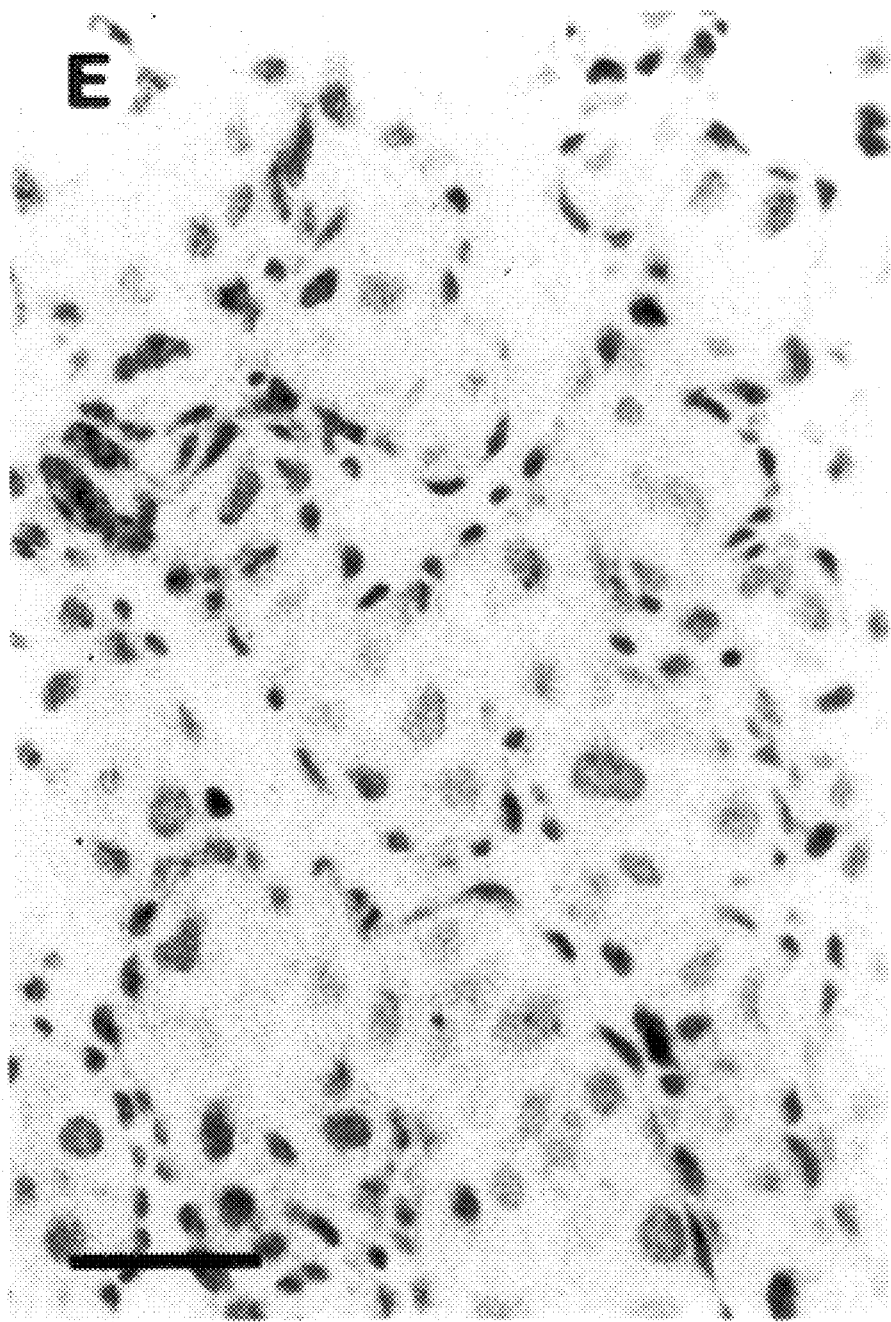
Figure 6F:
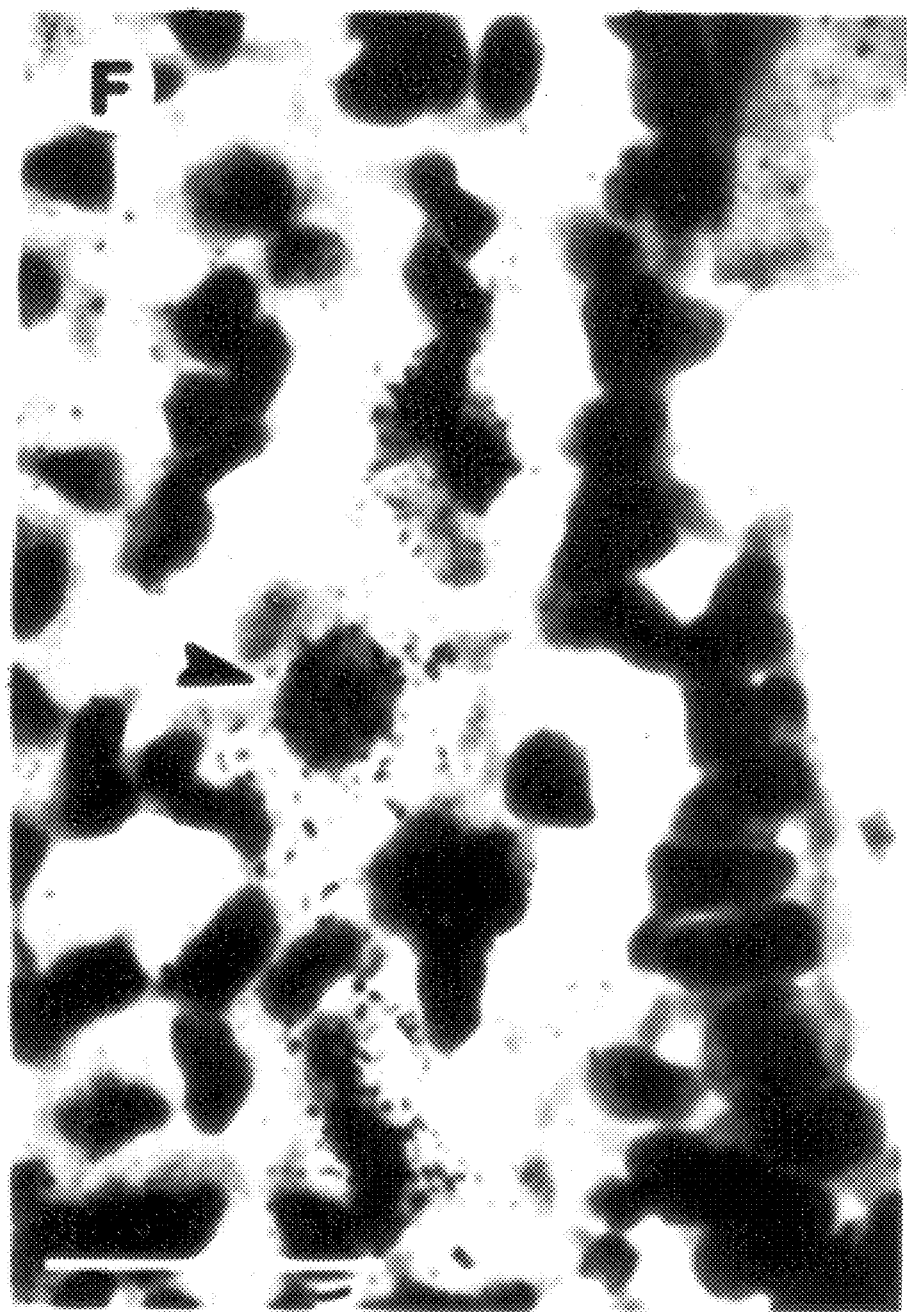
Figure 6:
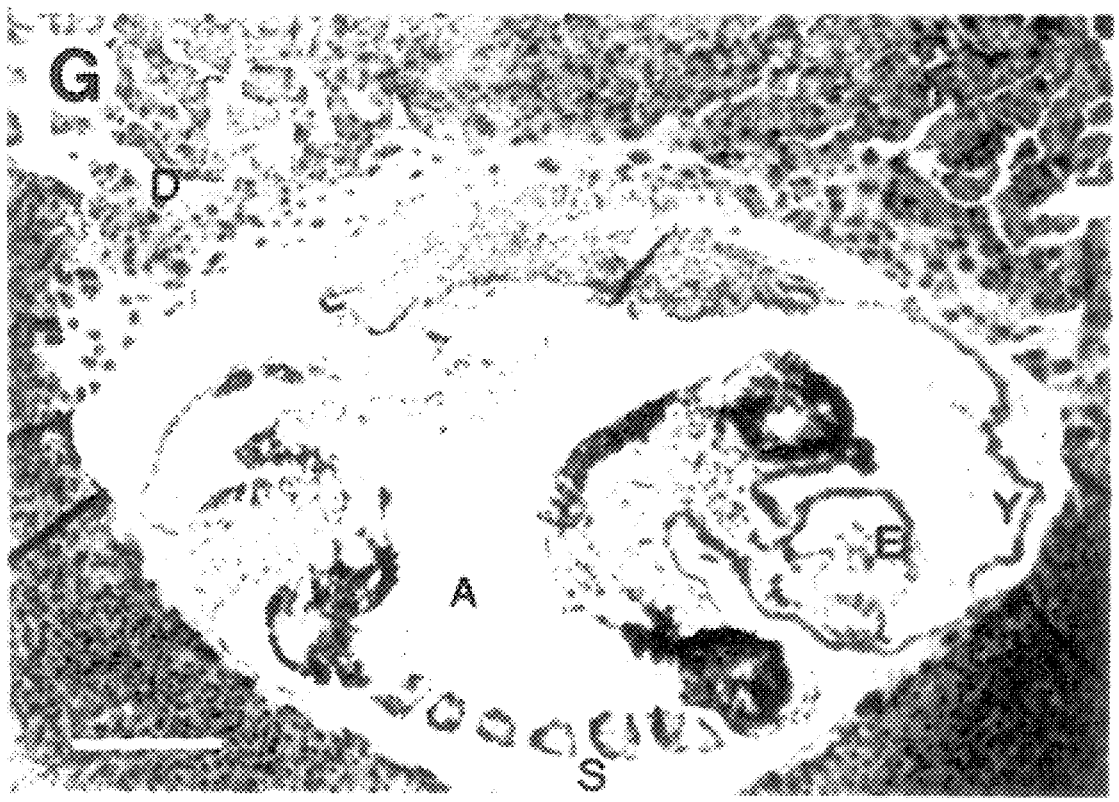

The present inventors' work suggested that tek is expressed in the presumptive precursors of endothelial cells, the angioblasts. First, tek expression was detected in both von Willebrand factor-positive cells as well as cells that appear to be progenitors of endothelial cells. Second, tek expression was observed in cells of non-endothelial morphology that in the avian system have been identified previously as angioblasts. It may also be significant that in the 8.5 day embryo, tek expression was identified in cells extending beneath the ventral surface of somites (FIG. 6, J). Analysis of serial sections revealed that some of these tek-expressing cells were actually contiguous with the somites. These cells may correspond to those described by Beddington, R. S. P. & Martin, P. (1989), *Mol.Cell.Med.*, 6, 263–274 who showed in mouse tissue transplantation studies that lacZ-expressing somite tissue, while devoid of endothelial cells prior to transplantation, possess cells capable of migrating and contributing to the host vasculature. Taken together, the present inventors' work suggests that tek expression may constitute one of the earliest mammalian endothelial cell lineage markers described to date.

The restricted expression of tek, imposes constraints on the cellular range of activity of the putative Tek receptor tyrosine kinase protein ligand, and suggests that the tek locus probably plays unique and important roles in the determination, migration, or proliferation of cells of the endothelial lineage.

Tek expression is very low in adults. However, it is likely that expression will be upregulated upon induction of angiogenesis. Accordingly, tek likely plays a role in angiogenesis, for example in tumor growth, in mature animals in addition to its role during development.

III. Preparation of Nucleic Acid Molecules and Proteins of the Invention

As hereinbefore mentioned, the present inventors have identified and sequenced a cDNA sequence encoding a novel receptor tyrosine kinase protein designated Tek.

Nucleic acid molecules of the present invention encoding the novel receptor tyrosine kinase protein of the present invention, or related, or analogous sequences, may be isolated and sequenced, for example, by synthesizing cDNAs from embryonic heart RNA by RT-PCR using degenerate oligonucleotide primers which amplify tyrosine kinase sequences such as the two degenerate tyrosine kinase oligonucleotide primers described by Wilks, A. F. ((1989) *Proc.Natl.Acad.Sci.*, 86, 1603–1607) and analysing the sequences of the clones obtained following amplification. Nucleic acid molecules of the present invention, or fragments thereof, encoding the novel receptor tyrosine kinase protein of the present invention, or parts thereof, may also be constructed by chemical synthesis and enzymatic ligation reactions using procedures known in the art.

The nucleic acid molecules of the present invention having a sequence which codes for the receptor tyrosine kinase protein of the invention, or an oligonucleotide fragment of the nucleic acid molecules may be incorporated in a known manner into a recombinant molecule which ensures good expression of the protein or part thereof. In general, a recombinant molecule of the invention contains a nucleic acid molecule, or an oligonucleotide fragment thereof, of the invention and an expression control sequence operatively linked to the nucleic acid molecule or oligonucleotide fragment. A nucleic acid molecule of the invention or an oligonucleotide fragment thereof, may be incorporated into a plasmid vector, for example, pECE. Suitable regulatory elements may be derived from a variety of sources, including bacterial, fungal, viral, mammalian, or insect genes. Selection of appropriate regulatory elements is dependent on the host cell chosen, and may be readily accomplished by one of ordinary skill in the art. Examples of regulatory elements include: a transcriptional promoter and enhancer or RNA polymerase binding sequence, a ribosomal binding sequence, including a translation initiation signal. Additionally, depending on the host cell chosen and the vector employed, other genetic elements, such as an origin of replication, additional DNA restriction sites, enhancers, sequences conferring inducibility of transcription, and selectable markers, may be incorporated into the expression vector.

The Tek receptor tyrosine kinase protein or isoforms or parts thereof, may be obtained by expression in a suitable host cell using techniques known in the art. Suitable host cells include prokaryotic or eukaryotic organisms or cell lines, for example, yeast, *E. coli* and mouse NIH 3B cells may be used as host cells. The protein or parts thereof may be prepared by chemical synthesis using techniques well known in the chemistry of proteins such as solid phase synthesis (Merrifield, 1964, J. Am. Chem. Assoc. 85:2149–2154) or synthesis in homogenous solution (Houbenweyl, 1987, Methods of Organic Chemistry, ed. E. Wansch, Vol. 15 I and II, Thieme, Stuttgart).

DNA sequences encoding Tek receptor tyrosine kinase protein, or a part thereof, may be expressed by a wide variety of prokaryotic and eukaryotic host cells, including bacterial, mammalian, yeast or other fungi, viral, plant, or insect cells. Methods for transforming or transfecting such cells to express foreign DNA are well known in the art (see, e.g., Itakura et al., U.S. Pat. No. 4,704,362; Hinnen et al., PNAS USA 75:1929–1933, 1978; Murray et al., U.S. Pat. No. 4,801,542; Upshall et al., U.S. Pat. No. 4,935,349; Hagen et al., U.S. Pat. No. 4,784,950; Axel et al., U.S. Pat. No. 4,399,216; Goeddel et al., U.S. Pat. No. 4,766,075; and Sambrook et al. Molecular Cloning A Laboratory Manual, 2nd edition, Cold Spring Harbor Laboratory Press, 1989, all of which are incorporated herein by reference).

Bacterial host cells suitable for carrying out the present invention include *E. coli, B. subtilis, Salmonella typhimurium*, and various species within the genus' Pseudomonas, Streptomyces, and Staphylococcus, as : well as many other bacterial species well known to one of ordinary skill in the art. Representative examples of bacterial host cells include DH5α (Stratagene, LaJolla, Calif.), JM109 ATCC No. 53323, HB101 ATCC No. 33694, and MN294.

Bacterial expression vectors preferably comprise a promoter which functions in the host cell, one or more selectable phenotypic markers, and a bacterial origin of replication. Representative promoters include the β-lactamase (penicillinase) and lactose promoter system (see Chang et al., Nature 275:615, 1978), the trp promoter (Nichols and Yanofsky, Meth in Enzymology 101:155, 1983) and the tac promoter (Russell et al., Gene 20: 231, 1982). Representative selectable markers include various antibiotic resistance markers such as the kanamycin or ampicillin resistance genes. Many plasmids suitable for transforming host cells are well known in the art, including among others, pBR322 (see Bolivar et al., Gene 2:9S, 1977), the pUC plasmids pUC18, pUC19, pUC118, pUC119 (see Messing, Meth in Enzymology 101:20–77, 1983 and Vieira and Messing, Gene 19:259–268, 1982), and pNH8A, pNH16a, pNH18a, and Bluescript M13 (Stratagene, La Jolla, Calif.).

Yeast and fungi host cells suitable for carrying out the present invention include, among others *Saccharomyces cerevisiae*, the genera Pichia or Kluyveromyces and various species of the genus Aspergillus. Suitable expression vectors for yeast and fungi include, among others, $YC_p50$ (ATCC No. 37419) for yeast, and the amdS cloning vector pV3 (Turnbull, Bio/Technology 7:169, 1989). Protocols for the transformation of yeast are also well known to those of ordinary skill in the art. For example, transformation may be readily accomplished either by preparation of spheroplasts of yeast with DNA (see Hinnen et al., PNAS USA 75:1929, 1978) or by treatment with alkaline salts such as LiCl (see Itoh et al., J. Bacteriology 153:163, 1983). Transformation of fungi may also be carried out using polyethylene glycol as described by Cullen et al. (Bio/Technology 5:369, 1987).

Mammalian cells suitable for carrying out the present invention include, among others: COS (e.g., ATCC No. CRL 1650 or 1651), BHK (e.g., ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter, as well as other transcriptional and translational control sequences. Common promoters include SV40, MMTV, metallothionein-1, adenovirus Ela, CMV, immediate early, immunoglobulin heavy chain promoter and enhancer, and RSV-LTR. Protocols for the transfection of mammalian cells are well known to those of ordinary skill in the art. Representative methods include calcium phosphate mediated electroporation, retroviral, and protoplast fusion-mediated transfection (see Sambrook et al., supra).

Given the teachings provided herein, promoters, terminators, and methods for introducing expression vectors of an appropriate type into plant, avian, and insect cells may also be readily accomplished. For example, within one embodiment, tek or derivatives thereof may be expressed from plant cells (see Sinkar et al., J. Biosci (Bangalore) 11:47–58, 1987, which reviews the use of Agrobacterium rhizogenes vectors; see also Zambryski et al., Genetic Engineering, Principles and Methods, Hollaender and Setlow (eds.), Vol. VI, pp. 253–278, Plenum Press, New York, 1984, which describes the use of expression vectors for plant cells, including, among others, pAS2022, pAS2023, and pAS2034).

Tek receptor tyrosine kinase protein may be prepared by culturing the host/vector systems described above, in order to express the recombinant Tek receptor tyrosine kinase protein.

Conjugates of Tek receptor tyrosine kinase protein of the invention, or parts thereof, with other molecules, such as proteins or polypeptides, may be prepared. This may be accomplished, for example, by the synthesis of N-terminal or C-terminal fusion proteins. Thus, fusion proteins may be prepared by fusing, through recombinant techniques, the N-terminal or C-terminal of Tek receptor tyrosine kinase protein or parts thereof, and the sequence of a selected protein with a desired biological function. The resultant fusion proteins contain Tek receptor tyrosine kinase protein or a portion thereof fused to the selected protein. Examples of proteins which may be selected to prepare fusion proteins include lymphokines such as gamma interferon, tumor necrosis factor, IL-1, IL-2, IL-3, Il-4, IL-5, IL-6, IL-7, IL-8, IL-9, IL-10, IL-11, GM-CSF, CSF-1 and G-CSF. Particularly preferred molecules include the Fc portion of immunoglobulin molecules.

Sequences which encode the above-described molecules may generally be obtained from a variety of sources, including for example, depositories which contain plasmids encoding sequences including the American Type Culture Collection (ATCC, Rockville Md.), and the British Biotechnology Limited (Cowley, Oxford England). Examples of such plasmids include BBG 12 (containing the GM-CSF gene coding for the mature protein of 127 amino acids), BBG 6 (which contains sequences encoding gamma interferon), ATCC No. 39656 (which contains sequences encoding TNF), ATCC No. 20663 (which contains sequences encoding alpha interferon,) ATCC Nos. 31902 and 39517 (which contains sequences encoding beta interferon), ATCC No. 67024 (which contains a sequence which encodes Interleukin-1β), ATCC Nos. 39405, 39452, 39516, 39626 and 39673 (which contains sequences encoding Interleukin-2), ATCC Nos. 59399, 59398, and 67326 (which contain sequences encoding Interleukin-3), ATCC Nos. 57592 (which contains sequences encoding Interleukin-4). ATCC Nos. 59394 and 59395 (which contain sequences encoding Interleukin-5), and ATCC No. 67153 (which contains sequences encoding Interleukin-6.

Within a particularly preferred embodiment of the invention, tek is cloned into an expression vector as a fusion gene with the constant region of human immunoglobulin γ1. Briefly, the expression vectors pNUTΔGH and pVL1393 are prepared for cloning by digestion with SmaI followed by dephosphorylation by calf intestinal alkaline phosphatase. The linear product is isolated after agarose gel electrophoresis. The tek genes are then generated by polymerase chain reaction using the cloned tek cDNA as a template. In particular, the Tek fusion protein is synthesized from the extracellular domain of Tek receptor tyrosine kinase protein (amino acids 19 to 744, SEQ ID NO: 6 and FIG. 11B).

The constant region of an immunoglobulin, such as human γ1 gene may be prepared, for example, from pUCB7Ig monomer. Briefly, the $C_H$ gene is isolated by digestion with XbaI which cuts at the 3' end of the gene followed by treatment with E. coli DNA polymerase I in the presence of all four dNTPs in order to create a blunt end. The plasmid is then digested with BclI which cuts at the 5' end of the gene. The fragment containing the heavy chain gene is isolated after electrophoresis in an agarose gel.

The fusion tek amplified fragment is inserted into each prepared vector along with the heavy chain fragment. Orientation of the resulting plasmids is determined by PCR with one priming oligo which anneals to vector sequence and the other priming oligo which anneals to the insert sequence. Alternatively, appropriate restriction digests can be performed to verify the orientation. The sequence of the fusion tek/immunoglobulin constant region gene can be verified by DNA sequencing.

Phosphorylated receptor tyrosine kinase proteins of the invention, or parts thereof, may be prepared using the method described in Reedijk et al. The EMBO Journal 11(4):1365, 1992. For example, tyrosine phosphorylation may be induced by infecting bacteria harbouring a plasmid containing a nucleotide sequence of the invention or fragment thereof, with a λgt11 bacteriophage encoding the cytoplamic domain of the Elk tyrosine kinase. Bacteria containing the plasmid and bacteriophage as a lysogen are isolated. Following induction of the lysogen, the expressed receptor protein becomes phosphorylated.

Alternatively, tek may be expressed in non-human transgenic animals such as, rats, rabbits, sheep and pigs (see Hammer et al. (Nature 315:680–683, 1985), Palmiter et al. (Science 222:809–814, 1983), Brinster et al. (Proc Natl. Acad. Sci USA 82:44384442, 1985), Palmiter and Brinster (Cell. 41:343–345, 1985) and U.S. Pat. No. 4,736,866).

IV. Utility of the Nucleic Acid Molecules and Proteins of the Invention

The nucleic acid molecules of the invention or oligonucleotide fragments thereof, allow those skilled in the art to construct nucleotide probes for use in the detection of nucleotide sequences in biological materials. A nucleotide probe may be labelled with a radioactive label which provides for an adequate signal and has sufficient half-life such as $^{32}P$, $^{3}H$, $^{14}C$ or the like. Other labels which may be used include antigens that are recognized by a specific labelled antibody, fluorescent compounds, enzymes, antibodies specific for a labelled antigen, and chemiluminescense. An appropriate label may be selected having regard to the rate of hybridization and binding of the probe to the nucleotide to be detected and the amount of nucleotide available for hybridization. Labelled probes may be hybridized to nucleic acids on solid supports such as nitrocellulose filters or nylon membranes as generally described in Sambrook et al, 1989, Molecular Cloning, A Laboratory Manual (2nd Edition). The nucleotide probes may be used to detect genes, preferably in human cells, that encode proteins related to, or analogous to, the novel receptor tyrosine kinase protein of the invention.

The receptor tyrosine kinase protein of the invention or parts thereof, for example amino acids of the extracellular domain, carboxy terminal tail or catalytic domain, may be used to prepare monoclonal or polyclonal antibodies. Antibodies having specificity for Tek receptor tyrosine kinase protein may also be raised from fusion proteins created by expressing trpE-Tek fusion proteins in bacteria as described above.

Within the context of the present invention, antibodies are understood to include monoclonal antibodies, polyclonal antibodies, antibody fragments (e.g., Fab, and F(ab')$_2$ and recombinantly produced binding partners. Antibodies are understood to be reactive against Tek receptor tyrosine kinase protein if they bind with a $K_a$ of greater than or equal to $10^{-7}$ M. As will be appreciated by one of ordinary skill in the art, antibodies may be developed which not only bind to Tek protein, but which bind to a ligand of Tek protein, and which also block the biological activity of Tek protein. Such antibodies will be useful in the diagnosis and treatment of developmental disorders of endothelial cell growth, angiogenesis, vascularization, wound healing and tumorigenesis.

Conventional methods can be used to prepare the antibodies as discussed in more detail below. As to the details relating to the preparation of monoclonal antibodies reference can be made to Goding, J. W., Monoclonal Antibodies: Principles and Practice, 2nd Ed., Academic Press, London, 1986; U.S. Pat. Nos. RE 32,011, 4,902,614, 4,543,439, and 4,411,993 which are incorporated herein by reference; see also Monoclonal Antibodies, Hybridomas: A New Dimension in Biological Analyses, Plenum Press, Kennett, McKearn, and Bechtol (eds.), 1980, and Antibodies: A Laboratory Manual, Harlow and Lane (eds.), Cold Spring Harbor Laboratory Press, 1988, which are also incorporated herein by reference).

Other techniques may also be utilized to construct monoclonal antibodies (see William D. Huse et al., "Generation of a Large Combinational Library of the Immunoglobulin Repertoire in Phage Lambda," Science 246:1275–1281, December 1989; see also L. Sastry et al., "Cloning of the Immunological Repertoire in *Escherichia coli* for Generation of Monoclonal Catalytic Antibodies: Construction of a Heavy Chain Variable Region-Specific cDNA Library," Proc Natl. Acad. Sci USA 86:5728–5732, August 1989; see also Michelle Alting-Mees et al., "Monoclonal Antibody Expression Libraries: A Rapid Alternative to Hybridomas," Strategies in Molecular Biology 3:1-9, January 1990; these references, which are also incorporated herein by reference, describe a commercial system available from Stratacyte, La Jolla, Calif., which enables the production of antibodies through recombinant techniques).

Binding partners may also be constructed utilizing recombinant DNA techniques to incorporate the variable regions of a gene which encodes a specifically binding antibody. Within one embodiment, the genes which encode the variable region from a hybridoma producing a monoclonal antibody of interest are amplified using nucleotide primers for the variable region. These primers may be synthesized by one of ordinary skill in the art, or may be purchased from commercially available sources. Stratacyte (La Jolla, Calif.) sells primers for mouse and human variable regions including, among others, primers for $V_{Ha}$, $V_{Hb}$, $V_{Hc}$, $V_{Hd}$, $C_{H1}$, $V_L$ and $C_L$ regions. These primers may be utilized to amplify heavy or light chain variable regions, which may then be inserted into vectors such as ImmunoZAP™ H or ImmunoZAP™ L (Stratacyte), respectively. These vectors may then be introduced into *E. coli* for expression. Utilizing these techniques, large amounts of a single-chain protein containing a fusion of the VH and VL domains may be produced (See Bird et al., Science 242:423–426, 1988). In addition, such techniques may be utilized to change a "murine" antibody to a "human" antibody, without altering the binding specificity of the antibody.

Once suitable antibodies or binding partners have been obtained, they may be isolated or purified by many techniques well known to those of ordinary skill in the art (see Antibodies: A Laboratory Manual, Harlow and Lane (eds.), Cold Spring Harbor Laboratory Press, 1988). Suitable techniques include peptide or protein affinity columns, HPLC or RP-HPLC, purification on protein A or protein G columns, or any combination of these techniques.

The polyclonal or monoclonal antibodies may be used to detect the receptor tyrosine kinase protein of the invention in various biological materials, for example they may be used in an Elisa, radioimmunoassay or histochemical tests. Thus, the antibodies may be used to quantify the amount of a receptor tyrosine kinase protein of the invention in a sample in order to determine its role in particular cellular events or pathological states.

In particular, the polyclonal and monoclonal antibodies of the invention may be used in immunohistochemical analyses, for example, at the cellular and sub-subcellular level, to detect the novel receptor tyrosine kinase protein of the invention, to localise it to particular cells and tissues and to specific subcellular locations, and to quantitate the level of expression.

Cytochemical techniques known in the art for localizing antigens using light and electron microscopy may be used to detect the novel tyrosine kinase of the invention. Generally, an antibody of the invention may be labelled with a detectable substance and the novel receptor tyrosine kinase of the invention may be localised in tissue based upon the presence of the detectable substance. Examples of detectable substances include various enzymes, fluorescent materials, luminescent materials and radioactive materials. Examples of suitable enzymes include horseradish peroxidase, biotin, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive materials include radioactive iodine $I^{125}$, $I^{131}$ or tritium. Antibodies may also be coupled to electron dense substances, such as ferritin or colloidal gold, which are readily visualised by electron microscopy.

Radioactive labelled materials may be prepared by radiolabeling with $^{125}I$ by the chloramine-T method (Greenwood et al, Biochem. J. 89:114, 1963), the lactoperoxidase method (Marchalonis et al, Biochem. J. 124:921, 1971), the Bolton-Hunter method (Bolton and Hunter, Biochem. J. 133:529, 1973 and Bolton Review 18, Amersham International Limited, Buckinghamshire, England, 1977), the iodogen method (Fraker and Speck, Biochem. Biophys. Res. Commun. 80:849, 1978), the Iodo-beads method (Markwell Anal. Biochem. 125:427, 1982) or with tritium by reductive methylation (Tack et al., J. Biol. Chem. 255:8842, 1980).

Known coupling methods (for example Wilson and Nakane, in "Immunofluorescence and Related Staining Techniques", W. Knapp et al, eds, p. 215, Elsevier/North-Holland, Amsterdam & New York, 1978; P. Tijssen and E. Kurstak, Anal. Biochem. 136:451, 1984) may be used to prepare enzyme labelled materials. Fluorescent labelled materials may be prepared by reacting the material with umbelliferone, fluorescein, fluorescein isothiocyanate, dichlorotriazinylamine fluorescein, dansyl chloride, derivatives of rhodamine such as tetramethyl rhodamine isothiocyanate, or phycoerythrin.

Indirect methods may also be employed in which the primary antigen-antibody reaction is amplified by the introduction of a second antibody, having specificity for the antibody reactive against the novel tyrosine kinase of the invention. By way of example, if the antibody having specificity against the novel tyrosine kinase protein of the invention is a rabbit IgG antibody, the second antibody may be goat anti-rabbit gamma-globulin labelled with a detectable substance as described herein.

Where a radioactive label is used as a detectable substance, the novel tyrosine kinase of the invention may be localized by radioautography. The results of radioautography may be quantitated by determining the density of particles in the radioautographs by various optical methods, or by counting the grains.

As discussed above, the expression patterns found for the novel tyrosine kinase of the invention indicate that it plays unique and important roles in angiogenesis, cardiogenesis and tumorigenesis. Therefore, the above described methods for detecting nucleic acid molecules and fragments thereof and Tek protein and parts thereof, can be used to monitor angiogenesis, cardiogenesis and tumorigenesis by detecting and localizing the novel tyrosine kinase protein of the invention.

It would also be apparent to one skilled in the art that the above described methods may be used to study the developmental expression of Tek and, accordingly, will provide further insight into the role of Tek protein in angiogenesis, cardiogenesis and tumorigenesis.

The finding of a novel receptor tyrosine kinase which is only expressed in cells of the endothelial lineage permits the identification of substances such as ligands, which may affect angiogenesis and/or maintenance of cells of the endothelial lineage and which may play a role in tumorigenesis. Therefore, in accordance with a method of the invention ligands, and natural and synthetic derivatives of such ligands, which are capable of binding to, and in some cases activating the receptor tyrosine kinase protein of the invention, isoforms thereof, or part of the protein may be identified. The method involves reacting the novel receptor kinase protein of the invention, isoforms thereof, or part of the protein with at least one ligand which potentially is capable of binding to the protein, isoform or part of the protein, under conditions which permit the formation of ligand-receptor protein complexes, and assaying for ligand-receptor protein complexes, for free ligand or for non-complexed proteins or for activation of the receptor tyrosine kinase.

The ligand-receptor protein complexes, free ligand or non-complexed proteins receptor-ligand complex, may be isolated by conventional isolation techniques, for example, salting out, chromatography, electrophoresis, gel filtration, fractionation, absorption, polyacrylamide gel electrophoresis, agglutination, or combinations thereof. To facilitate the assay of the components, antibody against the receptor protein or the ligand, or a labelled receptor protein, or a labelled ligand may be utilized. Antibodies, receptor protein, or substance may be labelled with a detectable substance as described above.

The receptor tyrosine kinase protein, isoforms or parts thereof, or ligand used in the method of the invention may be insolubilized. For example, the receptor protein or ligand may be bound to a suitable carrier. Examples of suitable carriers are agarose, cellulose, dextran, Sephadex, Sepharose, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc. Insolubilized receptor tyrosine kinase protein or ligand thereof will include receptor tyrosine kinase protein or ligand thereof expressed on the surface of a cell.

The insolubilized receptor tyrosine kinase protein or ligand may be prepared by reacting the material with a suitable insoluble carrier using known chemical or physical methods, for example, cyanogen bromide coupling.

Conditions which permit the formation of ligand-receptor protein complexes may be selected having regard to factors such as the nature and amounts of the ligand and the receptor protein.

The receptor tyrosine kinase protein, parts thereof, or substances may also be expressed on the surface of a cell using the methods described herein.

In a preferred embodiment of the method, ligands are identified which are capable of binding to and activating the novel receptor tyrosine kinase protein of the invention. In this method the ligands which bind to and activate the novel receptor tyrosine kinase protein of the invention are identified by assaying for protein tyrosine kinase activity i.e. by assaying for phosphorylation of the tyrosine residues of the receptor.

Protein tyrosine kinase activity may be assayed using known techniques such as those using antiphosphotyrosine antibodies and labelled phosphorous. For example, immunoblots of the complexes may be analyzed by autoradiography ($^{32}$P-labelled samples) or may be blocked and probed with antiphosphotyrosine antibodies as described in Koch, C. A. et al (1989) Mol. Cell. Biol. 9, 4131–4140.

The ligands for many receptor tyrosine kinase proteins are cell-bound, either as they are associated with the cell surface via heparin and hepatocyte growth factor or because they are transmembrane proteins (Lyman et al. 1993, supra). Accordingly, a ligand for Tek protein may have a cell-bound form. A cell-bound ligand may be identified by reacting the receptor tyrosine kinase protein of the invention, an isoform or a part thereof with a cell suspected of expressing the ligand on the surface of the cell following the procedures generally described in Lyman et al., 1993, (Cell 75;1157–1167). Thus, the invention provides a method for identifying cells expressing a surface bound ligand of Tek protein and for specifically selecting for such cells.

By way of example, a cDNA encoding a ligand for Tek protein may be cloned by first constructing a fusion protein. The fusion protein may consist of the extracelluar domain of Tek protein (amino acids 19 to 744, SEQ ID NO: 6 and FIG. 11B). The fusion protein may be expressed and used as a probe to examine cells or cell lines for their capacity to bind the extracelluar domain of Tek protein (determined by flow cytometry). The identification of cells and cell lines that bind the extracellular domain may be facilitated by incorporating in the fusion protein a sequence encoding a marker protein for example, the Fc portion of human IgG which may be detected with labelled anti-human IgG antibodies. Cells or cell lines which bind the extracellular domain are presumed to express a cell-bound form of the ligand.

Following identification of a source of the Tek ligand, a cDNA expression library is constructed, following known techniques, using mRNA from the cells/cell lines which have been identified as binding the fusion protein containing the extracellular domain of Tek protein. cDNAs are then transfected into host cells which are then screened for their capacity to bind the extracellular domain of Tek protein. Individual clones which are capable of binding the extracellular domain of Tek protein are identified and the cDNAs are sequenced. The cDNAs may be used as hybridization probes to isolate genomic DNA encoding the ligand.

The invention also provides a method of using the novel proteins of the invention for assaying a medium for the presence of a substance that affects a tek effector system. In particular the method may be used to detect a suspected agonist or antagonist of a tek effector system. The agonist or antagonist may be an endogenous physiological substance or it may be a natural or synthetic drug.

The term "tek effector system" used herein refers to the interactions of a ligand, and the receptor tyrosine kinase protein of the invention, and includes the binding of a ligand to the receptor protein or any modifications to the receptor associated therewith, to form a ligand/receptor complex and activating tyrosine kinase activity thereby affecting signalling pathways, particularly those involved in the regulation of angiogenesis.

In accordance with one embodiment, a method is provided which comprises providing a known concentration of a receptor tyrosine kinase protein of the invention, isoforms thereof, or part of the protein, incubating the protein, isoforms thereof, or part of the protein, with a ligand which is capable of binding to the protein, isoforms thereof, or part of the protein, and a suspected agonist or antagonist substance under conditions which permit the formation of ligand-receptor protein complexes, and assaying for ligand-receptor protein complexes, for free ligand or for non-complexed proteins.

The ligand-receptor complex, free ligand or non-complexed proteins may be assayed as described above. Suitable ligands used in the assay method may be identified using the methods described above. The ligand may be a natural ligand or a synthetic derivative having similar biological activity.

The invention also makes it possible to screen for antagonists that inhibit the effects of an agonist of a tek effector system, but do not have any biological activity in the tek effector system. Thus, the invention may be used to assay for a substance that competes for the same ligand-binding site on the novel receptor tyrosine kinase protein of the invention.

It will be understood that the substances that can be assayed using the methods of the invention may act on one or more of the binding sites on the receptor tyrosine kinase or the ligand, including agonist binding sites, competitive antagonist binding sites, non-competitive antagonist binding sites or allosteric sites.

The methods of the invention make it possible to screen a large number of potential ligands for their ability to bind to the novel receptor tyrosine kinase protein of the present invention. The methods of the invention are therefore useful for identifying potential stimulators or inhibitors of angiogenesis, cardiogenesis or tumorigenesis.

The invention further contemplates a method for identifying a substance which is capable of binding to an activated receptor tyrosine kinase protein of the invention or an isoform or part of the activated protein, comprising reacting an activated receptor tyrosine kinase protein of the invention, or an isoform, or part of the protein, with at least one substance which potentially can bind with the receptor tyrosine kinase protein, isoform or part of the protein, under conditions which permit the formation of substance-receptor kinase protein complexes, and assaying for substance-receptor kinase protein complexes, for free substance, for non-complexed receptor kinase proteins, or for phosphorylation of the substance.

An activated receptor tyrosine kinase protein of the invention, or isoform or part thereof may be prepared by binding of a ligand to the extracellular domain of a receptor tyrosine kinase protein of the invention which results in activation of the catalytic domain. Such a ligand may be identified using the methods hereinbefore described. An activated receptor or part thereof, may also be prepared using the methods described for example in Reedijk et al. The EMBO Journal, 11(4):1365, 1992 for producing a tyrosine phosphorylated receptor or part thereof.

Conditions which permit the formation of substance-receptor protein complexes may be selected having regard to factors such as the nature and amounts of the substance and the receptor protein. The substance-receptor complex, free substance or non-complexed proteins may be isolated by conventional isolation techniques described above. Phosphorylation of the substance may be determined using for example, labelled phosphorous as described above.

In an embodiment of this method, intracellular ligands such as Src homology region 2 (SH2)-containing proteins which are capable of binding to a phosphorylated receptor tyrosine kinase protein of the invention may be identified. SH2-containing proteins refers to proteins containing a Src homology region 2 which is a noncatalytic domain of ~100 amino acids which was originally identified in the Vfps and Vsrc cytoplasmic tyrosine kinases by virtue of its effects on both catalytic activity and substrate phosphorylation (T. Pawson, Oncogene 3, 491 (1988) and I. Sadowski et al., Mol. Cell. Biol. 6, 4396 (1986)). (See also Koch et al., Science 252:668, 1991; Moran et al., PNAS USA 87:8622 and Anderson et al., Science 250:979, 1990 for discussions on SH2-containing proteins and the role of SH2 domains). SH2-containing proteins may function downstream of the Tek signalling pathway by binding to the activated receptor protein. Intracellular ligands which may be phosphorylated by the novel receptor tyrosine kinase protein of the invention may also be identified using the method of the invention.

The invention further provides a method for assaying for a substance that affects angiogenesis, cardiogenesis, or tumorigenesis comprising administering to a non-human animal or to a tissue of an animal, a substance suspected of affecting angiogenesis, cardiogenesis, or tumorigenesis and detecting, and optionally quantitating, the novel receptor tyrosine kinase of the invention in the non-human animal or tissue.

In another embodiment, the method may be used to assay for a substance that affects tumorigenesis, comprising administering a substance suspected of affecting tumorigenesis to a non-human animal model of tumorigenesis and detecting, and optionally quantitating, the novel protein kinase of the invention in the non-human animal. For example, the 3T3 cell transformation model in nude mice may be employed.

Substances which are capable of binding to the Tek protein of the invention or parts thereof, particularly ligands, and agonists and antagonists of the binding of ligands and Tek protein, identified by the methods of the invention, may be used for stimulating or inhibiting angiogenesis or cardiogenesis, or inhibiting tumorigenesis. The efficacy of these substances in the treatment of human conditions may be confirmed using non-human animal models, for example the models of tumorigenesis described above.

Cells, tissues, embryos, and non-human animals lacking in Tek expression or partially lacking in Tek expression may be developed using recombinant molecules of the invention in particular recombinant molecules containing sequences encoding the Tek protein having specific structural mutations such as replacement, deletion or insertion mutations in the Tek gene, or having one or more regulatory elements which differ from the transcriptional and translation elements of the native Tek protein. For example, the extracelluar domain or parts thereof, the transmembrane region or parts thereof; the tyrosine kinase domain or parts thereof, and; the carboxy terminal tail may be deleted. A recombinant molecule may be used to inactivate or alter the endogenous gene by homologous recombination, and thereby create a Tek deficient cell, tissue or animal. The recombinant molecule may also contain a reporter gene, as described herein, to facilitate monitoring of expression in the cells, tissues, etc.

Null alleles may be generated in cells, such as embryonic stem cells by a deletion mutation. A recombinant Tek gene may also be engineered to contain an insertion mutation which inactivates Tek. Such a construct may then be introduced into a cell, such as an embryonic stem cell, by a technique such as transfection, electroporation, injection etc. Cells lacking an intact Tek gene may then be identified, for example by Southern blotting, Northern Blotting or by assaying for expression of Tek protein using the methods described herein. Such cells may then be fused to embryonic stem cells to generate transgenic non-human animals deficient in Tek. Germline transmission of the mutation may be achieved, for example, by aggregating the embryonic stem cells with early stage embryos, such as 8 cell embryos, in vitro; transferring the resulting blastocysts into recipient females and; generating germline transmission of the resulting aggregation chimeras. Such a mutant animal may be used to define specific nerve cell populations, developmental patterns of cardiogenesis, and endothelial and highly vascularized tissue and in vivo processes, normally dependent on Tek expression.

By way of example, specific targeted mutations may be employed to generate a Tek receptor tyrosine kinase protein that is still competent to bind ligand, but which is unable to transduce a signal due to its lack of catalytic function. Such targeted mutations may be made in the highly conserved intracellular cytoplasmic domain, for example, by altering lysine$^{853}$ to alanine$^{853}$. A null allele of tek may also be created by deletion of several nucleotides within an exon. For example the last 52 base pairs of exon-1 may be deleted.

The following non-limiting examples are illustrative of the present invention:

EXAMPLES

The following materials and methods were utilized in the investigations outlined in Examples I to VI:

DNAs

AKR/J, DBA, and AKR/J×DBA recombinant inbred mouse DNAs were obtained from Jackson Labs (Bar Harbor, Maine), digested with AccI, blotted to Zeta-Probe nylon membrane (Bio-Rad), and probed with the 1.6 kb tek cDNA labelled by random priming (Feinberg, A. P. & Vogelstein, B. (1983) Analyt.Biochem., 132, 6–13). Hybridization was performed overnight at 65° in 200 mM sodium phosphate pH7.0, 7% sodium dodecyl sulfate (SDS), 1% bovine serum albumin (BSA), and 1 mM EDTA. Filters were washed twice at 55° in 2×SSC (1×SSC=0.15 M NaCl, 0.015 M sodium citrate pH7.0) and 0.1% SDS and twice in 0.2×SSC and 0.1% SDS, and exposed overnight to Kodak XAR-5 film.

Mice

Embryos and adult mouse tissues were obtained from random bred CD-1 stocks (Charles River, Quebec). Embryos were staged as Day 0.5 on the morning of a vaginal plug.

RNA Purification and Analysis

Total RNA was extracted from pools of 30 to 40 Day 9.5 and 12.5 murine embryonic hearts with RNAzol (CINNA/B10TECX Lab. Int.), with some added modifications. Briefly, tissues were washed with ice cold phosphate buffered saline (PBS) and homogenized in 2.5 ml of RNAzol. Chloroform (250 μl) was added and the tubes were mixed vigorously and then chilled on ice for 15 min. The suspension was centrifuged for 15 min at 4° after which the aqueous phase was collected and re-extracted twice more with phenol/chloroform/isoamyl alcohol (25:24:1; vol:vol:vol). The RNA was precipitated with an equal volume of isopropanol, collected by centrifugation, and the pellet resuspended in diethylpyrocarbonate (DEPC)-treated 0.4 M sodium acetate, pH5.2. The RNA were then reprecipitated with two volumes of 95% ethanol, washed with 70% and 95% ethanol, dried, and resuspended in DEPC treated 0.3 M sodium acetate, pH5.2. The RNA concentration was determined and the RNA stored at −70° until use.

Poly A—containing RNA was purified from a pool of 100 to 150 Day 12.5 murine embryonic hearts with a QuickPrep mRNA isolation kit (Pharmacia) as outlined by the supplier.

For Northern blot hybridization, 5 μg of poly A—containing RNA from 12.5 day embryonic heart was electrophoresed through a formaldehyde-agarose gel and blotted to a Zeta-Probe nylon membrane (Bio-Rad) according to established protocols (Sambrook et al., 1989, Molecular Cloning. Cold Spring Harbor Laboratory Press). The membrane was hybridized with a [$^{32}$P]-labelled antisense riboprobe synthesized from the 1.6 kb tek cDNA in run off reactions with SP6 RNA polymerase (Promega).

Reverse Transcription Coupled to the Polymerase Chain Reaction (RT-PCR)

First strand cDNA was synthesized in a total reaction volume of 20 μl containing 20 μg of total RNA, 200 units of Mo-MLV-reverse transcriptase (BRL), either 1 μg of oligo-d(T)$_{18}$ (Day 12.5 RNA) (Boerhinger Mannheim) or 2 μg of random hexamer primers (Day 9.5 RNA) (Boerhinger Mannheim), 1×PCR buffer (Cetus), 2.5 mM MgCl$_2$, 1 mM of dNTPs (Pharmacia), 40 units of RNAsin (Promega), and 12.5 mM dithiothreitol. The RNA was heated to 65° C. for 10 min and cooled quickly on ice prior to addition to the reaction components. The reaction was allowed to proceed for 1 h at 37° and then terminated by heating for 5 min at 95°. For PCR, the reaction mixture was adjusted to a final volume of 100 μl containing 1×PCR buffer, 1.5 mM MgCl$_2$, 800 μM dNTPs, and 1 μg of each of the two degenerate tyrosine kinase oligonucleotide primers described by Wilks, A. F. (1989) *Proc.Natl.Acad.Sci.*, 86, 1603–1607. Amplification was performed with a Ericomp thermocycler using the following parameters: denaturation for 2 min at 94°, annealing for 2 min at 42°, and extension for 4 min at 63°. After 40 cycles, the reaction products were collected by ethanol precipitation and electrophoresed through at 2% low-melt agarose (Sea Plaque) gel. In most cases a band of approximately 200 bp was visible within a background smear of ethidium bromide staining. This band was excised and recovered by three cycles of freeze-thaw in 100 μl of water. 10 μl of this solution was then subjected to a second round of PCR under the same conditions described above.

Cloning and Sequencing of RT-PCR Products

After the second round of amplification, 10 μl of the reaction mixture were analyzed on a gel for successful amplification. The remaining 90 μl were then ethanol precipitated, digested with EcoRI and BamHI, gel purified, and ligated to pGEM7Zf+ (Promega) digested with the same enzymes. The ligation mixture was then transformed into MV1190 competent cells, individual ampe colonies picked, plasmid DNA prepared, and the cDNA inserts analyzed by single track dideoxynucleotide sequencing (Sanger, F., Nicklen, S. & Coulson, A. R. (1977). *Proc.Natl.Acad.Sci.*, 74, 5463–5467). A single representative clone of each multiple isolate was sequenced in its entirety. Of the 58 clones analyzed, roughly 10% showed no sequence identity to tyrosine kinases and were disregarded.

Isolation of Additional tek cDNA Sequences

Approximately $10^6$ plaques from an amplified, random primed 13.5 day murine embryonic λgt10 cDNA library were hybridized with the 210 bp tek PCR product labelled with [$^{32}$P]-dCTP by PCR. Hybridization was carried out overnight at 55° in 50% formamide, 10% dextran sulfate (Pharmacia), 0.5% BLOTTO, 4×SSPE (1×SSPE=0.18 M NaCl, 10 mM $NaH_2PO_4$, 1 mM EDTA, pH7.4), 100 μg/ml sheared salmon sperm DNA, and $2×10^6$ cpm/ml of probe. Filters were washed at 55° twice in 2×SSC containing 0.1% SDS and twice in 0.2×SSC containing 0.1% SDS, dried, and exposed overnight to Kodak XAR-5 film. One clone was isolated from this screen and was found to contain a 1.6 kb cDNA. The sequence of the 1.6 kb cDNA was determined by the method of Sanger et al. (1977) from a set of anchored deletions generated with a standardized kit (Erase-A-Base, Promega).

In Situ Hybridization

Embryos isolated on Day 12.5 were dissected away from all extraembryonic tissues whereas embryos at earlier time points were recovered in utero. Embryos and adult tissues were fixed overnight in 4% paraformaldehyde, dehydrated with alcohols and xylenes, and embedded in paraffin. Tissues were sectioned at 6 μm thickness and mounted on 3-aminopropyltriethoxysilane treated slides (Sigma). After removal of paraffin the samples were treated with predigested pronase (Boerhinger Mannheim), acetylated with triethanolamine, dehydrated, and hybridized according to the protocol described by Frohman, N. B., Boyle, M. & Martin, G. R. (1990), *Development*, 1101 589–607.

Dark and bright field photomicroscopy was performed with a Leitz Vario Orthomat 2 photomicroscopic system. Adjacent sections probed with a tek sense probe produced no detectable signal above background.

Whole-mount in situ hybridizations were performed using a modification of existing procedures (Tautz, D. & Pfeifle, C. (1989). *Chromosoma*, 98,81–85; Hemmati-Brivanlou, A., Franck, D., Bolce, M. E., Brown, B. D., Sive, H. L. & Harland, R. M. (1990). *Development*, 110, 325–330; Conlon and Rossant, in prep.). The hybridization of single-stranded RNA probes labelled with digoxigenin was detected with antidigoxigenin antibodies coupled to alkaline phosphatase. The En2 cDNA was prepared as set forth in Joyner A. L. & Martin, G. R. (1987). *Genes and Dev.*, 1, 29–38 and expression of En2 is described in Davis, C. A., Holmyard, D. P., Millen, K. J. & 2JJoyner, A. L. (1991) *Development*, 111:, 287–298.

Immunohistochemistry

Sections were stained immunohistochemically for von Willebrand factor with a commercially available kit (Biomeda). After color development, slides were counterstained with Harris hematoxylin.

EXAMPLE I

Isolation and Characterization of tek from a Day 13.5 Total Mouse Embryo cDNA Library To identify and characterize tyrosine kinases expressed during murine cardiogenesis, cDNAs were synthesized from 9.5 and 12.5 day embryonic heart RNA by RT-PCR using degenerate oligonucleotide primers previously demonstrated to amplify tyrosine kinase sequences preferentially (Wilks, A. F. 1989, *Proc.Natl.Acad.Sci.*, 86, 1603–1607). Considerable cellular differentiation and morphogenesis have occurred within the cardiac region of the embryo by Day 9.5. At this stage the heart has developed from the primordial mesoderm cells of the cardiac plate into a primitive bent tube structure, consisting of two endothelial tubes enclosed within the developing myocardium. Between Day 9.5 and 12.5 the heart undergoes additional complex morphological changes in association with the formation of the four chambers and septa characteristic of the adult heart. Sequence analysis of 58 clones obtained following amplification revealed that whereas roughly 10% did not contain sequence similarities to protein kinases the remainder corresponded to 5 distinct cDNAS (Table 1—Identity and number of tyrosine kinase cDNA clones recovered from Day 9.5 and 12.5 murine embryonic heart by RT-PCR). Four of these cDNAs represented previously characterized tyrosine kinases including, bmk, c-src, c-abl, and the platelet derived growth factor receptor β-subunit (pdgfrb). The isolation of bmk, c-src, and c-abl is consistent with the broad tissue distribution of these kinases (Wang, J. Y. J. & Baltimore, D. (1983). *Mol.Cell.Biol.*, 3, 773–779; Ben-Neriah et al., (1986). *Cell*, 44, 577–586; Holtzman, D., Cook, W. & Dunn, A. (1987). *Proc.Natl.Acad.Sci.*, 84, 8325–8329; Renshaw, M. W., Capozza, M. A. & Wang, J. Y. J. (1988). *Mol.Cell.Biol.*, 8, 4547–4551). The recovery from embryonic heart of pdgfrb at a relatively high frequency may indicate that pdgfrb plays an important role in cardiogenesis, as has been suggested by recent studies demonstrating that the addition of PDGF-BB to explants of axolotol cardiac field mesoderm stimulates the production of beating bodies (Muslin, A. J. & Williams, L. T. (1991). *Development*, 112, 1095–1101) the fifth cDNA, which was also isolated at high frequency, was novel and for reasons that will become clear below was designated tek. The 210 bp RT-PCR-derived tek clone was subsequently used to isolate additional tek cDNA sequences.

FIG. 2 (or SEQ ID NO:3) shows the nucleotide sequence of a 1.6 kb tek cDNA isolated from a 13.5 day mouse embryo cDNA library. Translation of this sequence reveals a single large open reading frame that terminates with TAG at nucleotide 907, followed by 696 nucleotides of 3' untranslated sequence. Several features of the deduced amino acid sequence (or SEQ ID NO:4) suggest that the 1.6 kb tek cDNA encodes the cytoplasmic portion of a transmembrane RTK, consisting of the catalytic domain followed by a short carboxy-terminal tail of 33 amino acid residues.

FIG. 3 shows a comparison of the deduced amino acid sequence of tek (or SEQ ID NO:4) with that of other tyrosine kinases; Identical sequences are denoted by periods. Dashes were added to allow for optimal alignment. The kinase insert and conserved regions of the catalytic domain are indicated beneath the aligned sequences (Hanks, S. K., Quinn, A. M. & Hunter, T. (1988), *Science*, 241, 52). Comparative sequences shown are for human Ret (SEQ ID NO:15) (Takahashi, M. & Cooper, G. M. (1987). *Mol.Cell.Biol.*, 7, 1378–1385), and Jtk14 (SEQ ID NO:14) (Partanen, J., M äkelä, T. P., Alitalo, R., Lehväslaiho, H. & Alitalo, K. (1990) Proc.Natl.Acad.Sci., 87, 8913–8917) and murine Flg (SEQ ID NO:16) (Reid, H. H., Wilks, A. F. & Bernard, O. (1990) *Proc.Natl.Acad.Sci.*, 87, 1596–1600).

As shown in FIG. 3, the putative kinase domain contains several sequence motifs conserved among tyrosine kinases, including the tripeptide motif DFG, which is found in almost all known kinases, and the consensus ATP-binding site motifs GXGXXG (SEQ ID NO:7) followed by AXK 16 amino acid residues downstream (Hanks et al., 1988). Transmembrane RTK's possess a methionine residue within the motif WMAIESL of conserved region VIII of the catalytic domain (Hanks et al., 1988) as does tek, and the catalytic domain is interrupted by a putative 21 amino acid kinase insert, a structural motif not found in cytoplasmic tyrosine kinases (Hanks et al., 1988).

Comparison with other tyrosine kinases (FIG. 3) reveals that the deduced tek amino acid sequence shows 42% sequence identity to the mouse fibroblast growth factor receptor Flg (Reid et al., 1990; Safran, A., Avivi, A., Orr-Urtereger, A., Neufeld, G., Lonai, P., Givol, D. & Yarden, Y. (1990). *Oncogene*, 5, 635–643, Sambrook, J., Fritsch, E. F. & Maniatis, T. (1989). Molecular Cloning. Cold Spring Harbor Laboratory Press) and 45% to the transmembrane RTK encoded by the human c-ret proto-oncogene (Takahashi & Cooper, 1987). In addition, striking sequence identity is observed to a 65 amino acid residue sequence encoded by Jtk14, a putative tyrosine kinase cDNA isolated from differentiating human K562 cells by RT-PCR (Partanen et al., 1990). Taken together, the results suggest that tek encodes a novel RTK.

EXAMPLE II
Chromosomal Mapping of the tek Murine Locus

Mapping of the tek locus in mice was accomplished by monitoring the strain distribution pattern of an AccI restriction site polymorphism in recombinant inbred (RI) mouse strains derived from matings between AKR/J (A) and DBA/ 2J (D) mice. The tek cDNA detects bands of 6.5, 6.1, 1.3 and 6.5, 3.1, 1.3 kb in DNA from the A and D strains, respectively. Southern blot hybridization analysis of DNA from 24 RI mice with the 1.6 kb cDNA probe, and comparison of the segregation pattern with the Jackson Laboratory data base, revealed 95.8% cosegregation between tek and both brown and pmv-23, two loci that have previously been localized to mouse chromosome 4 (Lyon & Searle, 1989). Table 2 shows the cosegregation of the tek, brown, and pmv-23 loci in A×D strains. In Table 2 for each RI strain, the symbol shown indicates the presence of an allele characteristic of the progenitor from which the strain was derived (A, AKR/J; D, DBA/2J). These data place tek between the brown and pmv-23 loci within 3.8±1.9 centimorgans of each interval.

EXAMPLE III
Multiple tek-related Transcripts are Expressed in Embryonic Heart Tek expression in embryonic heart was examined by Northern blot hybridization using an antisense probe derived from the 1.6 kb tek cDNA. FIG. 4 shows a Northern blot hybridization analysis of tek expression in 12.5 day murine embryonic heart; Arrows on the left denote the position of migration of 28 S and 18 S ribosomal RNAs obtained from adjacent lane loaded with total RNA.

10 μg of yeast tRNA (lane 1) and 10 μg of total RNA from Py4-1 (lane 2), EOMA (lane 3) and MAE 22106 (lane 4) cells were hybridized in solution with [$^{32}$P]labelled tek, flk-1, and β-actin antisense RNA and digested with RNAse. Individual probes were added to RNA prepared from EH13.5 (lanes 5 to 7). Digestion products were analyzed on a 6% sequencing gel and autoradiographed for 24 hrs (lanes 5–7) and 48 hrs (lanes 1 to 4). The β-actin lanes were exposed for equal times. Relevant regions of the gel are shown.

FIG. 4 shows that the tek probe detects 4 transcripts of 4.5, 2.7, 2.2, and 0.8 kb in size in cardiac RNA from 12.5 day mouse embryos. These hybridizing species vary considerably in signal intensity, suggesting that they may differ in relative abundance, with expression of the 2.7 and 2.2 kb transcripts occurring at significantly higher levels than the 4.5 and 0.8 kb RNAs. While the exact relationship among these transcripts is unclear, it is possible that they arise by differential splicing, since the 1.6 kb tek cDNA detects a single genomic locus in mouse DNA by Southern blot hybridization at the same stringency.

EXAMPLE IV

In Situ Localization of tek Expression During Mouse Embryogenesis

To determine which cell types express tek during development, RNA in situ hybridization analyses were performed on mouse embryos with an antisense riboprobe synthesized from the 1.6 kb tek cDNA.

FIG. 5 shows the in situ hybridization analysis of tek expression in the 12.5 day embryo; A. Dark field illumination of a para-sagittal section. Bar: 600 μm. B. and C. Bright and dark field illumination respectively, of the heart region taken from a mid-sagittal section. Bar: 300 μm. IV and VI, fourth and sixth aortic arches; A, atrium; BA, basilar artery; CV, caudal vein; E, endocardium; L, liver; M, leptomeninges; Ma, mandible; My, myocardium; PC, pericardial cavity; RA, renal artery; SS, sino-auricular septum; SV, sinus venosus; V, ventricle.

Figure 5A:
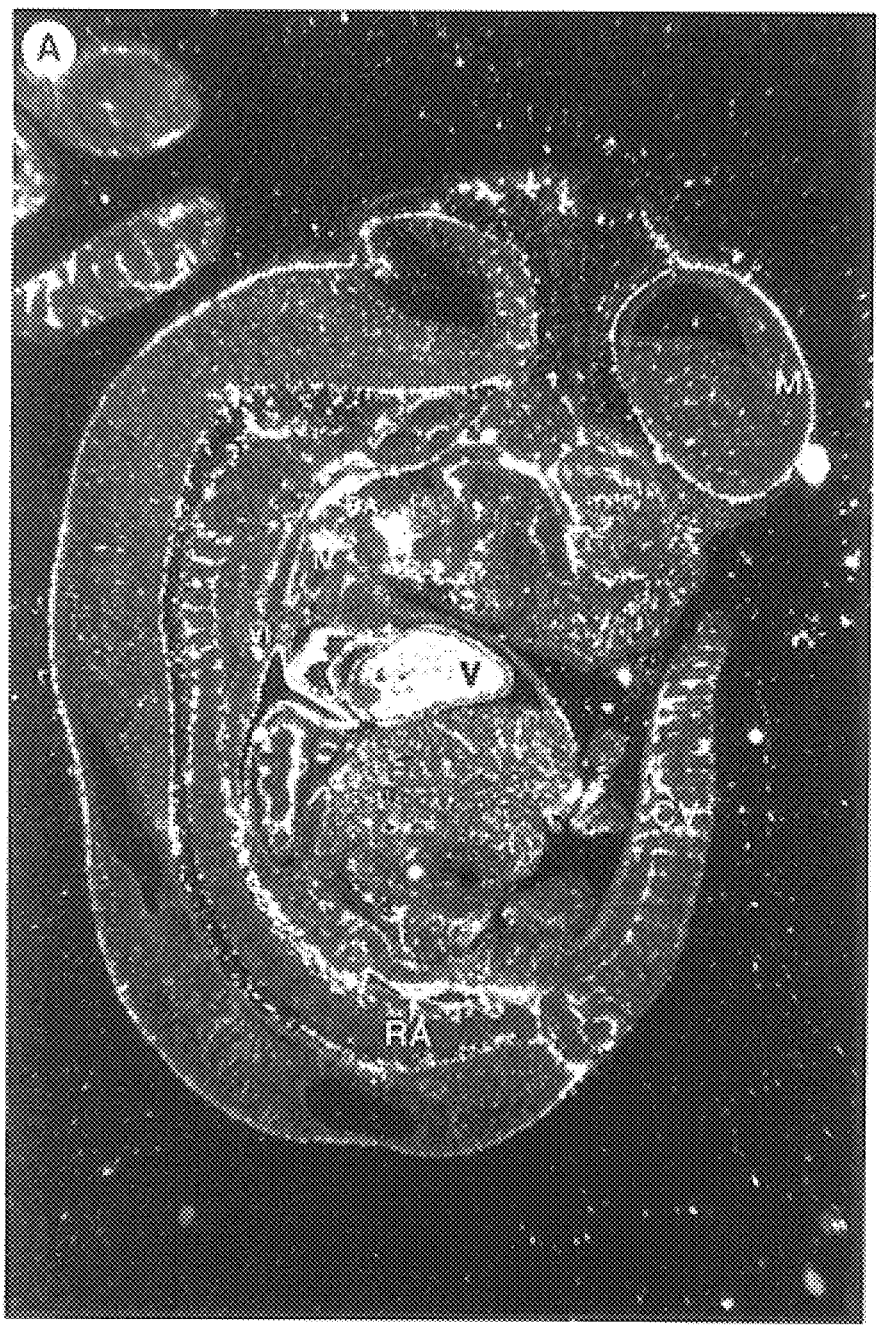
FIG. 5 shows the in situ hybridization analysis of expression of a DNA molecule of the invention in the 12.5 day embryo, (A) dark field illumination of a para-sagittal section, (B) and (C) bright and dark field illumination respectively, of a mid saggital section through the heart region.
Figure 5B:
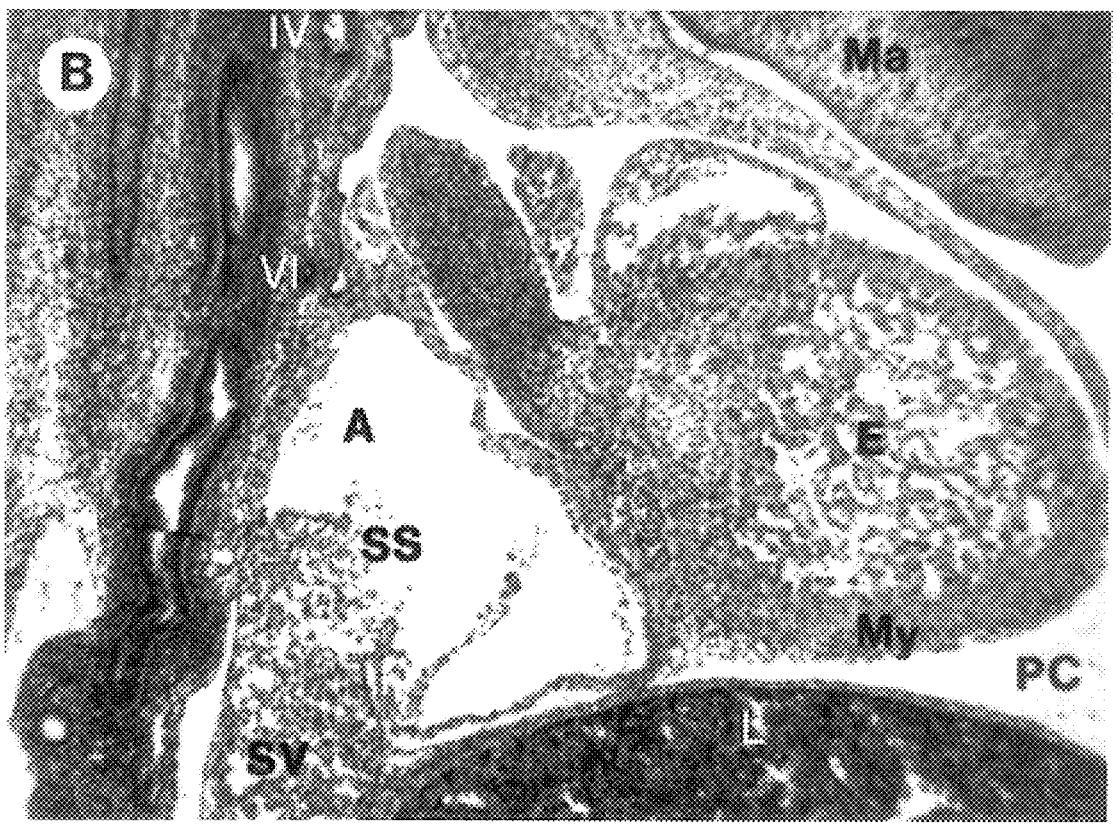
Figure 5C:

FIG. 5A shows that in 12.5 day mouse embryos, expression of tek is readily detected in the heart, the leptomeninges lining the brain and spinal cord, and the inner lining of major blood vessels, including the caudal vein and basilar and renal arteries. In addition, thin bands of hybridization are observed in the intersomite regions, corresponding to tek expression in the intersegmental vessels. Close examination of the region of the developing heart (FIG. 5B and 5C) reveals that tek is expressed in the endocardium, as well as in cells lining the lumina of the atria, the IV and VI aortic arches, the sinus venosus, and the sino-auricular septum. In addition, tek expression is observed in numerous small blood vessels perforating the liver and mandible. These observations, together with the overall pattern of hybridization seen in the 12.5 day embryo, demonstrate that tek is expressed in the endothelial cells of the tunica interna, the innermost lining of the blood vessels; hence the designation tunica interna endothelial cell kinase, tek.

More detailed information on tek expression was obtained through analysis of sections from earlier developmental stages. Hybridization to 6.5 and 7 day embryos revealed that while tek is expressed strongly in the inner lining of the small blood vessels and capillaries of the maternal decidua, no expression is observed in either the embryo itself or the ectoplacental cone. The absence of tek expression at these stages is consistent with the fact that at 6.5 to 7 days the embryo contains only a small amount of mesoderm from which endothelial cells are known to be derived.

FIG. 6 shows the expression of tek precedes that of von Willebrand factor in 8.5 day embryos; Adjacent transverse sections through an 8.5 day embryo fixed in utero were either hybridized in situ with an [$^{35}$S]-labelled tek probe or stained immunohistochemically for von Willebrand factor. A. Bright field illumination of tek expression, Bar: 300 µm. B. Dark field illumination of section in A. C. High magnification of a blood island, slightly out of the field shown in A, depicting silver grains over flat, elongated cells of endothelial-like morphology, Bar: 50 µm. D. Adjacent section to A at higher magnification showing absence of expression of von Willebrand factor in the embryo, Bar: 100 µm. E. Adjacent section to A at higher magnification showing expression of von Willebrand factor in the endothelial lining of the blood vessels of the maternal decidua. Bar: 200 µm. F. High magnification of cephalic region in A showing silver grains over a large, round cell of angioblast-like morphology (arrow). Bar: 50 µm. G. Bright field illumination of a sagittal section of an 8.5 day embryo hybridized in situ with an [$^{35}$S]-labelled tek probe. Bar: 300 µm. H. Dark field illumination of G. I. Higher magnification of heart region in A showing silver grains over cells with endothelial- and angioblast-like morphology in the developing endocardium. Bar: 100 µm. J. Higher magnification of somite region in A showing tek-expressing cells extending beneath, and possibly from, the ventral surface of the somites. Bar: 100 µm. A, amnion; Ag, presumptive angioblast; BI, blood island; D, maternal decidua; DA, dorsal aorta; E, endocardium; Ec, ectoplacental cone; En, endothelial cell; G. foregut; HV, head vein; NF, neural fold; S, somite; Y, yolk sac.

Figure 6H:
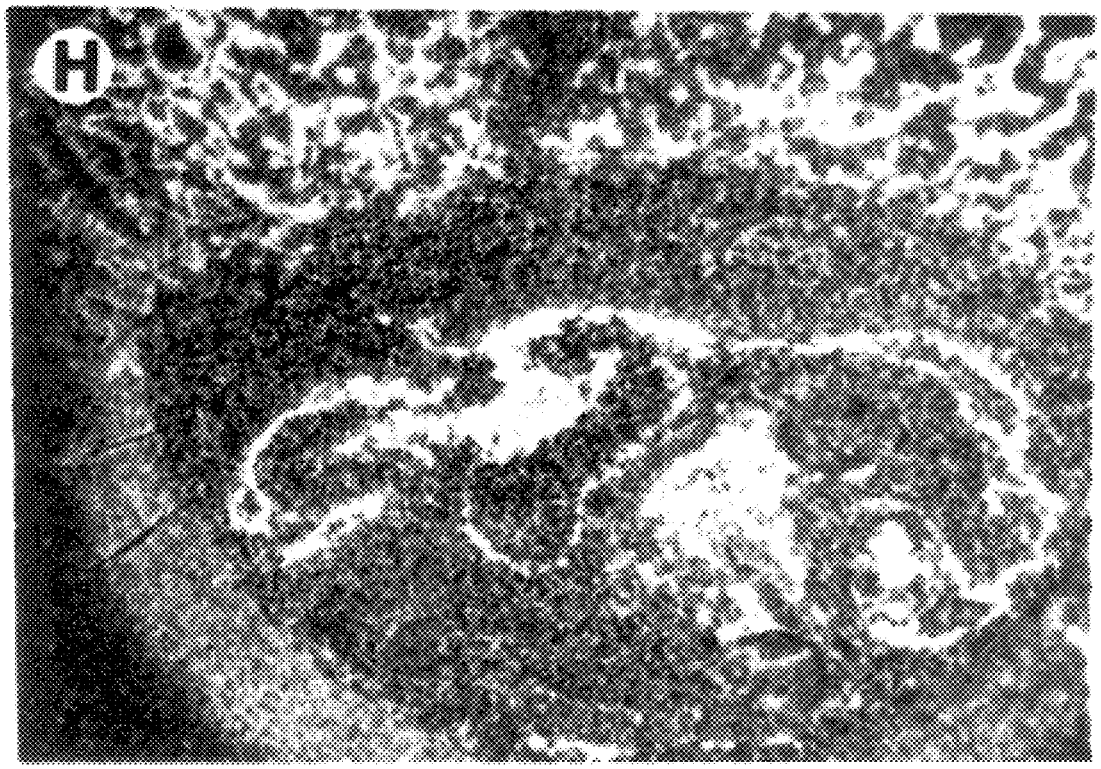
Figure 61:
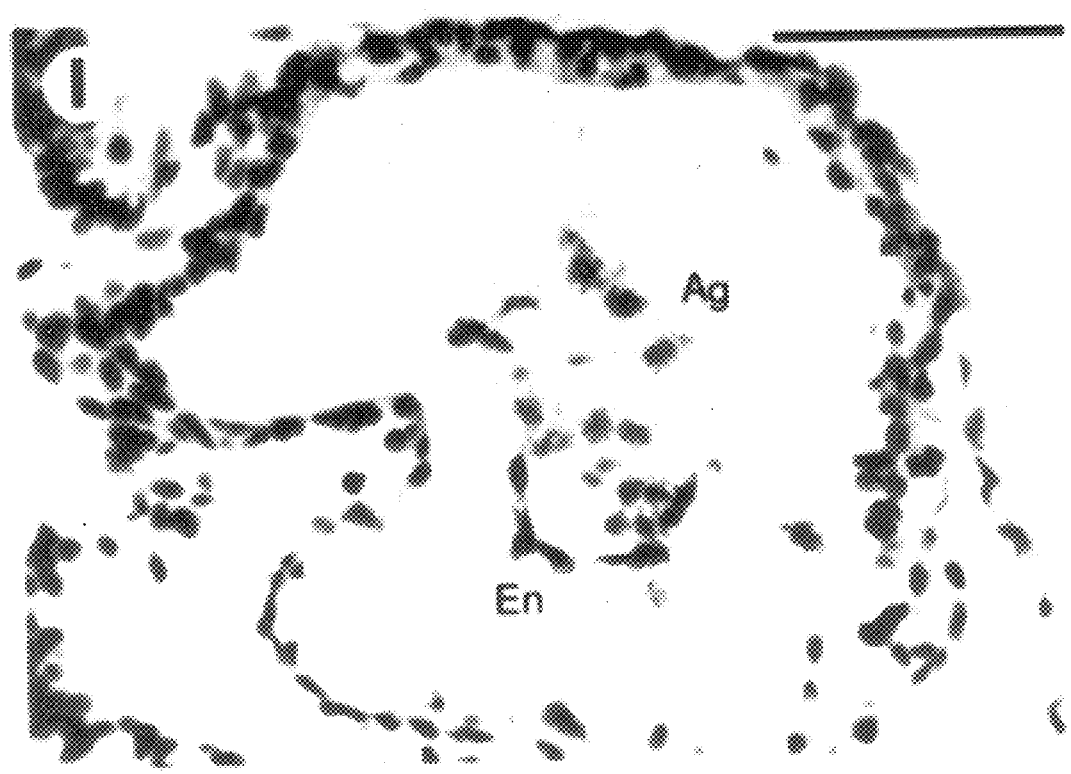
Figure 6J:
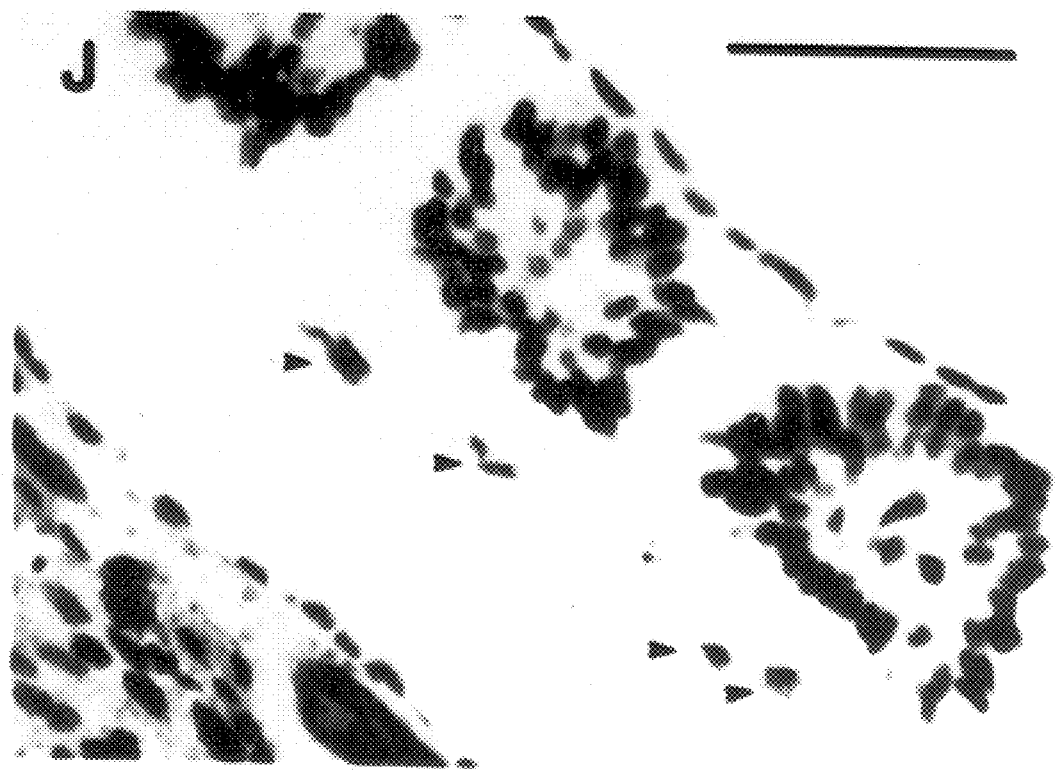

RNA in situ analysis of 8.0 day embryos revealed that tek expression first becomes detectable in the developing yolk sac and a few small clusters of cells in the cephalic mesenchyme. This expression becomes more pronounced by Day 8.5, at which time significant hybridization can be observed in the mesodermal component of the amnion (outer cell layer) and yolk sac (inner cell layer), as well as in the developing endocardium and the inner lining of the head veins and dorsal aortae (FIG. 6A and 6B). In addition, sagittal sections reveal numerous focal areas of hybridization throughout the cephalic mesenchyme in regions thought to contain developing vasculature, as well as a small number of tek-expressing cells extending beneath the ventral surface of the somites (FIG. 6H and 6J).

Whole mount in situ hybridization analysis confirmed and extended the above observations, as well as provided a three dimensional perspective on tek expression during embryogenesis. FIG. 7 shows tek expression in whole mount embryos; A., B., C. and D. tek expression in Day 8.0 embryos. E. tek mRNA distribution in a Day 9.5 embryo. F. En2 expression in a Day 8 embryo. I, II, III, first, second and third aortic arches; DA. dorsal aorta; E, endocardium; G, foregut pocket; H, heart; IS, intersegmental vessel; My, myocardium; ; NF, neural fold; OT; otic vesicle; V, vitelline vein; Y. yolk sac. Bars: 250 µm.

Figure 7A:
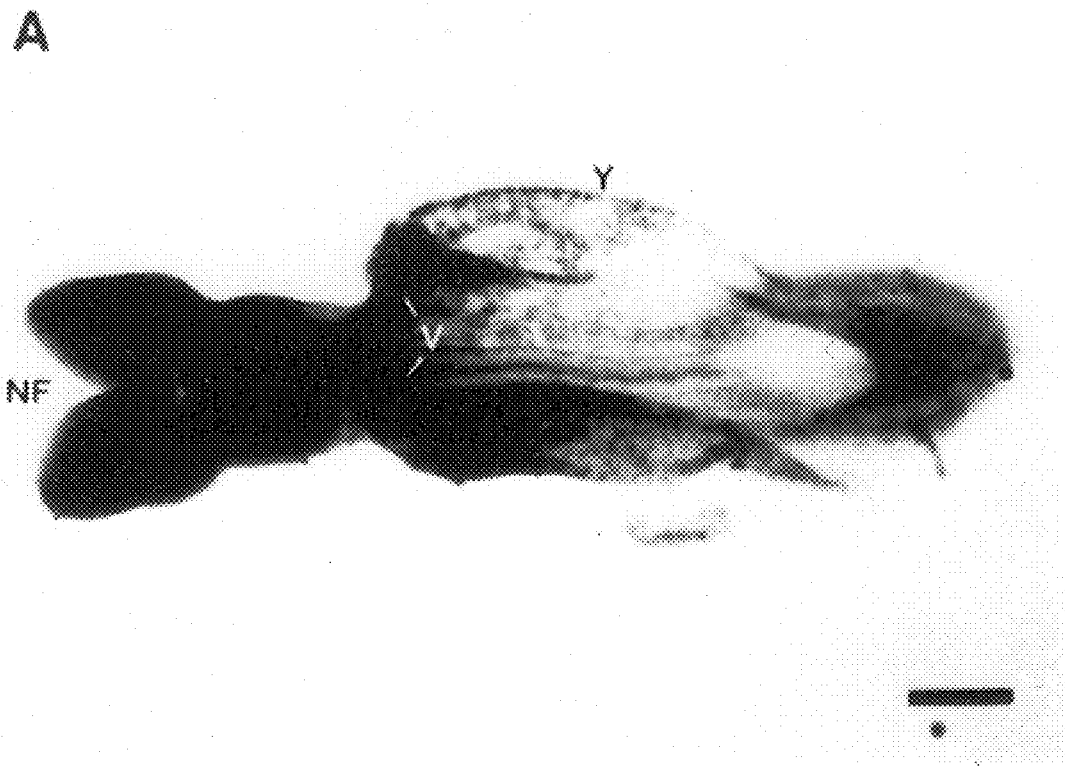
FIG. 7 shows expression of a DNA molecule of the invention in whole mount embryos(A, B, and C); expression in Day 8.0 embryos (D); mRNA distribution in a Day 9.5 embryo (E); and En2 expression in a Day 8 embryo (F)
Figure 7B:
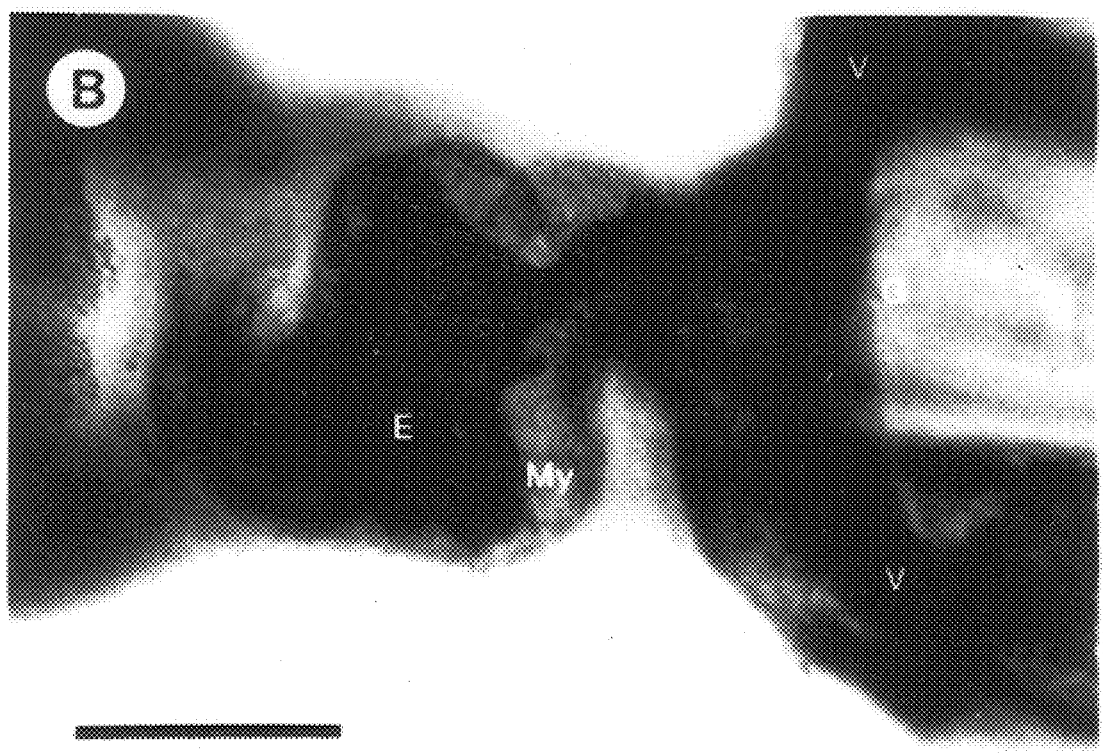
Figure 7C:
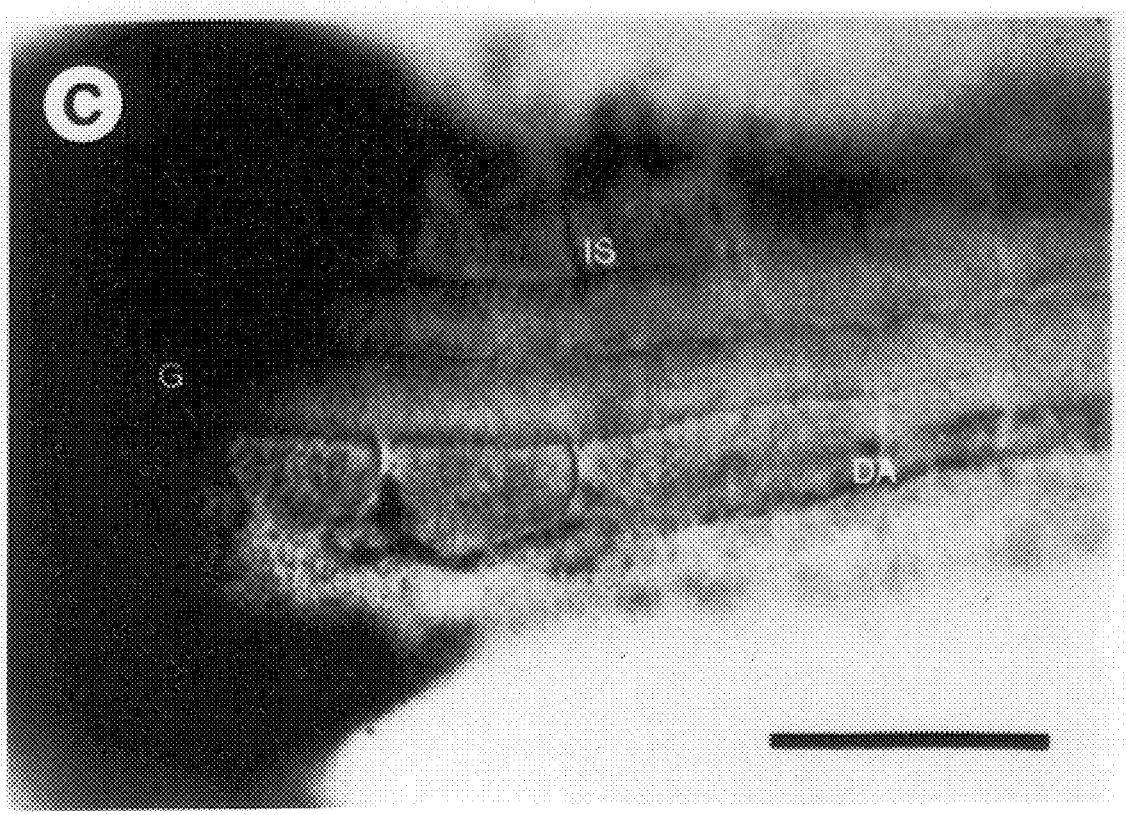
Figure 7D:
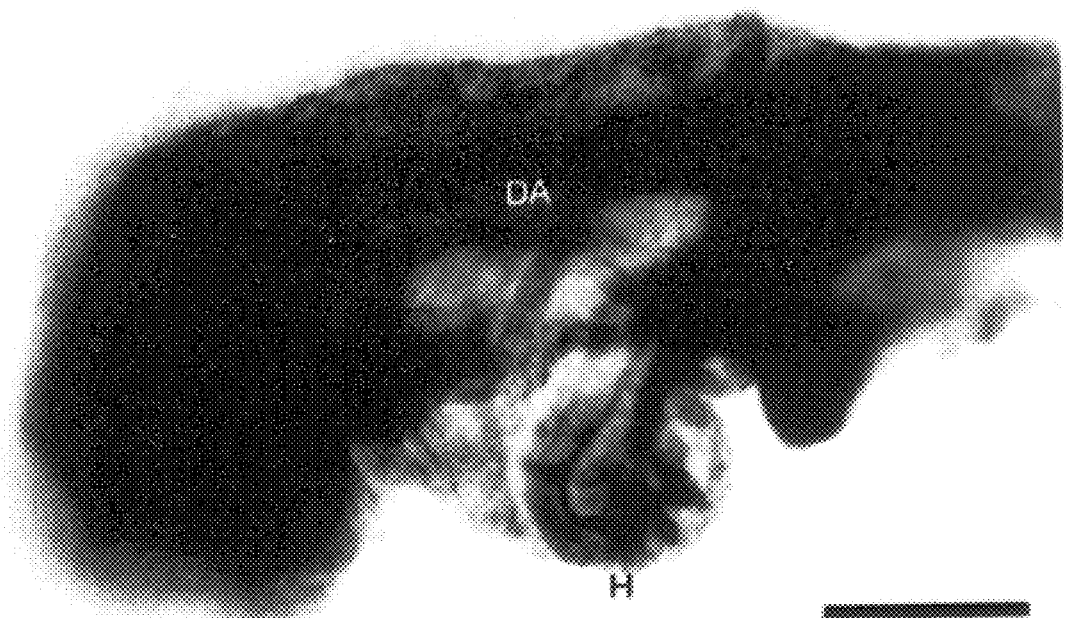
Figure 7E:
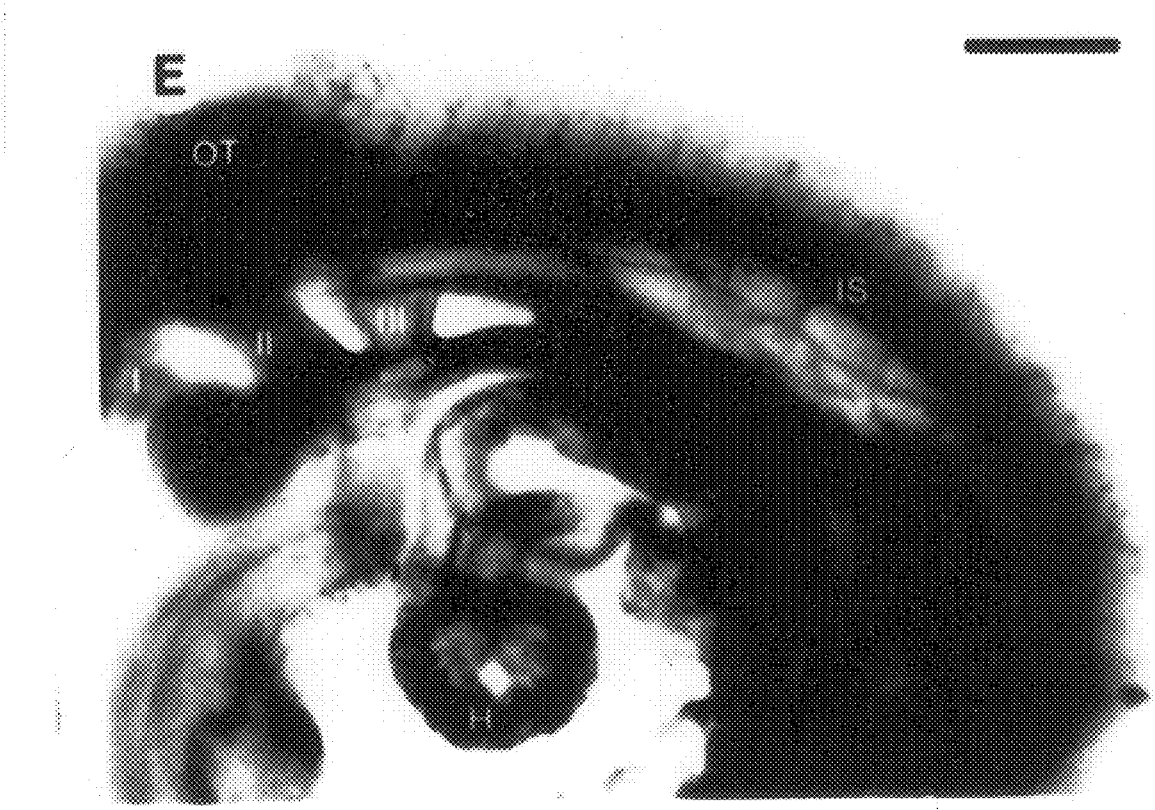
Figure 7F:
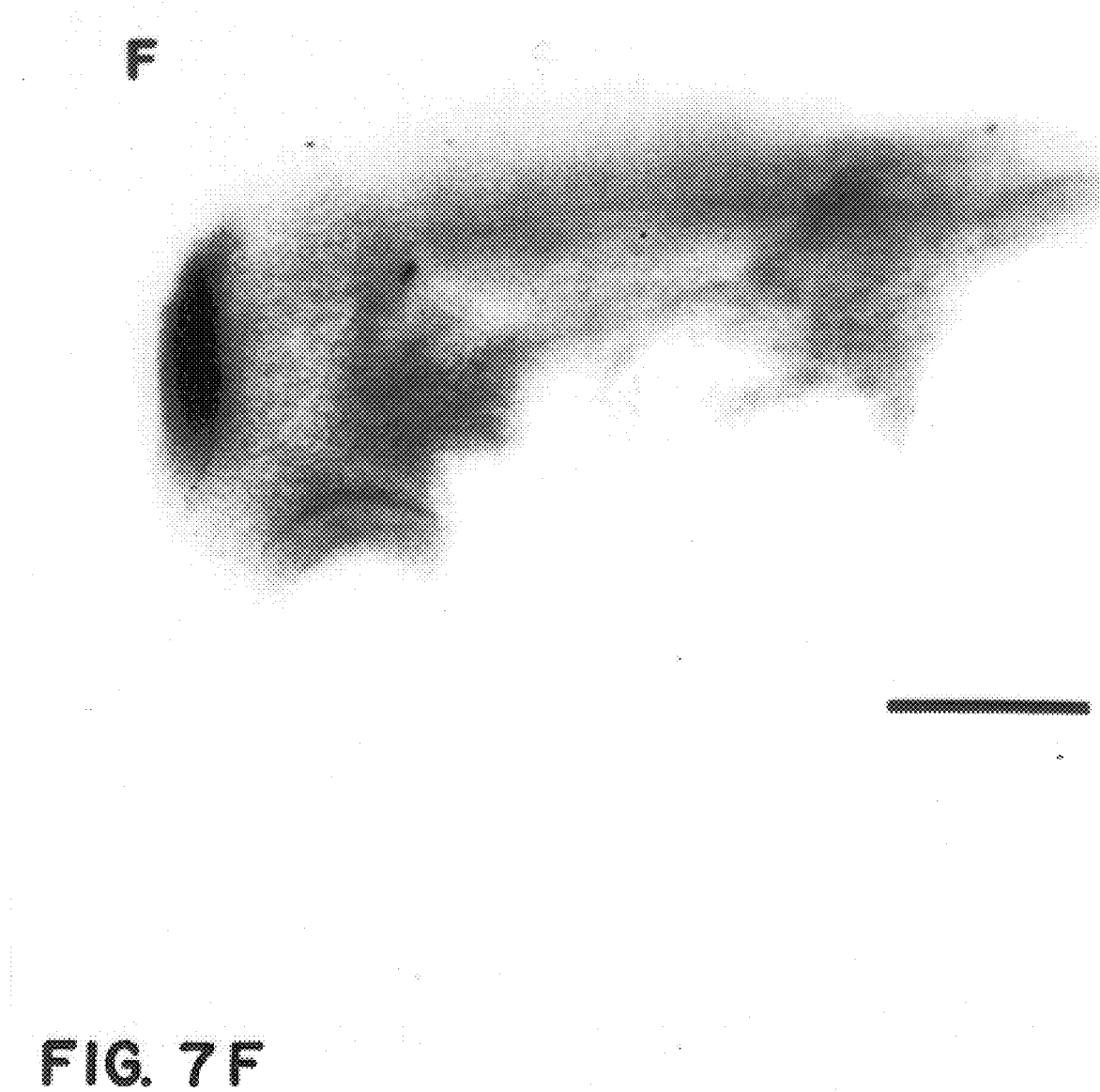

Consistent with our observations with sectioned material, localized tek expression was not observed on embryonic Day 7. The first detectable expression was seen about the time of first somite formation when signal was observed in the yolk sac, head mesenchyme, and heart. In Day 8.5 embryos, tek was found to be expressed in these same areas, and in the paired dorsal aortae, the vitelline veins, and in the forming intersegmental vessels (FIG. 7). By this time, tek expression was clearly confined to blood vessels within the embryo. On Day 9, tek expression was seen in addition, in the aortic arches and expression was very striking in the endocardium (FIG. 7E). Control hybridizations with an En-2 probe demonstrated the specificity of tek RNA detection (FIG. 7F).

EXAMPLE V

Expression of tek in Endothelial Cell Progenitors

The observation that tek is expressed between Day 8.0 and 8.5 in focal regions thought to represent developing blood vessels raised the possibility that tek might be expressed in endothelial cell progenitors. Indeed, close inspection of hybridized sections from 8 to 8.5 day embryos revealed that while the expression of tek in the maternal decidua is restricted to cells of an endothelial cell morphology, tek expressing cells in the embryo are of two morphologically distinct cell types. In the developing blood islands of the yolk sac, where tek expression is first detected, silver grains are localized predominantly to elongated cells with characteristic endothelial cell morphology (FIG. 6C). In contrast, within the cephalic mesenchyme, silver grains are frequently observed over large, round cells that, on the basis of similar morphology to cells described during avian embryogenesis (Pardanaud et al., 1987; Coffin & Poole, 1988; Noden, 1989; Noden, 1991), correspond to angioblasts, the presumptive progenitor of endothelial cells (FIG. 6F). Both cell types are observed in the developing endocardium (FIG. 6I) which, at later stages, is known to contain only fully mature endothelial cells.

To characterize more precisely the staging of tek expression within the endothelial lineage, sections adjacent to those used for in situ hybridization were stained immunohistochemically for von Willebrand factor, a well characterized marker of mature endothelial cells (Jaffe, E. A., Hoyer, L. W. & Nachman, R. L. (1973). J.Clin.Invest., 52, 2757–2764; Hormia, M., Lehto, V.-P. & Virtanen, I. (1984), Eur.J.Cell.Biol., 33, 217–228). FIG. 6B and H shows that whereas tek is expressed in both the maternal decidua and the embryo at Day 8.5, expression of von Willebrand factor is observed only in the tek-expressing, vascular endothelial cells of the maternal decidua (FIG. 6D and 6E). Hence tek expression precedes that of von Willebrand factor during embryogenesis. The same scenario is observed at later developmental stages during vascularization of individual organs.

Figure 8A:
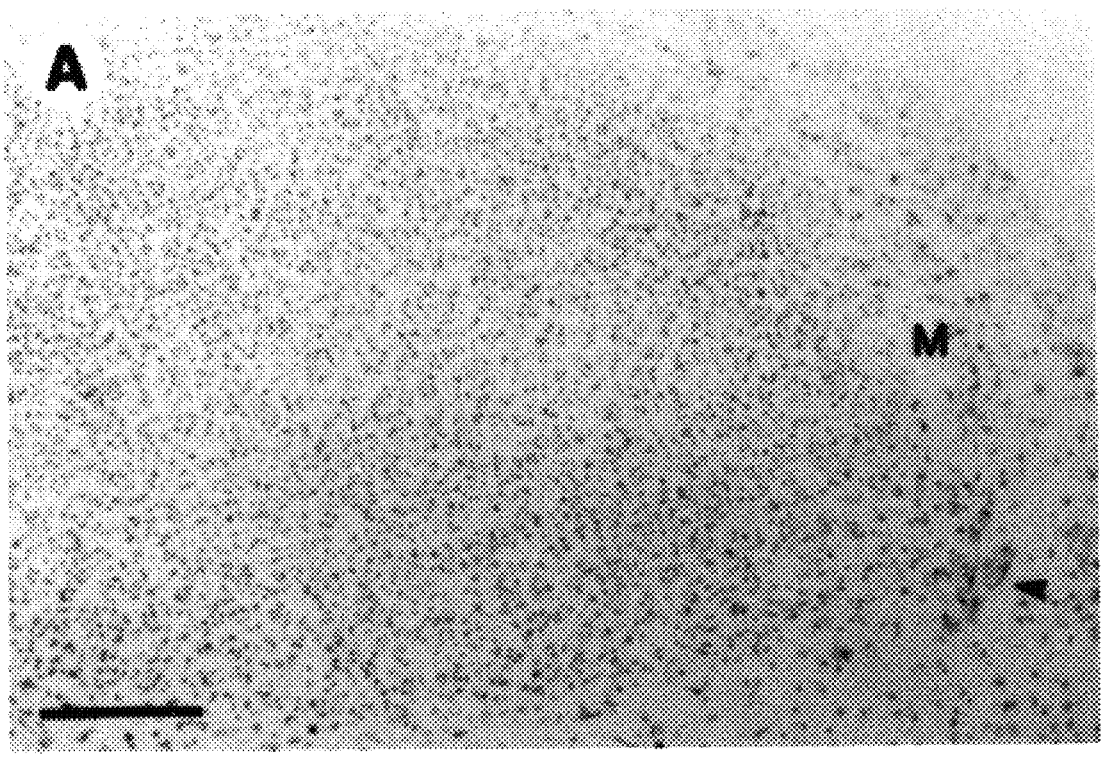
FIG. 8 shows the expression of a DNA molecule of the invention precedes that of von Willebrand factor in the developing leptomeninges and in particular the absence of immunohistochemical staining of von Willebrand factor in Day 12.5 leptomeninges (A); in situ detection of tek expression in Day 12.5 leptomeninges(B); staining of von Willebrand factor in Day 14.5 leptomeninges (C)
Figure 8B:
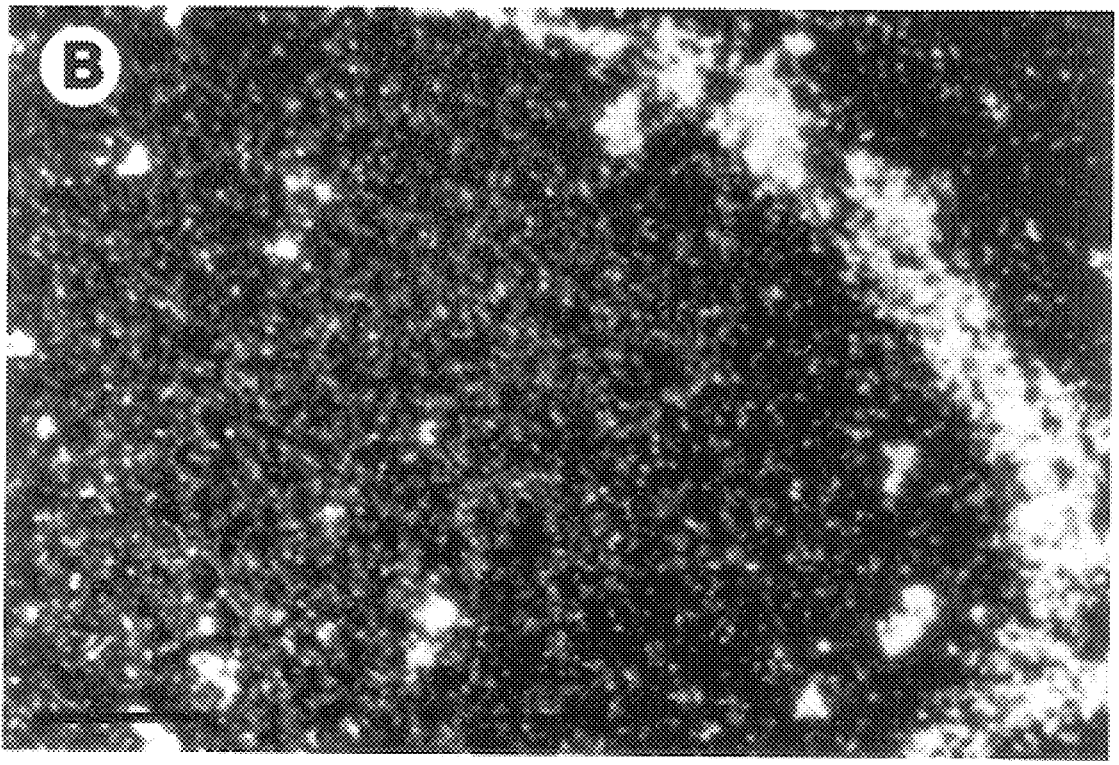
Figure 8C:
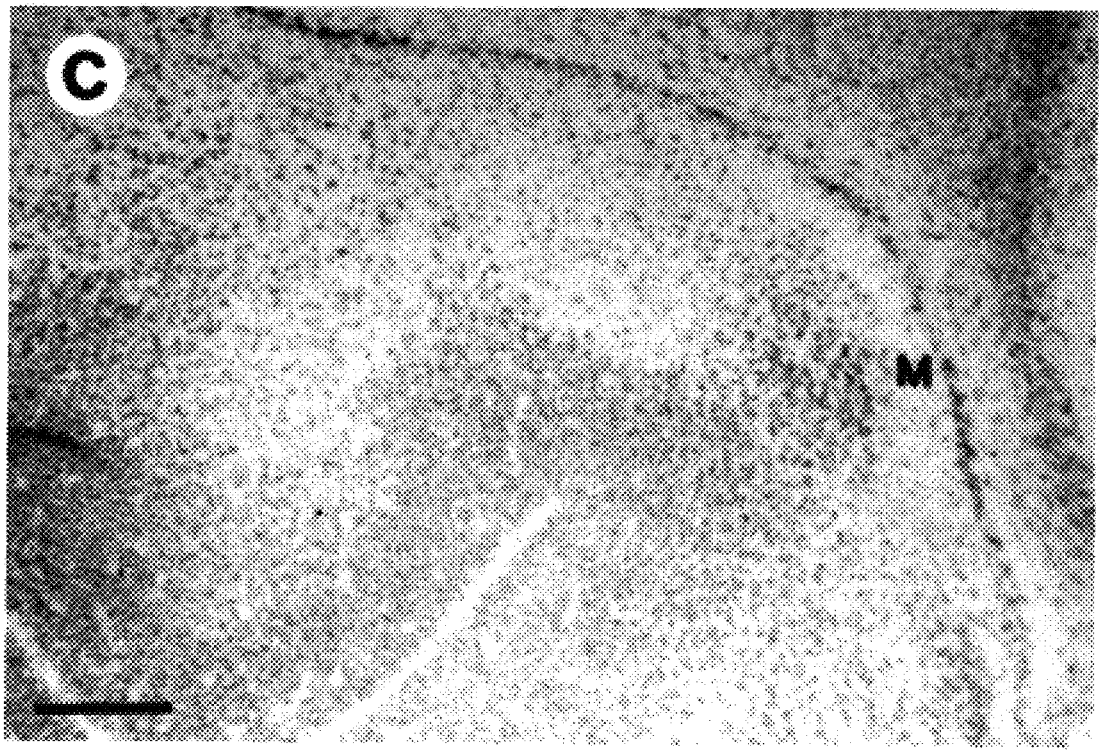

FIG. 8 shows the expression of tek precedes that of von Willebrand factor in the developing leptomeninges; A. Absence of immunohistochemical staining of von Willebrand factor in Day 12.5 leptomeninges. Arrow denotes a large blood vessel faintly positive for von Willebrand factor. B. In situ detection of tek expression in Day 12.5 leptomeninges. C. Staining of von Willebrand factor in Day 14.5 leptomeninges. Day 14.5 leptomeninges were positive for tek expression (not shown). M, leptomeninges. Bars: 200 µm.

FIG. 8 shows that in the 12.5 day embryo, the developing leptomeninges hybridizes strongly with tek but fails to stain positive for von Willebrand factor. By Day 14.5, however, expression of von Willebrand factor can be readily detected in the leptomeninges. Assuming that there is not a significant lag between transcription and translation of von Willebrand factor, these observations, together with those on the morphology of tek-expressing cells, suggest that tek is expressed in both mature endothelial cells and their progenitors.

EXAMPLE VI
tek is Expressed in Adult Vasculature

While the above results establish that tek is expressed during vascularization of the embryo, it was also of interest to determine whether expression of tek is maintained in endothelial cells of the adult. In situ hybridization analysis of a section through the heart region of a 3 week-old mouse revealed that tek is expressed in the endocardium as well as in the endothelial lining of major blood vessels, both arteries and veins, connecting with the adult heart (FIG. 9).

Figure 9A:
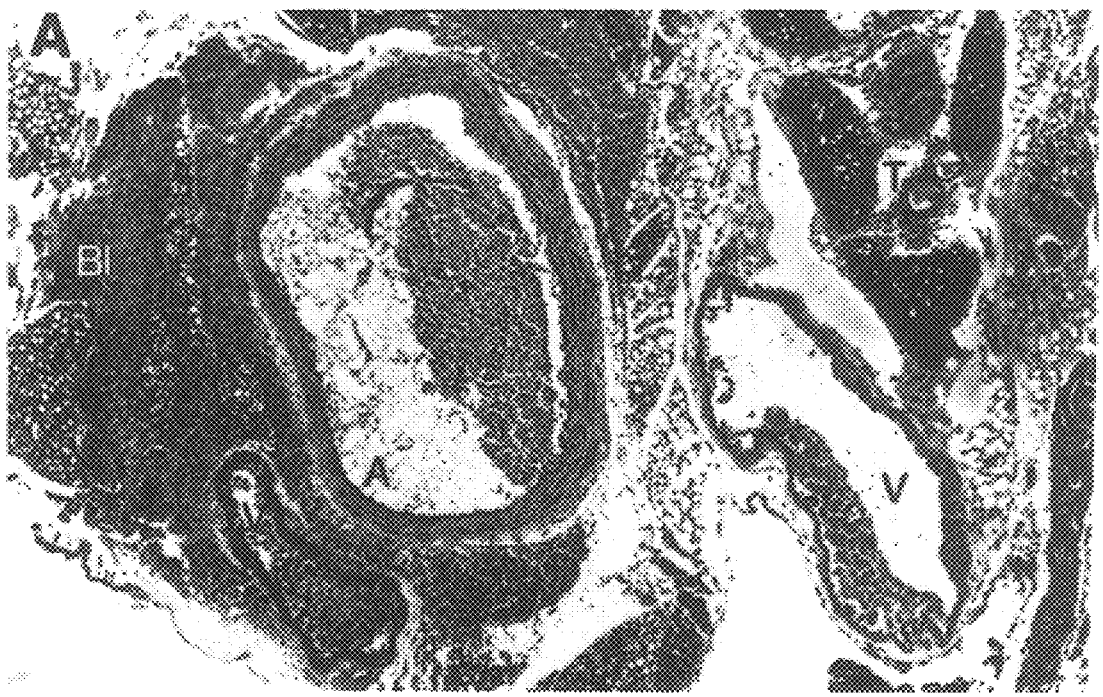
FIG. 9 shows the expression of a nucleic acid molecule of the invention in adult vasculature and in particular bright field illumination of a section through the upper heart region of a 3 week-old mouse hybridized with an [$^{35}$S]-labelled probe (A); bright field illumination showing expression in endothelial cells lining the artery and vein respectively (B) and (C)
Figure 9B:
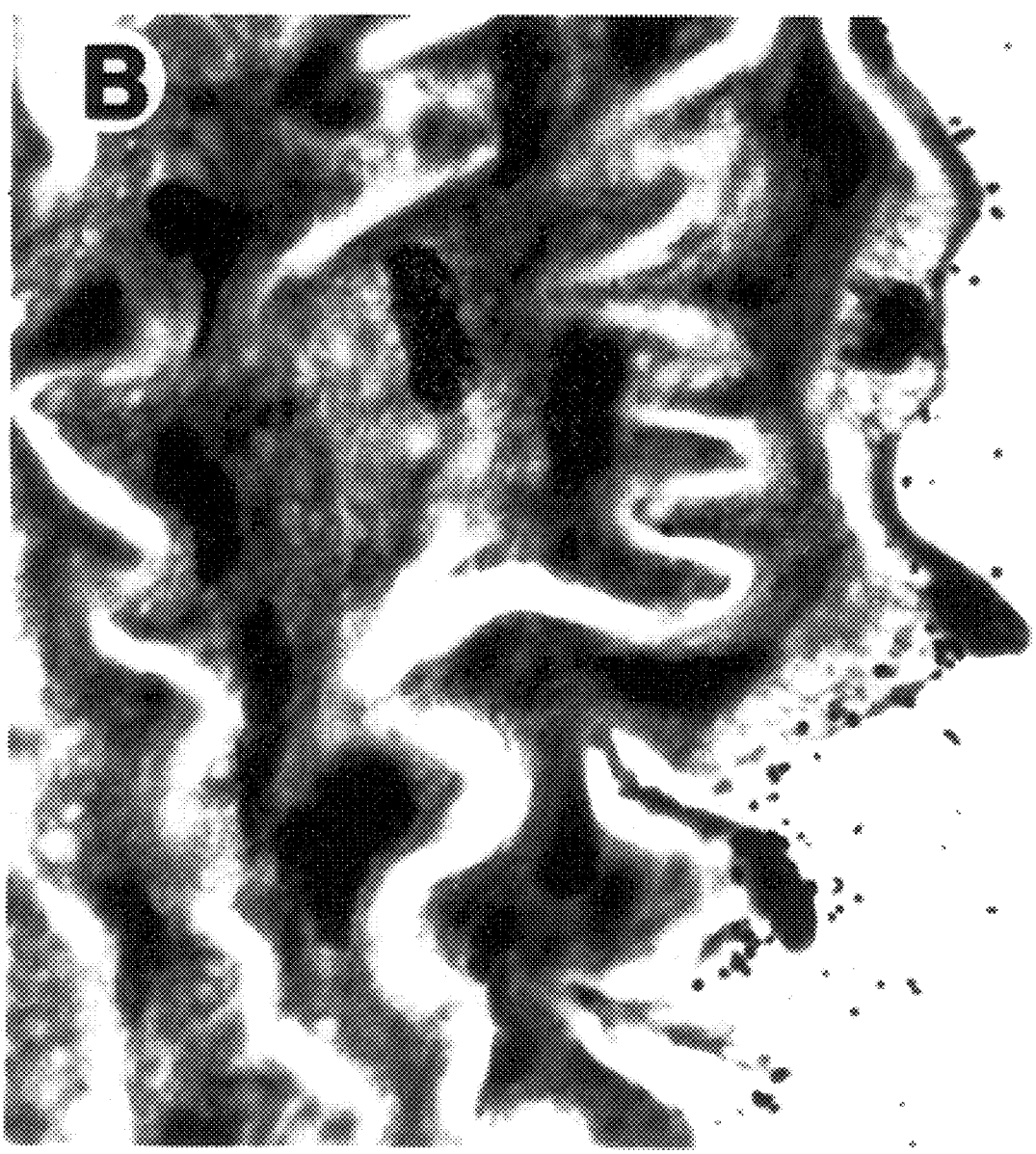
Figure 9:
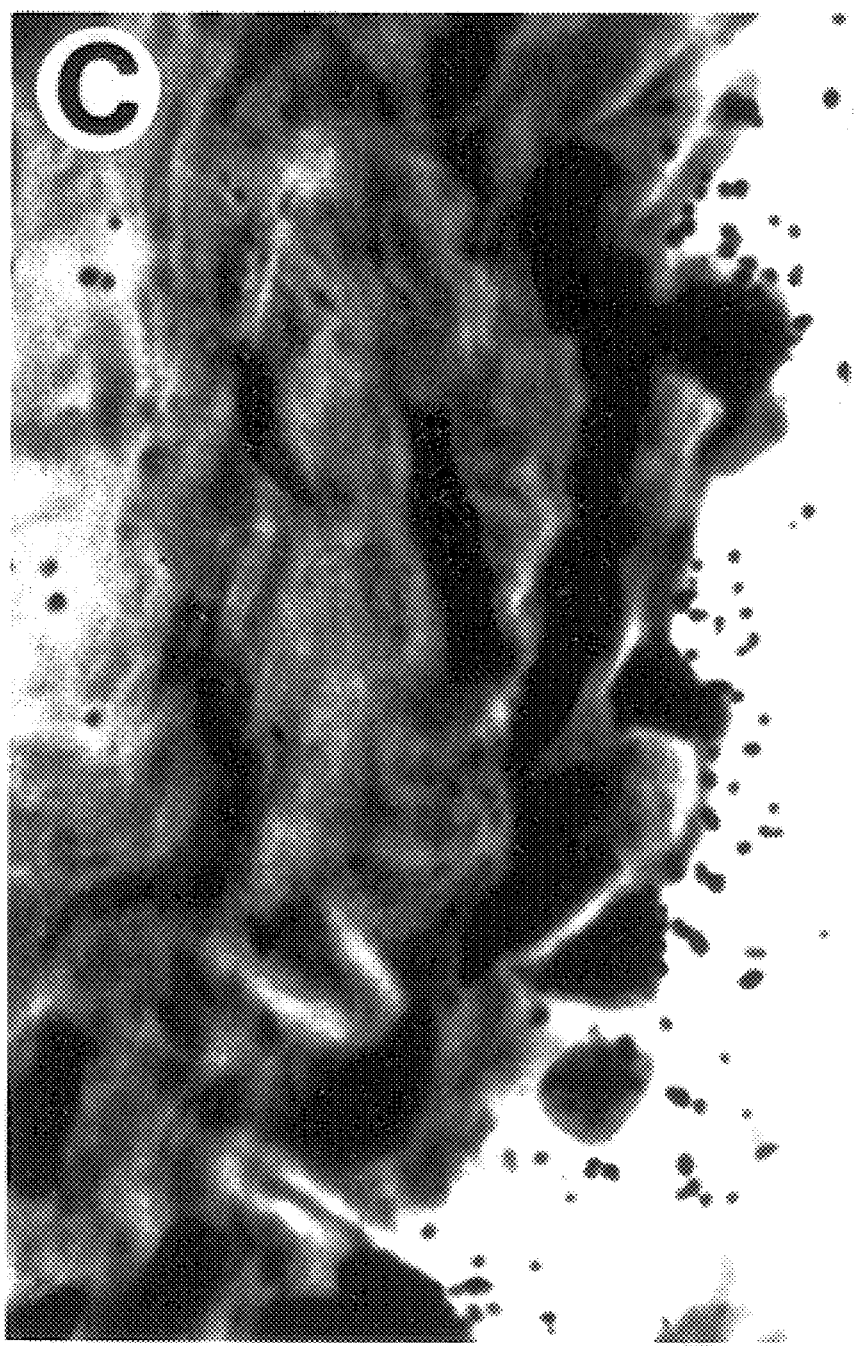

FIG. 9 shows the expression of tek in adult vasculature. A. Bright field illumination of a section through the upper heart region of a 3 week-old mouse hybridized with an [$^{35}$S]-labelled tek probe. Bar: 20 μm. B. and C.

Bright field illumination showing tek expression in endothelial cells lining the artery and vein respectively. Bar: 1 μm. Immunohistochemical staining of adjacent sections revealed that structures positive for tek expression also stained positive for von Willebrand factor. A, artery; Bl, extravasated blood; T, trachea; V, vein.).

The intensity of the hybridization signal observed for these structures is considerably lower than that observed for the endocardium and blood vessels of 12.5 day embryos hybridized and processed in parallel. This could indicate that mature endothelial cells, which are thought to be resting, have a different quantitative or qualitative requirement for expression of tek.

EXAMPLES VII to X

The following materials and methods were utilized in the investigations outlined in Examples VII to X:

DNAs

Tek- and tie-specific probes corresponding to sequences encoding the FNIII repeats (see FIG. 13A) were prepared as follows: The tek cDNA was digested with Pst I to yield a 0.95 kb fragment spanning sequences N1399 to 2344 (see FIG. 11B and SEQ ID NO:5). The tie-specific probe was generated by reverse transcription linked to PCR with two tie-specific oligonucleotides designed from the published sequence (5'$^{1288}$TTGCGGACAGTGGGTTCTGGGAGT (SEQ ID NO:9) and 5'$^{2414}$CGATGCAGGCAGCTTCT-GCGGAT (SEQ ID NO:10)) and RNA prepared from the human leukemia cell line, KG-1, which was previously shown to express tie (Partanen et al., Mol. Cell Biol. 12:1698–1707, 1992). First strand synthesis was done with random Hexamers (Pharmacia) according to established protocols (Sambrook et al., *Molecular Cloning: A Laboratory Manual*, 2nd ed. Cold Spring Harbor Laboratory Press, Cold Spring Harbor, N.Y., 1989). The cDNA/RNA mixture was then treated with 0.1 NaOH, neutralized with HCl, and an aliquot used as template for PCR. PCR was performed in 100 μl containing: 10 μl of 10× reaction buffer 1 (Stratagene), 10 μl dimethyl sulfoxide, 2 μg of each oligonucleotide, 200 μM of dNTPs and 2.5 units of Pfu polymerase (Stratagene). This reaction mixture was then cycled 30 times as follows: 94° for 45 sec, 52° for 2 min, 72° for 3 min, after which the products were resolved in a low-melt agarose gel. A major species of 1.1 kb was excised and restriction mapped to ascertain that the correct DNA fragment had been amplified. The tie-specific cDNA was amplified by PCR and purified as above.

Probes were labelled by random priming (Feinberg et al., Anal. Biochem. 132:6–13, 1983) with a kit according to the protocol supplied by the manufacturer (Pharmacia). Hybridization to immobilized DNA was performed overnight at 65° in 200 mM sodium phosphate pH7.0, 7% sodium dodecyl sulphate (SDS; BDH), 15% Formamide (BDH), 1% bovine serum albumin (BSA; Sigma), and 1 mM EDTA. Filters were washed twice at 55° in 2×SSC (1×SSC=0.15 M NaCl, 0.015 M sodium citrate pH7.0) and 0.1% SDS and twice in 0.2×SSC and 0.1% SDS, and exposed overnight to Kodak XAR-5 film.

Mice

Embryos and adult mouse tissues were obtained as described above for Examples I to VI.

RNA Purification and Analysis

Total RNA was extracted from cell pellets with RNAzol (CINNA/BIOTECX Lab. Int.) as described above for Examples I to VI. Poly A—containing RNA was purified from a pool of 150 Day 12.5 murine embryonic hearts with a QuickPrep mRNA isolation kit (Pharmacia) as outlined by the supplier.

Tek, flk-1, and β-actin transcripts were detected by RNAse protection analysis with a kit (Ambion) according to conditions recommended by the vendor. RNA antisense probes were generated by run-off transcription with a kit (Promega) in the presence of $^{32}$[P]-CTP (3000 Ci/mmol;Dupont) following subcloning of cDNA fragments into either pGEM7zf+ or pBluescript II SK—. Probes corresponded to sequences 2416 to 2683 for flk-1 (Matthews et al. *Proc. Natl. Acad. Sci. USA* 87:8913–8917, 1991), 1257 to 1633 for tek and 883 to 970 for β-actin. The flk-1 sequences were isolated from a Day 13.5 embryo cDNA library. The β-actin probe was provided by F. Shalaby. Digestion products were resolved in a 6% sequencing gel containing 8 M urea.

cDNA Cloning

Poly A-selected RNA (5 μg) from Day 12.5 embryonic heart (EH12.5) was used as template to make double-stranded cDNA using a You-Prime cDNA Synthesis Kit (Pharmacia) as outlined by the supplier. The reverse transcription reaction was supplemented with 1000 units of Super Script MMLV reverse transcriptase (BRL). Double-stranded cDNAs were ligated to adaptors, fractionated in a low-melt agarose gel, and molecules 2 to 4.5 kb in size were liberated by digestion with β-Agarase I (BioLabs). The cDNAs were then precipitated with ethanol and ligated to EcoR I-digested and dephosphorylated lambda Zap II arms (Stratagene). The ligation products were packaged in vitro using Gigapack II packaging extracts according to the protocol provided (Stratagene).

Figure 11A:
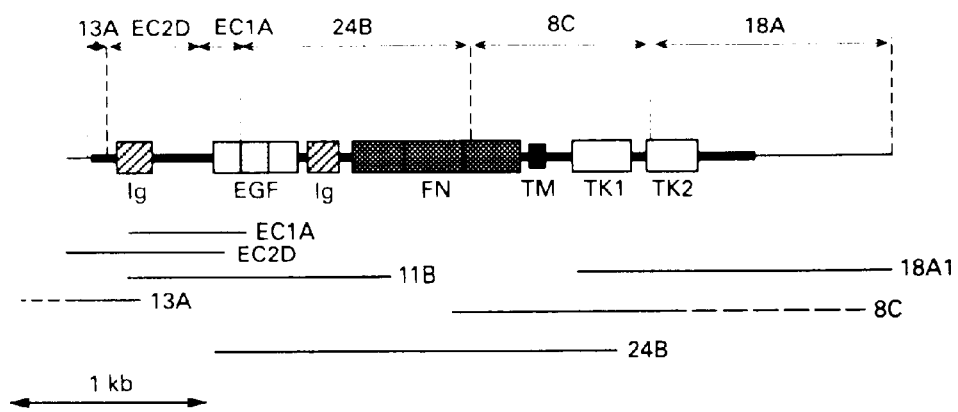
FIG. 11A shows the cDNAs used to assemble the tek cDNA.
Figure 11B:
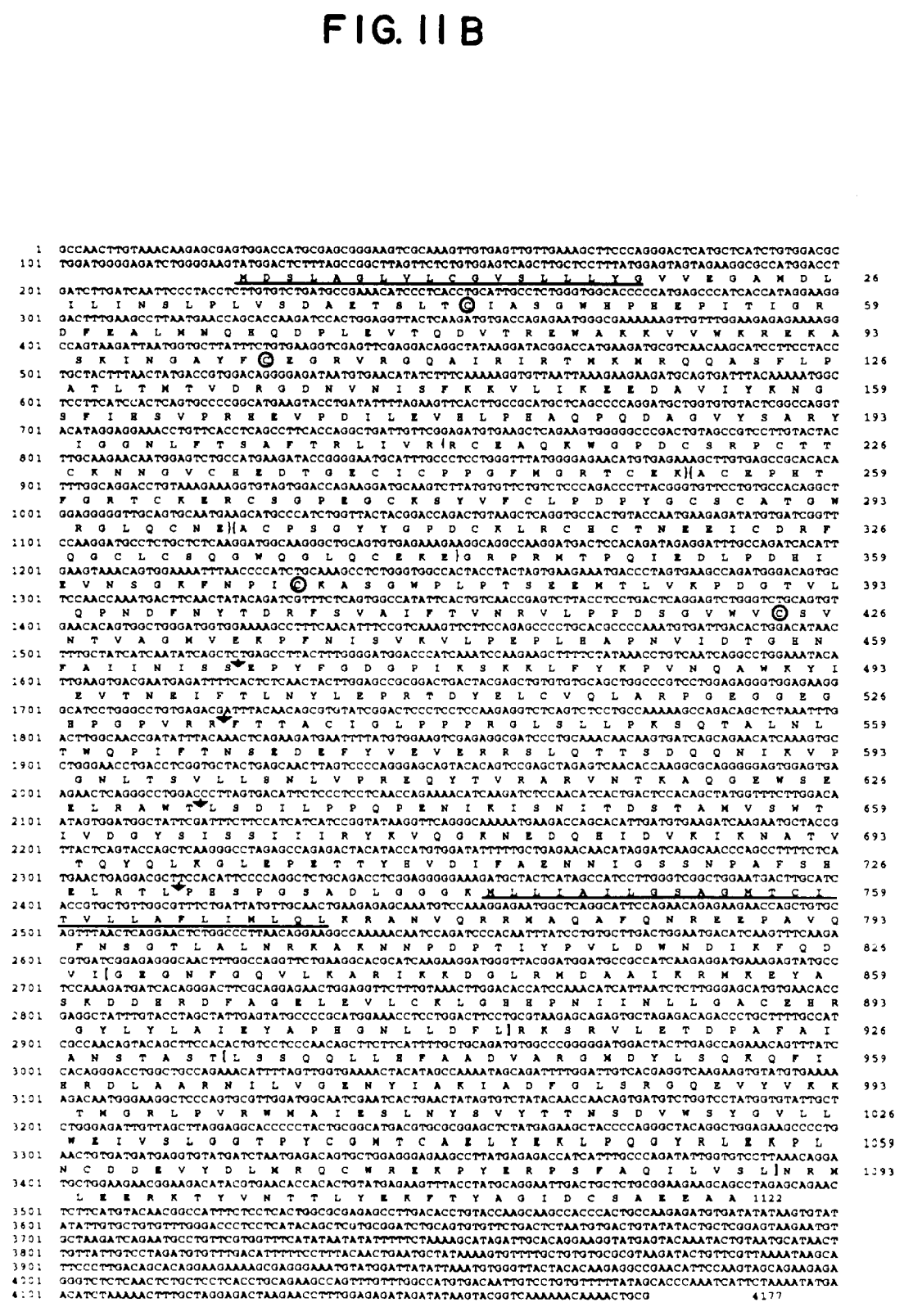

Filters containing the unamplified EH12.5 library (1.3× 10$^6$ plaques) were hybridized with clone 18a1 (see FIG. 11A). This screen produced 72 positive clones, the two largest of which (FIG. 11A; clones 8C and 24B) were sequenced in their entirety. To clone the 5' end of tek, a nested PCR strategy was employed on EH12.5 phage DNA using two tek-specific primers designed to hybridize to sequences 887 and 912 (EC1 primer) and 786 to 807 (EC2 primer) of the coding strand and a primer specific for the T7 polymerase binding site within the phage arm. Template phage DNA from 10$^{10}$ plaque forming units was purified by the polyethylene agglutination procedure (Sambrook et al., 1989). The PCR reaction was run through a first cycle in the absence of T7 primer in a volume of 100 μl containing 50 ng of phage DNA, and EC1 primer (1 μM) in 1×PCR buffer containing 50 mM KCl, 10 mM Tris-Cl pH 8.3, 1.5 mM MgCl$_2$, 0.1% gelatin, 200 mM dNTPs (Pharmacia). The DNA was denatured at 94° for 1 minute, annealed to the ECl primer at 55° for 1 minute, and reacted with Taq polymerase (2.5 units; Cetus) for 2 minutes at 72°. The T7 primer was then added at 1 μM and PCR continued for 40 cycles under the same conditions. The products were collected by ethanol precipitation and analyzed on a 1.5% low-melt agarose gel (Seaplaque, FMC). A band of approximately 600 bp was visible within a background smear extending up to 2 kb. The 600 bp band was excised, released from the gel by β-agarase I treatment as described by the supplier, digested with EcoR I (found within the λZapII multiple cloning site) and Hind III found at position 881 in the tek cDNA, and ligated to pGem7Zf+ (Promega) resulting in clone EC1A. The remainder of the PCR products from 0.6 to 2 kb were recovered as above, and submitted to a second round of PCR using EC2 and T7 primers under the same conditions as described earlier. The longest product obtained, 800 bp, was subcloned in pGem4Z (Promega) after digestion with EcoR I and Sph I found within the overlapping 600 bp EC1A clone resulting in clone EC2D.

To identify potential PCR-generated sequence artifacts, duplicate filters containing the EH12.5 library were probed with the PCR generated ECLA clone and a 5' fragment of clone 24B (see FIG. 11A). Two clones were obtained which hybridized with both of these probes as well as the EC2 primer. These two clones, 11b and 13a (see FIG. 11A), were sequenced in their entirety.

The tek cDNA was sequenced on both strands using a T7 DNA-Pol sequencing kit (Pharmacia) according to conditions recommended by the vendor. The complete sequence was deduced by sequencing subcloned cDNA fragments and by using tek-specific primers. The cDNA sequence has been deposited. in Genbank/EMBL under accession number X67553.

Tek Antibodies

A DNA fragment encoding the C-terminal 43 amino acid residues of Tek was prepared by PCR and subcloned into pGEX3X (Pharmacia). The glutathione-S-transferase-Tek (GST-Tek) fusion protein produced in *E. coli* was purified by affinity chromatography with glutathione-sepharose 4B (Pharmacia) and used to immunize rabbits according to established protocols (Harlow et al., *Antibodies: A Laboratory Manual*, Cold Spring Harbor Laboratory Press; Cold Spring Harbor, N.Y., 1988). Tek-specific serum was subsequently purified by absorption to a DHFR-Tek fusion protein (Qiagen), containing the Tek cytoplasmic domain (nucleotides 2254–3477), which had been cross-linked to CNBr activated Sepharose 4B.

Detection of the Tek Protein

COS cells were transfected by the calcium phosphate co-precipitation method (Chen et al., *Mol. Cell Biol.* 7:2745–2752, 1987) with an expression plasmid, pcDtek, containing the tek cDNA cloned into the EcoR I site of pcDNA1 (Invitrogen). Transfected cells were allowed to recover for 16 hr in normal medium (DMEM containing 10% bovine calf serum), after which they were washed three times with PBS, and metabolically labelled for 16 hr with 200 μCi [$^{35}$S]-methionine (DuPont, 1000 Ci/mmol) in 3 ml of methionine-deficient medium for 16 hours. The [$^{35}$S]-labelled cells were washed 3 times with ice-cold PBS and lysed in RIPA buffer (50 mM HEPES, pH 7.5, 150 mM NaCl, 1% Triton-X100, 0.1% SDS, 1 mM EDTA) supplemented with 1 mM PMSF, 10 μg/ml leupeptin, 10 μg/ml pepstatin A, 10 μg/ml aprotinin, and 10 μg/ml soya bean trypsin inhibitor. The cells lysates were cleared by centrifugation (12,000×g at 4° for 15 min) and then incubated overnight at 4° with 4 μg of affinity purified Tek antibodies. The immunocomplexes were collected on protein A-sepharose beads in RIPA buffer (Pharmacia), and then washed 3 times with RIPA buffer, twice with LiCl wash buffer (50 mM Tris-Cl, pH 7.5, 200 mM LiCl), and once with RIPA buffer. The resulting immunocomplexes were boiled in sample buffer and analyzed by SDS-PAGE. Radioactive proteins were detected by fluorography (EN$^3$HANCE;DuPont).

For detection of Tek by Western blotting, lysates were prepared from Py4-1 cells and Day 13.5 mouse embryonic hearts and umbilical veins by boiling of tissues and cell pellets in sample buffer, followed by sonication and centrifugation to remove insoluble material. The extracts were separated on a 7% SDS polyacrylamide gel, transferred to nitrocellulose filters and blocked overnight with 5% BSA and 1% ovalbumin in TBST (50 mM Tris-Cl, pH 7.5, 150 mM NaCl, 0.1% Tween 20). The blocked filters were then incubated with affinity purified Tek antibodies in the above blocking solution plus 0.5% SDS and 0.1% NP-40, washed extensively with TBST containing 0.5% SDS, reblocked with BSA and ovalbumin in TBS, and finally incubated with Protein A-horseradish peroxidase conjugate (BioRad) in TBSN (50 mM Tris-Cl, pH7.5, 150 mM NaCl, 0.2% NP-40) at 1:500 dilution for 30 minutes. The filters were washed 5 times in TBSN and developed by the ECL chemiluminescence method (Amersham).

Cells

The Py4-1, MAE 22106, and EOMA cell lines have been described previously (Dubois et al., Exp. Cell. Res. 196:302–313, 1991; Obeso et al., Lab. Invest. 63:259–269, 1990). Cells were cultured in DMEM containing 10% fetal bovine serum (Hy-Clone).

EXAMPLE VII
Isolation and Characterization of Tek from a Day 12.5 Embryonic Mouse Heart Tissue cDNA Library To acquire additional tek sequences, a cDNA library was constructed from RNA prepared from Day 12.5 embryonic heart tissue. From 12 tek-hybridizing clones that were subsequently selected and characterized, 7 different overlapping cDNAs were identified and used to assemble a contiguous tek cDNA of 4177 nucleotides (N) (FIGS. 11A and 11B).

FIG. 11A is a schematic representation of the cDNAs used to assemble the tek cDNA and the predicted structure of the encoded gene product. The regions corresponding to the Ig-like, EGF-like, and FNIII repeats are depicted by hatched, stippled, and cross-hatched boxes, respectively. The transmembrane and kinase regions are depicted by solid and open boxes, respectively. SEQ ID NO: 5 and FIG. 11B shows the nucleotide sequence and deduced amino acid sequence of the 4177N tek cDNA. The two cysteines in each Ig-like loop are circled and the EGF-like repeats are bracketed. The beginning and end of each FNIII repeat are indicated by arrowheads. Both the putative signal peptide and transmembrane regions are underlined; the kinase domain is framed by square brackets.

The assembly of this cDNA revealed that two of the overlapping tek-hybridizing clones, 13A and 8C, also contained sequences of unknown origin. The novel sequences in the 3'-half of clone 8C contained stop codons in all three reading frames, were extremely AT-rich, and bore no relationship to those of other tyrosine kinases. The novel 265N at the 5' end of clone 13A were not represented in any other overlapping tek cDNA or genomic clones isolated; moreover, the point at which these sequences diverged from those in genomic DNA did not correspond to a consensus splice acceptor site. Therefore, while the possibility that the novel sequence in clones 13A and 8C are derived from the tek locus could not be excluded, the simplest interpretation is that these sequences were acquired as a cDNA cloning artifact.

Conceptual translation of the 4177N tek cDNA (SEQ ID NO: 5 and FIG. 11B) revealed a single large open reading frame extending from a putative initiation codon, ATG, at N124 to an in-frame stop codon, TAG, at N3490. The sequence surrounding the putative initiation codon conforms to the optimum consensus sequence for initiation of translation (Kozak, Nucleic Acids Res. 12:1451–1459, 1984). In addition, the 18 amino acid residues encoded immediately after the putative initiation codon are sufficiently hydrophobic to constitute a signal peptide. While the sequences downstream of the termination codon do not contain a polyadenylation signal, they are fairly AT-rich, as is frequently characteristic of 3' untranslated sequences. Since stop codons are found in all three reading frames both upstream and downstream of the single large open reading frame, it follows that the 4177N tek cDNA probably contains all of the Tek coding sequences.

FIG. 11A shows that the predicted 1,122 residue protein encoded by the tek cDNA has several structural motifs that, together, set it apart from other RTKs. Within the extracellular domain, three distinct types of structural motifs can be identified, including immunoglobulin-like loops, EGF-like repeats, and fibronectin type III (FNIII) repeats. Briefly, two immunoglobulin-like loops, with characteristically placed cysteines (Williams & Barclay, Annu. Rev. Immunol. 6:381–405, 1988), are present between residues 19 and 209 and 344 and 467 (SEQ ID NO: 5 and FIG. 11B). These two immunoglobulin-like loops are separated from one another by three tandem EGF-like repeats that show homology to similar motifs found in other cell-surface proteins, such as Tie and Notch (FIG. 12A). Moreover, the second immunoglobulin-like loop is followed by three regions showing homology to FNIII repeats found in polypeptides such as DLAR and fibronectin (FIG. 12B).

FIGS. 12A and 12B shows a sequence comparison between Tek and Tie. FIG. 12A is a sequence comparison of the Tek (SEQ ID NO:23) EGF-like repeats (SEQ ID NO:17–19) with those of Tie (SEQ ID NO:20–22) (Partanen et al., 1992), EGF (Gray et al., Nature, 303, 722–725, 1983) and Notch (SEQ ID NO:24) (Rebay et al., Cell, 67, 687–699, 1991). The consensus sequence is written below. Upper case letters denote 100% conservation; lower case letters, greater than 70% conservation. Conserved cysteines and glycines are denoted by open and cross-hatched boxes, respectively. FIG. 12B is a sequence alignment of the three mouse Tek (SEQ ID NO:25, 27 and 29) and human Tie (SEQ ID NO:26, 28, and 30) (Partanen et al., 1992) FNIII repeats with a representative FNIII repeat from Drosophila DLAR (SEQ ID NO:32) (Streuli et al., 1988; Streuli et al., 1989) and rat fibronectin (SEQ ID NO:34) (Scwarzbauer et al., 1987). The deduced consensus is given below. Upper case letters denote 100% conservation; lower case letters, greater than 60% conservation.

The extracellular domain of Tek receptor tyrosine kinase protein is, therefore, particularly complex, representing a composite of three different structural motifs that are usually not found collectively within a single RTK.

Anchoring of Tek receptor tyrosine kinase protein in the membrane is most probably achieved by the highly hydrophobic stretch of residues that extends between positions 745 and 771 and which is followed by the two basic residues, lysine and arginine (SEQ ID NO: 5 and FIG. 11B). When this putative transmembrane region is used to define the boundary of the Tek extracellular domain, 8 consensus sites for potential N-linked glycosylation are present within the extracellular portion of the molecule.

The catalytic region of Tek receptor tyrosine kinase protein, which starts at residue 829, is interrupted by a 21-amino acid insert at residue 913 (SEQ ID NO: 5 and FIG. 11B). Interestingly, the kinase insert does not contain a tyrosine residue whose phosphorylation in other RTKs has been implicated as the site for binding of downstream substrates (Anderson et al., 1990; Escobedo et al., 1991; Klippel et al., 1992). However, Tek does contain a 32-amino acid residue carboxyl tail that contains tyrosine residues (FIG. 11B). Tek receptor tyrosine kinase protein may therefore mediate signal transduction by binding of downstream signalling molecules to these tyrosine residues when they are phosphorylated, as has been found for other RTKs, such as FGFR-1 and EGFR (Mohammadi et al., Mol. Cell. Biol. 11, 5068–5078, 1991; Margolis et al. EMBO. J., 9, 4375–4380, 19.

EXAMPLE VIII
Tek Expression in Cultured Endothelial Cells

The finding that tek expression is restricted to angioblasts and endothelial cells, both in the embryo and in the adult, prompted analysis of several cell lines of endothelial origin for expression of tek. To obtain additional insight into the character of these cell populations, they were also examined for expression of flk-1 (Matthews et al. 1991), which encodes an RTK whose expression may also be restricted to cells of the endothelial lineage, but which appears to precede that of tek by approximately one day in the developing embryo.

Figure 14:
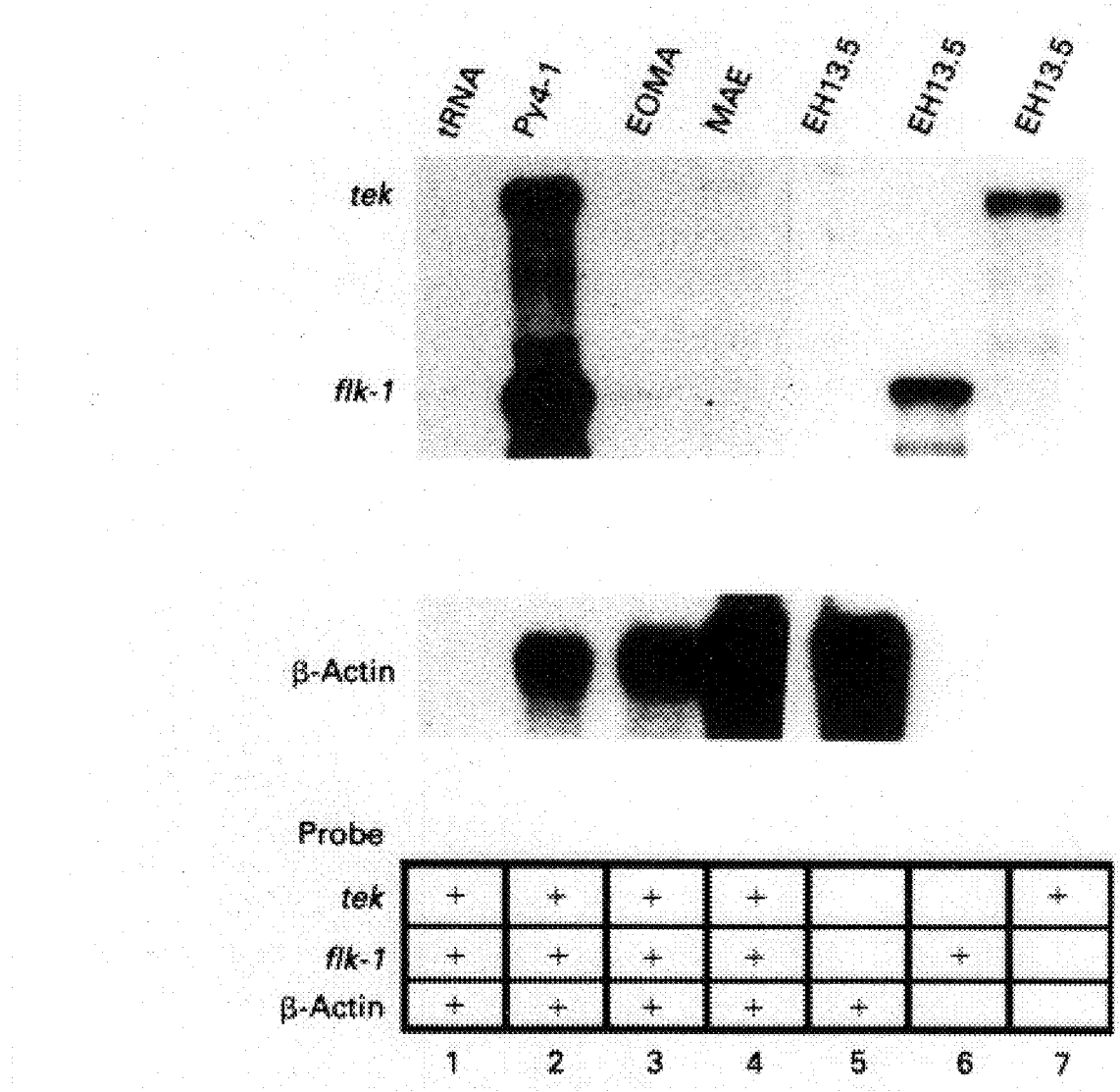
FIG. 14 shows tek and Flk-1 expression in cell lines of endothelial origin.

FIG. 14 shows the profile of tek and flk-1 expression detected by RNAse protection analysis in Py4-1, a transformed cell line established from a haemangioma originating in a polyoma middle T antigen-expressing transgenic mouse (Dubois et al., 1991); EOMA, a cell line derived from a spontaneously arising haemangioma (Obeso et al., 1990); and MAE 22106, an endothelial cell line cultured from normal mouse aorta (Pendl et al., Dev. Biol.). The results show that whereas both tek and flk-1 are expressed in Day 13.5 embryonic heart, and in Py4-1 cells at relatively high levels, the EOMA cell line expresses detectable levels of flk-1 but not tek RNA, while the MAE 22106 cell line expresses detectable levels of tek but not flk-1. The detection of tek and flk-1 transcripts in these cell populations is consistent with the in situ hybridization studies showing that these two genes are expressed in cells of the endothelial lineage. However, the finding that both tek and flk-1 are expressed at significant levels in only one of the three endothelial cell lines examined is of interest. This apparent discordance in tek and flk-1 expression in cell lines could reflect the intrinsic heterogeneity that has been documented for endothelial cell populations cultured from different anatomical sites (Gerritsen, Biochem. Pharmacol., 36, 2701–2711, 1987 Gumkowski et al., Blood Vessels, 24, 11–23, 1987), the differential retention of expression of these markers following malignant transformation or in vitro culture, or the differential expression of these two RTKs in different cell lines that correspond to cells of the endothelial lineage at different stages of differentiation. This latter possibility stems from the observation that expression of flk-1 not only precedes that of tek during embryogenesis but, also, that flk-1 appears to be down-regulated in endothelial cells as they differentiate, whereas tek is not. In any event, these results provide further evidence that tek and flk-1 are differentially regulated.

EXAMPLE IX
Expression of Tek Receptor Tyrosine Kinase Protein

To characterize the protein encoded by the tek cDNA, COS cells were transfected with a mammalian expression vector containing tek (as described above). Cell extracts prepared from metabolically labelled transfectants were analyzed for Tek receptor tyrosine kinase protein expression by immunoprecipitation with affinity-purified antibody directed against the carboxy terminal 43-amino acid residues.

Figure 15B:
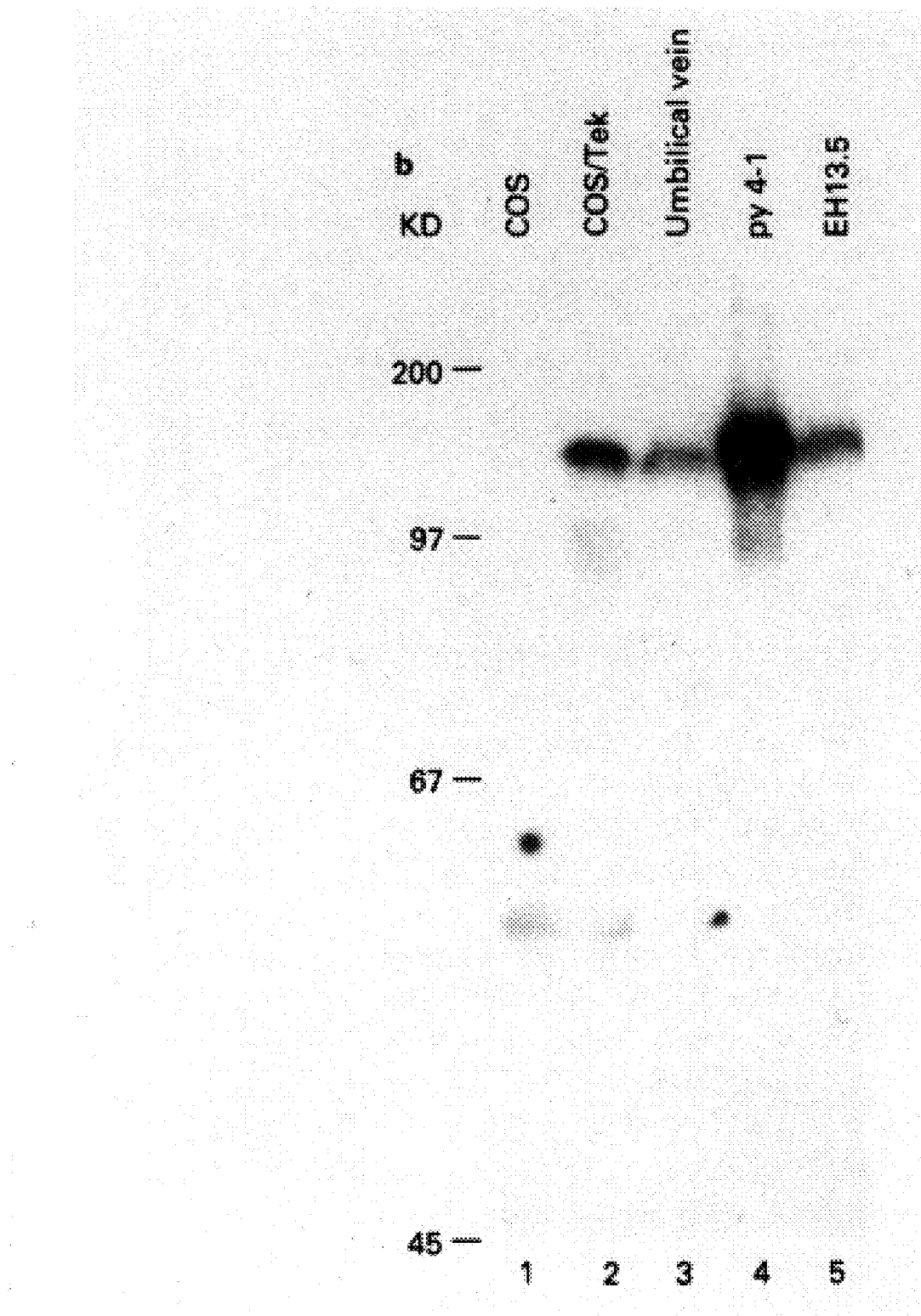
FIG. 15B shows that tek directs synthesis of a 140-kDa protein by Western analysis.

FIGS. 15A and 15B shows that tek directs the synthesis of a 140 kDa protein. FIG. 15A shows immunoprecipitation of Tek from transfected COS cells. Untransfected (lane 1) and transfected (lane 2) COS cells were labelled with [$^{35}$S]-methionine and lysates were prepared. The lysates were then subjected to immunoprecipitation with anti-Tek serum as described above. Antibody specificity was determined by the addition of 100 μg of GST-Tek fusion protein (competitor) to the antibody prior to the addition of cell extract (lane 3). FIG. 15B is a Western analysis of Tek expression in COS, Py4-1 cells and in embryonic tissues. Protein samples from untransfected and transfected COS cells, umbilical vein, Py4-1 cells, and Day 13.5 embryonic heart tissue (lanes 1 to 5, respectively) were analyzed for the presence of Tek receptor tyrosine kinase protein using affinity purified Tek antibodies.

FIG. 15A shows that a 140 kDa protein was specifically precipitated from transfected but not untransfected COS cells. Moreover, this 140 kDa protein could be detected immunologically by Western analysis (FIG. 15B, lane 2) and its immunoprecipitation could be competed by a GST fusion protein containing the 43-residue carboxy terminal segment to which the antibody was raised (FIG. 15A, lane 3). The apparent size of the encoded Tek protein, 140 kDa, is approximately 20 kDa greater than that predicted by the deduced amino acid sequence (126 kDa). The larger size of the detected protein presumably indicates that Tek is a glycosylated cell surface protein.

The protein encoded by the tek cDNA in transfected COS cells was compared with that encoded by the native gene in tissues and a cell line previously shown to express tek. FIG. 15B shows that cell lysates prepared from umbilical vein, Py4-1 cells, and Day 13.5 embryonic heart all contained a 140 kDa protein that reacted specifically with Tek antibody and which comigrated with the species detected in transfected COS cells. A slightly faster migrating species was also detected in Py4-1 cells. This species most likely represents an incompletely glycosylated form of Tek receptor tyrosine kinase protein, although it may be a distinct cross-reacting polypeptide. Taken together, these results indicate that the tek cDNA shown in SEQ ID NO:5 and FIG. 11B contains the complete coding information for the native Tek receptor tyrosine kinase protein.

EXAMPLE X
Tek is not the Murine Homolog of Tie

Tek shows some similarities to a human RTK, designated Tie, (Partanen et al., 1992). First, expression of tie was reported to be restricted to endothelial cells, as was observed for tek. Second, tie was mapped to human chromosome 1p33 to 1p34, a region which shows synteny with the interval to which tek was mapped on mouse chromosome 4 (See Example II). And third, tie, unlike all previously described members of the RTK family, encoded a molecule with virtually the same multidomain structure as Tek receptor tyrosine kinase protein. In fact, comparison of the primary structure of Tek and Tie proteins revealed considerable sequence similarity in the cytoplasmic region and the EGF-like repeats of the extracellular domain; however, this sequence similarity dropped off markedly in the immunoglobulin-like loops and the FNIII repeats (see FIGS. 12A and 12B). The relatively low sequence similarity within these subregions implied that tek might not be the murine homolog of tie. To resolve this issue, the pattern of hybridizing bands detected in digests of mouse and human genomic DNA by tek and tie probes containing sequences corresponding to equivalent regions (the FNIII repeats) of their respective genes (see FIG. 13A) was compared.

Figure 13:
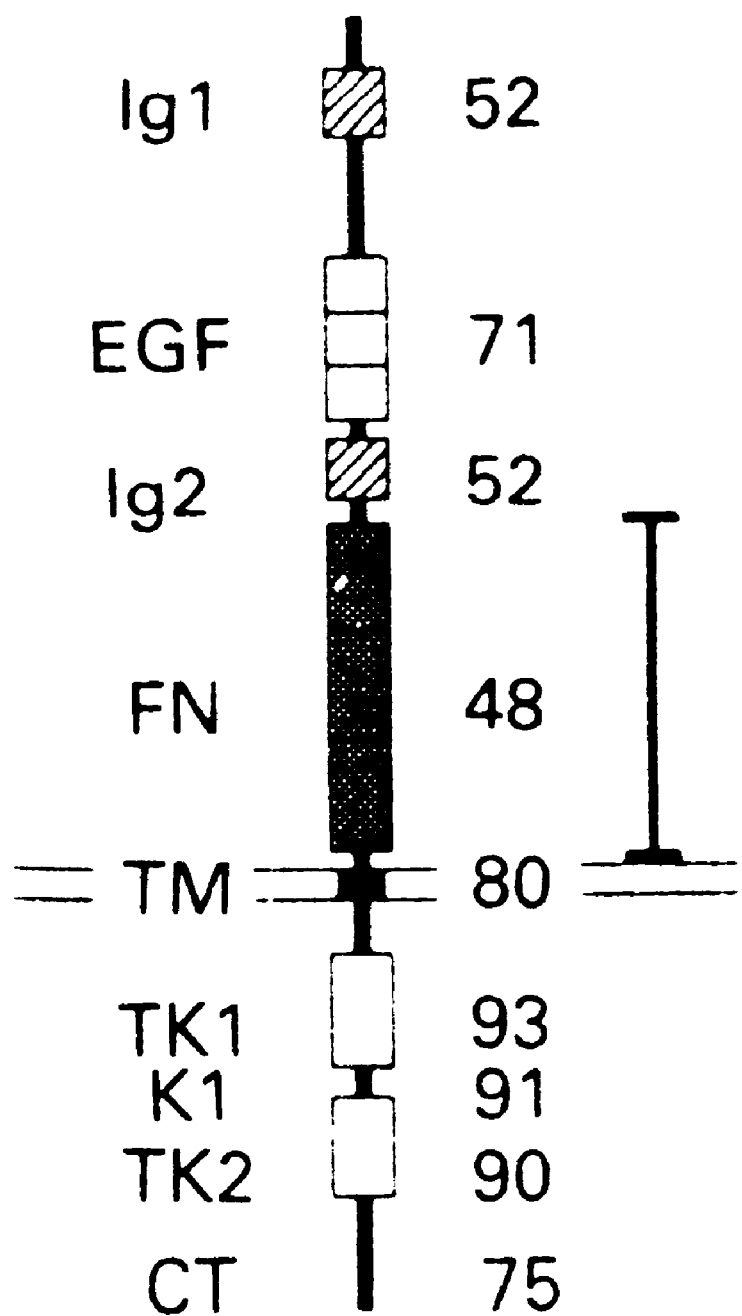
FIG. 13A shows the structural relationship between Tek and Tie by a comparison of structural motifs.
FIG. 13B shows the structural relationship between Tek and Tie by Southern analysis.
Figure 13B:
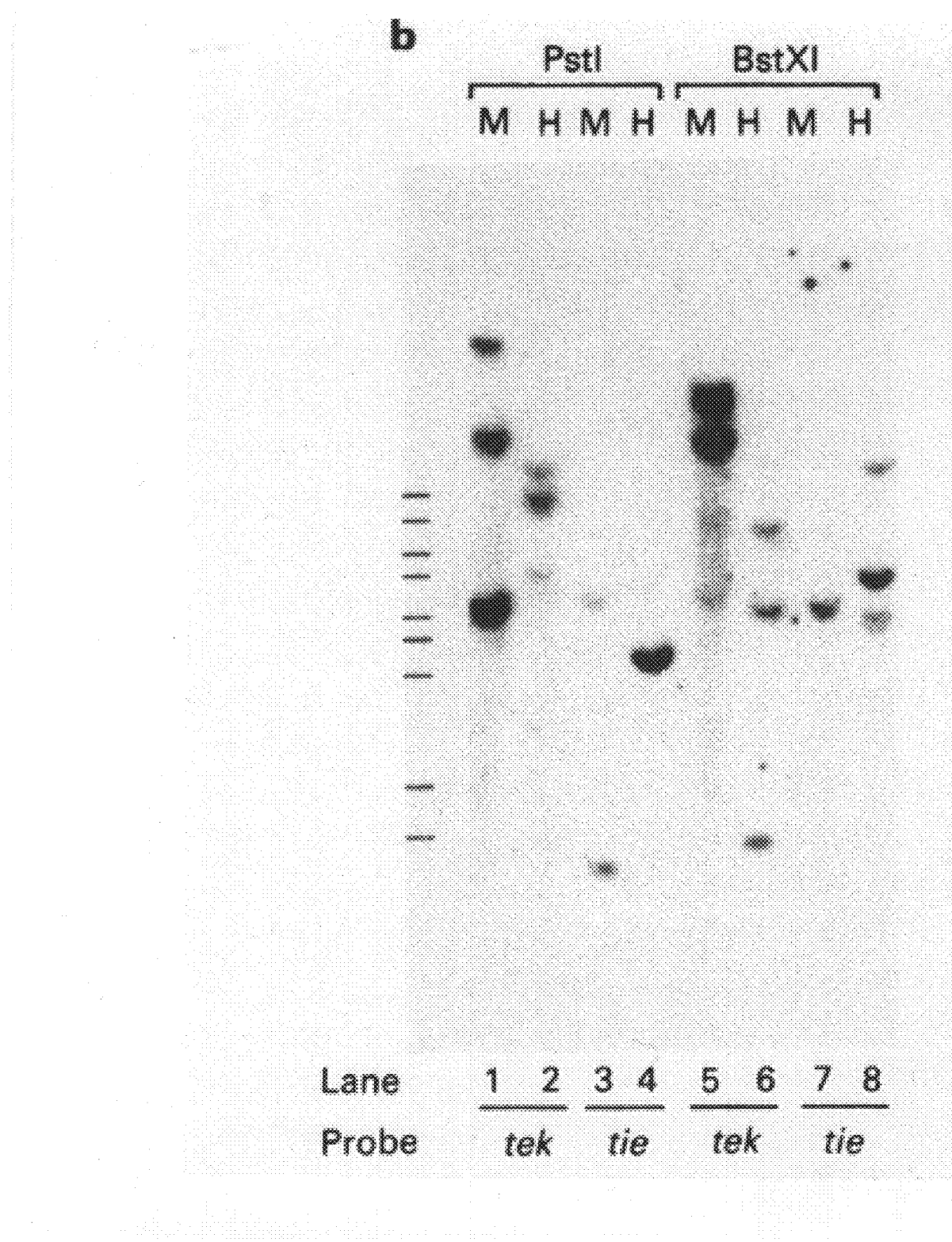

FIGS. 13A and 13B show the relationship between tek and tie. FIG. 13A shows the structural relationship between Tek and Tie. Structural motifs are depicted as described in respect to FIG. 11A and the numbers denote per cent sequence similarity between corresponding regions of the two receptors. The bar indicates the cDNA region of tek and tie used as probes in panel B. FIG. 13B shows a Southern analysis of mouse (lanes 1,3,5, and 7) and human (lanes 2,4,6, and 8) DNAs digested with either Pst I (lanes 1 to 4) or with BstX I (lanes 5 to 8). Immobilized DNAs were hybridized with either the tek- (lanes 1,2,5, and 6) or tie- (lanes 3,4,7, and 8) specific probes depicted in FIG. 13A. The position of the molecular weight markers, (8.4, 7.2, 6.4, 5.7, 4.8, 4.3, 3.7, 2.3 and 1.9 kb) are depicted to the left of the panel.

FIG. 13B shows that whereas the tek probe hybridized with 4 Pst I fragments of 15.4, 10, 4.7, and 2.4 kb (lane 1) and 5 BstX I fragments of 12.2, 11.5, 9.6, 7, and 5 kb (lane 5) in digests of mouse DNA, the tie probe detected 2 PstI fragments of 5 and 2.1 kb (lane 3) and 2 BstX I fragments of 6.9 and 4.7 kb (lane 7). Consistent with these results, the tek and tie probes also hybridized with different sized Pst I and BstX I fragments in human DNA. Thus, tek and tie are distinct, but closely related, members of a novel RTK gene subfamily.

EXAMPLE XI
Chromosomal Mapping of the Human Tek Locus

Figure 16:
FIG. 16 shows a G-banded partial metaphase spread with silver grain at 9p21 (arrow)
Figure 17:
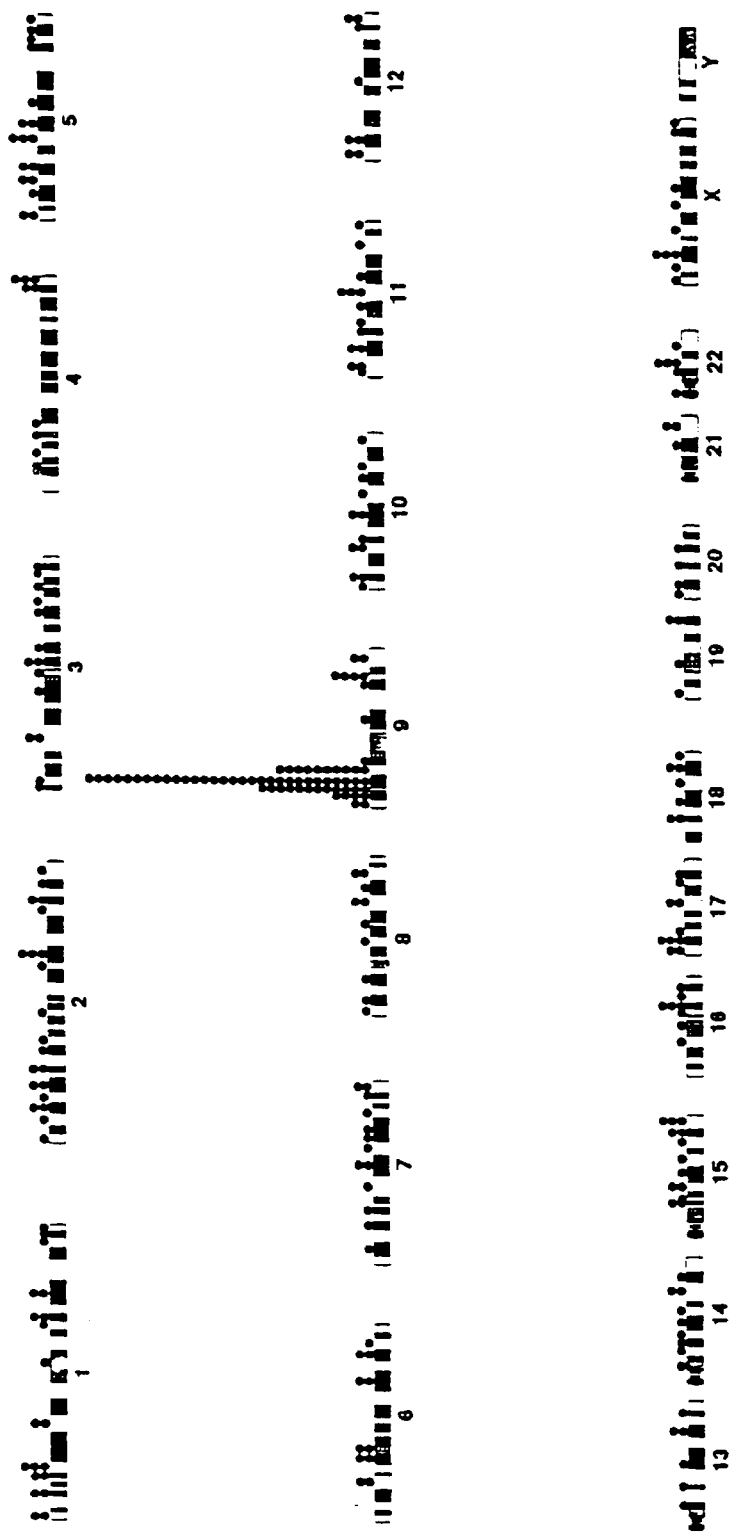
FIG. 17 shows silver grain distribution on a human karyotype following in situ hybridization with a tek probe.

In situ hybridization was used to map the human tek gene. An XbaI-digest of ptek cDNA was labelled to a specific activity of 9×10$^7$ cpm/μg DNA with [$^3$H]-dTTP and [$^3$H]-dATP (New Englan Nuclear) using a multiprime DNA labelling system (Amersham, #RPN1600Y). In situ hybridization to BrdU-synchronized peripheral blood lymphocytes was performed using the method of Harper and Sanders (1981, Chromosoma 83:431). Briefly, metaphase chromosomes on slides were denatured for 2 minutes at 70° C. in 70% deionized formamide, 2× SSC. Slides were then dehydrated in ethanol. The probe hybridization mixture consisted of 50% deionized formamide, 10% dextran sulfate, 2× SSC (pH 6.0), 0.2 μg/ml probe DNA, and 1 mg/ml sonicated salmon sperm DNA. The probe was denatured in the hybridization solution at 70° C. for 5 minutes. Fifty microliters of hybridization mix were placed on each slide. Slides were overlaid with cover-slips, sealed with rubber cement, and incubated at 37° C. overnight. Posthybridization washes were three times in 50% deionized formamide, 2× SSC for 3 minutes and five times for 3 minutes in 2× SSC (pH 7.0) at 39° C. The slides were sequentially dehydrated in ethanol. They were coated with Kodak NTB/2 emulsion, exposed for 3–5 weeks at 4° C., and developed (Harper and Saunders, 1981, supra). Chromosomes were stained with a modified fluorescence, 0.25% Wright's stain procedure (Lin et al., 1995, Cytogenet. Cell Genet. 39:269). The positions of silver grains directly over or touching well-banded metaphase chromosomes (FIG. 16) were mapped to an ISCN idiogram (FIG. 17).

The analysis of the distribution of 300 silver grains following in situ sublocalization revealed a significant clustering of grains on the short arm of chromosome 9. 59 silver grains were observed on this region, with a peak distribution at 9p21 (P<0.0001). The assignment of Tek to human chromosome 9p21 rather than to 1p33-34 which is the map location of Tie, demonstrates that during evolution, the region of mouse chromosome 4, to which both of these RTKs map, has been fragmented and distributed to human chromosomes 1 and 9. This is in keeping with earlier data demonstrating that these two regions of the human chromosome are known to share senteny to mouse chromosome 4.

The human chromosome 9p21 region has been shown to be deleted or rearranged in many types of neoplasia (Fountain et al., 1992; Taguchi et ali., 1993; Olopade et al., 1992; Rowley and Diaz, 1992). The latent oncogenic potential of receptor tyrosine kinase proteins and their known activation or gene amplification in malignancy suggests that if Tek receptor tyrosine kinase protein is indeed playing a role in these neoplasms it is most likely not due to a loss of heterozygosity, but to an activation of the Tek locus. The identification of a new non-random rearrangement involving (8,9)(q12; p21) in lymphoid malignancies (Huret et al., 1990) suggests that activation of the Tek locus may be responsible for these or other types of neoplasia.

EXAMPLE XII

The following methods were used in the investigations described in Example XII: Generation of the tek$^{A853}$ Dominant-Negative Transgenes and Transgenic Embryos The codon for lysine 853 was altered by oligonucleotide directed mutagenesis (Amersham) to the codon encoding an alanine residue. The entire cDNA fragment used in this mutagenesis was completely sequenced before subcloning back into the full length tek cDNA. The mutated cDNA (tek$^{A853}$) was cloned into the mammalian expression vector pECE (Ellis et al., 1987, Proc. Natl. Acad. Sci. U.S.A. 84:5101–5105) and transfected into COS cells as described previously. Metabolic labelling and tyrosine kinase assays were done with an anti-Tek antibody as described (Lhotak and Pawson, 1993, Mol. Cell Biol. 13:7071–7079). Two of the three transgenes were made by cloning the tek$^{A853}$ cDNA upstream of the SV40 polyadenylation (polyA) sequences (BamHI- XbaI) and then cloning this cassette downstream of the large β-actin promoter (Gift of V. Giguiere, Hospital for Sick Children, Toronto, Canada) or the 7.2 kb tek promoter. The polyoma-promoter driven transgene was constructed by cloning the tek$^{A853}$ cDNA without the SV40 polyA sequences into pdPX$_{13}$Bla$_3$MT$_5$ (Bautch et al., 1987, Cell 66:257–270) in which the sequences coding for polyoma middle T-antigen had been removed by BstXI digestion. These transgenes all contained 3' untranslated sequences from the tek cDNA, thus whether transcription terminated at the tek polyA sequences or the viral polyA sequences is not known. DNA from these constructs were prepared and injected into fertilized oocytes, as previously described (Logan et al., 1993). Embryos were analyzed on days 9.5 and 10.5 post-injection and were genotyped by PCR analysis of yolk sac DNA prepared as described (Frohman et al., 1990), utilizing a primer which annealed within the tek 3' untranslated sequence (CCTCACCTGCAGAAGCCAGTTTGT) (SEQ ID NO:11) and primers within either the SV40 (GTGGTTTGTCCAACTCATCAATG) (SEQ ID NO:12) or polyoma (CTACCATAATCCAGTCTACTGC) (SEQ ID NO:13) PolyA sequences. tek Targeting Vector The tek genomic clone used in these studies was obtained from a 129Sv mouse strain library. The targeting vector consisted of a long arm 7.2 kb Asp718I-BglII genomic fragment located 5' of the tek coding sequences and a short arm of 0.7 kb extending from XbaI to the EcoRI sites immediately 3' of the first exon (see FIG. 20). These two fragments were cloned on either side of the phosphoglycerate kinase (PGK)—neo expression cassette of the PPNT vector (Tybulewicz et al., 1991, Cell 65:1153–1163) such that the direction of neo transcription was in the same orientation as tek. Upon homologous recombination, this vector will delete approximately 0.7 kb of genomic sequences which includes 14 bp of untranslated sequence, the first 52 nucleotides of the protein-coding sequence and approximately 650 bp of the first intron.

Generation of Transgenic Mice Carrying a Tek cDNA Encoding a Dominant-Negative Tek Receptor Tyrosine Kinase Protein To further assess rapidly the role of the Tek signalling pathway in mouse development, a mutation was introduced within the tek cDNA which altered the codon for lysine 853 to encode an alanine residue. This lysine residue and its surrounding amino acids are found in a region within the intracellular cytoplasmic domain that is highly conserved in all tyrosine kinases and alteration of this residue is known to abolish catalytic function (Nocka et al., 1990, EMBO J. 9:1805–1813 and; Reith et al., 1990, Genes and Development 4:390–400). Thus, altering lysine$^{853}$ to alanine$^{853}$ should generate a Tek molecule that is still competent to bind ligand, but which is unable to transduce a signal due to its lack of catalytic function. To determine whether the lysine to alanine mutation at codon 853 affected the intrinsic tyrosine kinase activity of Tek protein, this mutated tek cDNA (tek$^{A853}$) was introduced into COS cells and extracts from these cells were analyzed for Tek activity.

Figure 18:
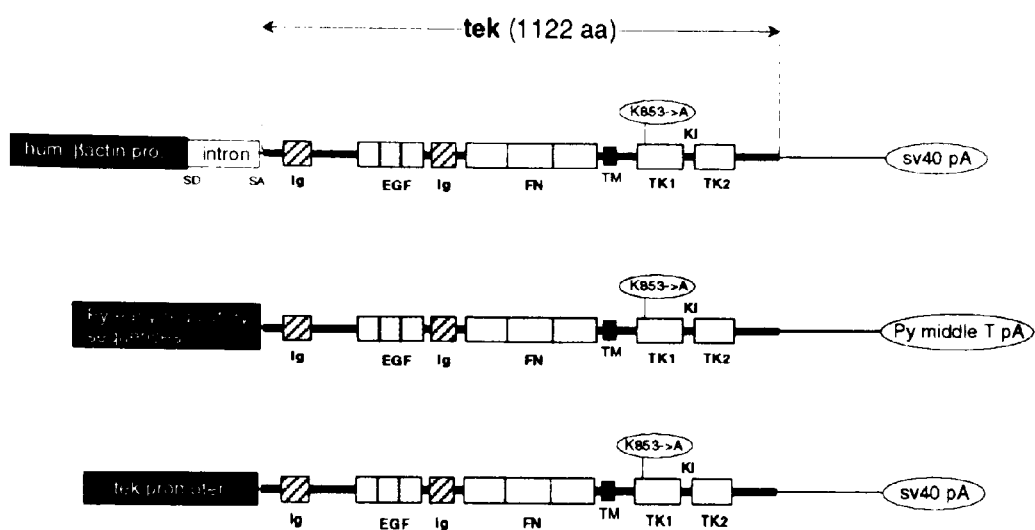
FIG. 18A is a schematic showing the transgene used to drive the expression of the dominant-negative mutant tek$^{A853}$ cDNA.
FIG. 18B is a gel showing that tek$^{A853}$ protein (DN) is catalytically inactive compared to wild type (WT) tek protein.

FIG. 18A is a schematic showing the transgenes used to drive the expression of the dominant-negative mutant tek$^{A853}$ cDNA. The solid box represents the promoter region for each transgene; the splice donor (SD) and acceptor (SA) of the β-actin promoter are indicated; the Immunoglobulin- (Ig), epidermal growth factor- (EGF), and fibronectin type III-like (FN) repeats found in the extracellular region of Tek are depicted by cross-hatched, stippled and open boxes, respectively; the smaller solid box represents the transmembrane region (TM). The two kinase domains (TK1 & TK2) are depicted by open boxes separated by the kinase insert (KI); ovals at the end of each transgene represent the different viral polyadenylation sequences. The oval above TK1 represents the position of the Lys→Ala853 mutation.

Figure 18B:
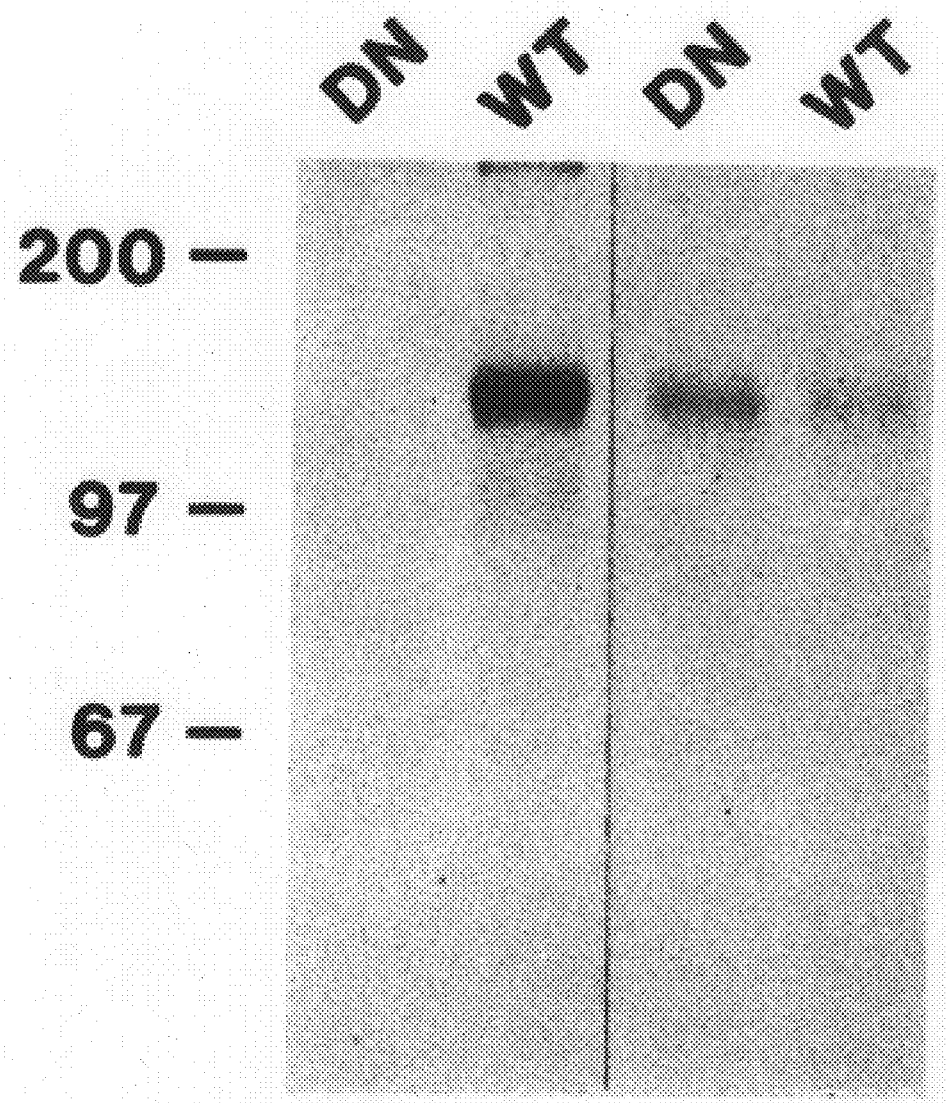

FIG. 18B shows that Tek$^{853}$ is catalytically inactive. Both the tek$^{A853}$ and wild type tek cDNAs were expressed in COS cells using the mammalian expression vector, pECE. Transfected COS cells were metabolically labelled with [$^{35}$S]-methionine and immunoprecipitated with anti-Tek antiserum. The immunoprecipitates were split and a portion used in an in vitro kinase assay (left two lanes) while the other was electrophoresed in a gel similar to the one used to analyze the products of the kinase assay but after electrophoresis the gel was processed for fluorography (right two lanes). DN, dominant-negative mutant tek$^{A853}$; WT, wild type tek cDNA.

As noted above, Tek$^{A853}$ protein was catalytically inactive in autophosphorylation and phosphorylation of exogenously added substrate (FIG. 18B, and data not shown). Moreover, the engineered mutation did not alter the length of the protein as judged by its gel mobility (FIG. 18B).

The β-actin, polyoma and tek promoters were used to drive expression of the tek$^{A853}$ cDNA within the endothelial cell lineage of transgenic mice (FIG. 18A and 18B). The β-actin promoter element is thought to be active in virtually all cells and thus should drive transgene expression early within the endothelial lineage and at relatively high levels. Transgenic animals expressing polyoma middle T-antigen driven by its promoter succumb to endotheliomas (Bautch et al., 1987, Cell 51:529–538; Williams et al., 1988, Cell 52:121–131) and endothelial cells isolated from these tumors express the transgene (Dubois et al., 1991, Exp. Cell Res. 196:302–313). Thus we reasoned that the polyoma early promoter sequences would be a good candidate for driving transgene expression within the endothelial cell lineage. Finally, we also employed a 7.2 kb DNA fragment that lies immediately upstream of the tek coding region which we have shown recapitulates the endogenous tek expression profile during early mouse development.

Figure 19A:
FIG. 19 shows developmentally delayed tek$^{A853}$ transgenic embryos as follows: 19A shows a non-transgenic control, 19B shows a tek promoter developmentally delayed embryo and 19C shows a polyoma driven developmentally delayed embryo.
Figure 19B:
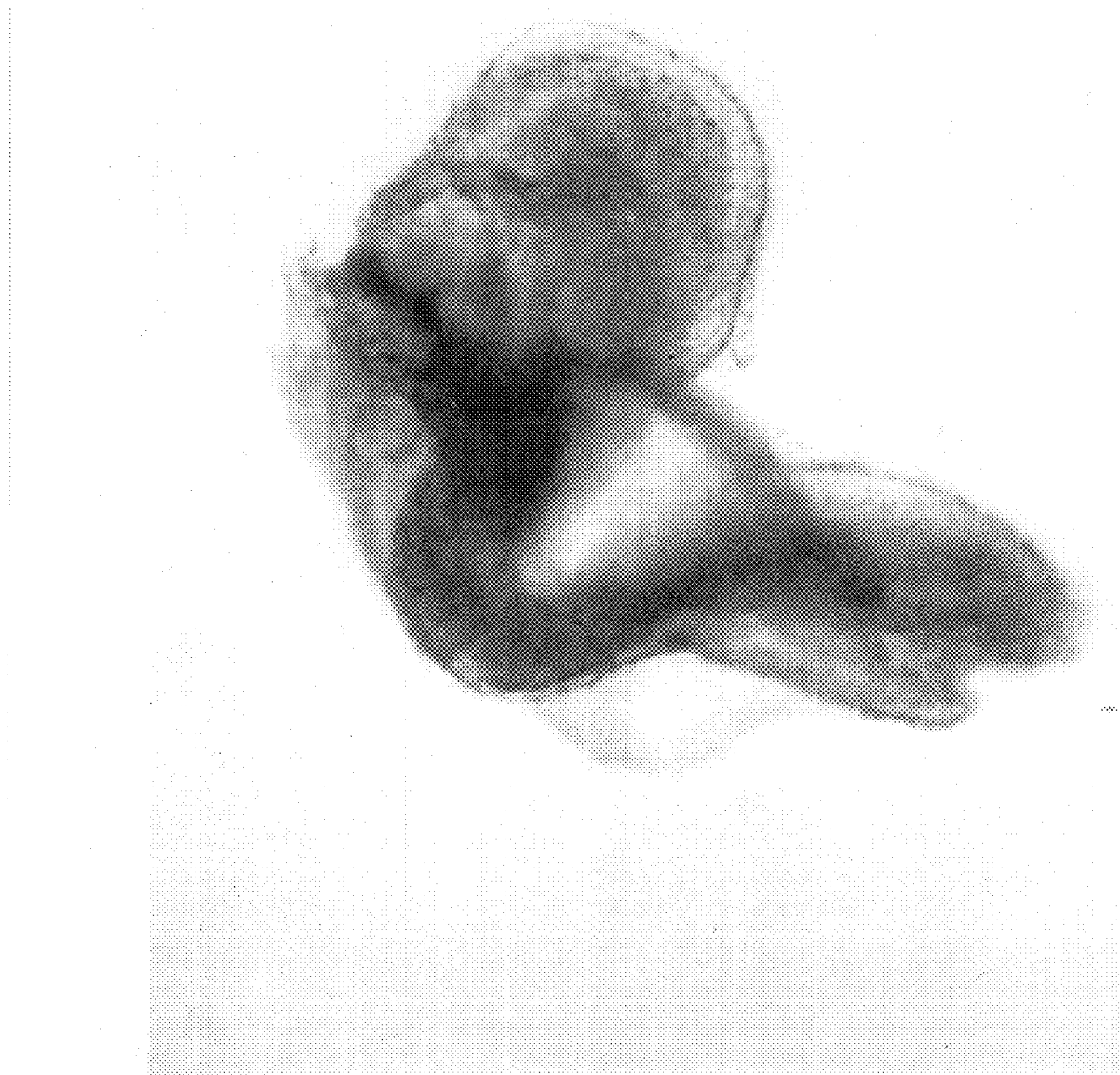
Figure 19C:
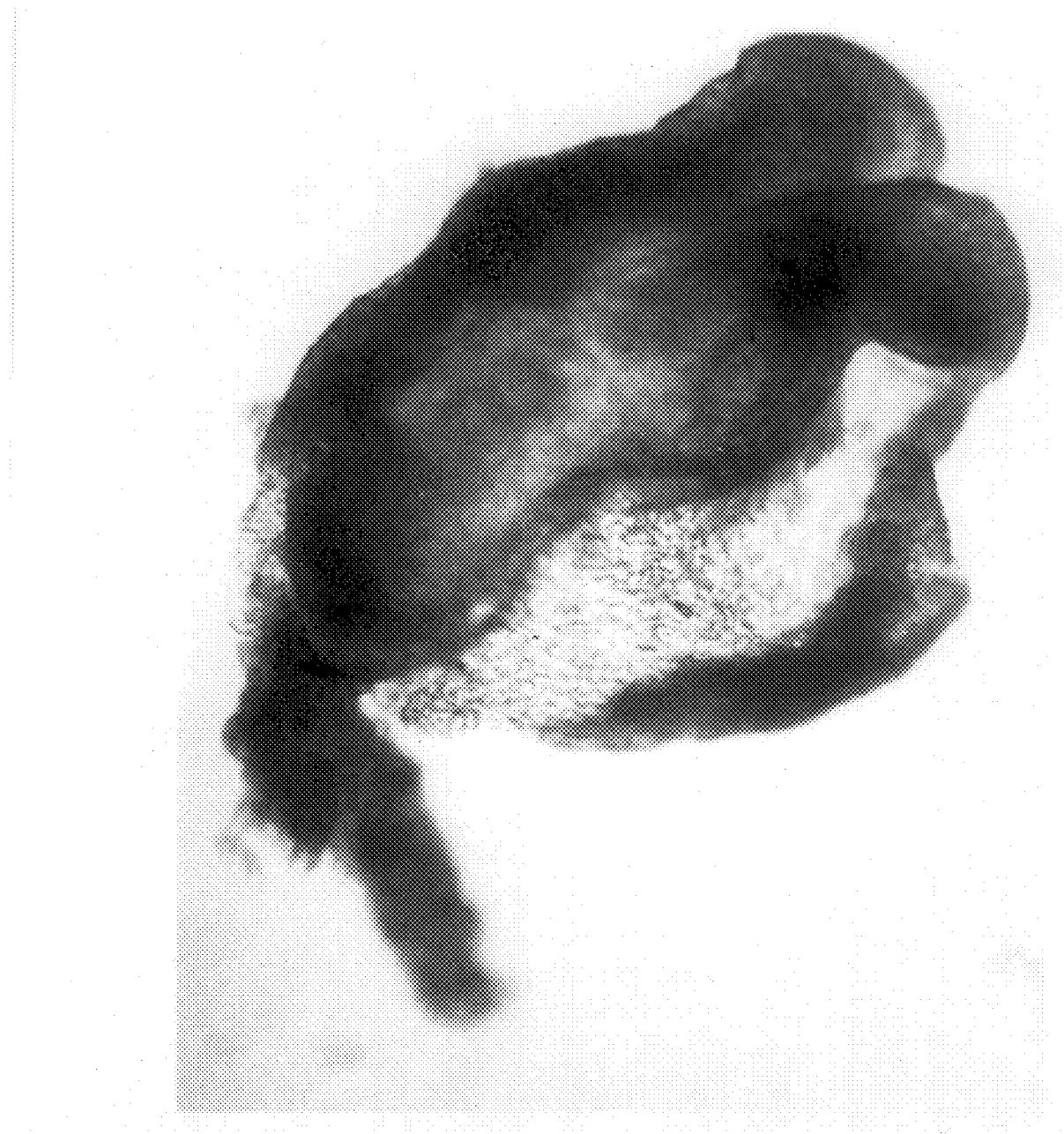

Tek$^{A853}$ Transgenic Mice are Developmentally Delayed and Exhibit a Defect in Their Endothelium Based on the assumption that Tek receptor tyrosine kinase may play a critical role in the endothelial cell lineage, transgenic founder embryos were removed on Days 9.5 and 10.5 of gestation, two to three days after the onset of tek expression. As shown in Table 3, embryos transgenic for the β-actin-tek$^{A853}$ transgene showed no discernible phenotype. In contrast, two out of 6 transgenic embryos containing the tek-promoter-tek$^{A853}$ transgene were delayed or arrested in their development (Table 3 and FIGS. 19A, B and C). In particular, FIGS. 19A and 19B show that tek$^{A853}$ transgenic mice are developmentally delayed and exhibit a defect in their endothelium. FIG. 19A shows a non-transgenic littermate taken from the same experiment as the embryo in panel B. FIG. 19B shows a tek promoter driven developmentally delayed embryo. FIG. 19C shows a polyoma driven developmentally delayed embryo. All embryos were recovered at E9.5 and were photographed at the same magnification.

Interestingly, one of the embryos isolated on E9.5 had an enlarged pericardial cavity and contained few blood cells in the vessels of the yolk sac. This was likely due to hemorrhaging into the yolk sac cavity, as primitive red blood cells were observed there. Furthermore, 5 out of 19 transgenic polyoma-promoter-tek$^{A853}$ embryos exhibited a developmental delay phenotype (Table 3). Of these delayed embryos, two appeared to have arrested early in development around Day 8.0 as judged by the closure of their neural folds. The three other embryos were delayed in their development to varying levels, but appeared morphologically normal when compared to embryos of the same size. One embryo was developmentally arrested, but proved to be negative for the presence of the transgene by PCR. This embryo was an amorphous mass which was undergoing resorption suggesting that its development arrested prior to the onset of tek expression and thus was considered to be phenotypically distinct.

Histological analysis of the developmentally delayed transgenic embryos was carried out on all tek$^{A853}$ mutants isolated on Day 9.5 (Table 3), but was not performed on Day 10.5 mutants due to severe necrosis of the specimens. FIGS. 21A–D shows a histological examination of the heart regions from dominant-negative tek$^{A853}$ transgenic and tek$^{Asp}$ heterozygous and homozygous embryos. E9.5 transgenic embryos, containing the tek$^{A853}$ transgene driven by either the tek-promoter (FIG. 21A) or the polyoma early sequences (FIG. 21B). tek$^{Asp}$ heterozygous (FIG. 21C) and homozygous (FIG. 21D) embryos. tek$^{Asp}$ heterozygous embryos (FIG. 21C) showed normal (arrowheads) while mutant transgenic tek-promoter-(FIG. 21A) and polyoma-promoter-tek$^{A853}$ (FIG. 21B) and the tek$^{Asp}$ homozygous (FIG. 21D) embryos showed degenerating endothelium (arrows) within their heart regions. All sections are photographed at the same magnification. Bar: 10 μm.

Figure 21A:
FIG. 21 shows a histological examination of the heart region of mouse E9.5 transgenic embryos as follows: 21A shows an embryo, containing the tek$^{A853}$ transgene driven by the tek-promoter, 21B shows an embryo containing the tek$^{A853}$ transgene driven by the polyoma early sequence, 21C shows tek$^{\Delta sp}$ heterozygous embryos and 21D shows tek$^{\Delta sp}$ homozygous embryos.
Figure 21B:
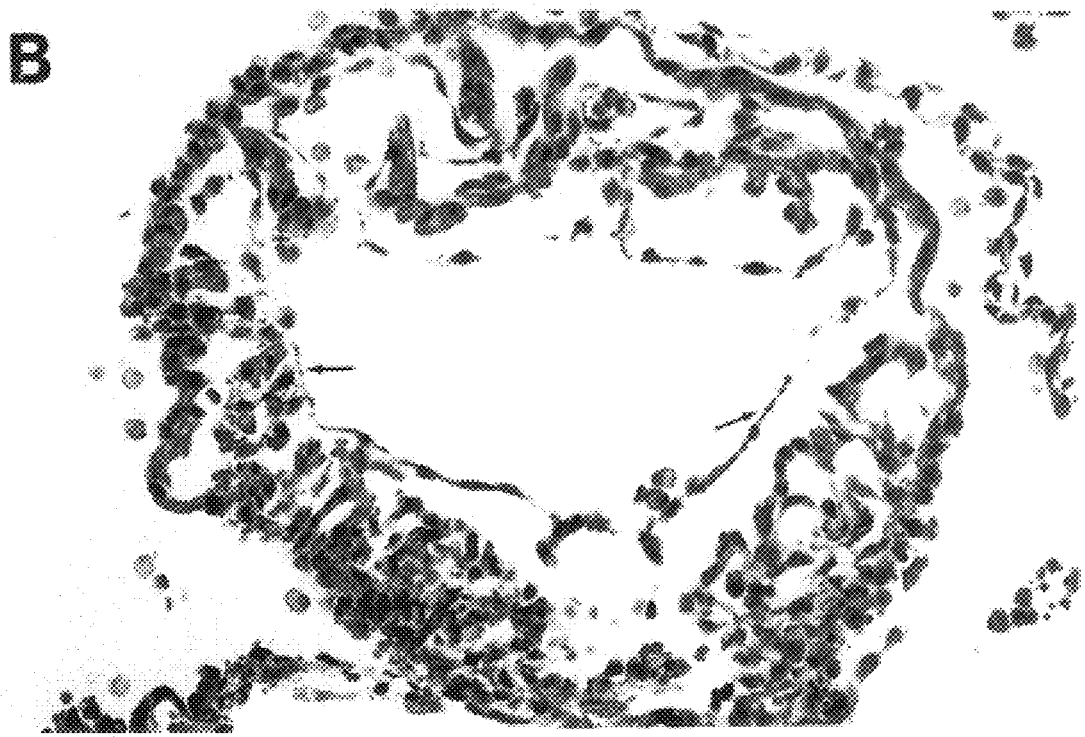
Figure 21C:
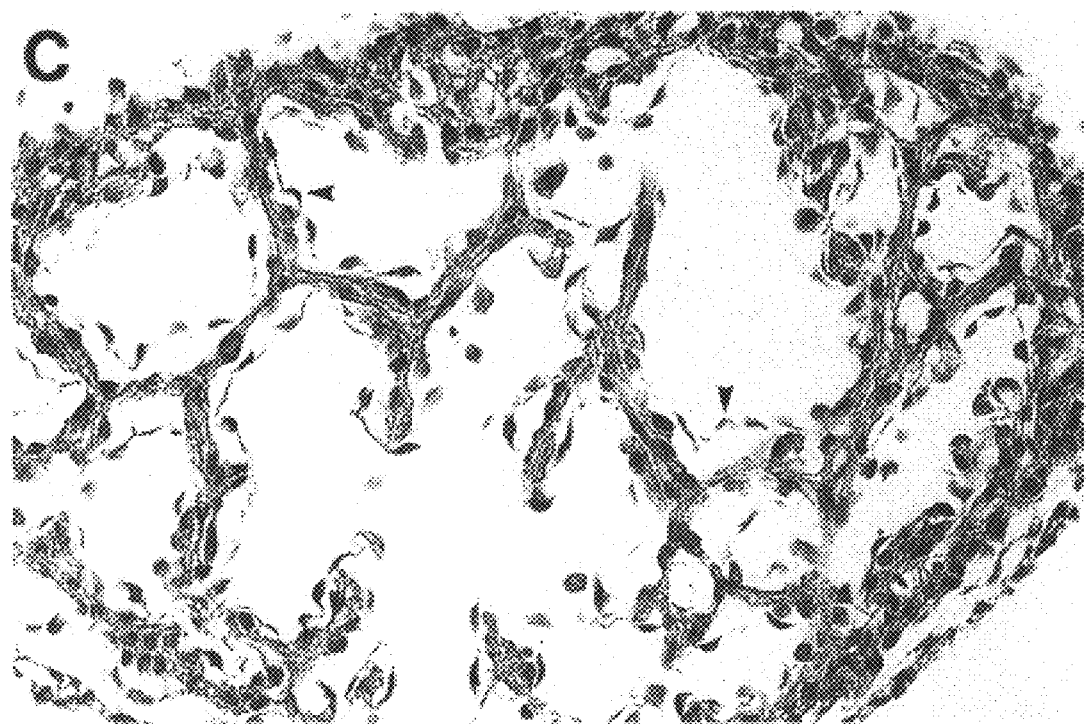

The heart of the tek-promoter-tek$^{A853}$ mutant embryos was reduced in size when compared to their normal littermates (FIGS. 21A & C, respectively). The organization of the trabeculae within the heart appeared to be relatively normal; however, there was a reduction in the number and complexity of the branching structures (FIG. 21A & C). The endothelial cells of the endocardium of the heart were fewer in number and had a short ribbon-like structure which may reflect degeneration. The developmentally delayed embryos observed after microinjection of the ployoma-promoter-tek$^{A853}$ transgene manifested phenotypes which varied in their severity. Histological analysis of three of these mutants revealed no clear pathological abnormalities, although subtle abnormalities could not be excluded. In contrast, the embryo shown in FIG. 21B represents the most extreme mutant where a defect could clearly be distinguished. Thin sections of the heart depicted a pathology virtually indistinguishable from that observed for tek$^{Asp}$ targeted homozygous mutant embryos (see below). The development and number of trabeculae within this polyoma-promoter-tek$^{853}$ and tek$^{Asp}$ targeted homozygous mutant hearts was severely reduced and the extent of myocardial development adversely affected (FIGS. 21B & D). The endothelial cells of the endocardium were few in number and not closely associated with the myocardium. In addition, the endothelial cells had small granules on their surfaces, which may be calcium deposits indicating cell death or cellular degeneration. Transgene expression levels could not be ascertained by RNA in situ analysis using probes directed against the viral polyadenylation sequences, suggesting that either they were not used and that the tek polyadenylation sequences within the tek cDNA were utilized or that the levels were too low to be detected.

No other overt phenotype was observed for any of the tek$^{A853}$-dominant-negative embryos, demonstrating that expression of this protein in other cellular compartments had no effect. Moreover, the fact that a phenotype was seen with the endothelial specific tek-promoter argues that the observed phenotypes for both the tek- and polyoma-promoter driven transgenes were intrinsic to a defect in the vascular endothelium.

EXAMPLE XIII

The following methods were used in the investigations described in Example XIII:

Generation and Genotyping of tek$^{Asp}$ Mice

R1 (Nagy et al., 1993, Proc. Natl. Acad. Sci. 90:8424–8428) ES cells were propagated, electroporated, plated and selected as described (Joyner et al., 1989, Nature 338:153–156). Selection in gancyclovir resulted in an enrichment of 7- and 32-fold in the two experiments. Four targeted clones were identified (1 in 232 and 3 in 55, respectively). Taken together, the frequency of homologous recombination was approximately 1 in 960 G418$^R$ clones. The identification of targeted events was accomplished by Southern blot analysis on ES cell DNA extracted directly in 24 well culture dishes as described (Wurst and Joyner, 1993, "Production of Targeted Embryonic Stem Cell Clones", in Gene Targeting, A. L. Joyner, ed. New York, Oxford University Press, pp. 33–61) and digested with BglII. A 0.3 kb AccI-BglII genomic DNA fragment located immediately 3' to the short arm was used as probe. This probe recognizes a wild-type fragment of 2.5 kb and a targeted fragment of 1.9 kb (see FIG. 20B).

Confirmation of a correctly targeted event was accomplished by Southern analysis of DNA extracted from heterozygous mice and digested with multiple enzymes. The probes used were the 3' external and two other internal probes consisting of the neo coding sequences and a genomic DNA fragment of 0.4 kb (Spe I-Bgl II) found 5' to the protein coding sequences (data not shown). No non-repetitive probes could be found 5' of the Asp718I site. Injection of ES cells carrying the tek$^{Asp}$ mutation into C57BL/6J blastocysts was performed as described previously (Joyner et al., 1989, Nature 338:153–156). Genotyping of offspring was carried out on DNA extracted from either tails or the dissected heads of embryos. Genotyping of LacZ transgenic animals were determined by Southern analysis using LacZ coding sequences as probe. Histology and LacZ staining Midday of the vaginal plug was considered as Day 0.5 post-coitum in the staging of embryos. To date all embryos with a cobblestone-like appearing yolk sac were homozygous for the tek$^{Asp}$ mutation. Therefore, to conserve material, embryos used in the LacZ-expression studies were judged to be homozygous for the tek$^{\Delta sp}$ mutation based on this criteria. Staining for the presence of β-galactosidase in whole-mount embryos was performed as described (Logan et al., 1993, Development 117:905–916). Stained embryos were postfixed in formalin at room temperature overnight and processed for wax embedding, sectioned at 6 µm and counter-stained with nuclear-fast-red. Quantification of the number of LacZ-expressing (blue) endothelial cells was accomplished by selecting a single section of an embryo and counting the number of endoderm and blue endothelial cells per blood island. Subsequent histological analysis of these mutants revealed other abnormalities characteristic of homozygous mutants which confirmed the phenotyping. For histological and RNA in situ analysis, the heads of embryos were removed for DNA extraction and genotyping prior to fixing the embryos overnight in freshly prepared 4% paraformaldehyde at 4° C. After fixation embryos were processed for wax embedding, sectioned at 4–6 µm and either used for RNA in situ analysis or stained with hematoxylin-eosin.

Disruption of the Tek Gene in ES Cells and Germ-line Transmission of the Mutation To create a null allele of tek, the last 52 base pairs of exon-1 were deleted (FIG. 20A), encoding the first 17 amino acids of Tek protein, by homologous recombination in ES cells. This deletion removes both the start of translation and the signal peptide. Therefore, this mutant is referred to as tek$^{\Delta sp}$. A positive/negative-type targeting vector (Mansour et al., 1993, Development 117:13–28) was engineered by cloning 7.2 kb of 5' genomic sequence upstream of a bacterial neomycin (neo) cassette (Tybulewicz et al., 1991, Cell 65:1153–1163) and 0.7 kb of 3' genomic sequences downstream.

Figure 20A:
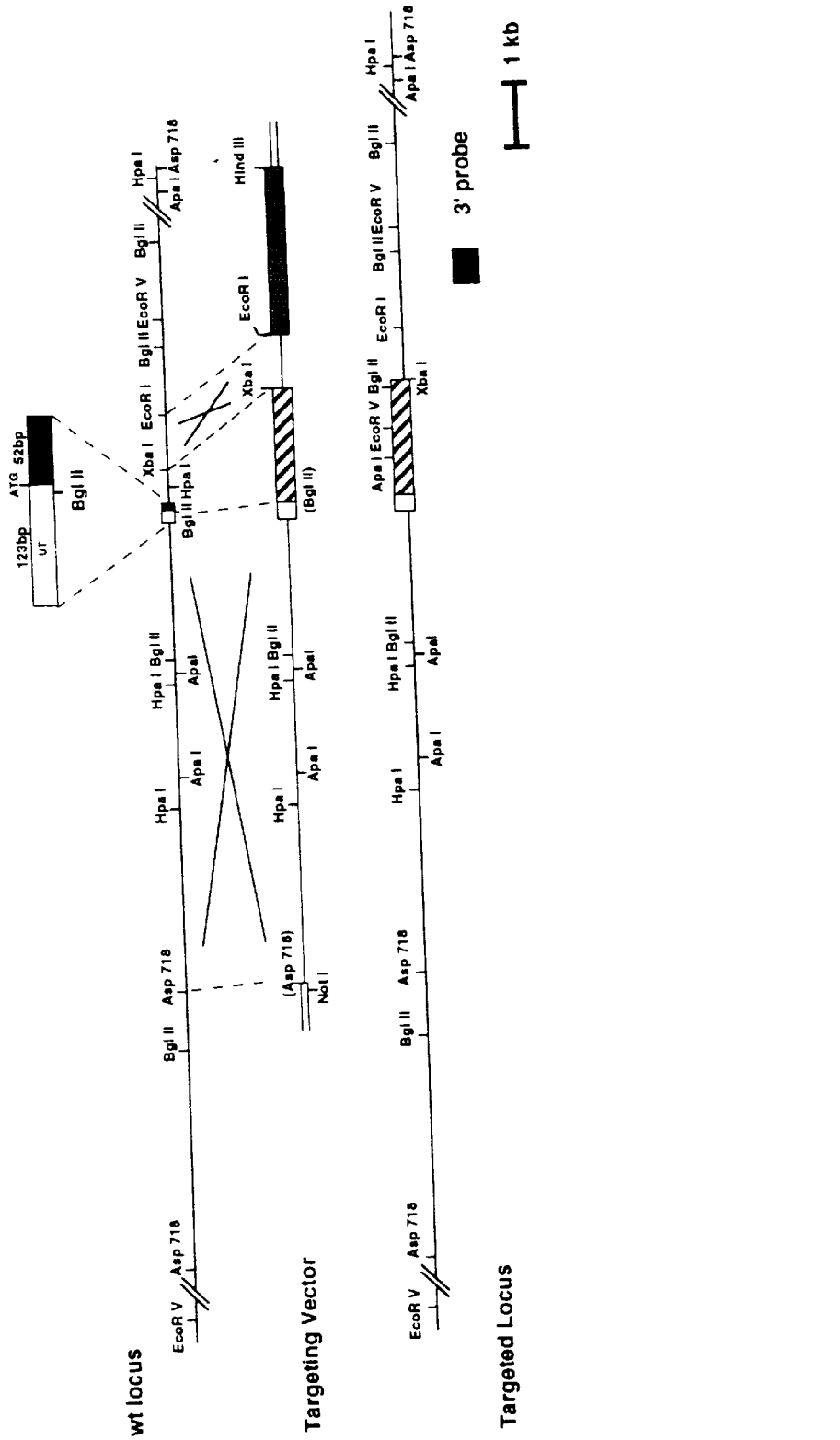
FIG. 20A is a schematic showing the strategy used to disrupt the coding sequence of the first exon of the tek gene, generating the mutation tek$^{\Delta sp}$.
Figure 20:
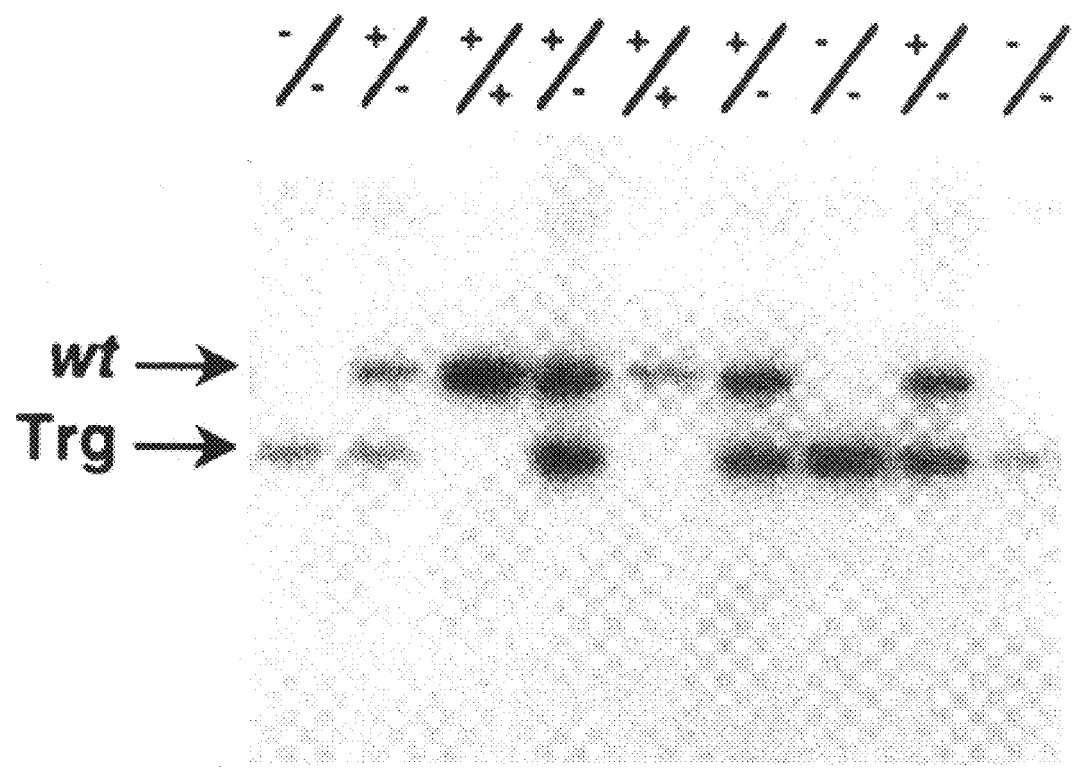
FIG. 20B shows the presence of a tek$^{\Delta sp}$ specific fragment (Trg) and wild type tek (wt) in DNA from day 9.5 embryos from a tek$^{\Delta sp}$/+heterozygous F1 intercross.

In the Figures, FIGS. 20A and B show disruption of the tek locus and Southern blot analysis of wild type, tek$^{\Delta sp}$ heterozygous and homozygous DNA. FIG. 20A is a schematic showing the strategy used to disrupt the coding sequences of the first exon of the tek gene, generating the mutation tek$^{\Delta sp}$. The closed box represents the protein-coding sequences; open box represents the untranslated sequences. The PGK-neo expression cassette, represented by a crossed hatched box, was inserted in the same transcriptional orientation as the tek gene. The stippled box represents the PGK-tk expression cassette fused to plasmid sequences represented by small, open-ended boxes. The XbaI and EcoRI restriction maps sites are not indicated 5' of the first exon. The brackets around the 5' Asp718 I site signify that the site was destroyed as a consequence of cloning. The location of the 3' external probe is indicated by a closed box beneath the predicted targeted locus.

FIG. 20B DNA extracted from Day 9.5 embryos from a tek$^{\Delta sp}$/+heterozygous F$_1$ intercross. The presence of the tek$^{\Delta sp}$ specific fragment is indicated, Trg. The number of wild type (+/+), heterozygous (+/−) and homozygous (−/−) embryos (2, 4 and 3, respectively) were at the predicted Mendelian frequency.

In two separate experiments, linearized targeting vector was electroporated into RI ES cells as described above. A properly targeted event was observed (FIG. 20B and data not shown) by Southern blot with both a 3' external and internal probes. Two independent ES cell lines carrying the tek$^{\Delta sp}$ allele were injected into host C57BL/6J blastocysts to generate Chimeras that transmitted the mutation to their offspring.

tek$^{\Delta sp}$ Homozygous Mice Die During Gestation

Mice heterozygous for the tek$^{\Delta sp}$ mutation had no apparent abnormalities and were fertile. Intercrosses of mice derived from both independent ES cell clones were carried out between either outbred (129SvJ×C57BL/6J) F$_1$ or inbred 129SvJ F$_1$ mice to allow analysis on two genetic backgrounds. No differences in phenotype were observed on either of the two genetic backgrounds or the two targeted ES cell lines.

F$_1$ intercrosses of tek$^{\Delta sp}$/+mice produced no live offspring homozygous for the tek$^{\Delta sp}$ allele (Table 4). Mothers from these intercrosses were therefore sacrificed and embryos were genotyped. At E9.5 some embryos from the heterozygous cross were visibly defective, showing some signs of necrosis and their hearts were not beating. These embryos were all homozygous for the teksP mutation (Table 4) No live homozygous mutant embryos were found beyond E9.5 (Table 4). At E12.5, none of the embryos (0/35) were teksP homozygotes; however, there were 8 severely necrosed implantations, suggesting that tek$^{\Delta sp}$ homozygous embryos implanted, but then died. Genotyping of embryos isolated on E9.5 demonstrated that the proportion of embryos that were wild type, heterozygous and homozygous for the tepsP allele followed the expected Mendelian frequency, confirming that Tek is not required for implantation of the embryo (FIG. 20B and Table 4).

Hemorrhaging of tek$^{\Delta sp}$/tek$^{\Delta sp}$ Embryos

FIGS. 22A–F shows a histological analysis of homozygous tek mutant embryos and normal littermates. In particular, the Figures show Sections through the embryonic portion of the placenta from tek$^{\Delta sp}$ heterozygous (22A) and homozygous (22D) embryos showing the accumulation of fetal blood cells in the placental sinuses in homozygous embryos. These sections also illustrate the decreased number of endothelial cells in the sinus of mutants as compared to normal littermates (arrowheads). Bar: 10 µm. Thin sections taken through the dorsal aortic region of heterozygous (22B) and homozygous (22E) embryos showing the collapsed aorta (da) and extravasated blood (arrows). Bar: 30 µm. Stained thin sections through the yolk sac of tek$^{\Delta sp}$ heterozygous (22C) and homozygous (22F) embryos showing the distended yolk sac vessels and the decreased number of endothelial cells lining the yolk sac vessels (arrowheads). Bars: 30 µm.

FIG. 23A–D shows the yolk sac vasculature of tek$^{\Delta sp}$ homozygous embryos contain fewer endothelial cells. tek-promoter-lacz transgene expression in Day 8.5 normal (23A) and tek$^{\Delta sp}$ homozygous (23C) embryos shows a reduced number of blue staining endothelial cells in the homozygous mutants. The decreased number of blue cells (arrowheads) is even more dramatic in the yolk sac of Day 9.0 tek$^{\Delta sp}$ homozygous (23D) embryos as compared to normal embryos (23B). Bar:50 µm.

FIGS. 24A–D shows the embryonic vasculature of tek$^{\Delta sp}$ homozygous embryos contain fewer endothelial cells. The trunk (24A, 24C) and heart (24B, 24D) regions of a E9.0 tek$^{\Delta sp}$ homozygous (24A, 24B) and wild type (24C, 24D) embryos. A lower levels of lacZ expression is seen in the intersegmental vessels (is) and endocardium (e) of mutants. Dorsal aorta, da. Bars: 50 µm.

In summary, the data show that Day 8.5 embryos homozygous for the tek$^{\Delta sp}$ mutation were readily discernible by the grossly abnormal morphology of their yolk sacs, which were engorged with blood and had a cobble-stone-like appearance (FIG. 22F & 23A–D). To date all embryos with this morphologically distinct yolk sac that have been genotyped have been homozygous tek$^{\Delta sp}$ (9/9).

Figure 22:
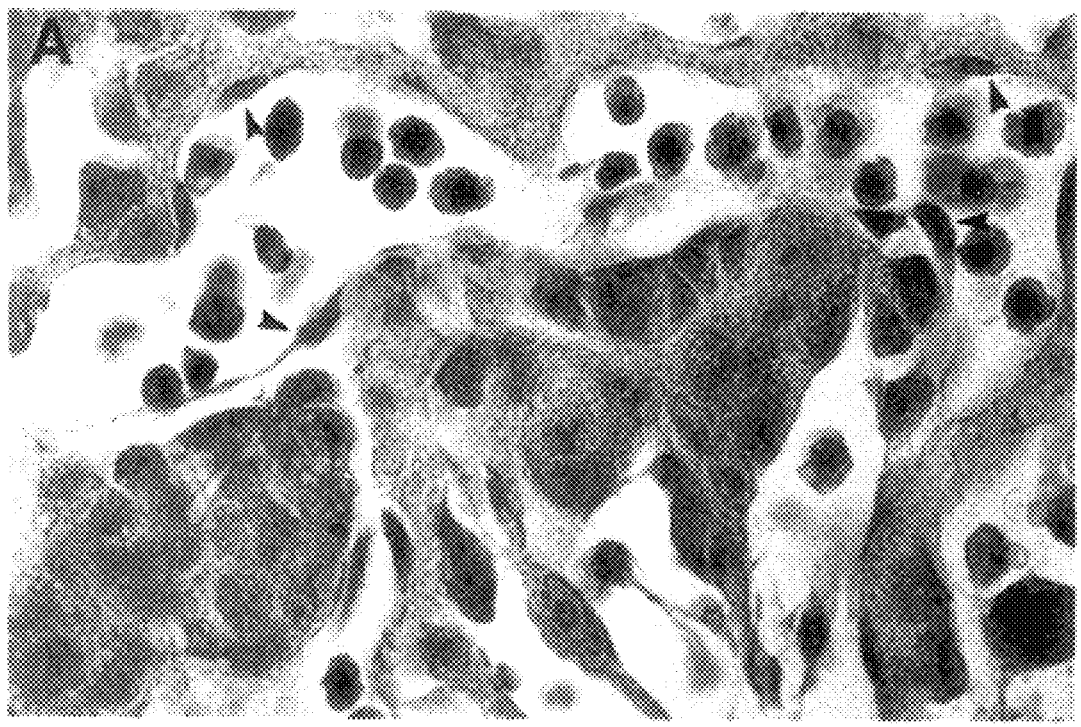
FIG. 22 shows a histological analysis of tek$^{\Delta sp}$ mutant embryos and normal littermates as follows: 21A shows the embryonic portion of the placenta from heterozygous embryos, 21B shows the dorsal aortic region of heterozygous embryos, 21C shows the yolk sac of heterozygous embryos, 21D shows the embryonic portion of the placenta from tek$^{\Delta sp}$ homozygous embryos, 21E shows the dorsal aortic region of homozygous embryos and, 21F shows the yolk sac of homozygous embryos.
Figure 22B:
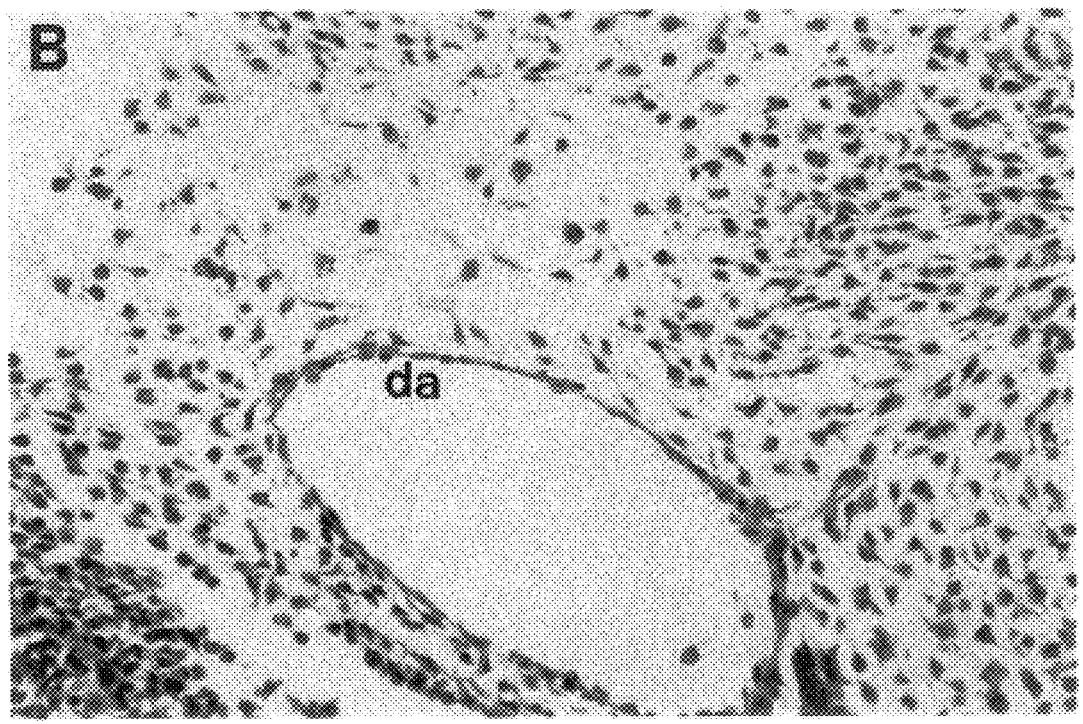
Figure 22:
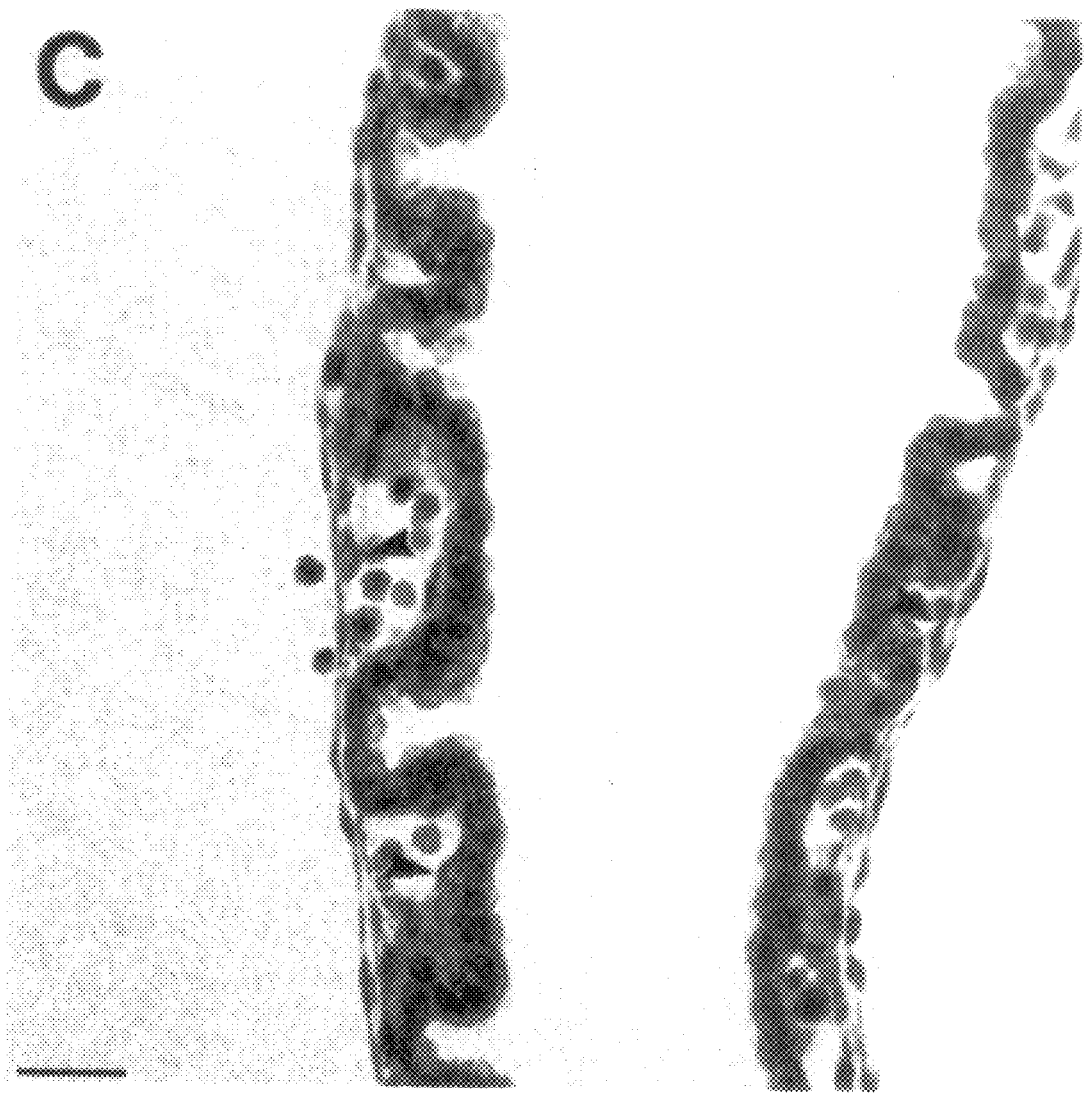
Figure 22:
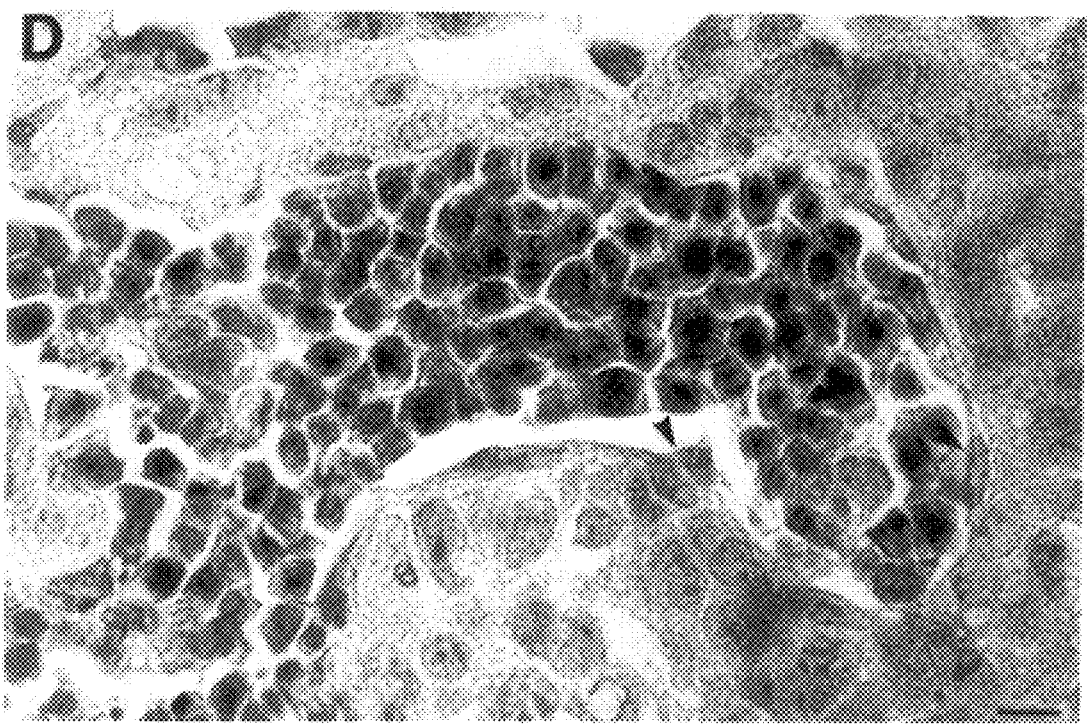
Figure 22E:
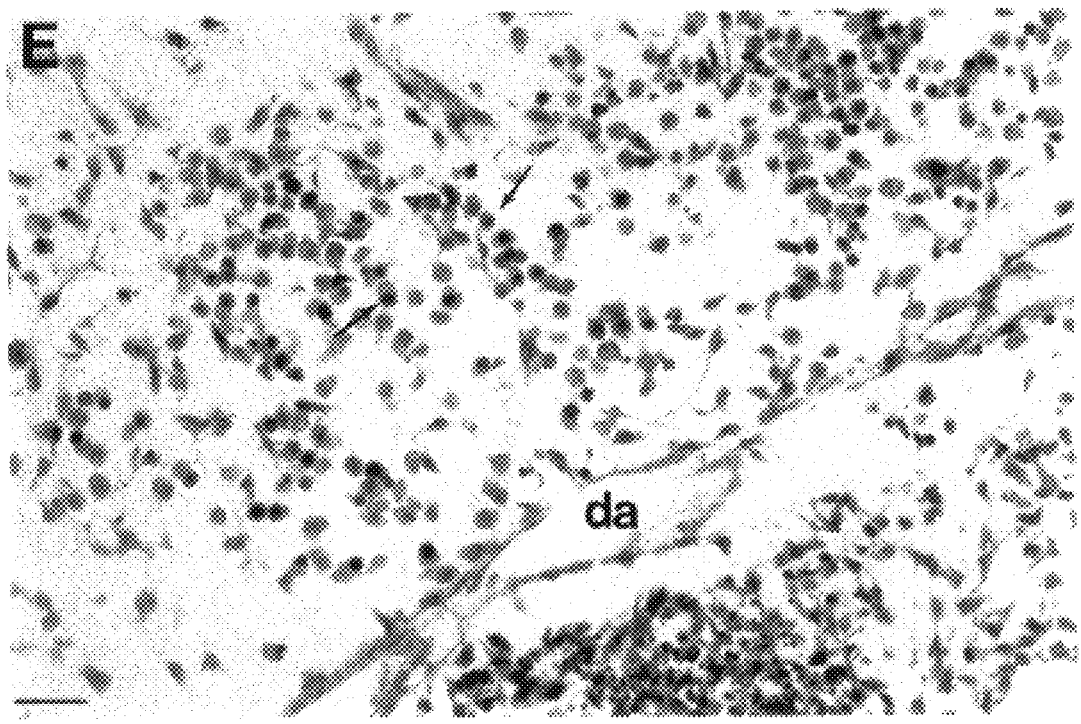
Figure 22F:
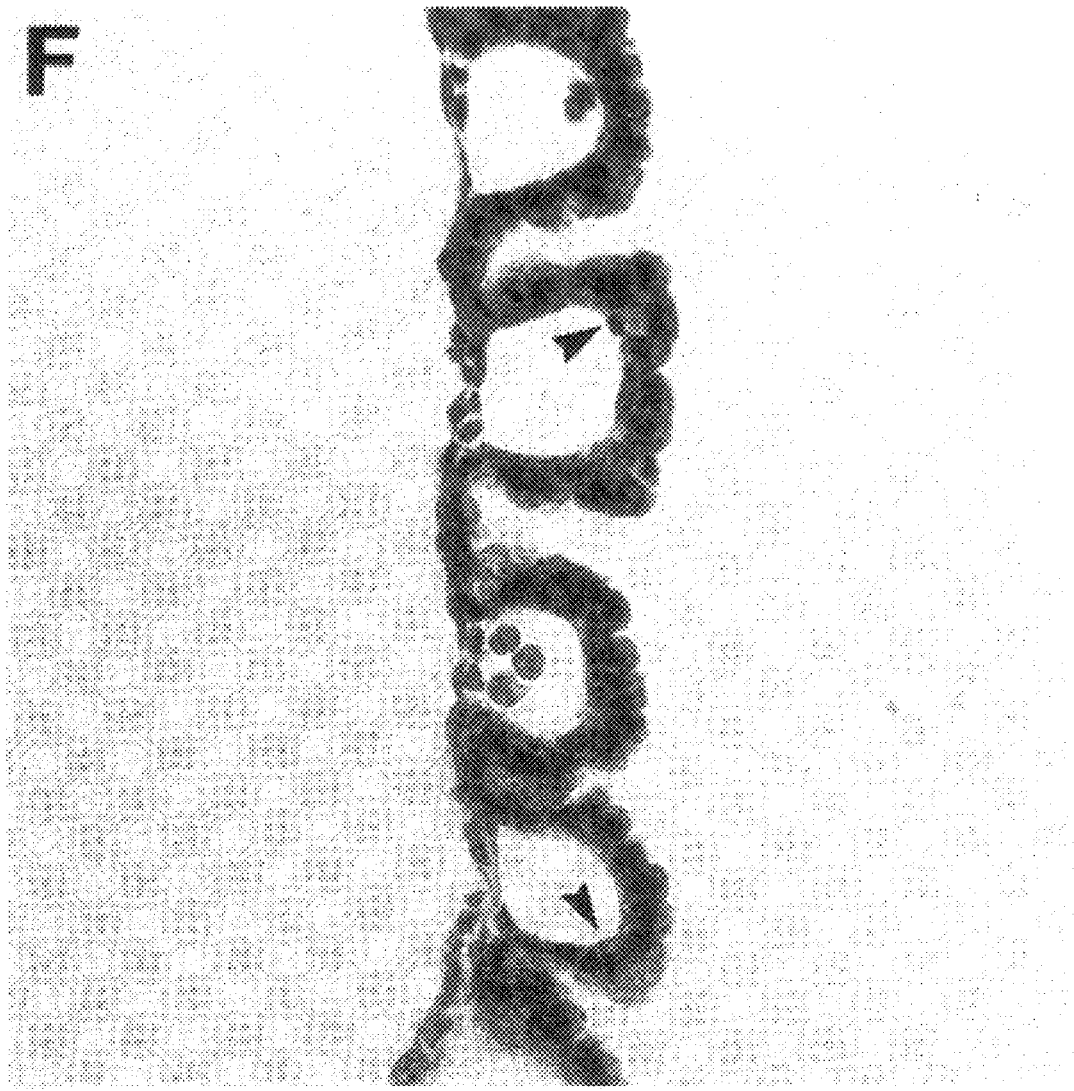
Figure 23:
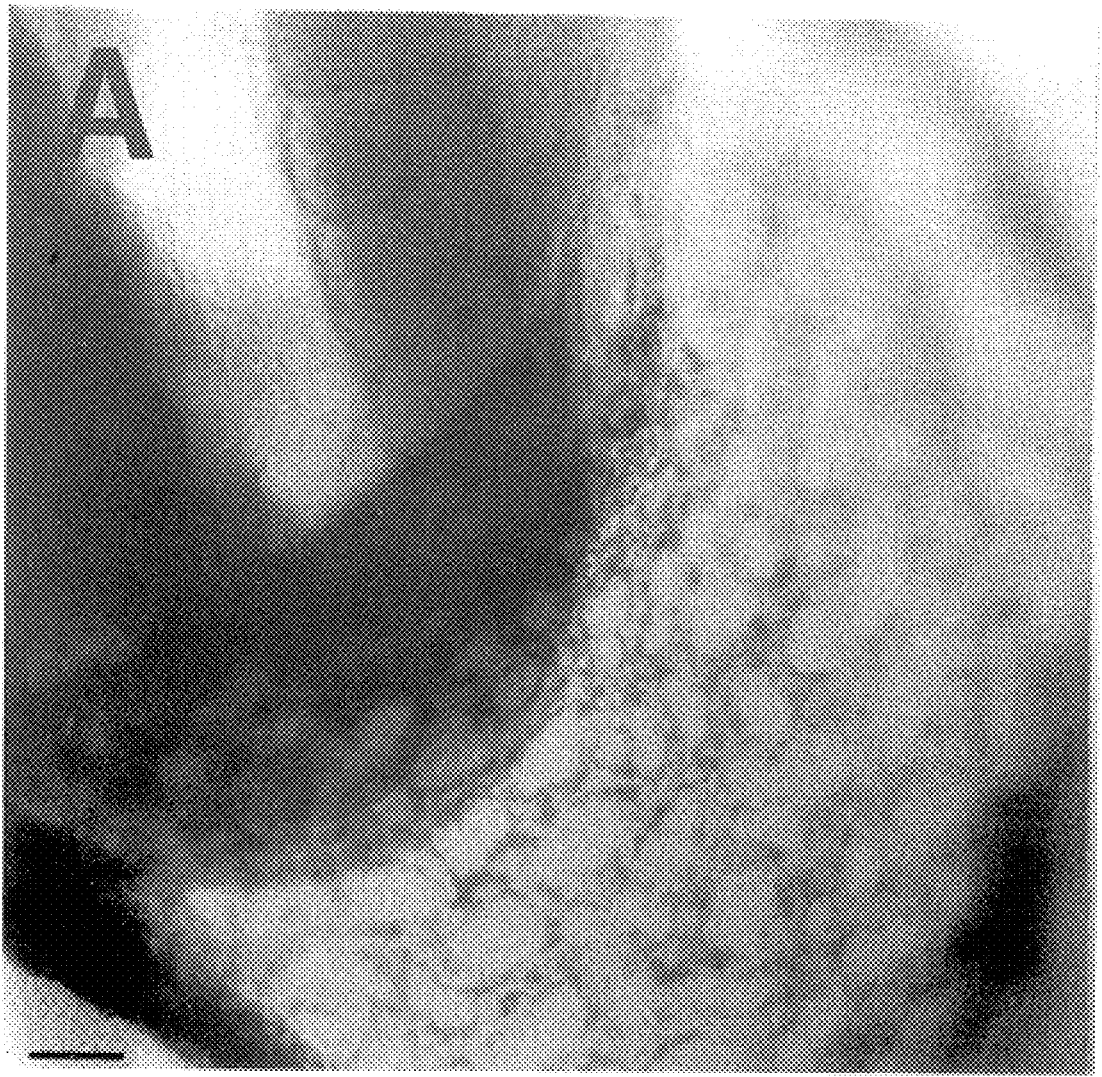
FIG. 23 shows tek-promoter-lacZ expression in the yolk sac vasculature of normal and tek$^{\Delta sp}$ homozygous embryos as follows: 23A shows expression in Day 8.5 normal embryos, 23B shows expression in Day 9.0 normal embryos, 23C shows expression in Day 8.5 homozygous mutants and, 23D shows expression in Day 9.0 homozygous mutants.
Figure 23:
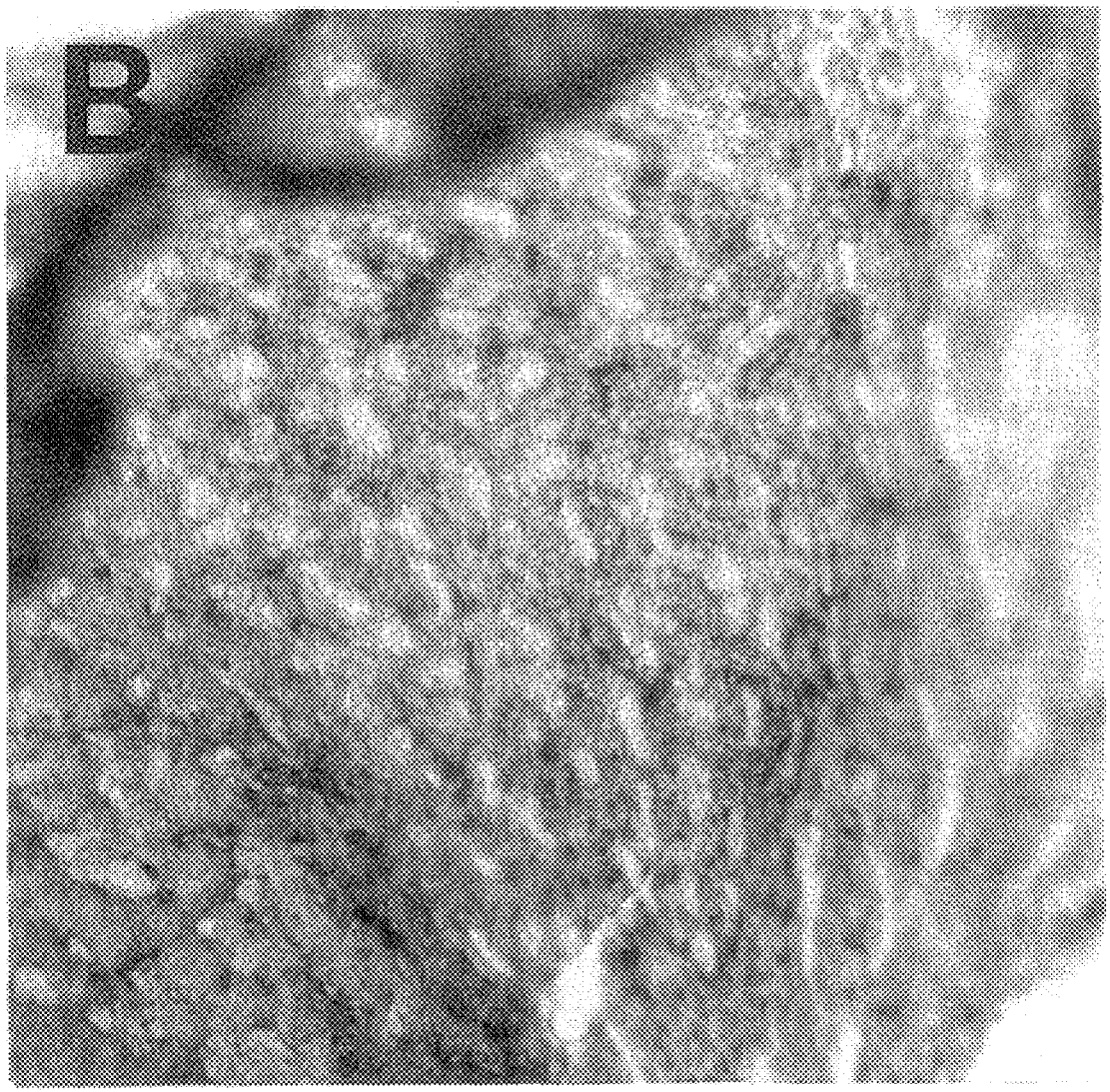
Figure 23:
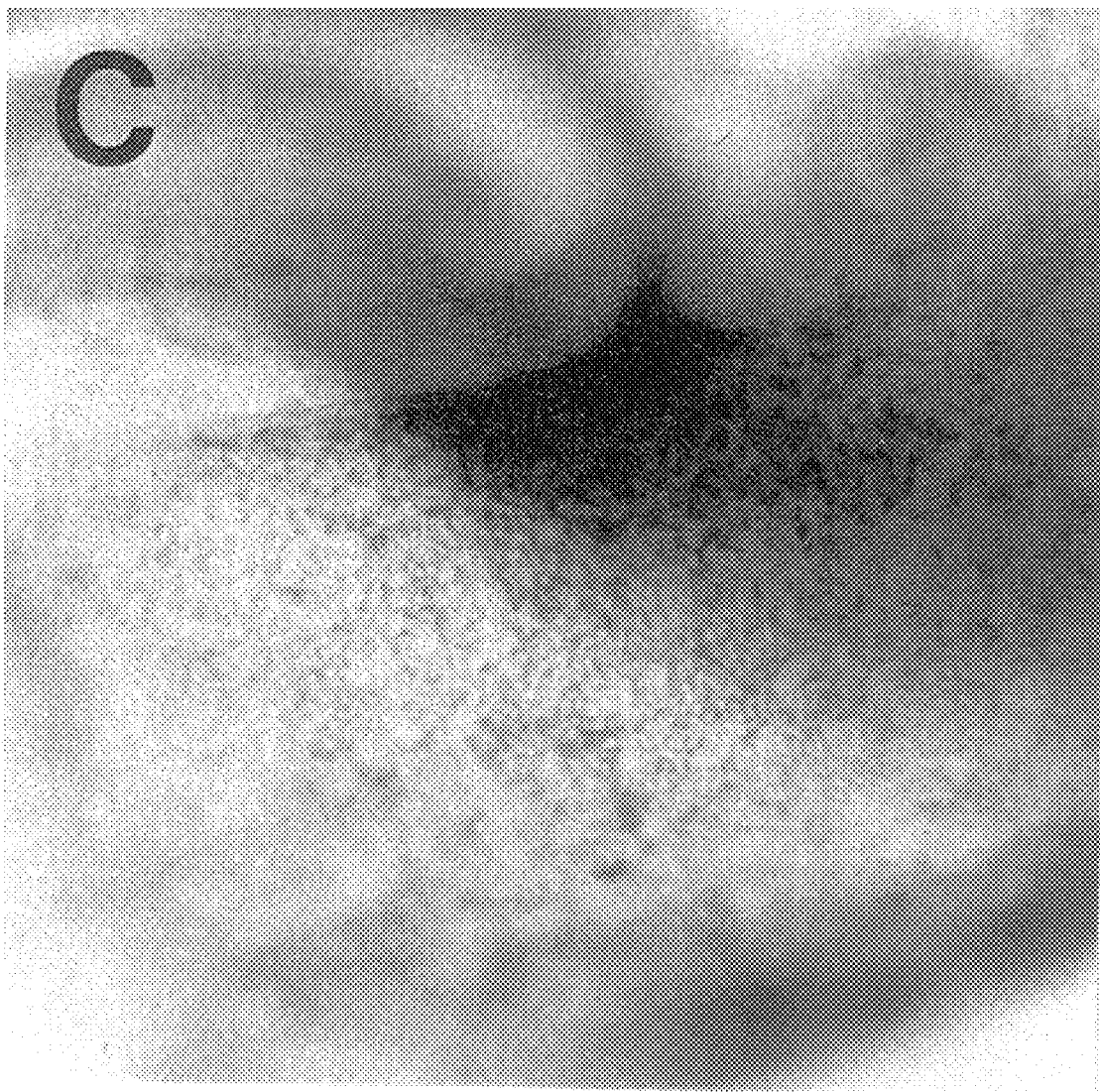
Figure 23:
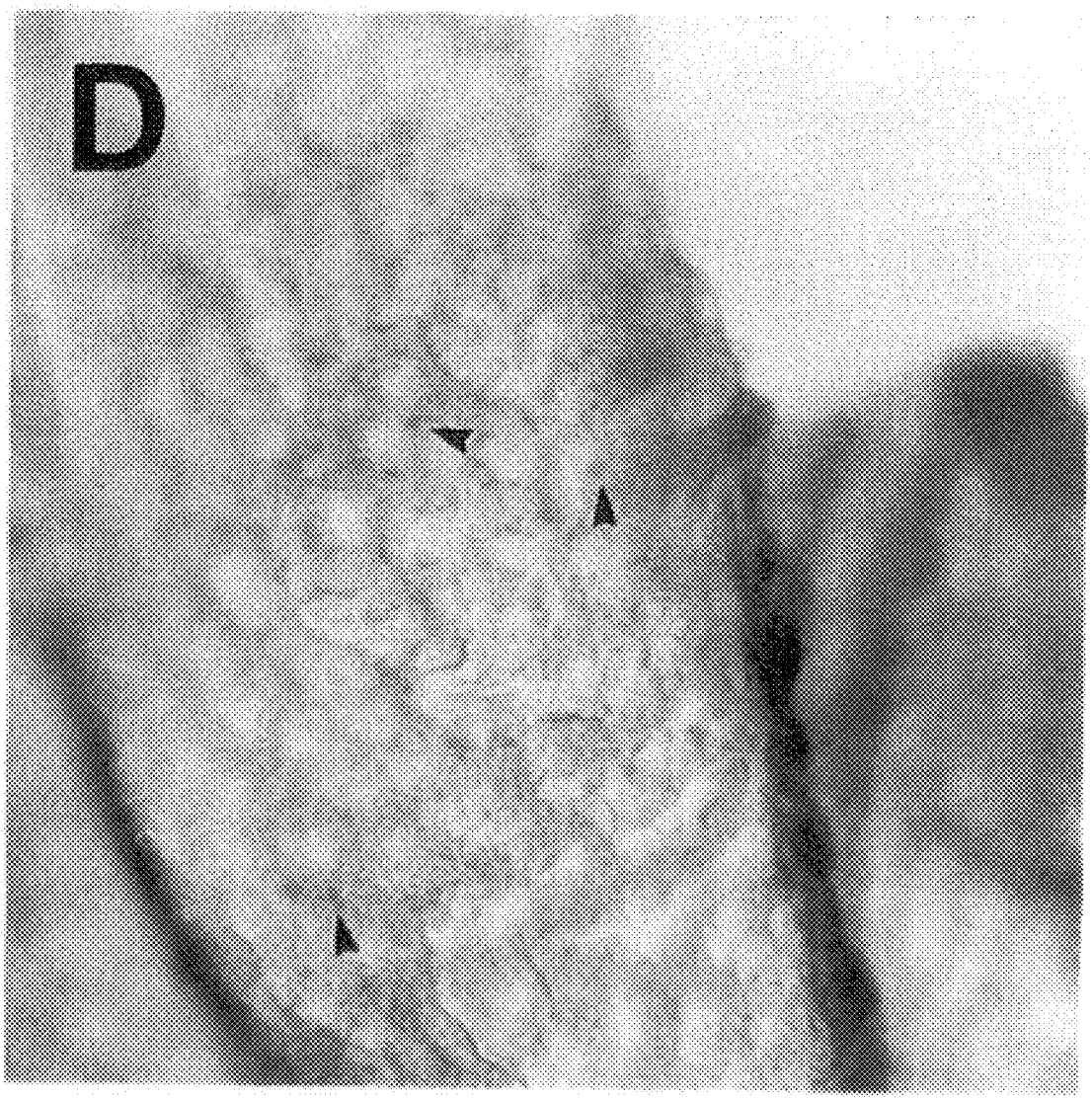
Figure 24:
FIG. 24 shows tek-promoter-lacz expression in the embryonic vasculature of normal and tek$^{\Delta sp}$ homozygous embryos as follows: 24A shows expression in the trunk region of E9.0 tek$^{\Delta sp}$ homozygous embryos, 24B shows expression in the heart region of E9.0 tek$^{\Delta sp}$ homozygous embryos, 24C shows expression in the trunk region of wild type embryos and, 24D shows expression in the heart region of wild type embryos.
Figure 24:
Figure 24:
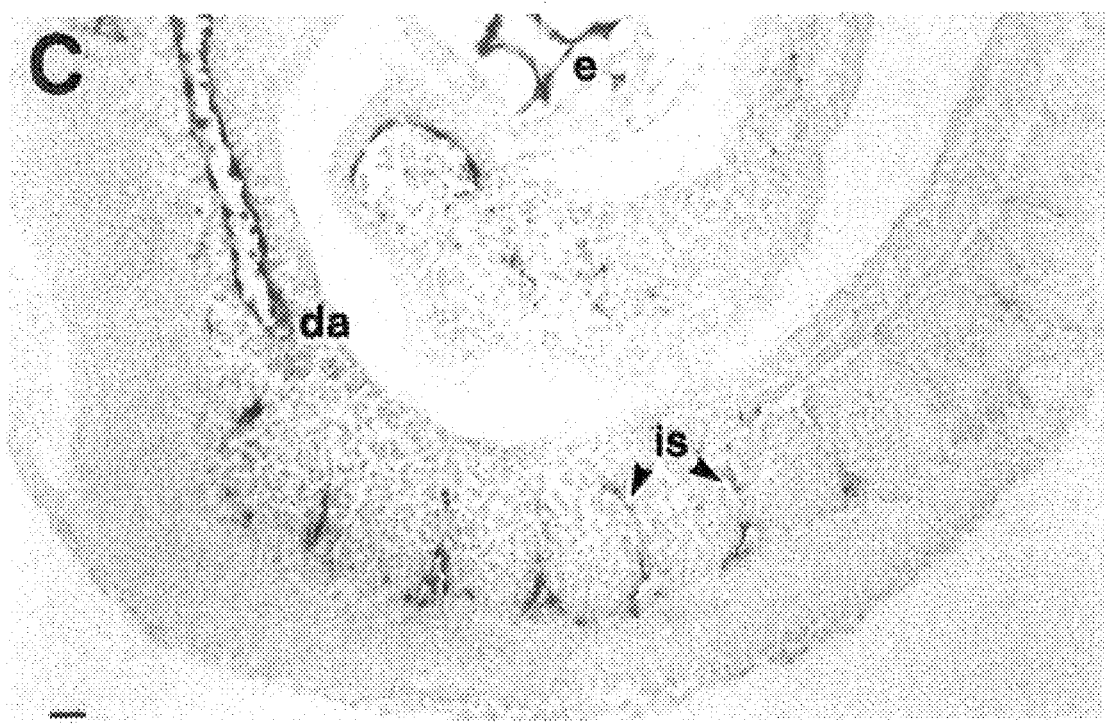
Figure 24:

The histological analysis of the yolk sacs from wild-type or heterozygous embryos harvested on E9.5 revealed that the blood vessels in the yolk sac appeared distended (FIGS. 23C & D) and were very often packed with blood (FIG. 24C & D). In contrast, several yolk sacs isolated from homozygous embryos contained little or no blood (FIG. 22F). Prior to dissection of these embryos, however, blood could be detected in the yolk sac cavity, indicating that the lack of blood in the yolk sac vasculature was due to hemorrhaging. In addition, the yolk sac vessels contained considerably fewer endothelial cells (FIG. 22F) than heterozygous littermates (FIG. 22C). Furthermore, vascular hemorrhaging of homozygous embryos could also be detected histologically when the trunk region was examined. Primitive blood cells could be seen throughout the body of the embryo distributed among the mesenchymal cells (FIGS. 22B & E). The dorsal aorta in heterozygous embryos was well defined with endothelial cells lining the lumen of the vessel and there was no blood in the trunk (FIG. 22B). In contrast, in homozygous embryos the endothelium of the dorsal aorta was disorganized and appeared to have ruptured, resulting in blood cells in the body (FIG. 22E). Localized hemorrhaging of the embryonic vasculature most likely results in a decrease in the embryonic blood pressure which may explain the accumulation of blood in the yolk sac vasculature and embryonic portion of the placenta (FIG. 22D). This region of the placenta also had very few endothelial cells in the sinuses as compared to a heterozygous littermate (FIGS. 22A & D). These results clearly demonstrate that $tek^{Asp}/tek^{Asp}$ embryos have a striking deficiency in the endothelium, resulting in hemorrhaging and pooling of blood in body cavities.

Figure 21D:
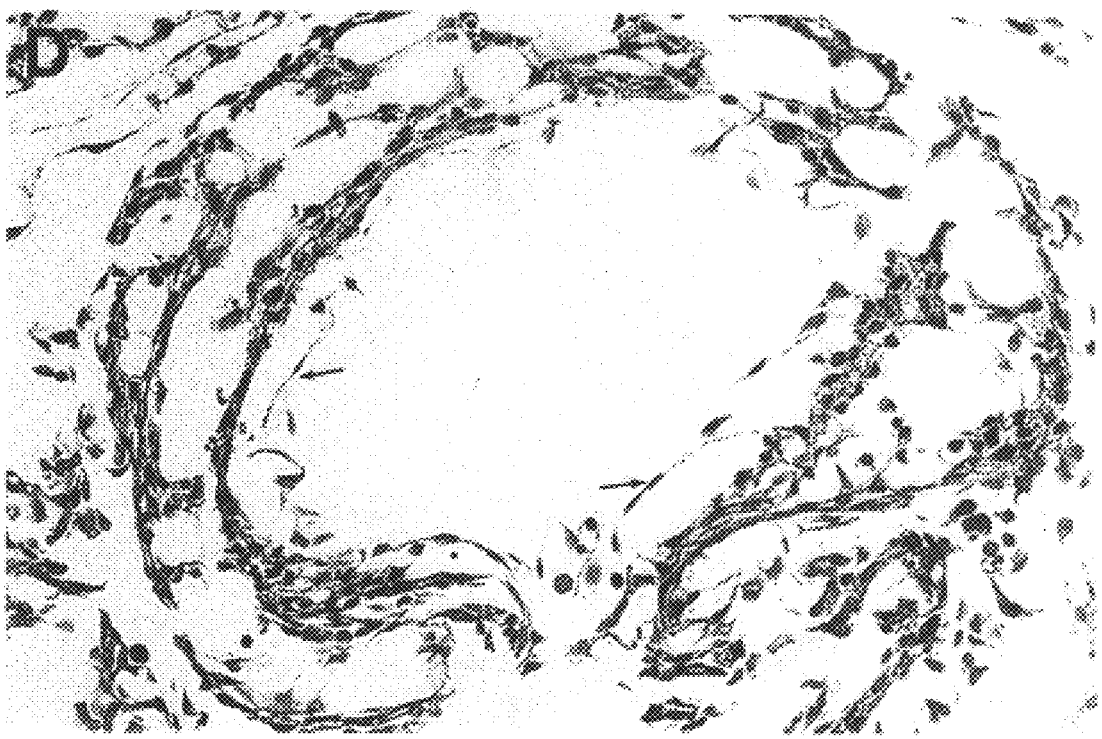

The hearts of $tek^{Asp}$ homozygous embryos were severely under-developed (FIG. 21D). The myocardium of E9.5 mutant embryos did not possess a detailed organization of trabeculae and the overall growth of the myocardium seems to be reduced. Furthermore, fewer endothelial cells were seen in the endocardium (FIG. 21D).

Analysis of flk-1, tek, and tie expression in $tek^{Asp}$ embryos

That there were few remaining endothelial cells in homozygous embryos was confirmed by RNA in situ hybridization of sections prepared from both $tek^{Asp}$ homozygous and heterozygous embryos with a flk-1 antisense riboprobe. Both heterozygous and homozygous embryos (data not shown) contained flk-1-positive cells organized in a distinctive vascular network. However, the flk-1 positive cells in homozygous mutant embryos were present in discontinuous chains, suggesting that the vessels contained a sparsely populated endothelium (data not shown). Moreover the levels of flk-1 expression were lower in the homozygous mutants. Adjacent sections probed for the expression of tek and tie demonstrated that tie transcripts were present albeit at lower levels than in heterozygous embryos (data not shown), whereas no tek signals could be detected in homozygous $tek^{Asp}$ embryos (data not shown). These results demonstrate that the $tek^{Asp}$ mutant allele does not produce a normal transcript, confirming that it is a null allele. Very interestingly, these results also demonstrate that tie expression in endothelial cells is not dependent on prior expression of tek.

$tek^{Asp}/tek^{Asp}$ Embryos Have a Reduced Number of Endothelial Cells

In order to follow the fate of tek expressing endothelial cells in mutant embryos, a tek-promoter-LacZ transgene gene was crossed onto the $tek^{Asp}$ mutant background. Adult mice bearing the tek-promoter-lacZ, $tek^{Asp}/+$ genotype were then used to generate homozygous embryos carrying the $tek^{Asp}$ mutation and the transgene. The tek-promoter-lacZ transgenic line used in these studies expresses the LacZ reporter gene in a manner which virtually recapitulates the endogenous tek expression profile.

Based on β-galactosidase (β-gal) activity, $tek^{Asp}$ homozygous embryos isolated on E8.5 and E9.0 contained a normally patterned vasculature in both extra- and embryonic tissues (FIGS. 24A–D and data not shown). Moreover, the size of normal and homozygous embryos at these gestational ages were the same (FIGS. 24A–D and data not shown), suggesting that the growth of the embryo up to E9.0 is not dependent on Tek. However, it is clear that the level of β-gal staining in these homozygous embryos was reduced (FIGS. 24A–D and 25A–D, and data not shown). Histological examination of E9.0 homozygous embryos confirmed that proper patterning of the vasculature was initiated (FIGS. 24A & B, and data not shown). Furthermore, the endocardium and other vascular structures of mutant embryos formed correctly but contained only low levels of LacZ expression, in keeping with the low levels of flk-1 and tie expression detected in these cells (FIG. 24A–D and data not shown).

FIGS. 25A–D show endothelial cells in the yolk sac of $tek^{Asp}$ homozygous embryos express low levels of the tek-lacZ transgene. Thin sections taken from the yolk sacs presented in FIGS. 25A–D illustrate tek-promoter-lacz expression (arrowheads) in the endothelial cells of E8.5 (25A,C) and E9.0 (25B,D) $tek^{Asp}$ homozygous (25C,D) and wild type (25A,B) embryos. These photomicrographs show both a reduction in the number of blue staining endothelial cells and a decrease in the levels of β-Galactosidase activity in the mutants. In addition, increased blood cell number can be seen in the blood vessels of $tek^{Asp}$ homozygous embryos. Bars: A&C=25 μm; B&D=12.5 μm.

Figure 25:
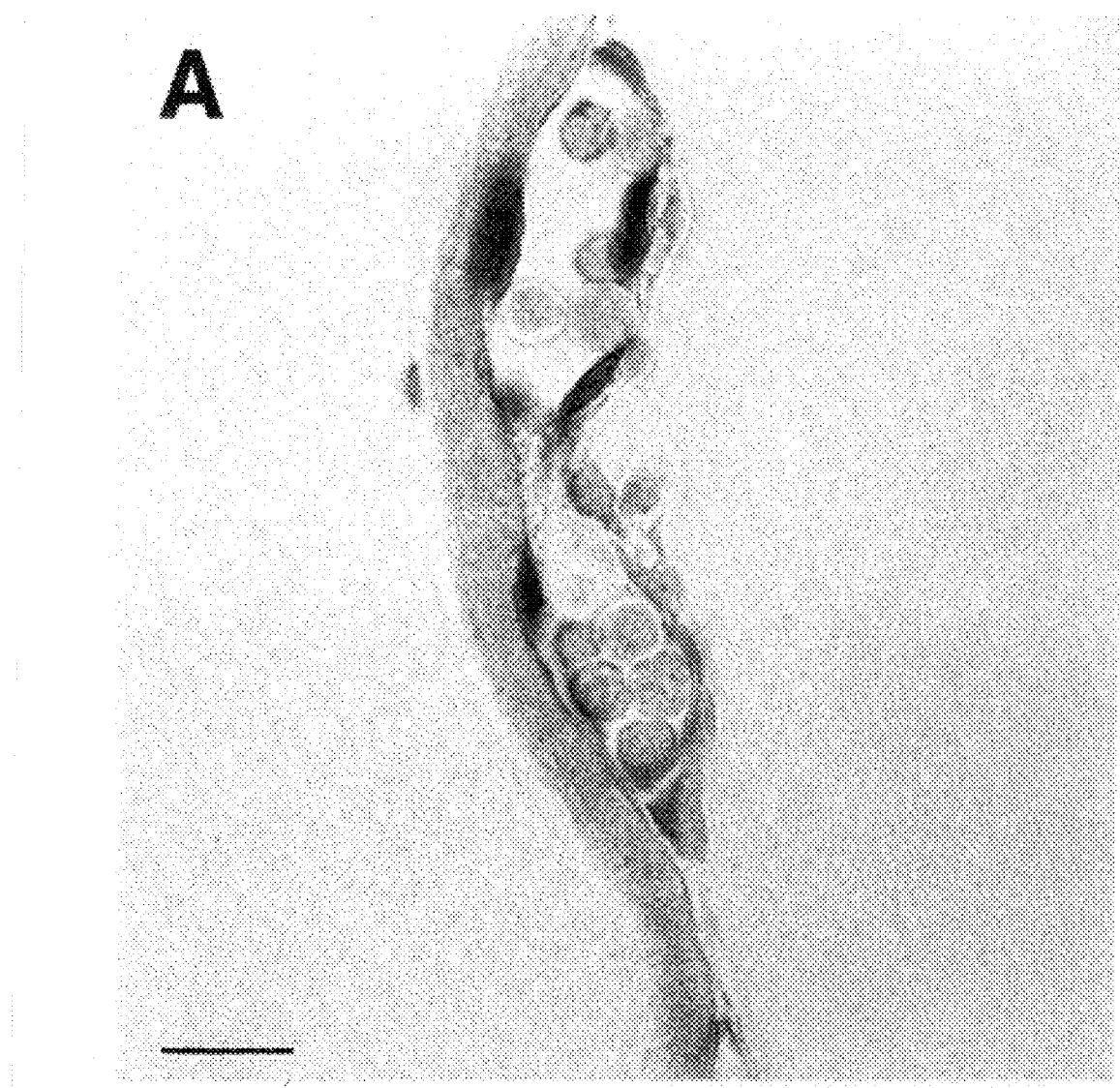
FIG. 25 shows expression of the tek-promoter-lacZ transgene in tek$^{\Delta sp}$ homozygous embryos as follows: 25A shows expression in the endothelial cells of E8.5 wild type embryos, 25B shows expression in the endothelial cells of E9.0 wild type embryos, 25C shows expression in the endothelial cells of E8.5 tek$^{\Delta sp}$ homozygous embryos and 25D shows expression in the endothelial cells of E9.0 tek$^{\Delta sp}$ homozygous embryos.
Figure 25B:
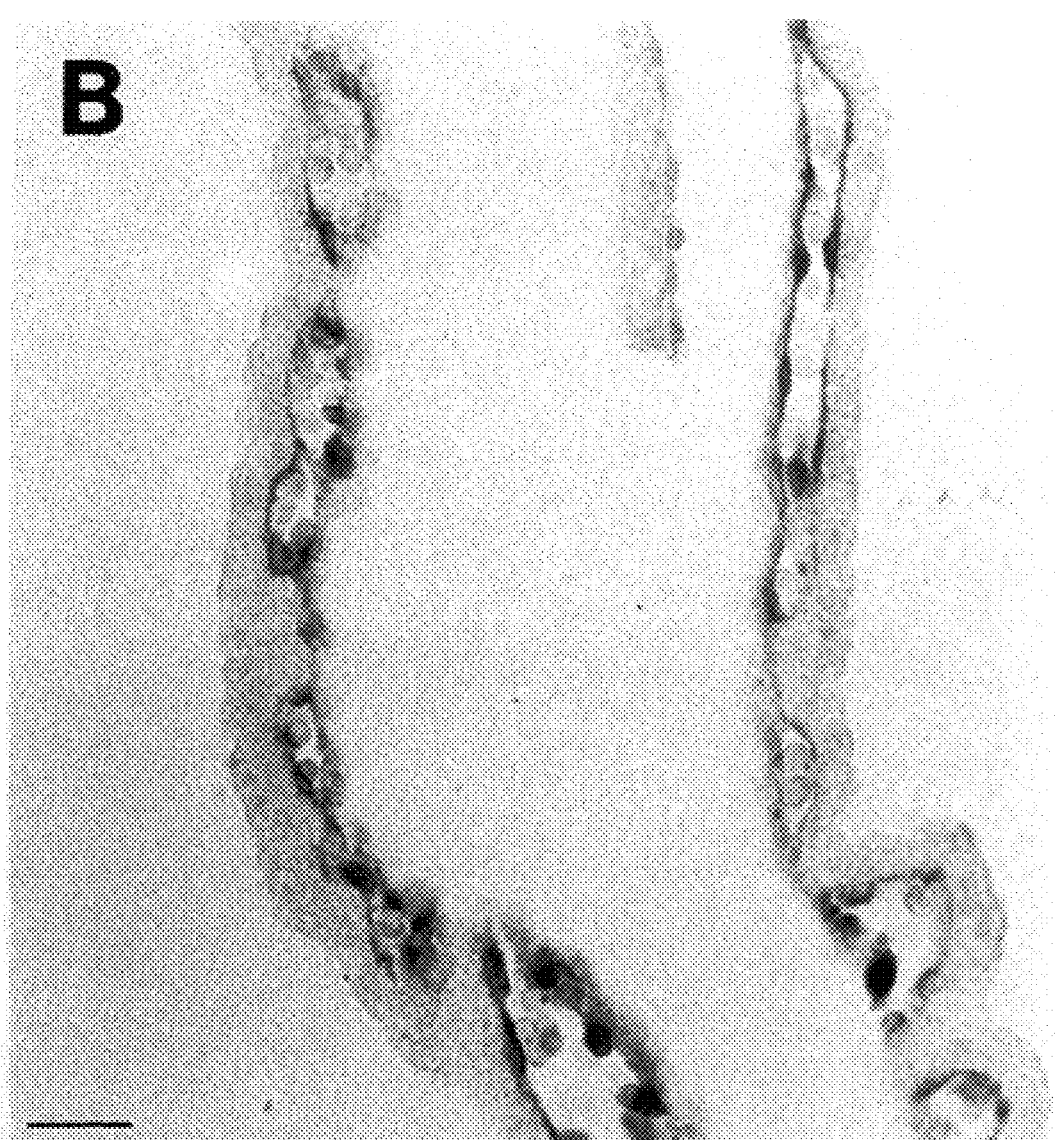
Figure 25:
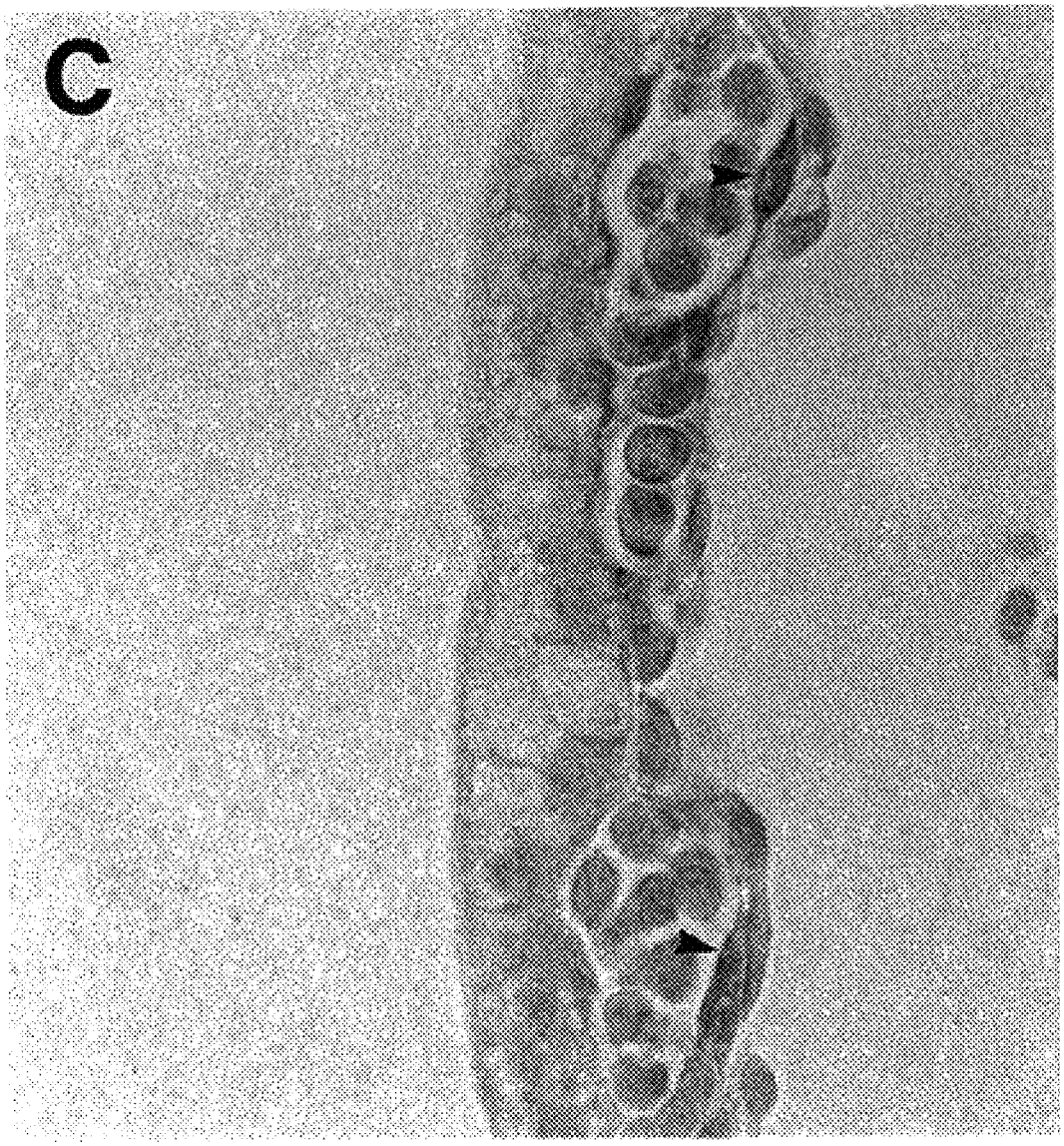
Figure 25:
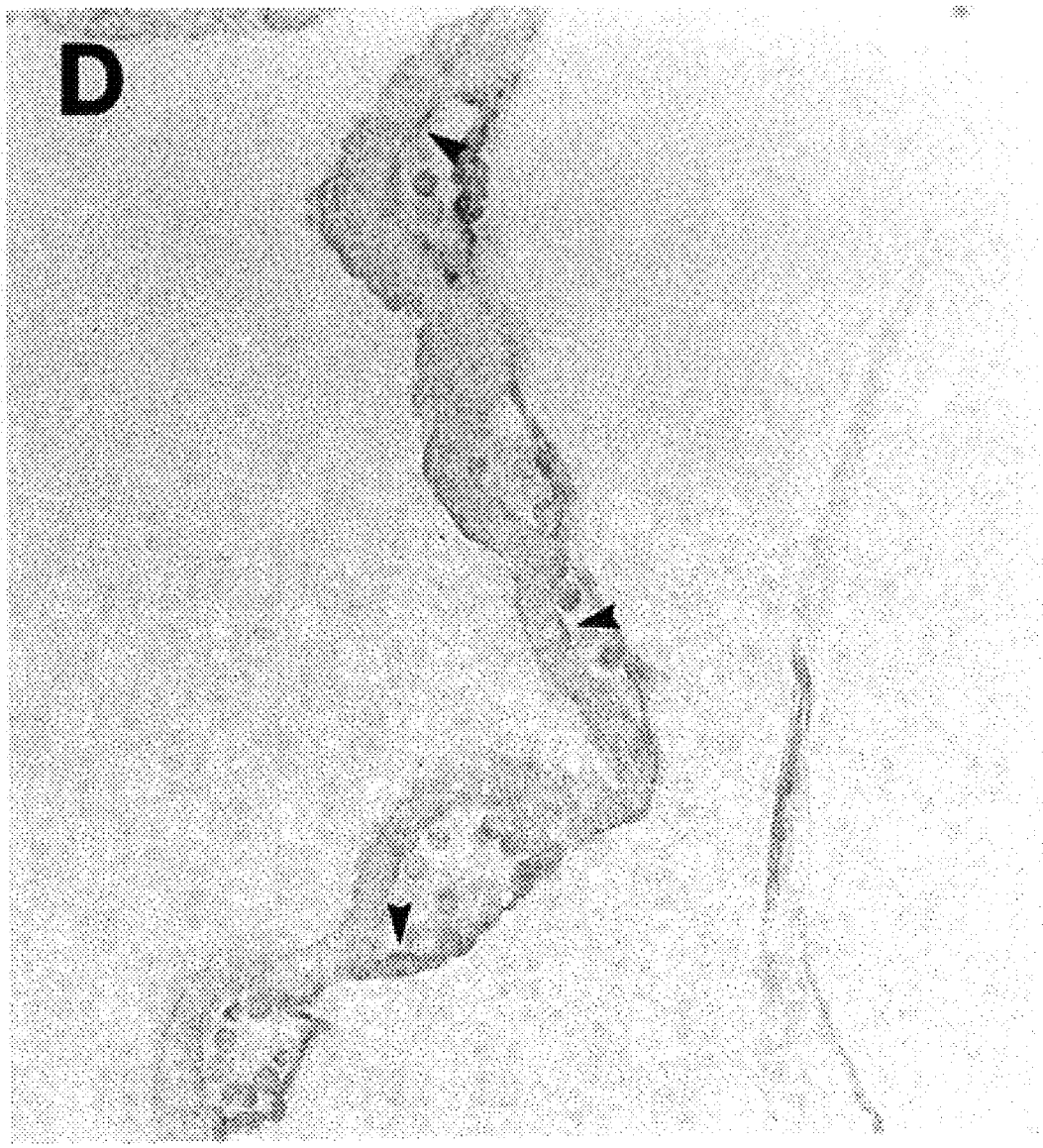

As shown in the Figures, histological analysis of the yolk sacs of $tek^{Asp}$ homozygous mutants revealed that the number of lacZ expressing endothelial cells lining the blood islands was reduced in E8.5 $tek^{Asp}$ homozygous embryos (FIG. 25C) compared to their normal littermates (FIG. 25A). This decrease in cell number and staining intensity was even more accentuated in sections taken from E9.0 homozygous embryos (FIGS. 25B & D). The blood islands also contained cells with an endothelial cell-like morphology which did not stain blue, whereas this was never observed in normal transgenic mice.

Table 5 summarizes the number of blue endothelial cells found in the yolk sacs of transgenic embryos. The number of endoderm cells found in each blood island did not vary significantly for any of the embryos and thus was used to normalize the values. Day 8.5 $tek^{Asp}$ homozygous embryos possessed approximately 30% fewer endothelial cells within the blood islands as compared to their normal littermates. On E9.0, one half day later in development, 75% fewer endothelial cells were detected in the yolk sac of $tek^{Asp}$ homozygous mutant embryos. These results clearly demonstrate that the number of endothelial cells present within homozygous embryos at the times analyzed is significantly lower than that of their normal littermates and that as development progresses the number of endothelial cells decreases. Moreover, the very low levels of LacZ expression detected in many cells suggests that these cells are probably compromised metabolically and are dying.

TABLE 1

| Protein tyrosine kinase cDNAs isolated by RT-PCR | | | | | |
|---|---|---|---|---|---|
| Embryonic Age | cDNA | | | | |
| (Days) | tek | pdgfrb | c-abl | c-src | bmk |
| 9.5 | 26 | 7 | 2 | 1 | 1 |
| 12.5 | 5 | 10 | — | — | — |

TABLE 2

Cosegregation of the tek, brown, and pmv-23 loci in A × D strains.

| Locus | 1 | 2 | 3 | 6 | 7 | 8 | 9 | 10 | 11 | 12 | 13 | 14 | 15 | 16 | 18 | 20 | 21 | 22 | 23 | 24 | 25 | 26 | 27 | 28 |
|---|---|---|---|---|---|---|---|---|---|---|---|---|---|---|---|---|---|---|---|---|---|---|---|---|
| tek | D | D | A | D | D | A | A | A | D | A | D | A | D | D | D | D | A | D | D | A | D | D | D | D |
| brown | D | D | A | D | D | A | A | A | D | A | A | A | D | D | D | D | A | D | A | A | D | D | D | D |
| pmv-23 | D | D | A | D | D | A | D | A | D | A | D | D | D | A | D | D | A | D | D | A | D | D | D | A |

TABLE 3

Delayed development among Tek$^{A853}$ Dominant-Negative Transgenic Embryos

| Transgene | Total Embryos Recovered | Total Transgenic (TG) | Total Devel Delayed (DD) | DD-TG/DD |
|---|---|---|---|---|
| Polyoma-tek$^{A853}$ | 126 | 19 | 6$^\#$ | 5*/6 |
| tek-tek$^{A853}$ | 64 | 6 | 2$^\#$ | 2/2 |
| β-actin-tek$^{A853}$ | 20 | 6 | 0 | — |

*One embryo comprised a small amorphous mass of necrotic cells that was undergoing resorption at the time of assay. As such, it was considered to be phenolypically distinct from the group of transgenic embryos showing the TeK$^{A853}$ dominant negative phenotype.

$^\#$All embryos were obtained for analysis on E9.5 except that two were discovered with the polyoma driven transgene on E10.5 and 1 with the tek-promoter on E10.5.

TABLE 4

Genotypes of progeny of $F_1$ intercrosses of tek$^{\Delta sp}$/+ heterzygous mice

| | Genotypes | | | | | |
|---|---|---|---|---|---|---|
| | neonates | | | E9.5 | | |
| Clone | +/+ | +/− | −/− | +/+ | +/− | −/− |
| 24 | 108 | 57 | 0 | 9 | 6 | 7 |
| 19 | 11 | 4 | 0 | 3 | 1 | 1 |
| Total | 119 | 61 | 0 | 12 | 7 | 8 |

Genotyping was carried out by Southern analysis on DNA extracted from tails or from the dissected head of embryos

TABLE 5

The ratio of endoderm cells to LacZ-positive cells in the yolk sacs of embryos of F1 intercrosses of tek-LacZ/tek-LacZ; tek$^{\Delta sp}$/+ mice.

| Gestational Age (Days) | tek Geno-type | Total number of endoderm cells per blood island$^\#$ | Total number of LacZ$^+$ expressing cells per blood island | Number of LacZ$^+$ cells per 100 endoderm cells |
|---|---|---|---|---|
| 8.5 | +/− | 7.8 ± 0.9 (24) | 4.5 ± 0.7 | 54 ± 12 |
| 8.5 | −/− | 6.1 ± 1.1 (45) | 1.0 ± 0.8 | 35 ± 7 |
| 9.0 | +/− | 11.8 ± 0.3 (27) | 4.7 ± 0.6 | 39 ± 6 |
| 9.0 | −/− | 11.8 ± 3 (21) | 1.1 ± 0.9 | 8 ± 4 |

$^\#$Numbers reflect the mean ± S.D. and the number in brackets represents the number of blood islands counted per section.

We claim:

1. An isolated and purified polypeptide comprising amino acids 19 to 744 of SEQ ID NO: 6.

2. A fusion protein comprising a polypeptide as claimed in claim 1 and a lymphokine or an immunoglobulin molecule.

3. A fusion protein comprising a polypeptide as claimed in claim 1 and interferon, tumor necrosis factor, Il-1, Il-2, IL-3, Il-4, IL-5, IL-6, IL-7, IL-8, IL-9, IL-10, IL-11, GM-CSF, CSF-1, or G-CSF.

4. An isolated and purified receptor tyrosine kinase protein comprising SEQ ID NO:2, NO:4, or NO: 6.

5. An isolated and purified protein consisting of the amino acid sequence of amino acids 19 to 744 of SEQ. ID. NO: 6.

* * * * *

SEQUENCE LISTING (1) GENERAL INFORMATION:

(iii) NUMBER OF SEQUENCES: 32

(2) INFORMATION FOR SEQ ID NO:1:

(i) SEQUENCE CHARACTERISTICS:
      (A) LENGTH: 4175 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (v) FRAGMENT TYPE: N-terminal (vi) ORIGINAL SOURCE:
      (A) ORGANISM: Mus musculus
      (B) STRAIN: CD-1

(D) DEVELOPMENTAL STAGE: Embryo
(F) TISSUE TYPE: Heart (vii) IMMEDIATE SOURCE:
    (B) CLONE: Tek (viii) POSITION IN GENOME:
    (A) CHROMOSOME/SEGMENT: 4
    (B) MAP POSITION: Between the brown and pmv-23 loci (ix) FEATURE:
    (A) NAME/KEY: CDS
    (B) LOCATION: 124..3478

(xi) SEQUENCE DESCRIPTION: SEQ ID NO:1:

```
GCCAACTTGT AAACAAGAGC GAGTGGACCA TGCGAGCGGG AAGTCGCAAA GTTGTGAGTT      60

GTTGAAAGCT TCCCAGGGAC TCATGCTCAT CTGTGGACGC TGGATGGGGA GATCTGGGGA     120

AGT ATG GAC TCT TTA GCC GGC TTA GTT CTC TGT GGA GTC AGC TTG CTC       168
    Met Asp Ser Leu Ala Gly Leu Val Leu Cys Gly Val Ser Leu Leu
    1               5                   10                  15

CTT TAT GGA GTA GTA GAA GGC GCC ATG GAC CTG ATC TTG ATC AAT TCC       216
Leu Tyr Gly Val Val Glu Gly Ala Met Asp Leu Ile Leu Ile Asn Ser
                20                  25                  30

CTA CCT CTT GTG TCT GAT GCC GAA ACA TCC CTC ACC TGC ATT GCC TCT       264
Leu Pro Leu Val Ser Asp Ala Glu Thr Ser Leu Thr Cys Ile Ala Ser
            35                  40                  45

GGG TGG CAC CCC CAT GAG CCC ATC ACC ATA GGA AGG GAC TTT GAA GCC       312
Gly Trp His Pro His Glu Pro Ile Thr Ile Gly Arg Asp Phe Glu Ala
        50                  55                  60

TTA ATG AAC CAG CAC CAA GAT CCA CTG GAG GTT ACT CAA GAT GTG ACC       360
Leu Met Asn Gln His Gln Asp Pro Leu Glu Val Thr Gln Asp Val Thr
    65                  70                  75

AGA GAA TGG GCG AAA AAA GTT GTT TGG AAG AGA GAA AAG GCC AGT AAG       408
Arg Glu Trp Ala Lys Lys Val Val Trp Lys Arg Glu Lys Ala Ser Lys
80                  85                  90                  95

ATT AAT GGT GCT TAT TTC TGT GAA GGT CGA GTT CGA GGA CAG GCT ATA       456
Ile Asn Gly Ala Tyr Phe Cys Glu Gly Arg Val Arg Gly Gln Ala Ile
                100                 105                 110

AGG ATA CGG ACC ATG AAG ATG CGT CAA CAA GCA TCC TTC CTA CCT GCT       504
Arg Ile Arg Thr Met Lys Met Arg Gln Gln Ala Ser Phe Leu Pro Ala
            115                 120                 125

ACT TTA ACT ATG ACC GTG GAC AGG GGA GAT AAT GTG AAC ATA TCT TTC       552
Thr Leu Thr Met Thr Val Asp Arg Gly Asp Asn Val Asn Ile Ser Phe
        130                 135                 140

AAA AAG GTG TTA ATT AAA GAA GAA GAT GCA GTG ATT TAC AAA AAT GGC       600
Lys Lys Val Leu Ile Lys Glu Glu Asp Ala Val Ile Tyr Lys Asn Gly
    145                 150                 155

TCC TTC ATC CAC TCA GTG CCC CGG CAT GAA GTA CCT GAT ATT TTA GAA       648
Ser Phe Ile His Ser Val Pro Arg His Glu Val Pro Asp Ile Leu Glu
160                 165                 170                 175

GTT CAC TTG CCG CAT GCT CAG CCC CAG GAT GCT GGT GTG TAC TCG GCC       696
Val His Leu Pro His Ala Gln Pro Gln Asp Ala Gly Val Tyr Ser Ala
                180                 185                 190

AGG TAC ATA GGA GGA AAC CTG TTC ACC TCA GCC TTC ACC AGG CTG ATT       744
Arg Tyr Ile Gly Gly Asn Leu Phe Thr Ser Ala Phe Thr Arg Leu Ile
            195                 200                 205

GTT CGG AGA TGT GAA GCT CAG AAG TGG GGG CCC GAC TGT AGC CGT CCT       792
Val Arg Arg Cys Glu Ala Gln Lys Trp Gly Pro Asp Cys Ser Arg Pro
        210                 215                 220

TGT ACT ACT TGC AAG AAC AAT GGA GTC TGC CAT GAA GAT ACC GGG GAA       840
Cys Thr Thr Cys Lys Asn Asn Gly Val Cys His Glu Asp Thr Gly Glu
    225                 230                 235
```

-continued

| | | |
|---|---|---|
| TGC ATT TGC CCT CCT GGG TTT ATG GGG AGA ACA TGT GAG AAA GCT TGT<br>Cys Ile Cys Pro Pro Gly Phe Met Gly Arg Thr Cys Glu Lys Ala Cys<br>240                   245                   250                   255 | 888 |
| GAG CCG CAC ACA TTT GGC AGG ACC TGT AAA GAA AGG TGT AGT GGA CCA<br>Glu Pro His Thr Phe Gly Arg Thr Cys Lys Glu Arg Cys Ser Gly Pro<br>                260                   265                   270 | 936 |
| GAA GGA TGC AAG TCT TAT GTG TTC TGT CTC CCA GAC CCT TAC GGG TGT<br>Glu Gly Cys Lys Ser Tyr Val Phe Cys Leu Pro Asp Pro Tyr Gly Cys<br>                   275                   280                   285 | 984 |
| TCC TGT GCC ACA GGC TGG AGG GGG TTG CAG TGC AAT GAA GCA TGC CCA<br>Ser Cys Ala Thr Gly Trp Arg Gly Leu Gln Cys Asn Glu Ala Cys Pro<br>             290                   295                   300 | 1032 |
| TCT GGT TAC TAC GGA CCA GAC TGT AAG CTC AGG TGC CAC TGT ACC AAT<br>Ser Gly Tyr Tyr Gly Pro Asp Cys Lys Leu Arg Cys His Cys Thr Asn<br>305                   310                   315 | 1080 |
| GAA GAG ATA TGT GAT CGG TTC CAA GGA TGC CTC TGC TCT CAA GGA TGG<br>Glu Glu Ile Cys Asp Arg Phe Gln Gly Cys Leu Cys Ser Gln Gly Trp<br>320                   325                   330                   335 | 1128 |
| CAA GGG CTG CAG TGT GAG AAA GAA GGC AGG CCA AGG ATG ACT CCA CAG<br>Gln Gly Leu Gln Cys Glu Lys Glu Gly Arg Pro Arg Met Thr Pro Gln<br>                   340                   345                   350 | 1176 |
| ATA GAG GAT TTG CCA GAT CAC ATT GAA GTA AAC AGT GGA AAA TTT AAC<br>Ile Glu Asp Leu Pro Asp His Ile Glu Val Asn Ser Gly Lys Phe Asn<br>             355                   360                   365 | 1224 |
| CCC ATC TGC AAA GCC TCT GGG TGG CCA CTA CCT ACT AGT GAA GAA ATG<br>Pro Ile Cys Lys Ala Ser Gly Trp Pro Leu Pro Thr Ser Glu Glu Met<br>370                   375                   380 | 1272 |
| ACC CTA GTG AAG CCA GAT GGG ACA GTG CTC CAA CCA AAT GAC TTC AAC<br>Thr Leu Val Lys Pro Asp Gly Thr Val Leu Gln Pro Asn Asp Phe Asn<br>385                   390                   395 | 1320 |
| TAT ACA GAT CGT TTC TCA GTG GCC ATA TTC ACT GTC AAC CGA GTC TTA<br>Tyr Thr Asp Arg Phe Ser Val Ala Ile Phe Thr Val Asn Arg Val Leu<br>400                   405                   410                   415 | 1368 |
| CCT CCT GAC TCA GGA GTC TGG GTC TGC AGT GTG AAC ACA GTG GCT GGG<br>Pro Pro Asp Ser Gly Val Trp Val Cys Ser Val Asn Thr Val Ala Gly<br>                   420                   425                   430 | 1416 |
| ATG GTG GAA AAG CCT TTC AAC ATT TCC GTC AAA GTT CTT CCA GAG CCC<br>Met Val Glu Lys Pro Phe Asn Ile Ser Val Lys Val Leu Pro Glu Pro<br>                   435                   440                   445 | 1464 |
| CTG CAC GCC CCA AAT GTG ATT GAC ACT GGA CAT AAC TTT GCT ATC ATC<br>Leu His Ala Pro Asn Val Ile Asp Thr Gly His Asn Phe Ala Ile Ile<br>             450                   455                   460 | 1512 |
| AAT ATC AGC TCT GAG CCT TAC TTT GGG GAT GGA CCC ATC AAA TCC AAG<br>Asn Ile Ser Ser Glu Pro Tyr Phe Gly Asp Gly Pro Ile Lys Ser Lys<br>465                   470                   475 | 1560 |
| AAG CTT TTC TAT AAA CCT GTC AAT CAG GCC TGG AAA TAC ATT GAA GTG<br>Lys Leu Phe Tyr Lys Pro Val Asn Gln Ala Trp Lys Tyr Ile Glu Val<br>480                   485                   490                   495 | 1608 |
| ACG AAT GAG ATT TTC ACT CTC AAC TAC TTG GAG CCG CGG ACT GAC TAC<br>Thr Asn Glu Ile Phe Thr Leu Asn Tyr Leu Glu Pro Arg Thr Asp Tyr<br>                   500                   505                   510 | 1656 |
| GAG CTG TGT GTG CAG CTG GCC CGT CCT GGA GAG GGT GGA GAA GGG CAT<br>Glu Leu Cys Val Gln Leu Ala Arg Pro Gly Glu Gly Gly Glu Gly His<br>             515                   520                   525 | 1704 |
| CCT GGG CCT GTG AGA CGA TTT ACA ACA GCG TGT ATC GGA CTC CCT CCT<br>Pro Gly Pro Val Arg Arg Phe Thr Thr Ala Cys Ile Gly Leu Pro Pro<br>530                   535                   540 | 1752 |
| CCA AGA GGT CTC AGT CTC CTG CCA AAA AGC CAG ACA GCT CTA AAT TTG<br>Pro Arg Gly Leu Ser Leu Leu Pro Lys Ser Gln Thr Ala Leu Asn Leu<br>545                   550                   555 | 1800 |

```
ACT TGG CAA CCG ATA TTT ACA AAC TCA GAA GAT GAA TTT TAT GTG GAA       1848
Thr Trp Gln Pro Ile Phe Thr Asn Ser Glu Asp Glu Phe Tyr Val Glu
560                 565                 570                 575

GTC GAG AGG CGA TCC CTG CAA ACA ACA AGT GAT CAG CAG AAC ATC AAA       1896
Val Glu Arg Arg Ser Leu Gln Thr Thr Ser Asp Gln Gln Asn Ile Lys
                580                 585                 590

GTG CCT GGG AAC CTG ACC TCG GTG CTA CTG AGC AAC TTA GTC CCC AGG       1944
Val Pro Gly Asn Leu Thr Ser Val Leu Leu Ser Asn Leu Val Pro Arg
            595                 600                 605

GAG CAG TAC ACA GTC CGA GCT AGA GTC AAC ACC AAG GCG CAG GGG GAG       1992
Glu Gln Tyr Thr Val Arg Ala Arg Val Asn Thr Lys Ala Gln Gly Glu
        610                 615                 620

TGG AGT GAA GAA CTC AGG GCC TGG ACC CTT AGT GAC ATT CTC CCT CCT       2040
Trp Ser Glu Glu Leu Arg Ala Trp Thr Leu Ser Asp Ile Leu Pro Pro
    625                 630                 635

CAA CCA GAA AAC ATC AAG ATC TCC AAC ATC ACT GAC TCC ACA GCT ATG       2088
Gln Pro Glu Asn Ile Lys Ile Ser Asn Ile Thr Asp Ser Thr Ala Met
640                 645                 650                 655

GTT TCT TGG ACA ATA GTG GAT GGC TAT TCG ATT TCT TCC ATC ATC ATC       2136
Val Ser Trp Thr Ile Val Asp Gly Tyr Ser Ile Ser Ser Ile Ile Ile
                660                 665                 670

CGG TAT AAG GTT CAG GGC AAA AAT GAA GAC CAG CAC ATT GAT GTG AAG       2184
Arg Tyr Lys Val Gln Gly Lys Asn Glu Asp Gln His Ile Asp Val Lys
            675                 680                 685

ATC AAG AAT GCT ACC GTT ACT CAG TAC CAG CTC AAG GGC CTA GAG CCA       2232
Ile Lys Asn Ala Thr Val Thr Gln Tyr Gln Leu Lys Gly Leu Glu Pro
        690                 695                 700

GAG ACT ACA TAC CAT GTG GAT ATT TTT GCT GAG AAC AAC ATA GGA TCA       2280
Glu Thr Thr Tyr His Val Asp Ile Phe Ala Glu Asn Asn Ile Gly Ser
    705                 710                 715

AGC AAC CCA GCC TTT TCT CAT GAA CTG AGG ACG CTT CCA CAT TCC CCA       2328
Ser Asn Pro Ala Phe Ser His Glu Leu Arg Thr Leu Pro His Ser Pro
720                 725                 730                 735

GGC TCT GCA GAC CTC GGA GGG GGA AAG ATG CTA CTC ATA GCC ATC CTT       2376
Gly Ser Ala Asp Leu Gly Gly Gly Lys Met Leu Leu Ile Ala Ile Leu
                740                 745                 750

GGG TCG GCT GGA ATG ACT TGC ATC ACC GTG CTG TTG GCG TTT CTG ATT       2424
Gly Ser Ala Gly Met Thr Cys Ile Thr Val Leu Leu Ala Phe Leu Ile
            755                 760                 765

ATG TTG CAA CTG AAG AGA GCA AAT GTC CAA AGG AGA ATG GCT CAG GCA       2472
Met Leu Gln Leu Lys Arg Ala Asn Val Gln Arg Arg Met Ala Gln Ala
        770                 775                 780

TTC CAG AAC AGA GAA GAA CCA GCT GTG CAG TTT AAC TCA GGA ACT CTG       2520
Phe Gln Asn Arg Glu Glu Pro Ala Val Gln Phe Asn Ser Gly Thr Leu
    785                 790                 795

GCC CTT AAC AGG AAG GCC AAA AAC AAT CCA GAT CCC ACA ATT TAT CCT       2568
Ala Leu Asn Arg Lys Ala Lys Asn Asn Pro Asp Pro Thr Ile Tyr Pro
800                 805                 810                 815

GTG CTT GAC TGG AAT GAC ATC AAG ATC GGA GAG GGC AAC TTT GGC CAG       2616
Val Leu Asp Trp Asn Asp Ile Lys Ile Gly Glu Gly Asn Phe Gly Gln
                820                 825                 830

GTT CTG AAG GCA CGC ATC AAG AAG GAT GGG TTA CGG ATG GAT GCC GCC       2664
Val Leu Lys Ala Arg Ile Lys Lys Asp Gly Leu Arg Met Asp Ala Ala
            835                 840                 845

ATC AAG AGG ATG AAA GAG TAT GCC TCC AAA GAT GAT CAC AGG GAC TTC       2712
Ile Lys Arg Met Lys Glu Tyr Ala Ser Lys Asp Asp His Arg Asp Phe
        850                 855                 860

GCA GGA GAA CTG GAG GTT CTT TGT AAA CTT GGA CAC CAT CCA AAC ATC       2760
Ala Gly Glu Leu Glu Val Leu Cys Lys Leu Gly His His Pro Asn Ile
    865                 870                 875
```

| | | |
|---|---|---|
| ATT AAT CTC TTG GGA GCA TGT GAA CAC CGA GGC TAT TTG TAC CTA GCT<br>Ile Asn Leu Leu Gly Ala Cys Glu His Arg Gly Tyr Leu Tyr Leu Ala<br>880                        885                     890                     895 | 2808 |
| ATT GAG TAT GCC CCG CAT GGA AAC CTC CTG GAC TTC CTG CGT AAG AGC<br>Ile Glu Tyr Ala Pro His Gly Asn Leu Leu Asp Phe Leu Arg Lys Ser<br>                   900                     905                     910 | 2856 |
| AGA GTG CTA GAG ACA GAC CCT GCT TTT GCC ATC GCC AAC AGT ACA GCT<br>Arg Val Leu Glu Thr Asp Pro Ala Phe Ala Ile Ala Asn Ser Thr Ala<br>         915                     920                     925 | 2904 |
| TCC ACA CTG TCC TCC CAA CAG CTT CTT CAT TTT GCT GCA GAT GTG GCC<br>Ser Thr Leu Ser Ser Gln Gln Leu Leu His Phe Ala Ala Asp Val Ala<br>             930                     935                     940 | 2952 |
| CGG GGG ATG GAC TAC TTG AGC CAG AAA CAG TTT ATC CAC AGG GAC CTG<br>Arg Gly Met Asp Tyr Leu Ser Gln Lys Gln Phe Ile His Arg Asp Leu<br>945                        950                     955 | 3000 |
| GCT GCC AGA AAC ATT TTA GTT GGT GAA AAC TAC ATA GCC AAA ATA GCA<br>Ala Ala Arg Asn Ile Leu Val Gly Glu Asn Tyr Ile Ala Lys Ile Ala<br>960                        965                     970                     975 | 3048 |
| GAT TTT GGA TTG TCA CGA GGT CAA GAA GTG TAT GTG AAA AAG ACA ATG<br>Asp Phe Gly Leu Ser Arg Gly Gln Glu Val Tyr Val Lys Lys Thr Met<br>             980                     985                     990 | 3096 |
| GGA AGG CTC CCA GTG CGT TGG ATG GCA ATC GAA TCA CTG AAC TAT AGT<br>Gly Arg Leu Pro Val Arg Trp Met Ala Ile Glu Ser Leu Asn Tyr Ser<br>         995                    1000                   1005 | 3144 |
| GTC TAT ACA ACC AAC AGT GAT GTC TGG TCC TAT GGT GTA TTG CTC TGG<br>Val Tyr Thr Thr Asn Ser Asp Val Trp Ser Tyr Gly Val Leu Leu Trp<br>            1010                   1015                   1020 | 3192 |
| GAG ATT GTT AGC TTA GGA GGC ACC CCC TAC TGC GGC ATG ACG TGC GCG<br>Glu Ile Val Ser Leu Gly Gly Thr Pro Tyr Cys Gly Met Thr Cys Ala<br>        1025                   1030                   1035 | 3240 |
| GAG CTC TAT GAG AAG CTA CCC CAG GGC TAC AGG CTG GAG AAG CCC CTG<br>Glu Leu Tyr Glu Lys Leu Pro Gln Gly Tyr Arg Leu Glu Lys Pro Leu<br>1040                  1045                  1050                   1055 | 3288 |
| AAC TGT GAT GAT GAG GTG TAT GAT CTA ATG AGA CAG TGC TGG AGG GAG<br>Asn Cys Asp Asp Glu Val Tyr Asp Leu Met Arg Gln Cys Trp Arg Glu<br>                    1060                  1065                  1070 | 3336 |
| AAG CCT TAT GAG AGA CCA TCA TTT GCC CAG ATA TTG GTG TCC TTA AAC<br>Lys Pro Tyr Glu Arg Pro Ser Phe Ala Gln Ile Leu Val Ser Leu Asn<br>              1075                  1080                  1085 | 3384 |
| AGG ATG CTG GAA GAA CGG AAG ACA TAC GTG AAC ACC ACA CTG TAT GAG<br>Arg Met Leu Glu Glu Arg Lys Thr Tyr Val Asn Thr Thr Leu Tyr Glu<br>        1090                   1095                   1100 | 3432 |
| AAG TTT ACC TAT GCA GGA ATT GAC TGC TCT GCG GAA GAA GCA GCC T<br>Lys Phe Thr Tyr Ala Gly Ile Asp Cys Ser Ala Glu Glu Ala Ala<br>       1105                   1110                   1115 | 3478 |
| AGAGCAGAAC TCTTCATGTA CAACGGCCAT TTCTCCTCAC TGGCGCGAGA GCCTTGACAC | 3538 |
| CTGTACCAAG CAAGCCACCC ACTGCCAAGA GATGTGATAT ATAAGTGTAT ATATTGTGCT | 3598 |
| GTGTTTGGGA CCCTCCTCAT ACAGCTCGTG CGGATCTGCA GTGTGTTCTG ACTCTAATGT | 3658 |
| GACTGTATAT ACTGCTCGGA GTAAGAATGT GCTAAGATCA GAATGCCTGT TCGTGGTTTC | 3718 |
| ATATAATATA TTTTTCTAAA AGCATAGATT GCACAGGAAG GTATGAGTAC AAATACTGTA | 3778 |
| ATGCATAACT TGTTATTGTC CTAGATGTGT TTGACATTTT TCCTTTACAA CTGAATGCTA | 3838 |
| TAAAAGTGTT TTGCTGTGTG CGCGTAAGAT ACTGTTCGTT AAAATAAGCA TTCCCTTGAC | 3898 |
| AGCACAGGAA GAAAAGCGAG GGAAATGTAT GGATTATATT AAATGTGGGT TACTACACAA | 3958 |
| GAGGCCGAAC ATTCCAAGTA GCAGAAGAGA GGGTCTCTCA ACTCTGCTCC TCACCTGCAG | 4018 |
| AAGCCAGTTT GTTTGGCCAT GTGACAATTG TCCTGTGTTT TTATAGCACC CAAATCATTC | 4078 |

```
TAAAATATGA ACATCTAAAA ACTTTGCTAG GAGACTAAGA ACCTTTGGAG AGATAGATAT    4138

AAGTACGGTC AAAAAACAAA ACTGCGCCAT GGTACCC                             4175
```

(2) INFORMATION FOR SEQ ID NO:2:

(i) SEQUENCE CHARACTERISTICS:
        (A) LENGTH: 1118 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asp Ser Leu Ala Gly Leu Val Leu Cys Gly Val Ser Leu Leu Leu
 1               5                  10                  15

Tyr Gly Val Val Glu Gly Ala Met Asp Leu Ile Leu Ile Asn Ser Leu
             20                  25                  30

Pro Leu Val Ser Asp Ala Glu Thr Ser Leu Thr Cys Ile Ala Ser Gly
         35                  40                  45

Trp His Pro His Glu Pro Ile Thr Ile Gly Arg Asp Phe Glu Ala Leu
     50                  55                  60

Met Asn Gln His Gln Asp Pro Leu Glu Val Thr Gln Asp Val Thr Arg
 65                  70                  75                  80

Glu Trp Ala Lys Lys Val Val Trp Lys Arg Glu Lys Ala Ser Lys Ile
                 85                  90                  95

Asn Gly Ala Tyr Phe Cys Glu Gly Arg Val Arg Gly Gln Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Arg Gly Asp Asn Val Asn Ile Ser Phe Lys
    130                 135                 140

Lys Val Leu Ile Lys Glu Glu Asp Ala Val Ile Tyr Lys Asn Gly Ser
145                 150                 155                 160

Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
        195                 200                 205

Arg Arg Cys Glu Ala Gln Lys Trp Gly Pro Asp Cys Ser Arg Pro Cys
    210                 215                 220

Thr Thr Cys Lys Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                245                 250                 255

Pro His Thr Phe Gly Arg Thr Cys Lys Glu Arg Cys Ser Gly Pro Glu
            260                 265                 270

Gly Cys Lys Ser Tyr Val Phe Cys Leu Pro Asp Pro Tyr Gly Cys Ser
        275                 280                 285

Cys Ala Thr Gly Trp Arg Gly Leu Gln Cys Asn Glu Ala Cys Pro Ser
    290                 295                 300

Gly Tyr Tyr Gly Pro Asp Cys Lys Leu Arg Cys His Cys Thr Asn Glu
305                 310                 315                 320

Glu Ile Cys Asp Arg Phe Gln Gly Cys Leu Cys Ser Gln Gly Trp Gln
                325                 330                 335

Gly Leu Gln Cys Glu Lys Glu Gly Arg Pro Arg Met Thr Pro Gln Ile
```

```
                    340              345              350
Glu Asp Leu Pro Asp His Ile Glu Val Asn Ser Gly Lys Phe Asn Pro
            355              360              365

Ile Cys Lys Ala Ser Gly Trp Pro Leu Pro Thr Ser Glu Glu Met Thr
370              375              380

Leu Val Lys Pro Asp Gly Thr Val Leu Gln Pro Asn Asp Phe Asn Tyr
385              390              395              400

Thr Asp Arg Phe Ser Val Ala Ile Phe Thr Val Asn Arg Val Leu Pro
            405              410              415

Pro Asp Ser Gly Val Trp Val Cys Ser Val Asn Thr Val Ala Gly Met
            420              425              430

Val Glu Lys Pro Phe Asn Ile Ser Val Lys Val Leu Pro Glu Pro Leu
            435              440              445

His Ala Pro Asn Val Ile Asp Thr Gly His Asn Phe Ala Ile Ile Asn
            450              455              460

Ile Ser Ser Glu Pro Tyr Phe Gly Asp Gly Pro Ile Lys Ser Lys Lys
465              470              475              480

Leu Phe Tyr Lys Pro Val Asn Gln Ala Trp Lys Tyr Ile Glu Val Thr
            485              490              495

Asn Glu Ile Phe Thr Leu Asn Tyr Leu Glu Pro Arg Thr Asp Tyr Glu
            500              505              510

Leu Cys Val Gln Leu Ala Arg Pro Gly Glu Gly Gly Glu Gly His Pro
            515              520              525

Gly Pro Val Arg Arg Phe Thr Thr Ala Cys Ile Gly Leu Pro Pro Pro
            530              535              540

Arg Gly Leu Ser Leu Leu Pro Lys Ser Gln Thr Ala Leu Asn Leu Thr
545              550              555              560

Trp Gln Pro Ile Phe Thr Asn Ser Glu Asp Glu Phe Tyr Val Glu Val
            565              570              575

Glu Arg Arg Ser Leu Gln Thr Thr Ser Asp Gln Gln Asn Ile Lys Val
            580              585              590

Pro Gly Asn Leu Thr Ser Val Leu Leu Ser Asn Leu Val Pro Arg Glu
            595              600              605

Gln Tyr Thr Val Arg Ala Arg Val Asn Thr Lys Ala Gln Gly Glu Trp
            610              615              620

Ser Glu Glu Leu Arg Ala Trp Thr Leu Ser Asp Ile Leu Pro Pro Gln
625              630              635              640

Pro Glu Asn Ile Lys Ile Ser Asn Ile Thr Asp Ser Thr Ala Met Val
            645              650              655

Ser Trp Thr Ile Val Asp Gly Tyr Ser Ile Ser Ser Ile Ile Ile Arg
            660              665              670

Tyr Lys Val Gln Gly Lys Asn Glu Asp Gln His Ile Asp Val Lys Ile
            675              680              685

Lys Asn Ala Thr Val Thr Gln Tyr Gln Leu Lys Gly Leu Glu Pro Glu
            690              695              700

Thr Thr Tyr His Val Asp Ile Phe Ala Glu Asn Asn Ile Gly Ser Ser
705              710              715              720

Asn Pro Ala Phe Ser His Glu Leu Arg Thr Leu Pro His Ser Pro Gly
            725              730              735

Ser Ala Asp Leu Gly Gly Gly Lys Met Leu Leu Ile Ala Ile Leu Gly
            740              745              750

Ser Ala Gly Met Thr Cys Ile Thr Val Leu Leu Ala Phe Leu Ile Met
            755              760              765
```

Leu Gln Leu Lys Arg Ala Asn Val Gln Arg Met Ala Gln Ala Phe
770             775                 780

Gln Asn Arg Glu Glu Pro Ala Val Gln Phe Asn Ser Gly Thr Leu Ala
785                 790                 795                 800

Leu Asn Arg Lys Ala Lys Asn Asn Pro Asp Pro Thr Ile Tyr Pro Val
                805                 810                 815

Leu Asp Trp Asn Asp Ile Lys Ile Gly Glu Gly Asn Phe Gly Gln Val
                820                 825                 830

Leu Lys Ala Arg Ile Lys Lys Asp Gly Leu Arg Met Asp Ala Ala Ile
                835                 840                 845

Lys Arg Met Lys Glu Tyr Ala Ser Lys Asp Asp His Arg Asp Phe Ala
850                 855                 860

Gly Glu Leu Glu Val Leu Cys Lys Leu Gly His His Pro Asn Ile Ile
865                 870                 875                 880

Asn Leu Leu Gly Ala Cys Glu His Arg Gly Tyr Leu Tyr Leu Ala Ile
                885                 890                 895

Glu Tyr Ala Pro His Gly Asn Leu Leu Asp Phe Leu Arg Lys Ser Arg
                900                 905                 910

Val Leu Glu Thr Asp Pro Ala Phe Ala Ile Ala Asn Ser Thr Ala Ser
                915                 920                 925

Thr Leu Ser Ser Gln Gln Leu Leu His Phe Ala Ala Asp Val Ala Arg
930                 935                 940

Gly Met Asp Tyr Leu Ser Gln Lys Gln Phe Ile His Arg Asp Leu Ala
945                 950                 955                 960

Ala Arg Asn Ile Leu Val Gly Glu Asn Tyr Ile Ala Lys Ile Ala Asp
                965                 970                 975

Phe Gly Leu Ser Arg Gly Gln Glu Val Tyr Val Lys Lys Thr Met Gly
                980                 985                 990

Arg Leu Pro Val Arg Trp Met Ala Ile Glu Ser Leu Asn Tyr Ser Val
                995                 1000                1005

Tyr Thr Thr Asn Ser Asp Val Trp Ser Tyr Gly Val Leu Leu Trp Glu
1010                1015                1020

Ile Val Ser Leu Gly Gly Thr Pro Tyr Cys Gly Met Thr Cys Ala Glu
1025                1030                1035                1040

Leu Tyr Glu Lys Leu Pro Gln Gly Tyr Arg Leu Glu Lys Pro Leu Asn
                1045                1050                1055

Cys Asp Asp Glu Val Tyr Asp Leu Met Arg Gln Cys Trp Arg Glu Lys
                1060                1065                1070

Pro Tyr Glu Arg Pro Ser Phe Ala Gln Ile Leu Val Ser Leu Asn Arg
                1075                1080                1085

Met Leu Glu Glu Arg Lys Thr Tyr Val Asn Thr Thr Leu Tyr Glu Lys
                1090                1095                1100

Phe Thr Tyr Ala Gly Ile Asp Cys Ser Ala Glu Glu Ala Ala
1105                1110                1115

(2) INFORMATION FOR SEQ ID NO:3:

(i) SEQUENCE CHARACTERISTICS:
        (A) LENGTH: 1601 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Mus musculus
        (D) DEVELOPMENTAL STAGE: Embryo (vii) IMMEDIATE SOURCE:
 (A) LIBRARY: Murine embryonic lambda gt10 cDNA library
 (B) CLONE: 1.6kb clone (viii) POSITION IN GENOME:
 (A) CHROMOSOME/SEGMENT: 4
 (B) MAP POSITION: Between the brown and pmv-23 loci (ix) FEATURE:
 (A) NAME/KEY: CDS
 (B) LOCATION: 1..903

(xi) SEQUENCE DESCRIPTION: SEQ ID NO:3:

```
ATC AAG TTT CAA GAC GTG ATC GGA GAG GGC AAC TTT GGC CAG GTT CTG        48
Ile Lys Phe Gln Asp Val Ile Gly Glu Gly Asn Phe Gly Gln Val Leu
 1               5                  10                  15

AAG GCA CGC ATC AAG AAG GAT GGG TTA CGG ATG GAT GCC GCC ATC AAG        96
Lys Ala Arg Ile Lys Lys Asp Gly Leu Arg Met Asp Ala Ala Ile Lys
                20                  25                  30

AGG ATG AAA GAG TAT GCC TCC AAA GAT GAT CAC AGG GAC TTC GCA GGA       144
Arg Met Lys Glu Tyr Ala Ser Lys Asp Asp His Arg Asp Phe Ala Gly
         35                  40                  45

GAA CTG GAG GTT CTT TGT AAA CTT GGA CAC CAT CCA AAC ATC ATT AAT       192
Glu Leu Glu Val Leu Cys Lys Leu Gly His His Pro Asn Ile Ile Asn
     50                  55                  60

CTC TTG GGA GCA TGT GAA CAC CGA GGC TAT TTG TAC CTA GCT ATT GAG       240
Leu Leu Gly Ala Cys Glu His Arg Gly Tyr Leu Tyr Leu Ala Ile Glu
 65                  70                  75                  80

TAT GCC CCG CAT GGA AAC CTC CTG GAC TTC CTG CGT AAG AGC AGA GTG       288
Tyr Ala Pro His Gly Asn Leu Leu Asp Phe Leu Arg Lys Ser Arg Val
                 85                  90                  95

CTA GAG ACA GAC CCT GCT TTT GCC ATC GCC AAC AGT ACA GCT TCC ACA       336
Leu Glu Thr Asp Pro Ala Phe Ala Ile Ala Asn Ser Thr Ala Ser Thr
            100                 105                 110

CTG TCC TCC CAA CAG CTT CTT CAT TTT GCT GCA GAT GTG GCC CGG GGG       384
Leu Ser Ser Gln Gln Leu Leu His Phe Ala Ala Asp Val Ala Arg Gly
        115                 120                 125

ATG GAC TAC TTG AGC CAG AAA CAG TTT ATC CAC AGG GAC CTG GCT GCC       432
Met Asp Tyr Leu Ser Gln Lys Gln Phe Ile His Arg Asp Leu Ala Ala
130                 135                 140

AGA AAC ATT TTA GTT GGT GAA AAC TAC ATA GCC AAA ATA GCA GAT TTT       480
Arg Asn Ile Leu Val Gly Glu Asn Tyr Ile Ala Lys Ile Ala Asp Phe
145                 150                 155                 160

GGA TTG TCA CGA GGT CAA GAA GTG TAT GTG AAA AAG ACA ATG GGA AGG       528
Gly Leu Ser Arg Gly Gln Glu Val Tyr Val Lys Lys Thr Met Gly Arg
                165                 170                 175

CTC CCA GTG CGT TGG ATG GCA ATC GAA TCA CTG AAC TAT AGT GTC TAT       576
Leu Pro Val Arg Trp Met Ala Ile Glu Ser Leu Asn Tyr Ser Val Tyr
            180                 185                 190

ACA ACC AAC AGT GAT GTC TGG TCC TAT GGT GTA TTG CTC TGG GAG ATT       624
Thr Thr Asn Ser Asp Val Trp Ser Tyr Gly Val Leu Leu Trp Glu Ile
        195                 200                 205

GTT AGC TTA GGA GGC ACC CCC TAC TGC GGC ATG ACG TGC GCG GAG CTC       672
Val Ser Leu Gly Gly Thr Pro Tyr Cys Gly Met Thr Cys Ala Glu Leu
    210                 215                 220

TAT GAG AAG CTA CCC CAG GGC TAC AGG CTG GAG AAG CCC CTG AAC TGT       720
Tyr Glu Lys Leu Pro Gln Gly Tyr Arg Leu Glu Lys Pro Leu Asn Cys
225                 230                 235                 240

GAT GAT GAG GTG TAT GAT CTA ATG AGA CAG TGC TGG AGG GAG AAG CCT       768
Asp Asp Glu Val Tyr Asp Leu Met Arg Gln Cys Trp Arg Glu Lys Pro
                245                 250                 255

TAT GAG AGA CCA TCA TTT GCC CAG ATA TTG GTG TCC TTA AAC AGG ATG       816
```

```
            Tyr Glu Arg Pro Ser Phe Ala Gln Ile Leu Val Ser Leu Asn Arg Met
                260                 265                 270

CTG GAA GAA CGG AAG ACA TAC GTG AAC ACC ACA CTG TAT GAG AAG TTT            864
Leu Glu Glu Arg Lys Thr Tyr Val Asn Thr Thr Leu Tyr Glu Lys Phe
        275                 280                 285

ACC TAT GCA GGA ATT GAC TGC TCT GCG GAA GAA GCA GCC TAGAGCAGAA             913
Thr Tyr Ala Gly Ile Asp Cys Ser Ala Glu Glu Ala Ala
        290                 295                 300

CTCTTCATGT ACAACGGCCA TTTCTCCTCA CTGGCGCGAG AGCCTTGACA CCTGTACCAA          973

GCAAGCCACC CACTGCCAAG AGATGTGATA TATAAGTGTA TATATTGTGC TGTGTTTGGG         1033

ACCCTCCTCA TACAGCTCGT GCGGATCTGC AGTGTGTTCT GACTCTAATG TGACTGTATA         1093

TACTGCTCGG AGTAAGAATG TGCTAAGATC AGAATGCCTG TTCGTGGTTT CATATAATAT         1153

ATTTTTCTAA AAGCATAGAT TGCACAGGAA GGTATGAGTA CAAATACTGT AATGCATAAC         1213

TTGTTATTGT CCTAGATGTG TTTGACATTT TTCCTTTACA ACTGAATGCT ATAAAAGTGT         1273

TTTGCTGTGT GCGCGTAAGA TACTGTTCGT TAAAATAAGC ATTCCCTTGA CAGCACAGGA         1333

AGAAAAGCGA GGGAAATGTA TGGATTATAT TAAATGTGGG TTACTACACA AGAGGCCGAA         1393

CATTCCAAGT AGCAGAAGAG AGGGTCTCTC AACTCTGCTC CTCACCTGCA GAAGCCAGTT         1453

TGTTTGGCCA TGTGACAATT GTCCTGTGTT TTTATAGCAC CCAAATCATT CTAAAATATG         1513

AACATCTAAA AACTTTGCTA GGAGACTAAG AACCTTTGGA GAGATAGATA TAAGTACGGT         1573

CAAAAAACAA AACTGCGCCA TGGTACCC                                            1601

(2) INFORMATION FOR SEQ ID NO:4:

(i) SEQUENCE CHARACTERISTICS:
        (A) LENGTH: 301 amino acids
        (B) TYPE: amino acid
        (D) TOPOLOGY: linear (ii) MOLECULE TYPE: protein (xi) SEQUENCE DESCRIPTION: SEQ ID NO:4:

Ile Lys Phe Gln Asp Val Ile Gly Glu Gly Asn Phe Gly Gln Val Leu
  1               5                  10                  15

Lys Ala Arg Ile Lys Lys Asp Gly Leu Arg Met Asp Ala Ala Ile Lys
            20                  25                  30

Arg Met Lys Glu Tyr Ala Ser Lys Asp Asp His Arg Asp Phe Ala Gly
        35                  40                  45

Glu Leu Glu Val Leu Cys Lys Leu Gly His His Pro Asn Ile Ile Asn
    50                  55                  60

Leu Leu Gly Ala Cys Glu His Arg Gly Tyr Leu Tyr Leu Ala Ile Glu
 65                  70                  75                  80

Tyr Ala Pro His Gly Asn Leu Leu Asp Phe Leu Arg Lys Ser Arg Val
                85                  90                  95

Leu Glu Thr Asp Pro Ala Phe Ala Ile Ala Asn Ser Thr Ala Ser Thr
           100                 105                 110

Leu Ser Ser Gln Gln Leu Leu His Phe Ala Ala Asp Val Ala Arg Gly
       115                 120                 125

Met Asp Tyr Leu Ser Gln Lys Gln Phe Ile His Arg Asp Leu Ala Ala
   130                 135                 140

Arg Asn Ile Leu Val Gly Glu Asn Tyr Ile Ala Lys Ile Ala Asp Phe
145                 150                 155                 160

Gly Leu Ser Arg Gly Gln Glu Val Tyr Val Lys Lys Thr Met Gly Arg
               165                 170                 175
```

```
Leu Pro Val Arg Trp Met Ala Ile Glu Ser Leu Asn Tyr Ser Val Tyr
        180                 185                 190

Thr Thr Asn Ser Asp Val Trp Ser Tyr Gly Val Leu Leu Trp Glu Ile
        195                 200                 205

Val Ser Leu Gly Gly Thr Pro Tyr Cys Gly Met Thr Cys Ala Glu Leu
        210                 215                 220

Tyr Glu Lys Leu Pro Gln Gly Tyr Arg Leu Glu Lys Pro Leu Asn Cys
225                 230                 235                 240

Asp Asp Glu Val Tyr Asp Leu Met Arg Gln Cys Trp Arg Glu Lys Pro
                245                 250                 255

Tyr Glu Arg Pro Ser Phe Ala Gln Ile Leu Val Ser Leu Asn Arg Met
                260                 265                 270

Leu Glu Glu Arg Lys Thr Tyr Val Asn Thr Thr Leu Tyr Glu Lys Phe
        275                 280                 285

Thr Tyr Ala Gly Ile Asp Cys Ser Ala Glu Glu Ala Ala
        290                 295                 300
```

(2) INFORMATION FOR SEQ ID NO:5:

(i) SEQUENCE CHARACTERISTICS:
        (A) LENGTH: 4176 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: N-terminal (vi) ORIGINAL SOURCE:
        (A) ORGANISM: Mus musculus
        (B) STRAIN: CD-1
        (D) DEVELOPMENTAL STAGE: Embryo
        (F) TISSUE TYPE: Heart (vii) IMMEDIATE SOURCE:
        (B) CLONE: Tek (viii) POSITION IN GENOME:
        (A) CHROMOSOME/SEGMENT: 4
        (B) MAP POSITION: Between the brown and pmv-23 loci (ix) FEATURE:
        (A) NAME/KEY: CDS
        (B) LOCATION: 124..3490

(xi) SEQUENCE DESCRIPTION: SEQ ID NO:5:

```
GCCAACTTGT AAACAAGAGC GAGTGGACCA TGCGAGCGGG AAGTCGCAAA GTTGTGAGTT      60

GTTGAAAGCT TCCCAGGGAC TCATGCTCAT CTGTGGACGC TGGATGGGGA GATCTGGGGA     120

AGT ATG GAC TCT TTA GCC GGC TTA GTT CTC TGT GGA GTC AGC TTG CTC       168
    Met Asp Ser Leu Ala Gly Leu Val Leu Cys Gly Val Ser Leu Leu
      1               5                  10                  15

CTT TAT GGA GTA GTA GAA GGC GCC ATG GAC CTG ATC TTG ATC AAT TCC       216
Leu Tyr Gly Val Val Glu Gly Ala Met Asp Leu Ile Leu Ile Asn Ser
                 20                  25                  30

CTA CCT CTT GTG TCT GAT GCC GAA ACA TCC CTC ACC TGC ATT GCC TCT       264
Leu Pro Leu Val Ser Asp Ala Glu Thr Ser Leu Thr Cys Ile Ala Ser
             35                  40                  45

GGG TGG CAC CCC CAT GAG CCC ATC ACC ATA GGA AGG GAC TTT GAA GCC       312
Gly Trp His Pro His Glu Pro Ile Thr Ile Gly Arg Asp Phe Glu Ala
         50                  55                  60
```

| | | |
|---|---|---|
| TTA ATG AAC CAG CAC CAA GAT CCA CTG GAG GTT ACT CAA GAT GTG ACC<br>Leu Met Asn Gln His Gln Asp Pro Leu Glu Val Thr Gln Asp Val Thr<br>65                         70                       75 | | 360 |
| AGA GAA TGG GCG AAA AAA GTT GTT TGG AAG AGA GAA AAG GCC AGT AAG<br>Arg Glu Trp Ala Lys Lys Val Val Trp Lys Arg Glu Lys Ala Ser Lys<br>80                       85                     90                     95 | | 408 |
| ATT AAT GGT GCT TAT TTC TGT GAA GGT CGA GTT CGA GGA CAG GCT ATA<br>Ile Asn Gly Ala Tyr Phe Cys Glu Gly Arg Val Arg Gly Gln Ala Ile<br>                   100                    105                   110 | | 456 |
| AGG ATA CGG ACC ATG AAG ATG CGT CAA CAA GCA TCC TTC CTA CCT GCT<br>Arg Ile Arg Thr Met Lys Met Arg Gln Gln Ala Ser Phe Leu Pro Ala<br>             115                    120                   125 | | 504 |
| ACT TTA ACT ATG ACC GTG GAC AGG GGA GAT AAT GTG AAC ATA TCT TTC<br>Thr Leu Thr Met Thr Val Asp Arg Gly Asp Asn Val Asn Ile Ser Phe<br>130                      135                    140 | | 552 |
| AAA AAG GTG TTA ATT AAA GAA GAA GAT GCA GTG ATT TAC AAA AAT GGC<br>Lys Lys Val Leu Ile Lys Glu Glu Asp Ala Val Ile Tyr Lys Asn Gly<br>             145                    150                   155 | | 600 |
| TCC TTC ATC CAC TCA GTG CCC CGG CAT GAA GTA CCT GAT ATT TTA GAA<br>Ser Phe Ile His Ser Val Pro Arg His Glu Val Pro Asp Ile Leu Glu<br>160                      165                    170                   175 | | 648 |
| GTT CAC TTG CCG CAT GCT CAG CCC CAG GAT GCT GGT GTG TAC TCG GCC<br>Val His Leu Pro His Ala Gln Pro Gln Asp Ala Gly Val Tyr Ser Ala<br>                   180                    185                   190 | | 696 |
| AGG TAC ATA GGA GGA AAC CTG TTC ACC TCA GCC TTC ACC AGG CTG ATT<br>Arg Tyr Ile Gly Gly Asn Leu Phe Thr Ser Ala Phe Thr Arg Leu Ile<br>             195                    200                   205 | | 744 |
| GTT CGG AGA TGT GAA GCT CAG AAG TGG GGG CCC GAC TGT AGC CGT CCT<br>Val Arg Arg Cys Glu Ala Gln Lys Trp Gly Pro Asp Cys Ser Arg Pro<br>210                      215                    220 | | 792 |
| TGT ACT ACT TGC AAG AAC AAT GGA GTC TGC CAT GAA GAT ACC GGG GAA<br>Cys Thr Thr Cys Lys Asn Asn Gly Val Cys His Glu Asp Thr Gly Glu<br>             225                    230                   235 | | 840 |
| TGC ATT TGC CCT CCT GGG TTT ATG GGG AGA ACA TGT GAG AAA GCT TGT<br>Cys Ile Cys Pro Pro Gly Phe Met Gly Arg Thr Cys Glu Lys Ala Cys<br>240                      245                    250                   255 | | 888 |
| GAG CCG CAC ACA TTT GGC AGG ACC TGT AAA GAA AGG TGT AGT GGA CCA<br>Glu Pro His Thr Phe Gly Arg Thr Cys Lys Glu Arg Cys Ser Gly Pro<br>                   260                    265                   270 | | 936 |
| GAA GGA TGC AAG TCT TAT GTG TTC TGT CTC CCA GAC CCT TAC GGG TGT<br>Glu Gly Cys Lys Ser Tyr Val Phe Cys Leu Pro Asp Pro Tyr Gly Cys<br>             275                    280                   285 | | 984 |
| TCC TGT GCC ACA GGC TGG AGG GGG TTG CAG TGC AAT GAA GCA TGC CCA<br>Ser Cys Ala Thr Gly Trp Arg Gly Leu Gln Cys Asn Glu Ala Cys Pro<br>290                      295                    300 | | 1032 |
| TCT GGT TAC TAC GGA CCA GAC TGT AAG CTC AGG TGC CAC TGT ACC AAT<br>Ser Gly Tyr Tyr Gly Pro Asp Cys Lys Leu Arg Cys His Cys Thr Asn<br>             305                    310                   315 | | 1080 |
| GAA GAG ATA TGT GAT CGG TTC CAA GGA TGC CTC TGC TCT CAA GGA TGG<br>Glu Glu Ile Cys Asp Arg Phe Gln Gly Cys Leu Cys Ser Gln Gly Trp<br>320                      325                    330                   335 | | 1128 |
| CAA GGG CTG CAG TGT GAG AAA GAA GGC AGG CCA AGG ATG ACT CCA CAG<br>Gln Gly Leu Gln Cys Glu Lys Glu Gly Arg Pro Arg Met Thr Pro Gln<br>                   340                    345                   350 | | 1176 |
| ATA GAG GAT TTG CCA GAT CAC ATT GAA GTA AAC AGT GGA AAA TTT AAC<br>Ile Glu Asp Leu Pro Asp His Ile Glu Val Asn Ser Gly Lys Phe Asn<br>             355                    360                   365 | | 1224 |
| CCC ATC TGC AAA GCC TCT GGG TGG CCA CTA CCT ACT AGT GAA GAA ATG<br>Pro Ile Cys Lys Ala Ser Gly Trp Pro Leu Pro Thr Ser Glu Glu Met<br>370                      375                    380 | | 1272 |

| | | | | | | | | | | | | | | | |
|---|---|---|---|---|---|---|---|---|---|---|---|---|---|---|---|
| ACC | CTA | GTG | AAG | CCA | GAT | GGG | ACA | GTG | CTC | CAA | CCA | AAT | GAC | TTC | AAC | 1320 |
| Thr | Leu | Val | Lys | Pro | Asp | Gly | Thr | Val | Leu | Gln | Pro | Asn | Asp | Phe | Asn |
| 385 | | | | | 390 | | | | | 395 | | | | | |

| TAT | ACA | GAT | CGT | TTC | TCA | GTG | GCC | ATA | TTC | ACT | GTC | AAC | CGA | GTC | TTA | 1368 |
| Tyr | Thr | Asp | Arg | Phe | Ser | Val | Ala | Ile | Phe | Thr | Val | Asn | Arg | Val | Leu |
| 400 | | | | | 405 | | | | | 410 | | | | | 415 |

| CCT | CCT | GAC | TCA | GGA | GTC | TGG | GTC | TGC | AGT | GTG | AAC | ACA | GTG | GCT | GGG | 1416 |
| Pro | Pro | Asp | Ser | Gly | Val | Trp | Val | Cys | Ser | Val | Asn | Thr | Val | Ala | Gly |
| | | | | 420 | | | | | 425 | | | | | 430 | |

| ATG | GTG | GAA | AAG | CCT | TTC | AAC | ATT | TCC | GTC | AAA | GTT | CTT | CCA | GAG | CCC | 1464 |
| Met | Val | Glu | Lys | Pro | Phe | Asn | Ile | Ser | Val | Lys | Val | Leu | Pro | Glu | Pro |
| | | | 435 | | | | | 440 | | | | | 445 | | |

| CTG | CAC | GCC | CCA | AAT | GTG | ATT | GAC | ACT | GGA | CAT | AAC | TTT | GCT | ATC | ATC | 1512 |
| Leu | His | Ala | Pro | Asn | Val | Ile | Asp | Thr | Gly | His | Asn | Phe | Ala | Ile | Ile |
| | | | 450 | | | | | 455 | | | | | 460 | | |

| AAT | ATC | AGC | TCT | GAG | CCT | TAC | TTT | GGG | GAT | GGA | CCC | ATC | AAA | TCC | AAG | 1560 |
| Asn | Ile | Ser | Ser | Glu | Pro | Tyr | Phe | Gly | Asp | Gly | Pro | Ile | Lys | Ser | Lys |
| 465 | | | | | 470 | | | | | 475 | | | | | |

| AAG | CTT | TTC | TAT | AAA | CCT | GTC | AAT | CAG | GCC | TGG | AAA | TAC | ATT | GAA | GTG | 1608 |
| Lys | Leu | Phe | Tyr | Lys | Pro | Val | Asn | Gln | Ala | Trp | Lys | Tyr | Ile | Glu | Val |
| 480 | | | | | 485 | | | | | 490 | | | | | 495 |

| ACG | AAT | GAG | ATT | TTC | ACT | CTC | AAC | TAC | TTG | GAG | CCG | CGG | ACT | GAC | TAC | 1656 |
| Thr | Asn | Glu | Ile | Phe | Thr | Leu | Asn | Tyr | Leu | Glu | Pro | Arg | Thr | Asp | Tyr |
| | | | | 500 | | | | | 505 | | | | | 510 | |

| GAG | CTG | TGT | GTG | CAG | CTG | GCC | CGT | CCT | GGA | GAG | GGT | GGA | GAA | GGG | CAT | 1704 |
| Glu | Leu | Cys | Val | Gln | Leu | Ala | Arg | Pro | Gly | Glu | Gly | Gly | Glu | Gly | His |
| | | | 515 | | | | | 520 | | | | | 525 | | |

| CCT | GGG | CCT | GTG | AGA | CGA | TTT | ACA | ACA | GCG | TGT | ATC | GGA | CTC | CCT | CCT | 1752 |
| Pro | Gly | Pro | Val | Arg | Arg | Phe | Thr | Thr | Ala | Cys | Ile | Gly | Leu | Pro | Pro |
| | | 530 | | | | | 535 | | | | | 540 | | | |

| CCA | AGA | GGT | CTC | AGT | CTC | CTG | CCA | AAA | AGC | CAG | ACA | GCT | CTA | AAT | TTG | 1800 |
| Pro | Arg | Gly | Leu | Ser | Leu | Leu | Pro | Lys | Ser | Gln | Thr | Ala | Leu | Asn | Leu |
| 545 | | | | | 550 | | | | | 555 | | | | | |

| ACT | TGG | CAA | CCG | ATA | TTT | ACA | AAC | TCA | GAA | GAT | GAA | TTT | TAT | GTG | GAA | 1848 |
| Thr | Trp | Gln | Pro | Ile | Phe | Thr | Asn | Ser | Glu | Asp | Glu | Phe | Tyr | Val | Glu |
| 560 | | | | | 565 | | | | | 570 | | | | | 575 |

| GTC | GAG | AGG | CGA | TCC | CTG | CAA | ACA | ACA | AGT | GAT | CAG | CAG | AAC | ATC | AAA | 1896 |
| Val | Glu | Arg | Arg | Ser | Leu | Gln | Thr | Thr | Ser | Asp | Gln | Gln | Asn | Ile | Lys |
| | | | | 580 | | | | | 585 | | | | | 590 | |

| GTG | CCT | GGG | AAC | CTG | ACC | TCG | GTG | CTA | CTG | AGC | AAC | TTA | GTC | CCC | AGG | 1944 |
| Val | Pro | Gly | Asn | Leu | Thr | Ser | Val | Leu | Leu | Ser | Asn | Leu | Val | Pro | Arg |
| | | | 595 | | | | | 600 | | | | | 605 | | |

| GAG | CAG | TAC | ACA | GTC | CGA | GCT | AGA | GTC | AAC | ACC | AAG | GCG | CAG | GGG | GAG | 1992 |
| Glu | Gln | Tyr | Thr | Val | Arg | Ala | Arg | Val | Asn | Thr | Lys | Ala | Gln | Gly | Glu |
| | | | 610 | | | | | 615 | | | | | 620 | | |

| TGG | AGT | GAA | GAA | CTC | AGG | GCC | TGG | ACC | CTT | AGT | GAC | ATT | CTC | CCT | CCT | 2040 |
| Trp | Ser | Glu | Glu | Leu | Arg | Ala | Trp | Thr | Leu | Ser | Asp | Ile | Leu | Pro | Pro |
| | 625 | | | | | 630 | | | | | 635 | | | | |

| CAA | CCA | GAA | AAC | ATC | AAG | ATC | TCC | AAC | ATC | ACT | GAC | TCC | ACA | GCT | ATG | 2088 |
| Gln | Pro | Glu | Asn | Ile | Lys | Ile | Ser | Asn | Ile | Thr | Asp | Ser | Thr | Ala | Met |
| 640 | | | | | 645 | | | | | 650 | | | | | 655 |

| GTT | TCT | TGG | ACA | ATA | GTG | GAT | GGC | TAT | TCG | ATT | TCT | TCC | ATC | ATC | ATC | 2136 |
| Val | Ser | Trp | Thr | Ile | Val | Asp | Gly | Tyr | Ser | Ile | Ser | Ser | Ile | Ile | Ile |
| | | | | 660 | | | | | 665 | | | | | 670 | |

| CGG | TAT | AAG | GTT | CAG | GGC | AAA | AAT | GAA | GAC | CAG | CAC | ATT | GAT | GTG | AAG | 2184 |
| Arg | Tyr | Lys | Val | Gln | Gly | Lys | Asn | Glu | Asp | Gln | His | Ile | Asp | Val | Lys |
| | | | 675 | | | | | 680 | | | | | 685 | | |

| ATC | AAG | AAT | GCT | ACC | GTT | ACT | CAG | TAC | CAG | CTC | AAG | GGC | CTA | GAG | CCA | 2232 |
| Ile | Lys | Asn | Ala | Thr | Val | Thr | Gln | Tyr | Gln | Leu | Lys | Gly | Leu | Glu | Pro |
| | | | 690 | | | | | 695 | | | | | 700 | | |

```
GAG ACT ACA TAC CAT GTG GAT ATT TTT GCT GAG AAC AAC ATA GGA TCA          2280
Glu Thr Thr Tyr His Val Asp Ile Phe Ala Glu Asn Asn Ile Gly Ser
705                 710                 715

AGC AAC CCA GCC TTT TCT CAT GAA CTG AGG ACG CTT CCA CAT TCC CCA          2328
Ser Asn Pro Ala Phe Ser His Glu Leu Arg Thr Leu Pro His Ser Pro
720                 725                 730                 735

GGC TCT GCA GAC CTC GGA GGG GGA AAG ATG CTA CTC ATA GCC ATC CTT          2376
Gly Ser Ala Asp Leu Gly Gly Gly Lys Met Leu Leu Ile Ala Ile Leu
            740                 745                 750

GGG TCG GCT GGA ATG ACT TGC ATC ACC GTG CTG TTG GCG TTT CTG ATT          2424
Gly Ser Ala Gly Met Thr Cys Ile Thr Val Leu Leu Ala Phe Leu Ile
        755                 760                 765

ATG TTG CAA CTG AAG AGA GCA AAT GTC CAA AGG AGA ATG GCT CAG GCA          2472
Met Leu Gln Leu Lys Arg Ala Asn Val Gln Arg Arg Met Ala Gln Ala
    770                 775                 780

TTC CAG AAC AGA GAA GAA CCA GCT GTG CAG TTT AAC TCA GGA ACT CTG          2520
Phe Gln Asn Arg Glu Glu Pro Ala Val Gln Phe Asn Ser Gly Thr Leu
785                 790                 795

GCC CTT AAC AGG AAG GCC AAA AAC AAT CCA GAT CCC ACA ATT TAT CCT          2568
Ala Leu Asn Arg Lys Ala Lys Asn Asn Pro Asp Pro Thr Ile Tyr Pro
800                 805                 810                 815

GTG CTT GAC TGG AAT GAC ATC AAG TTT CAA GAC GTG ATC GGA GAG GGC          2616
Val Leu Asp Trp Asn Asp Ile Lys Phe Gln Asp Val Ile Gly Glu Gly
            820                 825                 830

AAC TTT GGC CAG GTT CTG AAG GCA CGC ATC AAG AAG GAT GGG TTA CGG          2664
Asn Phe Gly Gln Val Leu Lys Ala Arg Ile Lys Lys Asp Gly Leu Arg
        835                 840                 845

ATG GAT GCC GCC ATC AAG AGG ATG AAA GAG TAT GCC TCC AAA GAT GAT          2712
Met Asp Ala Ala Ile Lys Arg Met Lys Glu Tyr Ala Ser Lys Asp Asp
    850                 855                 860

CAC AGG GAC TTC GCA GGA GAA CTG GAG GTT CTT TGT AAA CTT GGA CAC          2760
His Arg Asp Phe Ala Gly Glu Leu Glu Val Leu Cys Lys Leu Gly His
865                 870                 875

CAT CCA AAC ATC ATT AAT CTC TTG GGA GCA TGT GAA CAC CGA GGC TAT          2808
His Pro Asn Ile Ile Asn Leu Leu Gly Ala Cys Glu His Arg Gly Tyr
880                 885                 890                 895

TTG TAC CTA GCT ATT GAG TAT GCC CCG CAT GGA AAC CTC CTG GAC TTC          2856
Leu Tyr Leu Ala Ile Glu Tyr Ala Pro His Gly Asn Leu Leu Asp Phe
            900                 905                 910

CTG CGT AAG AGC AGA GTG CTA GAG ACA GAC CCT GCT TTT GCC ATC GCC          2904
Leu Arg Lys Ser Arg Val Leu Glu Thr Asp Pro Ala Phe Ala Ile Ala
        915                 920                 925

AAC AGT ACA GCT TCC ACA CTG TCC TCC CAA CAG CTT CTT CAT TTT GCT          2952
Asn Ser Thr Ala Ser Thr Leu Ser Ser Gln Gln Leu Leu His Phe Ala
    930                 935                 940

GCA GAT GTG GCC CGG GGG ATG GAC TAC TTG AGC CAG AAA CAG TTT ATC          3000
Ala Asp Val Ala Arg Gly Met Asp Tyr Leu Ser Gln Lys Gln Phe Ile
945                 950                 955

CAC AGG GAC CTG GCT GCC AGA AAC ATT TTA GTT GGT GAA AAC TAC ATA          3048
His Arg Asp Leu Ala Ala Arg Asn Ile Leu Val Gly Glu Asn Tyr Ile
960                 965                 970                 975

GCC AAA ATA GCA GAT TTT GGA TTG TCA CGA GGT CAA GAA GTG TAT GTG          3096
Ala Lys Ile Ala Asp Phe Gly Leu Ser Arg Gly Gln Glu Val Tyr Val
            980                 985                 990

AAA AAG ACA ATG GGA AGG CTC CCA GTG CGT TGG ATG GCA ATC GAA TCA          3144
Lys Lys Thr Met Gly Arg Leu Pro Val Arg Trp Met Ala Ile Glu Ser
        995                 1000                1005

CTG AAC TAT AGT GTC TAT ACA ACC AAC AGT GAT GTC TGG TCC TAT GGT          3192
Leu Asn Tyr Ser Val Tyr Thr Thr Asn Ser Asp Val Trp Ser Tyr Gly
    1010                1015                1020
```

| | | |
|---|---|---|
| GTA TTG CTC TGG GAG ATT GTT AGC TTA GGA GGC ACC CCC TAC TGC GGC<br>Val Leu Leu Trp Glu Ile Val Ser Leu Gly Gly Thr Pro Tyr Cys Gly<br>     1025                 1030                        1035 | | 3240 |
| ATG ACG TGC GCG GAG CTC TAT GAG AAG CTA CCC CAG GGC TAC AGG CTG<br>Met Thr Cys Ala Glu Leu Tyr Glu Lys Leu Pro Gln Gly Tyr Arg Leu<br>1040                1045                  1050                  1055 | | 3288 |
| GAG AAG CCC CTG AAC TGT GAT GAT GAG GTG TAT GAT CTA ATG AGA CAG<br>Glu Lys Pro Leu Asn Cys Asp Asp Glu Val Tyr Asp Leu Met Arg Gln<br>     1060                 1065                        1070 | | 3336 |
| TGC TGG AGG GAG AAG CCT TAT GAG AGA CCA TCA TTT GCC CAG ATA TTG<br>Cys Trp Arg Glu Lys Pro Tyr Glu Arg Pro Ser Phe Ala Gln Ile Leu<br>          1075                 1080                   1085 | | 3384 |
| GTG TCC TTA AAC AGG ATG CTG GAA GAA CGG AAG ACA TAC GTG AAC ACC<br>Val Ser Leu Asn Arg Met Leu Glu Glu Arg Lys Thr Tyr Val Asn Thr<br>              1090                 1095                  1100 | | 3432 |
| ACA CTG TAT GAG AAG TTT ACC TAT GCA GGA ATT GAC TGC TCT GCG GAA<br>Thr Leu Tyr Glu Lys Phe Thr Tyr Ala Gly Ile Asp Cys Ser Ala Glu<br>     1105                 1110                      1115 | | 3480 |
| GAA GCA GCC T AGAGCAGAAC TCTTCATGTA CAACGGCCAT TTCTCCTCAC<br>Glu Ala Ala<br>1120 | | 3530 |
| TGGCGCGAGA GCCTTGACAC CTGTACCAAG CAAGCCACCC ACTGCCAAGA GATGTGATAT | | 3590 |
| ATAAGTGTAT ATATTGTGCT GTGTTTGGGA CCCTCCTCAT ACAGCTCGTG CGGATCTGCA | | 3650 |
| GTGTGTTCTG ACTCTAATGT GACTGTATAT ACTGCTCGGA GTAAGAATGT GCTAAGATCA | | 3710 |
| GAATGCCTGT TCGTGGTTTC ATATAATATA TTTTTCTAAA AGCATAGATT GCACAGGAAG | | 3770 |
| GTATGAGTAC AAATACTGTA ATGCATAACT TGTTATTGTC CTAGATGTGT TTGACATTTT | | 3830 |
| TCCTTTACAA CTGAATGCTA TAAAAGTGTT TTGCTGTGTG CGCGTAAGAT ACTGTTCGTT | | 3890 |
| AAAATAAGCA TTCCCTTGAC AGCACAGGAA GAAAAGCGAG GGAAATGTAT GGATTATATT | | 3950 |
| AAATGTGGGT TACTACACAA GAGGCCGAAC ATTCCAAGTA GCAGAAGAGA GGGTCTCTCA | | 4010 |
| ACTCTGCTCC TCACCTGCAG AAGCCAGTTT GTTTGGCCAT GTGACAATTG TCCTGTGTTT | | 4070 |
| TTATAGCACC CAAATCATTC TAAAATATGA ACATCTAAAA ACTTTGCTAG GAGACTAAGA | | 4130 |
| ACCTTTGGAG AGATAGATAT AAGTACGGTC AAAAAACAAA ACTGCG | | 4176 |

(2) INFORMATION FOR SEQ ID NO:6:

(i) SEQUENCE CHARACTERISTICS:
        (A) LENGTH: 1122 amino acids
        (B) TYPE: amino acid
        (D) TOPOLOGY: linear (ii) MOLECULE TYPE: protein (xi) SEQUENCE DESCRIPTION: SEQ ID NO:6:

Met Asp Ser Leu Ala Gly Leu Val Leu Cys Gly Val Ser Leu Leu Leu
 1               5                  10                  15

Tyr Gly Val Val Glu Gly Ala Met Asp Leu Ile Leu Ile Asn Ser Leu
                20                  25                  30

Pro Leu Val Ser Asp Ala Glu Thr Ser Leu Thr Cys Ile Ala Ser Gly
            35                  40                  45

Trp His Pro His Glu Pro Ile Thr Ile Gly Arg Asp Phe Glu Ala Leu
        50                  55                  60

Met Asn Gln His Gln Asp Pro Leu Glu Val Thr Gln Asp Val Thr Arg
65                  70                  75                  80

Glu Trp Ala Lys Lys Val Val Trp Lys Arg Glu Lys Ala Ser Lys Ile
                85                  90                  95

-continued

```
Asn Gly Ala Tyr Phe Cys Glu Gly Arg Val Arg Gly Gln Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Arg Gly Asp Asn Val Asn Ile Ser Phe Lys
    130                 135                 140

Lys Val Leu Ile Lys Glu Glu Asp Ala Val Ile Tyr Lys Asn Gly Ser
145                 150                 155                 160

Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
        195                 200                 205

Arg Arg Cys Glu Ala Gln Lys Trp Gly Pro Asp Cys Ser Arg Pro Cys
    210                 215                 220

Thr Thr Cys Lys Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                245                 250                 255

Pro His Thr Phe Gly Arg Thr Cys Lys Glu Arg Cys Ser Gly Pro Glu
            260                 265                 270

Gly Cys Lys Ser Tyr Val Phe Cys Leu Pro Asp Pro Tyr Gly Cys Ser
        275                 280                 285

Cys Ala Thr Gly Trp Arg Gly Leu Gln Cys Asn Glu Ala Cys Pro Ser
    290                 295                 300

Gly Tyr Tyr Gly Pro Asp Cys Lys Leu Arg Cys His Cys Thr Asn Glu
305                 310                 315                 320

Glu Ile Cys Asp Arg Phe Gln Gly Cys Leu Cys Ser Gln Gly Trp Gln
                325                 330                 335

Gly Leu Gln Cys Glu Lys Glu Gly Arg Pro Arg Met Thr Pro Gln Ile
            340                 345                 350

Glu Asp Leu Pro Asp His Ile Glu Val Asn Ser Gly Lys Phe Asn Pro
        355                 360                 365

Ile Cys Lys Ala Ser Gly Trp Pro Leu Pro Thr Ser Glu Glu Met Thr
    370                 375                 380

Leu Val Lys Pro Asp Gly Thr Val Leu Gln Pro Asn Asp Phe Asn Tyr
385                 390                 395                 400

Thr Asp Arg Phe Ser Val Ala Ile Phe Thr Val Asn Arg Val Leu Pro
                405                 410                 415

Pro Asp Ser Gly Val Trp Val Cys Ser Val Asn Thr Val Ala Gly Met
            420                 425                 430

Val Glu Lys Pro Phe Asn Ile Ser Val Lys Val Leu Pro Glu Pro Leu
        435                 440                 445

His Ala Pro Asn Val Ile Asp Thr Gly His Asn Phe Ala Ile Ile Asn
    450                 455                 460

Ile Ser Ser Glu Pro Tyr Phe Gly Asp Gly Pro Ile Lys Ser Lys Lys
465                 470                 475                 480

Leu Phe Tyr Lys Pro Val Asn Gln Ala Trp Lys Tyr Ile Glu Val Thr
                485                 490                 495

Asn Glu Ile Phe Thr Leu Asn Tyr Leu Glu Pro Arg Thr Asp Tyr Glu
            500                 505                 510

Leu Cys Val Gln Leu Ala Arg Pro Gly Glu Gly Gly Glu Gly His Pro
        515                 520                 525
```

-continued

```
Gly Pro Val Arg Arg Phe Thr Thr Ala Cys Ile Gly Leu Pro Pro Pro
        530                 535                 540

Arg Gly Leu Ser Leu Leu Pro Lys Ser Gln Thr Ala Leu Asn Leu Thr
545                 550                 555                 560

Trp Gln Pro Ile Phe Thr Asn Ser Glu Asp Glu Phe Tyr Val Glu Val
                565                 570                 575

Glu Arg Arg Ser Leu Gln Thr Thr Ser Asp Gln Gln Asn Ile Lys Val
            580                 585                 590

Pro Gly Asn Leu Thr Ser Val Leu Leu Ser Asn Leu Val Pro Arg Glu
        595                 600                 605

Gln Tyr Thr Val Arg Ala Arg Val Asn Thr Lys Ala Gln Gly Glu Trp
    610                 615                 620

Ser Glu Glu Leu Arg Ala Trp Thr Leu Ser Asp Ile Leu Pro Pro Gln
625                 630                 635                 640

Pro Glu Asn Ile Lys Ile Ser Asn Ile Thr Asp Ser Thr Ala Met Val
                645                 650                 655

Ser Trp Thr Ile Val Asp Gly Tyr Ser Ile Ser Ser Ile Ile Ile Arg
            660                 665                 670

Tyr Lys Val Gln Gly Lys Asn Glu Asp Gln His Ile Asp Val Lys Ile
        675                 680                 685

Lys Asn Ala Thr Val Thr Gln Tyr Gln Leu Lys Gly Leu Glu Pro Glu
    690                 695                 700

Thr Thr Tyr His Val Asp Ile Phe Ala Glu Asn Asn Ile Gly Ser Ser
705                 710                 715                 720

Asn Pro Ala Phe Ser His Glu Leu Arg Thr Leu Pro His Ser Pro Gly
                725                 730                 735

Ser Ala Asp Leu Gly Gly Lys Met Leu Leu Ile Ala Ile Leu Gly
            740                 745                 750

Ser Ala Gly Met Thr Cys Ile Thr Val Leu Leu Ala Phe Leu Ile Met
        755                 760                 765

Leu Gln Leu Lys Arg Ala Asn Val Gln Arg Arg Met Ala Gln Ala Phe
    770                 775                 780

Gln Asn Arg Glu Glu Pro Ala Val Gln Phe Asn Ser Gly Thr Leu Ala
785                 790                 795                 800

Leu Asn Arg Lys Ala Lys Asn Asn Pro Asp Pro Thr Ile Tyr Pro Val
                805                 810                 815

Leu Asp Trp Asn Asp Ile Lys Phe Gln Asp Val Ile Gly Glu Gly Asn
            820                 825                 830

Phe Gly Gln Val Leu Lys Ala Arg Ile Lys Lys Asp Gly Leu Arg Met
        835                 840                 845

Asp Ala Ala Ile Lys Arg Met Lys Glu Tyr Ala Ser Lys Asp Asp His
850                 855                 860

Arg Asp Phe Ala Gly Glu Leu Glu Val Leu Cys Lys Leu Gly His His
865                 870                 875                 880

Pro Asn Ile Ile Asn Leu Leu Gly Ala Cys Glu His Arg Gly Tyr Leu
                885                 890                 895

Tyr Leu Ala Ile Glu Tyr Ala Pro His Gly Asn Leu Leu Asp Phe Leu
            900                 905                 910

Arg Lys Ser Arg Val Leu Glu Thr Asp Pro Ala Phe Ala Ile Ala Asn
        915                 920                 925

Ser Thr Ala Ser Thr Leu Ser Ser Gln Gln Leu Leu His Phe Ala Ala
    930                 935                 940

Asp Val Ala Arg Gly Met Asp Tyr Leu Ser Gln Lys Gln Phe Ile His
```

```
                945           950           955           960
Arg Asp Leu Ala Ala Arg Asn Ile Leu Val Gly Glu Asn Tyr Ile Ala
                    965               970               975
Lys Ile Ala Asp Phe Gly Leu Ser Arg Gly Gln Glu Val Tyr Val Lys
            980               985               990
Lys Thr Met Gly Arg Leu Pro Val Arg Trp Met Ala Ile Glu Ser Leu
        995               1000              1005
Asn Tyr Ser Val Tyr Thr Thr Asn Ser Asp Val Trp Ser Tyr Gly Val
    1010              1015              1020
Leu Leu Trp Glu Ile Val Ser Leu Gly Gly Thr Pro Tyr Cys Gly Met
1025              1030              1035              1040
Thr Cys Ala Glu Leu Tyr Glu Lys Leu Pro Gln Gly Tyr Arg Leu Glu
                1045              1050              1055
Lys Pro Leu Asn Cys Asp Asp Glu Val Tyr Asp Leu Met Arg Gln Cys
            1060              1065              1070
Trp Arg Glu Lys Pro Tyr Glu Arg Pro Ser Phe Ala Gln Ile Leu Val
        1075              1080              1085
Ser Leu Asn Arg Met Leu Glu Glu Arg Lys Thr Tyr Val Asn Thr Thr
    1090              1095              1100
Leu Tyr Glu Lys Phe Thr Tyr Ala Gly Ile Asp Cys Ser Ala Glu Glu
1105              1110              1115              1120
Ala Ala (2) INFORMATION FOR SEQ ID NO:7:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Gly Xaa Gly Xaa Xaa Gly
1               5

(2) INFORMATION FOR SEQ ID NO:8:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Trp Met Ala Ile Glu Ser Leu
1               5

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:9:

GACAG TGGGTTCTGG GAGT                                          24
```

(2) INFORMATION FOR SEQ ID NO:10:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:10:

```
CGATGCAGGC AGCTTCTGCG GAT                                          23
```

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:11:

```
CCTCACCTGC AGAAGCCAGT TTGT                                         24
```

(2) INFORMATION FOR SEQ ID NO:12:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:12:

```
GTGGTTTGTC CAACTCATCA ATG                                          23
```

(2) INFORMATION FOR SEQ ID NO:13:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:13:

```
CTACCATAAT CCAGTCTACT GC                                           22
```

(2) INFORMATION FOR SEQ ID NO:14:

(i) SEQUENCE CHARACTERISTICS:
        (A) LENGTH: 65 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: Jtk14

(xi) SEQUENCE DESCRIPTION: SEQ ID NO:14:

```
Ile His Arg Asp Leu Ala Ala Arg Asn Val Leu Val Gly Glu Asn Leu
 1               5                  10                  15
```

```
Ala Ser Lys Ile Ala Asp Phe Gly Leu Ser Arg Gly Glu Glu Val Tyr
             20                  25                  30

Val Lys Lys Thr Met Gly Arg Leu Pro Val Arg Trp Met Ala Ile Glu
             35                  40                  45

Ser Leu Asn Tyr Ser Val Tyr Thr Thr Lys Ser Asp Val Trp Ser Phe
 50                  55                  60

Gly
 65

(2) INFORMATION FOR SEQ ID NO:15:

(i) SEQUENCE CHARACTERISTICS:
        (A) LENGTH: 316 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: Ret (xi) SEQUENCE DESCRIPTION: SEQ ID NO:15:

Leu Val Leu Gly Lys Thr Leu Gly Glu Gly Glu Phe Gly Lys Val Val
 1               5                  10                  15

Lys Ala Thr Ala Phe His Leu Lys Gly Arg Ala Gly Tyr Thr Thr Val
             20                  25                  30

Ala Val Lys Met Leu Lys Glu Asn Ala Ser Pro Ser Glu Leu Arg Asp
             35                  40                  45

Leu Leu Ser Glu Phe Asn Val Leu Lys Gln Val Asn His Pro His Val
 50                  55                  60

Ile Lys Leu Tyr Gly Ala Cys Ser Gln Asp Gly Pro Leu Leu Leu Ile
 65                  70                  75                  80

Val Glu Tyr Ala Lys Tyr Gly Ser Leu Arg Gly Phe Leu Arg Glu Ser
             85                  90                  95

Arg Lys Val Gly Pro Gly Tyr Leu Gly Ser Gly Gly Ser Arg Asn Ser
            100                 105                 110

Ser Ser Leu Asp His Pro Asp Glu Arg Ala Leu Thr Met Gly Asp Leu
            115                 120                 125

Ile Ser Phe Ala Trp Gln Ile Ser Gln Gly Met Gln Tyr Leu Ala Glu
130                 135                 140

Met Lys Leu Val His Arg Asp Leu Ala Ala Arg Asn Ile Leu Val Ala
145                 150                 155                 160

Glu Gly Arg Lys Met Lys Ile Ser Asp Phe Gly Leu Ser Arg Asp Val
                165                 170                 175

Tyr Glu Glu Asp Pro Tyr Val Lys Arg Ser Gln Gly Arg Ile Pro Val
            180                 185                 190

Lys Trp Met Ala Ile Glu Ser Leu Phe Asp His Ile Tyr Thr Thr Gln
            195                 200                 205

Ser Asp Val Trp Ser Phe Gly Val Leu Leu Trp Glu Ile Val Thr Leu
            210                 215                 220

Gly Gly Asn Pro Tyr Pro Gly Ile Pro Pro Glu Arg Leu Phe Asn Leu
225                 230                 235                 240

Leu Lys Thr Gly His Arg Met Glu Arg Pro Asp Asn Cys Ser Glu Glu
                245                 250                 255

Met Tyr Arg Leu Met Leu Gln Cys Trp Lys Gln Glu Pro Asp Lys Arg
            260                 265                 270
```

```
Pro Val Phe Ala Asp Ile Ser Lys Asp Leu Glu Lys Met Met Val Lys
        275                 280                 285

Arg Arg Asp Tyr Leu Asp Leu Ala Ala Ser Thr Pro Ser Asp Ser Leu
        290                 295                 300

Ile Tyr Asp Asp Gly Leu Ser Glu Glu Glu Thr Pro
305                 310                 315
```

(2) INFORMATION FOR SEQ ID NO:16:

(i) SEQUENCE CHARACTERISTICS:
        (A) LENGTH: 313 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: FlgM (xi) SEQUENCE DESCRIPTION: SEQ ID NO:16:

```
Leu Val Leu Gly Lys Pro Leu Gly Glu Gly Cys Phe Gly Gln Val Val
1               5                   10                  15

Leu Ala Glu Ala Ile Gly Leu Asp Lys Asp Lys Pro Asn Arg Val Thr
            20                  25                  30

Lys Val Ala Val Lys Met Leu Lys Ser Asp Ala Thr Glu Lys Asp Leu
        35                  40                  45

Ser Asp Leu Ile Ser Glu Met Glu Met Met Lys Met Ile Gly Lys His
    50                  55                  60

Lys Asn Ile Ile Asn Leu Leu Gly Ala Cys Thr Gln Asp Gly Pro Leu
65                  70                  75                  80

Tyr Val Ile Val Glu Tyr Ala Ser Lys Gly Asn Leu Arg Glu Tyr Leu
                85                  90                  95

Gln Ala Arg Arg Pro Pro Gly Leu Glu Tyr Cys Tyr Asn Pro Ser His
            100                 105                 110

Asn Pro Glu Glu Gln Leu Ser Ser Lys Asp Leu Val Ser Cys Ala Tyr
        115                 120                 125

Gln Val Ala Arg Gly Met Glu Tyr Leu Ala Ser Lys Lys Cys Ile His
    130                 135                 140

Arg Asp Leu Ala Ala Arg Asn Val Leu Val Thr Glu Asp Asn Val Met
145                 150                 155                 160

Lys Ile Ala Asp Phe Gly Leu Ala Arg Asp Ile His His Ile Asp Tyr
                165                 170                 175

Tyr Lys Lys Thr Thr Asn Gly Arg Leu Pro Val Lys Trp Met Ala Pro
            180                 185                 190

Glu Ala Leu Phe Asp Arg Ile Tyr Thr His Gln Ser Asp Val Trp Ser
        195                 200                 205

Phe Gly Val Leu Leu Trp Glu Ile Phe Thr Leu Gly Gly Ser Pro Tyr
    210                 215                 220

Pro Gly Val Pro Val Glu Glu Leu Phe Lys Leu Leu Lys Glu Gly His
225                 230                 235                 240

Arg Met Asp Lys Pro Ser Asn Cys Thr Asn Glu Leu Tyr Met Met Met
                245                 250                 255

Arg Asp Cys Trp His Ala Val Pro Ser Gln Arg Pro Thr Phe Lys Gln
            260                 265                 270

Leu Val Glu Asp Leu Asp Arg Ile Val Ala Leu Thr Ser Asn Gln Glu
        275                 280                 285

Tyr Leu Asp Leu Ser Ile Pro Leu Asp Gln Tyr Ser Pro Ser Phe Pro
```

```
                      290              295              300
Asp Thr Arg Ser Ser Thr Cys Ser Ser
305                 310
```

(2) INFORMATION FOR SEQ ID NO:17:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: Tek1

(xi) SEQUENCE DESCRIPTION: SEQ ID NO:17:

```
Arg Cys Glu Ala Gln Lys Trp Gly Pro Asp Cys Ser Arg Pro Cys Thr
1               5                  10                  15

Thr Cys Lys Asn Asn Gly Val Cys His Glu Asp Thr Gly Glu Cys Ile
            20                  25                  30

Cys Pro Pro Gly Phe Met Gly Arg Thr Cys Glu Lys
        35                  40
```

(2) INFORMATION FOR SEQ ID NO:18:

(i) SEQUENCE CHARACTERISTICS:
        (A) LENGTH: 47 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: Tek2

(xi) SEQUENCE DESCRIPTION: SEQ ID NO:18:

```
Ala Cys Glu Pro His Thr Phe Gly Arg Thr Cys Lys Glu Arg Cys Ser
1               5                  10                  15

Gly Pro Glu Gly Cys Lys Ser Tyr Val Phe Cys Leu Pro Asp Pro Tyr
            20                  25                  30

Gly Cys Ser Cys Ala Thr Gly Trp Arg Gly Leu Gln Cys Asn Glu
        35                  40                  45
```

(2) INFORMATION FOR SEQ ID NO:19:

(i) SEQUENCE CHARACTERISTICS:
        (A) LENGTH: 41 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: Tek 3

(xi) SEQUENCE DESCRIPTION: SEQ ID NO:19:

```
Ala Cys Pro Ser Gly Tyr Tyr Gly Pro Asp Cys Lys Leu Arg Cys His
1               5                  10                  15

Cys Thr Asn Glu Glu Ile Cys Asp Arg Phe Gln Cys Leu Cys Ser Gln
            20                  25                  30

Gly Trp Gln Gly Leu Gln Cys Glu Lys
        35                  40
```

(2) INFORMATION FOR SEQ ID NO:20:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: protein (vi) ORIGINAL SOURCE:
       (A) ORGANISM: Homo sapiens (vii) IMMEDIATE SOURCE:
       (B) CLONE: Tie1

(xi) SEQUENCE DESCRIPTION: SEQ ID NO:20:

```
Gly Cys Gly Ala Gly Arg Trp Gly Pro Gly Cys Thr Lys Glu Cys Pro
 1               5                  10                  15
Gly Cys Leu His Gly Gly Val Cys His Asp His Asp Gly Glu Cys Val
             20                  25                  30
Cys Pro Pro Gly Phe Thr Gly Thr Arg Cys Glu Gln
         35                  40
```

(2) INFORMATION FOR SEQ ID NO:21:

(i) SEQUENCE CHARACTERISTICS:
        (A) LENGTH: 47 amino acids
        (B) TYPE: amino acid
        (C) STRANDEDNESS: single
        (D) TOPOLOGY: linear (ii) MOLECULE TYPE: protein (vi) ORIGINAL SOURCE:
       (A) ORGANISM: Homo sapiens (vii) IMMEDIATE SOURCE:
       (B) CLONE: Tie2

(xi) SEQUENCE DESCRIPTION: SEQ ID NO:21:

```
Ala Cys Arg Glu Gly Arg Phe Gly Gln Ser Cys Gln Glu Gln Cys Pro
 1               5                  10                  15
Gly Ile Ser Gly Cys Arg Gly Leu Thr Phe Cys Leu Pro Asp Pro Tyr
             20                  25                  30
Gly Cys Ser Cys Gly Ser Gly Trp Arg Gly Ser Gln Cys Gln Glu
         35                  40                  45
```

(2) INFORMATION FOR SEQ ID NO:22:

(i) SEQUENCE CHARACTERISTICS:
        (A) LENGTH: 42 amino acids
        (B) TYPE: amino acid
        (C) STRANDEDNESS: single
        (D) TOPOLOGY: linear (ii) MOLECULE TYPE: protein (vi) ORIGINAL SOURCE:
       (A) ORGANISM: Homo sapiens (vii) IMMEDIATE SOURCE:
       (B) CLONE: Tie3

(xi) SEQUENCE DESCRIPTION: SEQ ID NO:22:

```
Ala Cys Ala Pro Gly His Phe Gly Ala Asp Cys Arg Leu Gln Cys Gln
 1               5                  10                  15
Cys Gln Asn Gly Gly Thr Cys Asp Arg Phe Ser Gly Cys Val Cys Pro
             20                  25                  30
```

```
Ser Gly Trp His Gly Val His Cys Glu Lys
        35                  40
```

(2) INFORMATION FOR SEQ ID NO:23:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: EGF (xi) SEQUENCE DESCRIPTION: SEQ ID NO:23:

```
Asn Ser Asp Ser Pro Cys Pro Leu Ser Met Asp Gly Tyr Cys Leu His
1               5                  10                  15
Asp Gly Val Cys Met Tyr Ile Lys Ala Leu Asp Lys Tyr Ala Cys Asn
                20                  25                  30
Cys Val Val Gly Tyr Ile Gly Lys Arg Cys Gln Tyr
        35                  40
```

(2) INFORMATION FOR SEQ ID NO:24:

(i) SEQUENCE CHARACTERISTICS:
        (A) LENGTH: 45 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: Notch (xi) SEQUENCE DESCRIPTION: SEQ ID NO:24:

```
Gly Arg Tyr Cys Asp Lys Asp Ile Asp Glu Cys Ser Leu Ser Ser Phe
1               5                  10                  15
Cys Arg Asn Gly Ala Ser Cys Leu Asn Val Pro Gly Ser Tyr Arg Cys
                20                  25                  30
Leu Cys Thr Lys Gly Tyr Glu Gly Arg Asp Cys Ala Ile
        35                  40                  45
```

(2) INFORMATION FOR SEQ ID NO:25:

(i) SEQUENCE CHARACTERISTICS:
        (A) LENGTH: 66 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: TekFn1

(xi) SEQUENCE DESCRIPTION: SEQ ID NO:25:

```
Glu Pro Tyr Phe Gly Asp Gly Pro Ile Lys Ser Lys Lys Leu Phe Tyr
1               5                  10                  15
Lys Pro Val Asn Gln Ala Trp Lys Tyr Ile Glu Val Thr Asn Glu Ile
                20                  25                  30
Phe Thr Leu Asn Tyr Leu Glu Pro Arg Thr Asp Tyr Glu Leu Cys Val
        35                  40                  45
Gln Leu Ala Arg Pro Gly Glu Gly Gly Glu Gly His Pro Gly Pro Val
```

```
                50                  55                  60
Arg Arg
 65

(2) INFORMATION FOR SEQ ID NO:26:

(i) SEQUENCE CHARACTERISTICS:
        (A) LENGTH: 67 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens (vii) IMMEDIATE SOURCE:
        (B) CLONE: TieFn1

(xi) SEQUENCE DESCRIPTION: SEQ ID NO:26:

Phe Ser Gly Asp Gly Pro Ile Ser Thr Val Arg Leu His Tyr Arg Pro
 1               5                  10                  15

Gln Asp Ser Thr Met Asp Trp Ser Thr Ile Val Val Asp Pro Ser Glu
                20                  25                  30

Asn Val Thr Leu Met Asn Leu Arg Pro Lys Thr Gly Tyr Ser Val Arg
                35                  40                  45

Val Gln Leu Ser Arg Pro Gly Glu Gly Gly Glu Gly Ala Trp Gly Pro
                50                  55                  60

Pro Thr Leu
 65

(2) INFORMATION FOR SEQ ID NO:27:

(i) SEQUENCE CHARACTERISTICS:
        (A) LENGTH: 99 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: TekFn2

(xi) SEQUENCE DESCRIPTION: SEQ ID NO:27:

Phe Thr Thr Ala Cys Ile Gly Leu Pro Pro Pro Arg Gly Leu Ser Leu
 1               5                  10                  15

Leu Pro Lys Ser Gln Thr Ala Leu Asn Leu Thr Trp Gln Pro Ile Phe
                20                  25                  30

Thr Asn Ser Glu Asp Glu Phe Tyr Val Glu Val Glu Arg Arg Ser Leu
                35                  40                  45

Gln Thr Thr Ser Asp Gln Asn Ile Lys Val Pro Gly Asn Leu Thr
                50                  55                  60

Ser Val Leu Leu Ser Asn Leu Val Pro Arg Glu Gln Tyr Thr Val Arg
 65                  70                  75                  80

Ala Arg Val Asn Thr Lys Ala Gln Gly Glu Trp Ser Glu Glu Leu Arg
                85                  90                  95

Ala Asn Thr (2) INFORMATION FOR SEQ ID NO:28:

(i) SEQUENCE CHARACTERISTICS:
        (A) LENGTH: 100 amino acids
```

(B) TYPE: amino acid
            (C) STRANDEDNESS: single
            (D) TOPOLOGY: linear (ii) MOLECULE TYPE: protein (vi) ORIGINAL SOURCE:
            (A) ORGANISM: Homo sapiens (vii) IMMEDIATE SOURCE:
            (B) CLONE: TieFn2

(xi) SEQUENCE DESCRIPTION: SEQ ID NO:28:

Thr Thr Asp Cys Pro Glu Pro Leu Leu Gln Pro Trp Leu Glu Gly Trp
1               5                   10                  15

His Val Glu Gly Thr Asp Arg Leu Arg Val Ser Trp Ser Leu Pro Leu
            20                  25                  30

Val Pro Gly Pro Leu Val Gly Asp Gly Phe Leu Leu Arg Leu Trp Asp
        35                  40                  45

Gly Thr Arg Gly Gln Glu Arg Arg Glu Asn Val Ser Ser Pro Gln Ala
    50                  55                  60

Arg Thr Ala Leu Leu Thr Gly Leu Thr Pro Gly Thr His Tyr Gln Leu
65                  70                  75                  80

Asp Val Gln Leu Tyr His Cys Thr Leu Leu Gly Pro Ala Ser Pro Pro
                    85                  90                  95

Ala His Val Leu
            100

(2) INFORMATION FOR SEQ ID NO:29:

(i) SEQUENCE CHARACTERISTICS:
            (A) LENGTH: 99 amino acids
            (B) TYPE: amino acid
            (C) STRANDEDNESS: single
            (D) TOPOLOGY: linear (ii) MOLECULE TYPE: protein (vii) IMMEDIATE SOURCE:
            (B) CLONE: TekFn3

(xi) SEQUENCE DESCRIPTION: SEQ ID NO:29:

Leu Ser Asp Ile Leu Pro Pro Gln Pro Glu Asn Ile Lys Ile Ser Asn
1               5                   10                  15

Ile Thr Asp Ser Thr Ala Met Val Ser Trp Thr Ile Val Asp Gly Tyr
            20                  25                  30

Ser Ile Ser Ser Ile Ile Ile Arg Tyr Lys Val Gln Gly Lys Asn Glu
        35                  40                  45

Asp Gln His Ile Asp Val Lys Ile Lys Asn Ala Thr Val Thr Gln Tyr
    50                  55                  60

Gln Leu Lys Gly Leu Glu Pro Glu Thr Thr Tyr His Val Asp Ile Phe
65                  70                  75                  80

Ala Glu Asn Asn Ile Gly Ser Ser Asn Pro Ala Phe Ser Met Glu Leu
                    85                  90                  95

Arg Thr Leu (2) INFORMATION FOR SEQ ID NO:30:

(i) SEQUENCE CHARACTERISTICS:
            (A) LENGTH: 94 amino acids
            (B) TYPE: amino acid
            (C) STRANDEDNESS: single
            (D) TOPOLOGY: linear (ii) MOLECULE TYPE: peptide (vi) ORIGINAL SOURCE:
    (A) ORGANISM: Homo sapiens (vii) IMMEDIATE SOURCE:
    (B) CLONE: TieFn3

(xi) SEQUENCE DESCRIPTION: SEQ ID NO:30:

```
Leu Pro Pro Ser Gly Pro Pro Ala Pro Arg His Leu His Ala Gln Ala
1               5                   10                  15

Leu Ser Asp Ser Glu Ile Gln Leu Thr Trp Lys His Pro Glu Ala Leu
            20                  25                  30

Pro Gly Pro Ile Ser Lys Tyr Val Val Glu Val Gln Val Ala Gly Gly
                35                  40                  45

Ala Gly Asp Pro Leu Trp Ile Asp Val Asp Arg Pro Glu Glu Thr Ser
50                  55                  60

Thr Ile Ile Arg Gly Leu Asn Ala Ser Thr Arg Tyr Leu Phe Arg Met
65                  70                  75                  80

Arg Ala Ser Ile Gln Gly Leu Gly Asp Trp Ser Asn Thr Val
                85                  90
```

(2) INFORMATION FOR SEQ ID NO:31:

(i) SEQUENCE CHARACTERISTICS:
        (A) LENGTH: 104 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: Finc-rat (xi) SEQUENCE DESCRIPTION: SEQ ID NO:31:

```
Val Ser Asp Val Pro Arg Asp Leu Lys Val Ile Ala Ser Thr Pro Thr
1               5                   10                  15

Ser Leu Leu Ile Ser Trp Glu Pro Pro Ala Val Ser Val Arg Tyr Tyr
            20                  25                  30

Arg Ile Thr Tyr Gly Glu Thr Gly Gly Asn Ser Pro Val Gln Lys Phe
            35                  40                  45

Thr Val Pro Gly Ser Lys Ser Thr Ala Thr Ile Met Asn Ile Lys Pro
50                  55                  60

Gly Ala Asp Tyr Thr Ile Thr Leu Tyr Ala Val Thr Gly Arg Gly Asp
65                  70                  75                  80

Ser Pro Ala Ser Ser Lys Phe Val Ser Ile Asn Tyr Gln Thr Lys Ile
                85                  90                  95

Asp Lys Pro Ser Gln Asn Gln Val
            100
```

(2) INFORMATION FOR SEQ ID NO:32:

(i) SEQUENCE CHARACTERISTICS:
        (A) LENGTH: 96 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: DLar (xi) SEQUENCE DESCRIPTION: SEQ ID NO:32:

```
Pro Gly Ala Pro Pro Arg Asn Ile Thr Ala Ile Ala Thr Ser Ser Thr
1               5                   10                  15

Thr Ile Ser Leu Ser Trp Leu Pro Pro Pro Val Glu Arg Ser Asn Gly
            20              25              30

Arg Ile Ile Tyr Tyr Lys Val Phe Phe Val Glu Val Gly Arg Glu Asp
        35              40              45

Asp Glu Ala Thr Thr Met Thr Leu Asn Met Thr Ser Ile Val Leu Asp
    50              55              60

Glu Leu Lys Arg Trp Thr Glu Tyr Lys Ile Trp Val Leu Ala Gly Thr
65              70              75              80

Ser Val Gly Asp Gly Pro Arg Ser His Pro Ile Ile Leu Arg Thr Gln
            85              90              95
```